(12) United States Patent
McComas et al.

(10) Patent No.: US 7,601,722 B2
(45) Date of Patent: Oct. 13, 2009

(54) ARYL SULFAMIDE DERIVATIVES AND METHODS OF THEIR USE

(75) Inventors: Casey Cameron McComas, Phoenixville, PA (US); Stephen Todd Cohn, Spring, TX (US); Andrew Fensome, Wayne, PA (US); Joel Adam Goldberg, Philadelphia, PA (US); Charles William Mann, Plymouth Meeting, PA (US); Michael Anthony Marella, Limerick, PA (US); David John O'Neill, Collegeville, PA (US); Joseph Peter Sabatucci, Collegeville, PA (US); Eugene Anthony Terefenko, Center Valley, PA (US); Eugene John Trybulski, Huntingdon Valley, PA (US); An Thien Vu, Pottstown, PA (US); Richard Page Woodworth, Jr., North Wales, PA (US); Puwen Zhang, Audubon, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/955,018

(22) Filed: Dec. 12, 2007

(65) Prior Publication Data

US 2008/0167303 A1    Jul. 10, 2008

Related U.S. Application Data

(60) Provisional application No. 60/869,644, filed on Dec. 12, 2006.

(51) Int. Cl.
   *A61K 31/496*    (2006.01)
   *A61K 31/5377*   (2006.01)
   *C07D 413/06*    (2006.01)
   *C07D 403/06*    (2006.01)

(52) U.S. Cl. .............. 514/254.03; 514/234.2; 544/134; 544/368

(58) Field of Classification Search .......... 548/125, 548/134; 514/234.2, 254.03; 544/134, 268
See application file for complete search history.

(56) References Cited

U.S. PATENT DOCUMENTS

| | | |
|---|---|---|
| 3,177,221 A | 4/1965 | Carson |
| 5,681,841 A | 10/1997 | Himmelsbach et al. |
| 5,763,469 A | 6/1998 | Delucca |
| 6,329,366 B1 | 12/2001 | Fairhurst et al. |
| 2003/0013874 A1 | 1/2003 | Goehring et al. |
| 2003/0078419 A1 | 4/2003 | Butler et al. |
| 2006/0063769 A1 | 3/2006 | Ishihara et al. |
| 2007/0072918 A1 | 3/2007 | McComas et al. |

FOREIGN PATENT DOCUMENTS

| | | |
|---|---|---|
| WO | WO 2006/114706 A | 11/2006 |
| WO | WO 2007/041258 A | 4/2007 |

OTHER PUBLICATIONS

"Tautomer." Retrieved online via Internet [Jan. 8, 2009], URL: http://en.wikipedia.org/wiki/Tautomer.*

* cited by examiner

*Primary Examiner*—Kamal A Saeed
*Assistant Examiner*—Samantha L Shterengarts
(74) *Attorney, Agent, or Firm*—Doina G. Ene; A. David Joran; David Kurlandsky

(57) ABSTRACT

The present invention is directed to aryl sulfamide derivatives of formula I:

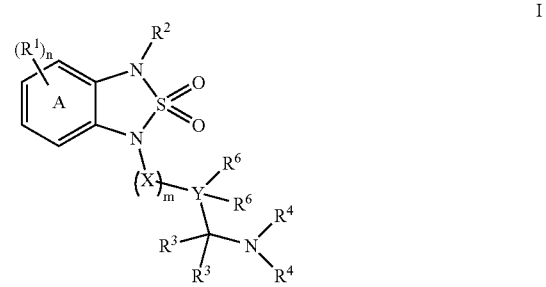

or a pharmaceutically acceptable salt, stereoisomer or tautomer thereof, which are monoamine reuptake inhibitors, compositions containing these derivatives, and methods of their use for the prevention and treatment of conditions, including, inter alia, vasomotor symptoms, sexual dysfunction, gastrointestinal disorders and genitourinary disorder, depression disorders, endogenous behavioral disorders, cognitive disorders, diabetic neuropathy, pain, and other diseases or disorders.

58 Claims, No Drawings

ARYL SULFAMIDE DERIVATIVES AND METHODS OF THEIR USE

CROSS-REFERENCE TO RELATED APPLICATIONS

This application claims the benefit under 35 U.S.C. §119 (e) to U.S. Provisional Application Ser. No. 60/869,644, filed Dec. 12, 2006, which is hereby incorporated by reference in its entirety.

FIELD

The present invention relates to aryl sulfamide derivatives, which are monoamine reuptake inhibitors, compositions containing these derivatives, and methods of their use for the prevention and treatment of diseases or disorders including vasomotor symptoms, depression disorders, endogenous behavioral disorders, cognitive disorders, sexual dysfunction, or pain conditions, in particular vasomotor symptoms.

BACKGROUND

Vasomotor symptoms (VMS), referred to as hot flushes and night sweats, are the most common symptoms associated with menopause, occurring in 60% to 80% of all women following natural or surgically-induced menopause. VMS are likely an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women.

VMS are caused by fluctuations of sex steroid levels and can be disruptive and disabling in both males and females. A hot flush can last up to thirty minutes and vary in their frequency from several times a week to multiple occurrences per day. The patient experiences a hot flush as a sudden feeling of heat that spreads quickly from the face to the chest and back and then over the rest of the body. It is usually accompanied by outbreaks of profuse sweating, and may sometimes occur several times an hour, and it often occurs at night. Hot flushes and outbreaks of sweats occurring during the night can cause sleep deprivation. Psychological and emotional symptoms are also observed, such as nervousness, fatigue, irritability, insomnia, depression, memory loss, headache, anxiety, nervousness or inability to concentrate, and are caused by the sleep deprivation following hot flush and night sweats (Kramer et al., In: Murphy et al., 3$^{rd}$ Int'l Symposium on Recent Advances in Urological Cancer Diagnosis and Treatment-Proceedings, Paris, France: SCI: 3-7 (1992)).

Hot flushes may be even more severe in women treated for breast cancer for several reasons. Many survivors of breast cancer are given tamoxifen, the most prevalent side effect of which is hot flush, and many women treated for breast cancer undergo premature menopause from chemotherapy Women with a history of breast cancer are also generally been denied estrogen therapy because of concerns about potential recurrence of breast cancer (Loprinzi, et al., Lancet, 2000, 356 (9247): 2059-2063).

Men also experience hot flushes following steroid hormone (androgen) withdrawal. This is true in cases of age-associated androgen decline (Katovich, et al., Proceedings of the Society for Experimental Biology & Medicine, 1990, 193 (2): 129-35) as well as in extreme cases of hormone deprivation associated with treatments for prostate cancer (Berendsen, et al., European Journal of Pharmacology, 2001, 419(1): 47-54. As many as one-third of these patients will experience persistent and frequent symptoms severe enough to cause significant discomfort and inconvenience.

The precise mechanism of these vasomotor symptoms is unknown but generally is thought to represent disturbances to normal homeostatic mechanisms controlling thermoregulation and vasomotor activity (Kronenberg et al., "Thermoregulatory Physiology of Menopausal Hot Flashes: A Review," Can. J. Physiol. Pharmacol., 1987, 65:1312-1324).

The fact that estrogen treatment (e.g. estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (J. Pharmacology & Experimental Therapeutics, 1986, 236(3) 646-652). It is hypothesized that estrogens modulate NE and 5-HT levels providing homeostasis in the thermoregulatory center of the hypothalamus. The descending pathways from the hypothalamus via brainstem/ spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al., Lancet, 2000, 356:2059-2063; Stearns et al., JAMA, 2003, 289:2827-2834) compared to doses used to treat the behavioral aspects of depression. The interplay of the CNS/ PNS in the pathophysiology of VMS supports the claims that the norepinephrine system could be targeted to treat VMS.

Although VMS are most commonly treated by hormone therapy, some patients cannot tolerate estrogen treatment (Berendsen, Maturitas, 2000, 36(3): 155-164, Fink et al., Nature, 1996, 383(6598): 306). In addition, hormone replacement therapy is usually not recommended for women or men with or at risk for hormonally sensitive cancers (e.g. breast or prostate cancer). Thus, non-hormonal therapies (e.g. fluoxetine, paroxetine [SRIs] and clonidine) are being evaluated clinically. WO9944601 discloses a method for decreasing hot flushes in a human female by administering fluoxetine. Other options have been studied for the treatment of hot flushes, including steroids, alpha-adrenergic agonists, and beta-blockers, with varying degree of success (Waldinger et al., Maturitas, 2000, 36(3): 165-168).

$\alpha_2$-Adrenergic receptors play a role in thermoregulatory dysfunctions (Freedman et al., Fertility & Sterility, 2000, 74(1): 20-3). These receptors are located both pre- and post-synaptically and mediate an inhibitory role in the central and peripheral nervous system. There are four distinct subtypes of the adrenergic$_{\alpha 2}$ receptors, i.e., are $\alpha_{2A}$, $\alpha_{2B}$, $\alpha_{2C}$ and $\alpha_{2D}$ (Mackinnon et al., TIPS, 1994, 15: 119; French, Pharmacol. Ther., 1995, 68: 175). A non-select $\alpha_2$-adrenoceptor antagonist, yohimbine, induces a flush and an $\alpha_2$-adrenergic receptor agonist, clonidine, alleviates the yohimbine effect (Katovich, et al., Proceedings of the Society for Experimental Biology & Medicine, 1990, 193(2): 129-35, Freedman et al., Fertility & Sterility, 2000, 74(1): 20-3). Clonidine has been used to treat hot flush. However, using such treatment is associated with a number of undesired side effects caused by high doses necessary to abate hot flush described herein and known in the related arts.

Chronic pain comes in many forms, including visceral, inflammatory or neuropathic and crosses all therapeutic areas. It is a debilitating condition that exerts a high social cost in terms of productivity, economic impact and quality of life and current therapies have limited efficacy. Currently, first-line pharmacological treatments for neuropathic pain (i.e., diabetic neuropathy and post-herpetic neuralgia) and fibromyalgia include off-label use of the tricyclic (TCA) antidepressants (e.g., amitriptyline) and anticonvulsants (e.g., gabapentin) (Collins et al., *J. Pain Symptom Manage.* 2000, 20(6):449-58; and Marcus Expert *Opin Pharmacother.* 2003, 4(10): 1687-95). However, these therapies are only effective in 30-50% of patients and produce only a partial reduction in pain (~50%). In addition, the clinical benefits of these therapies are often outweighed by the side effects, including dry mouth and sedation. Therefore, newer classes of compounds including non-TCA antidepressants are being evaluated preclinically and clinically for chronic pain indications, and recently duloxetine was approved for the treatment of diabetic neuropathy. Although more tolerable than the older tricyclic antidepressants, these newer compounds are not devoid of side effects that include sexual dysfunction, weight gain and nausea.

While the precise pathophysiological mechanisms involved in the development and maintenance of chronic pain states are not fully understood, the pathways involved in pain perception and modulation have been well described and characterized (Gebhart, In: Yaksh T L, editor. Spinal afferent processing, New York: Plenum, 1986. pp 391-416; Fields, et al., *Annual Review of Neuroscience* 1991,14: 219-245; Fields, et al. In: Wall P D, Melzack R, editors. Textbook of pain, London: Churchill Livingstone, 1999, pp 309-329; Millan, et al. *Progress in Neurobiology;* 2002, 66:355-474). A major component of this descending pain inhibitory system involves the noradrenergic pathway (Zhuo, et al., *Brain Research* 1991; 550:35-48; Holden, et al. *Neuroscience* 1999; 91: 979-990). It is assumed that norepinephrine (NE), and to a lesser extent serotonin (5-HT) reuptake inhibitor NRIs and SRIs, attenuate pain by preventing presynaptic reuptake of NE/5-HT leading to increased postsynaptic NE/5-HT levels and sustained activation of this descending pain inhibitory pathway. A meta-analysis of antidepressants and neuropathic pain comparing the efficacy of known NRIs, mixed NRI/SRIs and SRIs determined that compounds with NRI activity were more effective in reducing pain, and that select SRIs did not significantly differ from placebo (Collins et al., *J. Pain Symptom Manage.* 2000, 20(6): 449-58). This analysis suggests that compounds with greater NRI versus SRI activity will be more effective for the treatment of pain.

Given the complex multifaceted nature of pain and of thermoregulation and the interplay between the CNS and PNS in maintaining thermoregulatory the homeostasis, multiple therapies and approaches can be developed to target the treatment of pain and vasomotor symptoms. The present invention provides novel compounds and compositions containing these compounds directed to these and other important uses.

SUMMARY

The present invention is directed to aryl sulfamide derivatives, which are monoamine reuptake inhibitors, compositions containing these derivatives, and methods of their use for the prevention and treatment of conditions, including, inter alia, vasomotor symptoms (such as hot flush), sexual dysfunction (such as desire-related or arousal-related dysfunction), gastrointestinal disorders and genitourinary disorder (such as stress incontinence or urge incontinence), chronic fatigue syndrome, fibromyalgia syndrome, depression disorders (such as major depressive disorder, generalized anxiety disorder, panic disorder, attention deficit disorder with or without hyperactivity, sleep disturbance, and social phobia), diabetic neuropathy, pain, and combinations thereof.

One aspect of the invention provides a compound of formula I:

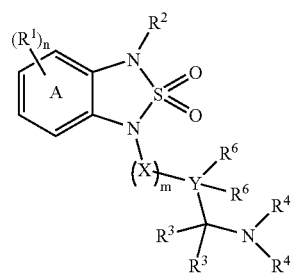

I or a pharmaceutically acceptable salt, stereoisomer or tautomer thereof;

wherein:

n is an integer from 0 to 4;

m is an integer from 0 to 6;

X is, independently at each occurrence, $C(R^7)_2$, $N(R^3)$, O, S, $S(=O)$, or $S(=O)_2$;

Y is C; or

Y and an adjacent X together form $-CR^7=CR^7-$, $-C\equiv C-$, or arylenyl substituted with 0-3 $R^{10}$;

$R^1$ is, independently at each occurrence, H, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;

$R^2$ is aryl substituted with 0-3 $R^9$ or heteroaryl substituted with 0-3 $R^9$;

$R^3$ is, independently at each occurrence, H, halo, hydroxy, alkyl substituted with 0-3 $R^{13}$, a heterocyclic ring, aryl substituted with 0-3 $R^{12}$, or heteroaryl substituted with 0-3 $R^{12}$;

$R^4$ is, independently at each occurrence, H, alkyl substituted with 0-3 $R^{13}$, arylalkyl substituted with 0-3 $R^{13}$ or heteroarylmethyl substituted with 0-3 $R^{13}$;

$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;

$R^6$ is, independently at each occurrence, H, hydroxy, $C_1$-$C_4$ alkyl, $C_1$-$C_6$ alkoxy, halo, aryl substituted with 0-3 $R^1$, heteroaryl substituted with 0-3 $R^1$, $-N(R^3)_2$, $-S(R^3)$, or $-R^8-O-R^3$; or both $R^6$ groups form a cycloalkyl, a heterocyclic ring, $=O$ or $=N-OH$;

provided that if each $R^3$ is H, each X is $CH_2$, and either each $R^6$ is H or one $R^6$ is hydroxy; then, both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, or a heterocyclic ring, F, or $CF_3$; and where any additional N atom may be optionally substituted with $C_1$-$C_4$ alkyl;

$R^7$ is, independently at each occurrence, H, hydroxy, alkoxy, or $C_1$-$C_4$ alkyl;

$R^8$ is, independently at each occurrence, straight or branched alkylenyl;

or one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, F, or $CF_3$; and where any additional N atom may be optionally substituted with alkyl;

or both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, a heterocyclic ring, F, or $CF_3$; and where any additional N atom may be optionally substituted with alkyl;

or one of said $R^6$ or one of said $R^7$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl;

$R^9$ is, independently at each occurrence, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide, alkylamido, or arylamido;

$R^{10}$ is, independently at each occurrence, alkyl, alkoxy, halo, $CF_3$, $OCF_3$, hydroxy, alkanoyloxy, nitro, nitrile, alkenyl, or alkynyl;

$R^{11}$ is, independently at each occurrence, alkyl, alkoxy, halo, $CF_3$, $OCF_3$, hydroxy, alkanoyloxy, nitro, nitrile, alkenyl, or alkynyl;

$R^{12}$ and $R^{13}$ are each, independently at each occurrence, alkyl, alkoxy, halo, $CF_3$, $OCF_3$, hydroxy, hydroxyalkyl, aminoalkyl, a heterocyclic ring, alkanoyloxy, nitro, nitrile, alkenyl, or alkynyl; and wherein 1-3 carbon atoms in ring A may optionally be replaced with N.

In a more particular embodiment, $R^4$ and $R^7$, taken together, do not form a piperidinyl ring.

Another aspect of the invention provides a compound of formula II:

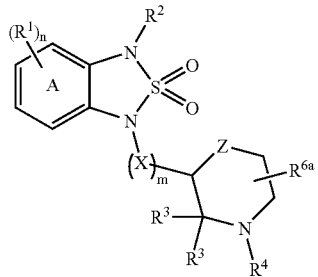

II or a pharmaceutically acceptable salt, stereoisomer or tautomer thereof;

wherein:

n is an integer from 0 to 4;

m is an integer from 1 to 6;

X is, independently at each occurrence, $C(R^7)_2$, $N(R^3)$, O, S, $S(\!=\!O)$, or $S(\!=\!O)_2$;

Z is O, $N(R^3)$, S, or $C(R^7)_2$;

$R^1$ is, independently at each occurrence, H, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;

$R^2$ is aryl substituted with 0-3 $R^9$ or heteroaryl substituted with 0-3 $R^9$;

$R^3$ is, independently at each occurrence, H, $C_1$-$C_4$ alkyl, aryl substituted with 0-3 $R^{12}$, or heteroaryl substituted with 0-3 $R^{12}$;

$R^4$ is H, $C_1$-$C_6$ alkyl, arylalkyl substituted with 0-3 $R^{13}$ or heteroarylmethyl substituted with 0-3 $R^{13}$;

$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;

$R^{6a}$ is H, $C_1$-$C_4$ alkyl, $C_1$-$C_6$ alkoxy, halo, aryl substituted with 0-3 $R^1$, heteroaryl substituted with 0-3 $R^1$, $-N(R^3)_2$, $-S(R^3)$, or $-R^8-O-R^3$;

$R^7$ is, independently at each occurrence, H, hydroxy, $C_1$-$C_6$ alkoxy, or $C_1$-$C_4$ alkyl;

$R^8$ is, independently at each occurrence, straight or branched $C_1$-$C_6$ alkylenyl;

or one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl;

$R^9$ is, independently at each occurrence, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide, alkylamido, or arylamido;

$R^{10}$ is, independently at each occurrence, alkyl, alkoxy, halo, $CF_3$, $OCF_3$, hydroxy, alkanoyloxy, nitro, nitrile, alkenyl, or alkynyl;

$R^{11}$ is, independently at each occurrence, alkyl, alkoxy, halo, $CF_3$, $OCF_3$, hydroxy, alkanoyloxy, nitro, nitrile, alkenyl, or alkynyl;

$R^{12}$ and $R^{13}$ are each, independently at each occurrence, alkyl, alkoxy, halo, $CF_3$, $OCF_3$, hydroxy, hydroxyalkyl, aminoalkyl, a heterocyclic ring, alkanoyloxy, nitro, nitrile, alkenyl, or alkynyl; and wherein 1-3 carbon atoms in ring A may optionally be replaced with N.

Another aspect of the invention provides a composition, comprising:

a. at least one compound of formula I or formula II; and b. at least one pharmaceutically acceptable carrier.

Another aspect of the invention provides a method for treating or preventing a condition selected from the group consisting of a vasomotor symptom, sexual dysfunction, gastrointestinal disorder, genitourinary disorder, chronic fatigue syndrome, fibromyalgia syndrome, depression disorder, diabetic neuropathy, endogenous behavioral disorder, cognitive disorder, pain, and combinations thereof in a subject in need thereof, comprising the step of:

administering to said subject an effective amount of a compound of formula I or formula II.

Another aspect of the invention provides a process for the preparation of a compound of formula I:

the process comprising:
(d) reacting a compound of formula IA:

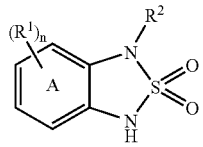

IA with a compound of formula IB:

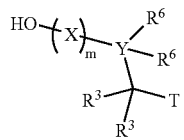

IB wherein,
T is an —N(R$^4$)$_2$ or an activating group;
wherein,
if T is —N(R$^4$)$_2$, then the compound of formula I is formed; or
if T is an activating group, then a compound of formula IC is formed:

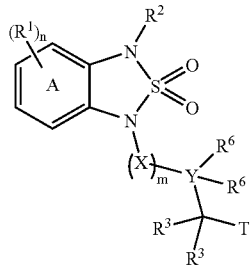

IC and the process further comprises:
(e) reacting the compound formula IC with —N(R$^4$)R$^P$ to form a compound of formula ID:

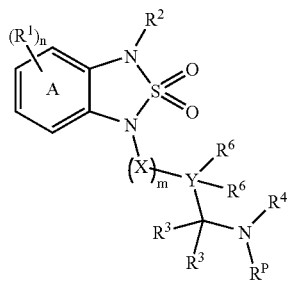

ID wherein,
R$^P$ is R$^4$ or a protecting group;
wherein,
if R$^P$ is R$^4$, the compound of formula I is formed; or if R$^P$ is a protecting group, the process further comprises:
(f) deprotecting the compound of formula ID to form a deprotected compound; and
(g) reacting the deprotected compound with an activated-R$^4$ group, provided that R$^4$ in the activated-R$^4$ group is not H;
wherein the compound of formula I is formed.

In another aspect of the invention, the compound of formula IA is prepared by:
(a) reacting a compound of formula IE:

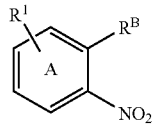

IE wherein R$^B$ is F or Cl;
with R$^2$—NH$_2$ to form a compound of formula IF:

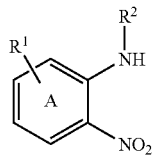

IF (b) hydrogenating the compound of formula IF to form a compound of formula IG:

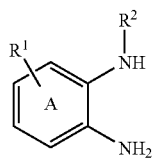

IG and (c) reacting the compound of formula IG with sulfamide in diglyme to form the compound of formula IA.

Another aspect of the invention provides a process for the preparation of a compound of formula I:

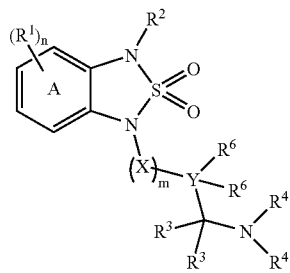

I or a pharmaceutically acceptable salt, stereoisomer or tautomer thereof;
wherein:
n is an integer from 0 to 4;
m is an integer from 0 to 6;
X is, independently at each occurrence, C(R$^7$)$_2$, N(R$^3$), O, S, S(=O), or S(=O)$_2$;
Y is C; or
Y and an adjacent X together form —CR$^7$=CR$^7$—, —C≡C—, or arylenyl substituted with 0-3 R$^{10}$;
R$^1$ is, independently at each occurrence, H, alkyl, alkoxy, halo, CF$_3$, OCF$_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;

$R^2$ is aryl substituted with 0-3 $R^9$ or heteroaryl substituted with 0-3 $R^9$;

$R^3$ is, independently at each occurrence, H, halo, hydroxy, alkyl substituted with 0-3 $R^{13}$, a heterocyclic ring, aryl substituted with 0-3 $R^{12}$, or heteroaryl substituted with 0-3 $R^{12}$;

$R^4$ is, independently at each occurrence, H, alkyl substituted with 0-3 $R^{13}$, arylalkyl substituted with 0-3 $R^{13}$ or heteroarylmethyl substituted with 0-3 $R^{13}$;

$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;

$R^6$ is, independently at each occurrence, H, hydroxy, $C_1$-$C_4$ alkyl, $C_1$-$C_6$ alkoxy, halo, aryl substituted with 0-3 $R^1$, heteroaryl substituted with 0-3 $R^1$, —$N(R^3)_2$, —$S(R^3)$, or —$R^8$—O—$R^3$; or both $R^6$ groups form a cycloalkyl, a heterocyclic ring, =O or =N—OH;

provided that if each $R^3$ is H, each X is $CH_2$, and either each $R^6$ is H or one $R^6$ is hydroxy; then, both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, or a heterocyclic ring, F, or $CF_3$; and where any additional N atom may be optionally substituted with $C_1$-$C_4$ alkyl;

$R^7$ is, independently at each occurrence, H, hydroxy, alkoxy, or $C_1$-$C_4$ alkyl;

$R^8$ is, independently at each occurrence, straight or branched alkylenyl;

or one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, F, or $CF_3$; and where any additional N atom may be optionally substituted with alkyl;

or both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, a heterocyclic ring, F, or $CF_3$; and where any additional N atom may be optionally substituted with alkyl;

or one of said $R^6$ or one of said $R^7$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl; provided that $R^4$ and $R^7$, taken together, do not form a piperidinyl ring;

$R^9$ is, independently at each occurrence, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide, alkylamido, or arylamido;

$R^{10}$ is, independently at each occurrence, alkyl, alkoxy, halo, $CF_3$, $OCF_3$, hydroxy, alkanoyloxy, nitro, nitrile, alkenyl, or alkynyl;

$R^{11}$ is, independently at each occurrence, alkyl, alkoxy, halo, $CF_3$, $OCF_3$, hydroxy, alkanoyloxy, nitro, nitrile, alkenyl, or alkynyl;

$R^{12}$ and $R^{13}$ are each, independently at each occurrence, alkyl, alkoxy, halo, $CF_3$, $OCF_3$, hydroxy, hydroxyalkyl, aminoalkyl, a heterocyclic ring, alkanoyloxy, nitro, nitrile, alkenyl, or alkynyl; and wherein 1-3 carbon atoms in ring A may optionally be replaced with N;

the process comprising:

(d) reacting $R^2(BOH)_2$ and a transitional metal salt with a compound of formula IH:

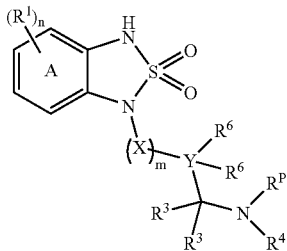

IH wherein, $R^P$ is $R^4$ or a protecting group; and if $R^P$ is $R^4$, the compound of formula I is formed; or if $R^P$ is a protecting group, the process further comprises:

(e) deprotecting the compound of formula IH to form a deprotected compound; and (g) reacting the deprotected compound with an activated-$R^4$ group, provided that $R^4$ group in the activated-$R^4$ group is not H;

wherein the compound of formula I is formed.

In another aspect of the invention, the compound of formula IH is prepared by:

(a) reacting a compound of formula IJ:

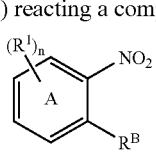

wherein $R^B$ is F or Cl;

with a compound of formula IK:

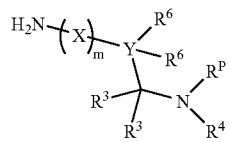

IK to form a compound of formula IL:

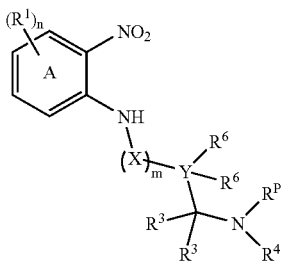

IL (b) hydrogenating the compound of formula IL to form a compound of formula IM:

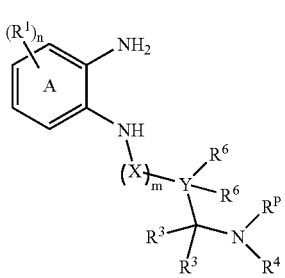

IM and (c) reacting the compound of formula IM with sulfamide and diglyme to form the compound of formula IH.

Other objects, features and advantages of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from this detailed description.

DETAILED DESCRIPTION

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "μL" means microliter(s), "mL" means milliliter(s), "mM" means millimolar, "M" means molar, "mmole" means millimole(s), "cm" means centimeters, "SEM" means standard error of the mean and "IU" means International Units. "Δ° C." and Δ "$ED_{50}$ value" means dose which results in 50% alleviation of the observed condition or effect (50% mean maximum endpoint).

"Norepinephrine transporter" is abbreviated NET.
"Human norepinephrine transporter" is abbreviated hNET.
"Serotonin transporter" is abbreviated SERT.
"Human serotonin transporter" is abbreviated hSERT.
"Norepinephrine reuptake inhibitor" is abbreviated NRI.
"Selective norepinephrine reuptake inhibitor" is abbreviated SNRI.
"Serotonin reuptake inhibitor" is abbreviated SRI.
"Selective serotonin reuptake inhibitor" is abbreviated SSRI.
"Norepinephrine" is abbreviated NE.
"Serotonin is abbreviated 5-HT.
"Subcutaneous" is abbreviated sc.
"Intraperitoneal" is abbreviated ip.
"Oral" is abbreviated po.

In the context of this disclosure, a number of terms are utilized. The term "treat," "treatment" or "treating" as used herein includes preventative (e.g., prophylactic), curative or palliative treatment.

The term "effective amount," as used herein, refers to an amount effective, at dosages, and for periods of time necessary, to achieve the desired result with respect to treatment of a given disease or disorder. An effective amount is also one in which any toxic or detrimental effects of the components are outweighed by the therapeutically beneficial effects. In particular, with respect to vasomotor symptoms, "effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

The effective amount of components of the present invention will vary from patient to patient not only with the particular compound, component or composition selected, the route of administration, and the ability of the components (alone or in combination with one or more additional active agents) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment. With respect to sexual dysfunction, gastrointestinal disorder, genitourinary disorder, chronic fatigue syndrome, fibromyalgia syndrome, depression disorder, diabetic neuropathy, or pain, the compounds of the present invention are administered at a dosage and for a time sufficient to treat the symptom or condition.

For example, for a patient, compounds of formula I, or a pharmaceutically acceptable salt thereof, may be administered, preferably, at a dosage of from about 0.1 mg/day to about 1500 mg/day, dosed one or two times daily, more preferably from about 1 mg/day to about 200 mg/day and most preferably from about 1 mg/day to 100 mg/day for a time sufficient to reduce and/or substantially eliminate the number and/or severity of hot flushes or symptom or condition of the sexual dysfunction, gastrointestinal disorder, genitourinary disorder, chronic fatigue syndrome, fibromyalgia syndrome, depression disorder, diabetic neuropathy, or pain.

The terms "component," "composition," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action.

The term "modulation" refers to the capacity to either enhance or inhibit a functional property of a biological activity or process; for example, receptor binding or signaling activity. Such enhancement or inhibition may be contingent on the occurrence of a specific event, such as activation of a signal transduction pathway and/or may be manifest only in particular cell types. The modulator is intended to comprise any compound; e.g., antibody, small molecule, peptide, oligopeptide, polypeptide, or protein, and is preferably small molecule, or peptide.

As used herein, the term "inhibitor" refers to any agent that inhibits, suppresses, represses, or decreases a specific activity, such as norepinephrine reuptake activity. The term "inhibitor" is intended to comprise any compound; e.g., antibody, small molecule, peptide, oligopeptide, polypeptide, or protein (preferably small molecule or peptide) that exhibits a partial, complete, competitive and/or inhibitory effect on mammalian (preferably the human norepinephrine reuptake or both serotonin reuptake and norepinephrine reuptake) thus diminishing or blocking (preferably diminishing) some or all of the biological effects of endogenous norepinephrine reuptake or of both serotonin reuptake and the norepinephrine reuptake.

Within the present invention, the compounds of formula I, may be prepared in the form of pharmaceutically acceptable salts. As used herein, the term "pharmaceutically acceptable salts" refers to salts prepared from pharmaceutically acceptable non-toxic acids, including inorganic salts and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferred is the hydrochloride salt.

"Administering," as used herein, means either directly administering a compound or composition of the present invention, or administering a prodrug, derivative or analog which will form an equivalent amount of the active compound or substance within the body.

The term "subject" or "patient" refers to an animal including the human species that is treatable with the compounds, compositions, and/or methods of the present invention. The term "subject" or "subjects" is intended to refer to both the male and female gender unless one gender is specifically indicated. Accordingly, the term "patient" comprises any mammal which may benefit from treatment or prevention of a disease or disorder, such as a human, especially if the mammal is female, either in the pre-menopausal, peri-menopausal, or post-menopausal period. Furthermore, the term patient includes female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

"Side effect" refers to a consequence other than the one(s) for which an agent or measure is used, as one or more adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and hot flushes (Janowsky, et al., *Journal of Clinical Psychiatry*, 1984, 45(10 Pt 2): 3-9), the entire disclosure of which is hereby incorporated by reference.

"Vasomotor symptoms," (also called "vasomotor instability symptoms" and "vasomotor disturbances") include, but are not limited to, hot flushes (flushes), insomnia, sleep disturbances, mood disorders, irritability, excessive perspiration, night sweats, fatigue, and the like, caused by, inter alia, thermoregulatory dysfunction.

The term "hot flush" (sometimes called "hot flash") is an art-recognized term that refers to an episodic disturbance in body temperature typically consisting of a sudden skin flushing, usually accompanied by perspiration in a subject.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause and the term "post-menopausal" means after the menopause. "Ovariectomy" means removal of an ovary or ovaries and can be effected according to Merchenthaler et al., *Maturitas*, 1998, 30(3): 307-316, the entire disclosure of which is hereby incorporated by reference.

The term "sexual dysfunction" includes, but is not limited to, conditions relating to disorders of sexual desire and/or arousal.

As used herein, "gastrointestinal and genitourinary disorders" includes irritable bowel syndrome, symptomatic GERD, hypersensitive esophagus, nonulcer dyspepsia, non-cardiac chest pain, biliary dyskinesia, sphincter of Oddi dysfunction, incontinence (i.e., urge incontinence, stress incontinence, genuine stress incontinence, and mixed incontinence, including the involuntary voiding of feces or urine, and dribbling or leakage or feces or urine which may be due to one or more causes including but not limited to pathology altering sphincter control, loss of cognitive function, overdistention of the bladder, hyperreflexia and/or involuntary urethral relaxation, weakness of the muscles associated with the bladder or neurologic abnormalities), interstitial cystitis (irritable bladder), and chronic pelvic pain (including, but not limited to vulvodynia, prostatodynia, and proctalgia).

As used herein, "chronic fatigue syndrome" (CFS) is a condition characterized by physiological symptoms selected from weakness, muscle aches and pains, excessive sleep, malaise, fever, sore throat, tender lymph nodes, impaired memory and/or mental concentration, insomnia, disordered sleep, localized tenderness, diffuse pain and fatigue, and combinations thereof, whether or not correlated with Epstein-Barr virus infection.

As used herein, "fibromyalgia syndrome" (FMS) includes FMS and other somatoform disorders, including FMS associated with depression, somatization disorder, conversion disorder, pain disorder, hypochondriasis, body dysmorphic disorder, undifferentiated somatoform disorder, and somatoform NOS. FMS and other somatoform disorders are accompanied by physiological symptoms selected from a generalized heightened perception of sensory stimuli, abnormalities in pain perception in the form of allodynia (pain with innocuous stimulation), abnormalities in pain perception in the form of hyperalgesia (increased sensitivity to painful stimuli), and combinations thereof.

As used herein, the term "depression disorder" includes major depressive disorder, generalized anxiety disorder, panic disorder, attention deficit disorder with or without hyperactivity, sleep disturbance, social phobia, and combinations thereof.

The compounds of the present invention can also be used to treat a cognitive disorder or an endogenous behavioral disorder. As used herein, a "cognitive disorder" includes changes or defects in alertness; mild cognitive impairment (MCI), characterized by problems with memory, language, or other mental functions which is severe enough to be noticeable or be detected by tests, but not serious enough to significantly interfere with daily life; cognitive disorder NOS (not otherwise specified), characterized by a syndrome of cognitive impairment that does not meet the criteria for delirium, dementia or amnesic disorders; age-related cognitive decline (ARCD); and cognitive arousal (such as increased arousal states). A cognition disorder can be idiopathic, or can be caused by a variety of other factors such as a congenital defect, alcohol or drug addiction, transient or permanent pharmacologic effects of drugs, organic or infectious disease (e.g., Alzheimer's disease, Parkinson's disease, AIDS), trauma (e.g., brain injury, stroke) or advanced age. As used herein, an "endogenous behavioral disorder" includes attention deficit disorder/attention deficit hyperactivity disorder (ADD/ADHD, including adult and pediatric forms of predominantly inattentive, predominantly hyperactive, or combined types), obsessive-compulsive disorder (OCD), oppositional or oppositional explosive defiant disorder (ODD/OEDD), anxiety and panic disorders (APD) and temper, rage and outburst behavior disorder (TROBD).

As used herein, "pain" includes both acute and chronic nociceptic or neuropathic pain, which includes centralized pain, peripheral pain, or combination thereof. The term includes many different types of pain, including, but not limited to, visceral pain, musculoskeletal pain, bony pain, cancer pain, inflammatory pain, and combinations thereof, such as lower back pain, atypical chest pain, headache such as cluster headache, migraine, herpes neuralgia, phantom limb pain, pelvic pain, myofascial face pain, abdominal pain, neck pain, central pain, dental pain, opioid resistant pain, visceral pain, surgical pain, bone injury pain, pain during labor and delivery, pain resulting from burns, post partum pain, angina pain, peripheral neuropathy and diabetic neuropathy, post-operative pain, and pain which is co-morbid with nervous system disorders described herein.

As used herein, the term "acute pain" refers to centralized or peripheral pain that is intense, localized, sharp, or stinging, and/or dull, aching, diffuse, or burning in nature and that occurs for short periods of time.

As used herein, the term "chronic pain" refers to centralized or peripheral pain that is intense, localized, sharp, or stinging, and/or dull, aching, diffuse, or burning in nature and that occurs for extended periods of time (i.e., persistent and/or regularly reoccurring), including, for the purposes of the present invention, neuropathic pain and cancer pain. Chronic pain includes neuropathic pain, hyperalgesia, and/or allodynia.

As used herein, the term "neuropathic pain" refers to chronic pain caused by damage to or pathological changes in the peripheral or central nervous systems. Examples of pathological changes related to neuropathic pain include prolonged peripheral or central neuronal sensitization, central sensitization related damage to nervous system inhibitory and/or exhibitory functions and abnormal interactions between the parasympathetic and sympathetic nervous systems. A wide range of clinical conditions may be associated with or form the basis for neuropathic pain including, for example, diabetes, post traumatic pain of amputation (nerve damage cause by injury resulting in peripheral and/or central sensitization such as phantom limb pain), lower back pain, cancer, chemical injury, toxins, other major surgeries, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, or viral or bacterial infections such as shingles or human immunodeficiency virus (HIV), and combinations thereof. Also included in the definition of neuropathic pain is a condition secondary to metastatic infiltration, adiposis dolorosa, burns, central pain conditions related to thalamic conditions, and combinations thereof.

As used herein, the term "hyperalgesia" refers to pain where there is an increase in sensitivity to a typically noxious stimulus.

As used herein, the term "allodynia" refers to an increase in sensitivity to a typically non-noxious stimulus.

As used herein, the term "visceral pain" refers to pain associated with or resulting from maladies of the internal organs, such as, for example, ulcerative colitis, irritable bowel syndrome, irritable bladder, Crohn's disease, rheumatologic (arthralgias), tumors, gastritis, pancreatitis, infections of the organs, biliary tract disorders, and combinations thereof.

As used herein, the term "female-specific pain" refers to pain that may be acute and/or chronic pain associated with female conditions. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes, and combinations thereof.

"Alkyl," as used herein, refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms or 1 to 6 carbon atoms ($C_1$-$C_6$) being preferred, and with from about 1 to about 4 carbon atoms, herein referred to as "lower alkyl", being more preferred. Alkyl groups include, but are not limited to, methyl, ethyl, n-propyl, isopropyl, n-butyl, isobutyl, t-butyl, n-pentyl, cyclopentyl, cyclopropyl, isopentyl, neopentyl, n-hexyl, isohexyl, cyclohexyl, cyclooctyl, adamantyl, 3-methylpentyl, 2,2-dimethylbutyl, and 2,3-dimethylbutyl. A branched alkyl group has at least 3 carbon atoms (e.g., an isopropyl group), and in various embodiments, has up to 6 carbon atoms, i.e., a branched lower alkyl group. A branched alkyl group has at least 3 carbon atoms (e.g., an isopropyl group), and in various embodiments, has up to 6 carbon atoms, i.e., a branched lower alkyl group. Examples of branched lower alkyl groups include, but are not limited to:

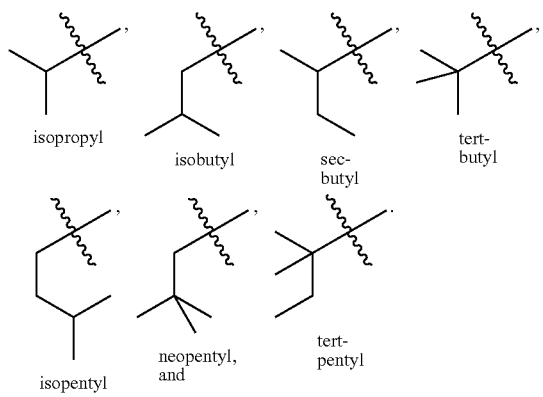

isopropyl, isobutyl, sec-butyl, tert-butyl, isopentyl, neopentyl, and tert-pentyl "Alkenyl," as used herein, refers to an alkyl group of at least two carbon atoms having one or more double bonds, wherein alkyl is as defined herein. Preferred alkenyl groups have from 2 to 6 carbon atoms ($C_2$-$C_6$). Alkenyl groups can be optionally substituted.

"Alkynyl," as used herein, refers to an alkyl group of at least two carbon atoms having one or more triple bonds, wherein alkyl is as defined herein. Preferred alkynyl groups have from 2 to 6 carbon atoms ($C_2$-$C_6$). Alkynyl groups can be optionally substituted.

"Alkylenyl", "alkenylenyl", "alkynylenyl", and "arylenyl" refer to the subsets of alkyl, alkenyl, alkynyl and aryl groups, respectively, as defined herein, including the same residues as alkyl, alkenyl, alkynyl, and aryl but having two points of attachment within a chemical structure. Examples of $C_1$-$C_6$alkylenyl include methylenyl (—$CH_2$—), ethylenyl (—$CH_2CH_2$—), propylenyl (—$CH_2CH_2CH_2$—), and dimethylpropylenyl (—$CH_2C(CH_3)_2CH_2$—). Likewise, examples of $C_2$-$C_6$alkenylenyl include ethenylenyl (—CH=CH—) and propenylenyl (—CH=CH—$CH_2$—). Examples of $C_2$-$C_6$alkynylenyl include ethynylenyl (—C≡C—) and propynylenyl (—C≡C—$CH_2$—).

Examples of arylenyl groups include phenylenyl;

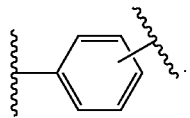

Preferably, arylenyl groups contain 6 carbon atoms ($C_6$).

"Halo," as used herein, refers to chloro, bromo, fluoro, and iodo.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons ($C_6$-$C_{10}$) being preferred. Non-limiting examples include, for example, phenyl, naphthyl, anthracenyl, and phenanthrenyl.

"Heteroaryl," as used herein, refers to an optionally substituted, mono-, di-, tri-, or other multicyclic aromatic ring system that includes at least one, and preferably from 1 to about 4 heteroatom ring members selected from sulfur, oxygen and nitrogen. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring," as used herein, refers to a stable 4- to 12-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than two. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

"Alkoxy," as used herein, refers to the group R—O— where R is an alkyl group, as defined herein. Preferred alkoxy groups have from 1 to 6 carbon atoms ($C_1$-$C_6$).

"Arylalkyl," as used herein, refers to the group R'—R— where R' is an aryl group, as defined herein, and R is an alkyl group, as defined herein. Preferred arylalkyl groups have from 7 to 16 carbon atoms ($C_7$-$C_{16}$).

"Heteroarylalkyl," as used herein, refers to the group R"—R— where R" is a heteroaryl group, as defined herein, and R is an alkyl group, as defined herein.

"Heteroarylmethyl," as used herein, refers to the group R"—$CH_2$—where R" is a heteroaryl group, as defined herein.

"Alkanoyloxy," as used herein, refers to the group R—C(=O)—O— where R is an alkyl group, as defined herein, of 1 to 5 carbon atoms ($C_1$-$C_5$).

"Alkylsulfoxide," as used herein, refers to as used herein, refers to —S(=O)—R, where R is alkyl, as defined herein. Preferred alkysulfoxide groups have from 1 to 6 carbon atoms ($C_1$-$C_6$).

"Arylsulfoxide," as used herein, refers to as used herein, refers to —S(=O)—R', where R' is aryl, as defined herein. Preferred arylsulfoxide groups have from 6 to 10 carbon atoms ($C_6$-$C_{10}$).

"Alkylsulfone," as used herein, refers to —S(=O)$_2$—R, where R is alkyl, as defined herein. Preferred alkylsulfone groups have from 1 to 6 carbon atoms ($C_1$-$C_6$).

"Arylsulfone," as used herein, refers to —S(=O)$_2$—R', where R' is aryl, as defined herein. Preferred arylsulfone groups have from 6 to 10 carbon atoms ($C_6$-$C_{10}$).

"Alkylsulfonamide," as used herein, refers to —NR—S(=O)$_2$—R, where each R is independently, alkyl, as defined above, or the NR part may also be NH. Preferred alkylsulfonamide groups have from 1 to 6 carbon atoms ($C_1$-$C_6$).

"Arylsulfonamide," as used herein, refers to —NR—S(=O)$_2$—R', where R is H or alkyl, as defined herein, and R' is aryl, as defined herein. Preferred arylsulfonamide groups have from 6 to 10 carbon atoms ($C_6$-$C_{10}$).

"Heteroarylsulfonamide," as used herein, refers to —NR—S(=O)$_2$—R", where R is H or alkyl, as defined herein, and R" is aryl, as defined herein.

"Alkylamido," as used herein, refers to —NR—C(=O)—R, where each R is independently, alkyl, as defined above, or the NR part may also be NH. Preferred alkylamido groups have from 1 to 6 carbon atoms ($C_1$-$C_6$).

"Arylamido," as used herein, refers to —NR—C(=O)—R", where R is H or alkyl, as defined herein, and R" is aryl, as defined herein. Preferred arylamido groups have from 6 to 10 carbon atoms ($C_6$-$C_{10}$).

"Phenylamido," as used herein, refers to —NR—C(=O)-phenyl, where R is H or alkyl, as defined above.

As used herein, the terms "optionally substituted" or "substituted or unsubstituted" are intended to refer to the optional replacement of up to four hydrogen atoms with up to four independently selected substituent groups as defined herein. Unless otherwise specified, suitable substituent groups independently include hydroxyl, nitro, amino, imino, cyano, halo, thio, sulfonyl, aminocarbonyl, carbonylamino, carbonyl, oxo, guanidine, carboxyl, formyl, alkyl, perfluoroalkyl, alkylamino, dialkylamino, alkoxy, alkoxyalkyl, alkylcarbonyl, arylcarbonyl, alkylthio, aryl, heteroaryl, a heterocyclic ring, cycloalkyl, hydroxyalkyl, carboxyalkyl, haloalkyl, alkenyl, alkynyl, arylalkyl, aryloxy, heteroaryloxy, heteroarylalkyl, and the like. Substituent groups that have one or more available hydrogen atoms can in turn optionally bear further independently selected substituents, to a maximum of three levels of substitutions. For example, the term "optionally substituted alkyl" is intended to mean an alkyl group that can optionally have up to four of its hydrogen atoms replaced with substituent groups as defined above (i.e., a first level of substitution), wherein each of the substituent groups attached to the alkyl group can optionally have up to four of its hydrogen atoms replaced by substituent groups as defined above (i.e., a second level of substitution), and each of the substituent groups of the second level of substitution can optionally have up to four of its hydrogen atoms replaced by substituent groups as defined above (i.e., a third level of substitution).

Unless indicated otherwise, the nomenclature of substituents that are not explicitly defined herein are arrived at by naming the terminal portion of the functionality followed by the adjacent functionality toward the point of attachment. For example, the substituent "arylalkoxycarbonyl" refers to the group (aryl)-(alkyl)-O—C(O)—.

It is understood that the above definitions are not intended to include impermissible substitution patterns (e.g., methyl substituted with 5 fluoro groups, multiple consecutive oxygen atoms, or other noncompatible consecutive or proximal heteroatoms). Such impermissible substitution patterns are well known to the skilled artisan.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of another example, the term "5-9 membered heteroaryl group" is specifically intended to individually disclose a heteroaryl group having 5, 6, 7, 8, 9, 5-9, 5-8, 5-7, 5-6, 6-9, 6-8, 6-7, 7-9, 7-8, and 8-9 ring atoms.

The term "protecting group" or "$G_p$" with respect to amine groups, hydroxyl groups and sulfhydryl groups refers to forms of these functionalities which are protected from undesirable reaction with a protecting group known to those skilled in the art, such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; carbamates; e.g. BOC; imides, such as phthalimide, Fmoc, Cbz, PMB, benzyl, and dithiosuccinimide; and others. Examples of protected or capped sulfhydryl groups include, but are not limited to, thioethers such as S-benzyl thioether, and S-4-picolyl thioether; substituted S-methyl derivatives such as hemithio, dithio and aminothio acetals; and others.

Reference to "activated" or "an activating group" or "$G_a$" as used herein indicates having an electrophilic moiety bound to a substituent, capable of being displaced by a nucleophile. Examples of preferred activating groups are halogens, such as Cl, Br or I, and F; triflate; mesylate, or tosylate; esters; aldehydes; ketones; epoxides; and the like. An example of an activated group is acetylchloride, which is readily attacked by a nucleophile, such as piperidine group to form a N-acetylpiperidin functionality.

The term "deprotecting" refers to removal of a protecting group, such as removal of a benzyl or BOC group bound to an amine. Deprotecting may be preformed by heating and/or addition of reagents capable of removing protecting groups. In preferred embodiments, the deprotecting step involves addition of an acid, base, reducing agent, oxidizing agent, heat, or any combination thereof. One preferred method of removing BOC groups from amino groups is to add HCl in ethyl acetate. Many deprotecting reactions are well known in the art and are described in Protective Groups in Organic Synthesis, Greene, T. W., John Wiley & Sons, New York, N.Y., (1st Edition, 1981), the entire disclosure of which is herein incorporated by reference.

One aspect of the invention provides a compound of formula I:

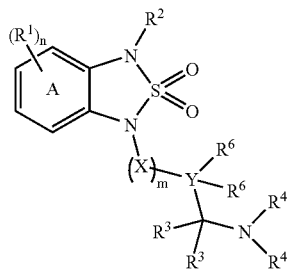

I or a pharmaceutically acceptable salt, stereoisomer or tautomer thereof;
wherein:
n is an integer from 0 to 4;
m is an integer from 0 to 6;
X is, independently at each occurrence, $C(R^7)_2$, $N(R^3)$, O, S, $S(=O)$, or $S(=O)_2$;
Y is C; or
Y and an adjacent X together form $—CR^7=CR^7—$, $—C≡C—$, or arylenyl substituted with 0-3 $R^{10}$;
$R^1$ is, independently at each occurrence, H, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;
$R^2$ is aryl substituted with 0-3 $R^9$ or heteroaryl substituted with 0-3 $R^9$;
$R^3$ is, independently at each occurrence, H, halo, hydroxy, alkyl substituted with 0-3 $R^{13}$, a heterocyclic ring, aryl substituted with 0-3 $R^{12}$, or heteroaryl substituted with 0-3 $R^{12}$;
$R^4$ is, independently at each occurrence, H, alkyl substituted with 0-3 $R^{13}$, arylalkyl substituted with 0-3 $R^{13}$ or heteroarylmethyl substituted with 0-3 $R^{13}$;
$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;
$R^6$ is, independently at each occurrence, H, hydroxy, $C_1$-$C_4$ alkyl, $C_1$-$C_6$ alkoxy, halo, aryl substituted with 0-3 $R^1$, heteroaryl substituted with 0-3 $R^1$, $—N(R^3)_2$, $—S(R^3)$, or $—R^8—O—R^3$; or both $R^6$ groups form a cycloalkyl, a heterocyclic ring, $=O$ or $=N—OH$;
provided that if each $R^3$ is H, each X is $CH_2$, and either each $R^6$ is H or one $R^6$ is hydroxy; then, both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, or a heterocyclic ring, F, or $CF_3$; and where any additional N atom may be optionally substituted with $C_1$-$C_4$ alkyl;
$R^7$ is, independently at each occurrence, H, hydroxy, alkoxy, or $C_1$-$C_4$ alkyl;
$R^8$ is, independently at each occurrence, straight or branched alkylenyl;
or
one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, F, or $CF_3$; and where any additional N atom may be optionally substituted with alkyl;
or
both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, a heterocyclic ring, F, or $CF_3$; and where any additional N atom may be optionally substituted with alkyl;
or
one of said $R^6$ or one of said $R^7$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl; provided that $R^4$ and $R^7$, taken together, do not form a piperidinyl ring;
$R^9$ is, independently at each occurrence, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide, alkylamido, or arylamido;
$R^{10}$ is, independently at each occurrence, alkyl, alkoxy, halo, $CF_3$, $OCF_3$, hydroxy, alkanoyloxy, nitro, nitrile, alkenyl, or alkynyl;
$R^{11}$ is, independently at each occurrence, alkyl, alkoxy, halo, $CF_3$, $OCF_3$, hydroxy, alkanoyloxy, nitro, nitrile, alkenyl, or alkynyl;
$R^{12}$ and $R^{13}$ are each, independently at each occurrence, alkyl, alkoxy, halo, $CF_3$, $OCF_3$, hydroxy, hydroxyalkyl, aminoalkyl, a heterocyclic ring, alkanoyloxy, nitro, nitrile, alkenyl, or alkynyl; and
wherein 1-3 carbon atoms in ring A may optionally be replaced with N.
In another embodiment,
$R^4$ and $R^6$, taken together, form a morpholinyl group optionally substituted with $C_1$-$C_4$ alkyl, F, or $CF_3$.
In another embodiment,
$R^4$ and $R^6$, taken together, form morpholin-2-yl.
In another embodiment,
$R^4$ and $R^6$, taken together, form (R)-morpholin-2-yl.
In another embodiment,
$R^4$ and $R^6$, taken together, form (S)-morpholin-2-yl.
In another embodiment,
n is an integer from 0 to 2.
In another embodiment,
m is an integer from 1 to 6.

In another embodiment, m is an integer from 2 to 6. More particularly, m is 1 to 5, 1 to 4, 1 to 3, 1 to 2, 2 to 5, 2 to 4, 2 to 3, 3 to 6, 3 to 5, 3 to 4, 4 to 6, or 4 to 5. In another embodiment, m is 1, m is 2, m is 3, m is 4, m is 5 or m is 6.

In another embodiment,
X is, independently at each occurrence, $C(R^7)_2$, $N(R^3)$, or O.

In another embodiment,
X is, independently at each occurrence, $C(R^7)_2$.

In another embodiment,
$R^1$ is, independently at each occurrence, alkyl, alkoxy, halo, $CF_3$, $OCF_3$ or nitrile.

In another embodiment,
$R^2$ is aryl substituted with 0-3 $R^9$.

In another embodiment,
$R^2$ is phenyl, fluoro-phenyl, difluoro-phenyl, trifluoro-phenyl, chloro-phenyl, fluoro-chloro-phenyl, bromo-phenyl, trifluoromethyl-phenyl trifluoromethoxy-phenyl, methyl-fluoro-phenyl, methoxy-fluoro-phenyl, or naphthyl.

In another embodiment,
$R^2$ is heteroaryl substituted with 0-3 $R^9$.

In another embodiment,
$R^2$ is pyridinyl, methyl-pyridinyl, ethyl-pyridinyl, methoxy-pyridinyl, or quinolinyl.

In another embodiment, $R^2$ is:

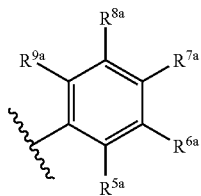

wherein,
each $R^{5a}$, $R^{6a}$, $R^{7a}$, $R^{8a}$ and $R^{9a}$ are independently selected from the group consisting of H, alkyl, alkoxy, halo, $CF_3$, $OCF_3$, hydroxy, alkanoyloxy, nitro, nitrile, alkenyl, alkynyl, aryl substituted, heteroaryl, alkylsulfoxide, alkylsulfone, alkylsulfonamide, arylsulfonamide, alkylamido, or arylamido.

In another embodiment, $R^{9a}$ is F. In another embodiment, $R^{5a}$, $R^{6a}$, $R^{7a}$ and $R^{8a}$ are H. In another embodiment, $R^{5a}$, $R^{6a}$, $R^{7a}$, $R^{8a}$ and $R^{9a}$ are independently H, halo, alkyl or alkoxy. In another embodiment, $R^{5a}$, $R^{6a}$, $R^{7a}$ and $R^{8a}$ are H. In another embodiment $R^{5a}$ is H or F, $R^{6a}$ is H or F, $R^{7a}$ is H or F, $R^{8a}$ is H or F and $R^{9a}$ is H or F. In another embodiment, $R^{5a}$, $R^{6a}$, $R^{7a}$, $R^{8a}$ and $R^{9a}$ are H, halo, alkyl or alkoxy.

In another embodiment,
$R^3$ is, independently at each occurrence, H, methyl, or phenyl.

In another embodiment,
$R^4$ is, independently at each occurrence, hydrogen, methyl, ethyl, cyclopropyl, or n-butyl.

In another embodiment,
both of said $R^4$, together with the nitrogen through which they are attached, form a heterocyclic ring of 4 to 7 atoms, where one carbon may be optionally replaced with N or O; where any carbon ring atom may be optionally substituted with one or two $C_1$-$C_4$ alkyl, F, or $CF_3$; and where any additional N atom may be optionally substituted with $C_1$-$C_4$ alkyl.

In another embodiment,
$R^5$ is, independently at each occurrence, alkyl, alkoxy, halo, or $OCF_3$.

In another embodiment,
$R^6$ is, independently at each occurrence, H methyl, or fluoro.

In another embodiment,
$R^7$ is, independently at each occurrence, H, methyl, or phenyl.

In another embodiment,
Y and an adjacent X together form —CH═CH—, —C≡C—, or phenylenyl.

In another embodiment,
m is an integer from 1 to 3;
X is, independently at each occurrence, $C(R^7)_2$, $N(R^3)$, or O;
Y is C;
$R^1$ is, independently at each occurrence, alkyl, alkoxy, halo, $CF_3$, or $OCF_3$;
$R^2$ is aryl substituted with 0-3 $R^9$ or heteroaryl substituted with 0-3 $R^9$;
$R^3$ is, independently at each occurrence, H or $C_1$-$C_4$ alkyl;
$R^4$ is, independently at each occurrence, H or $C_1$-$C_6$ alkyl;
$R^6$ is, independently at each occurrence, H, $C_1$-$C_4$ alkyl, or halo; and
$R^7$ is, independently at each occurrence, H or $C_1$-$C_4$ alkyl.

In another embodiment,
m is an integer from 0 to 1;
X is, independently at each occurrence, $C(R^7)_2$;
Y is C;
$R^1$ is, independently at each occurrence, alkyl, alkoxy, halo, $CF_3$, or $OCF_3$;
$R^2$ is aryl substituted with 0-3 $R^9$ or heteroaryl substituted with 0-3 $R^9$;
$R^3$ is, independently at each occurrence, H or $C_1$-$C_4$ alkyl;
$R^6$ is, independently at each occurrence, H, $C_1$-$C_4$ alkyl, or halo; and
$R^7$ is, independently at each occurrence, H or $C_1$-$C_4$ alkyl; or
both of said $R^4$, together with the nitrogen through which they are attached, form a heterocyclic ring of 4 to 7 atoms, where one carbon may be optionally replaced with N or O, where any carbon ring atom may be optionally substituted with one or two $C_1$-$C_4$ alkyl, F, or $CF_3$; and where any additional N atom may be optionally substituted with $C_1$-$C_4$ alkyl.

In another embodiment,
m is an integer from 0-1;
X is, independently at each occurrence, $C(R^7)_2$
Y is C
$R^1$ is, independently at each occurrence, alkyl, alkoxy, halo, $CF_3$, or $OCF_3$;
$R^2$ is aryl substituted with 0-3 $R^9$ or heteroaryl substituted with 0-3 $R^9$;
$R^3$ is, independently at each occurrence, H or $C_1$-$C_4$ alkyl;
$R^6$ is, independently at each occurrence, H, $C_1$-$C_4$ alkyl, or halo; and
$R^7$ is, independently at each occurrence, H or $C_1$-$C_4$ alkyl, or
one of said $R^6$ or one of said $R^7$ and one of said $R^4$, together with the nitrogen and carbon atoms through which they are attached, form a monocyclic or bicyclic heterocyclic ring of 3 to 12 atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl.

In another embodiment, the compound is selected from the group consisting of:

1-(morpholin-2-ylmethyl)-3-phenyl-1,3-dihydro-2,1,3-benzothiadiazole2,2-dioxide;
1-[(2R)-morpholin-2-ylmethyl]-3-phenyl-1,3-dihydro-2,1,3-benzothiadiazole 2,2-dioxide;
1-[(2S)-morpholin-2-ylmethyl]-3-phenyl-1,3-dihydro-2,1,3-benzothiadiazole 2,2-dioxide;
1-[(4-methylmorpholin-2-yl)methyl]-3-phenyl-1,3-dihydro-2,1,3-benzothiadiazole2,2-dioxide;
1-(2-chloro-4-fluorophenyl)-3-{2-[(3R,5S)-3,5-dimethylpiperazin-1-yl]ethyl}-1,3-dihydro-2,1,3-benzothiadiazole-2,2-dioxide;
1-(2-chloro-4-fluorophenyl)-3-{2-piperazin-1-ylethyl}-1,3-dihydro-2,1,3-benzothiadiazole-2,2-dioxide;
1-(4-fluoro-2-methylphenyl)-3-{2-piperazin-1-ylethyl}-1,3-dihydro-2,1,3-benzothiadiazole-2,2-dioxide;
1-(4-fluoro-2-methylphenyl)-3-{2-[(3R,5S)-3,5-dimethylpiperazin-1-yl]ethyl}-1,3-dihydro-2,1,3-benzothiadiazole-2,2-dioxide;
1-(4-fluoro-2-methoxyphenyl)-3-{2-piperazin-1-ylethyl}-1,3-dihydro-2,1,3-benzothiadiazole-2,2-dioxide;
1-[2-(2,5-diazabicyclo[2.2.1]hept-2-yl)ethyl]-3-phenyl-1,3-dihydro-2,1,3-benzothiadiazole-2,2-dioxide;
2-{2-[3-(2-fluorophenyl)-2,2-dioxido-2,1,3-benzothiadiazol-1(3H)-yl]ethoxy}ethanamine;
2-{2-[3-(2-fluorophenyl)-2,2-dioxido-2,1,3-benzothiadiazol-1(3H)-yl]ethoxy}-N-methylethanamine;
2-{2-[3-(2-fluorophenyl)-2,2-dioxido-2,1,3-benzothiadiazol-1(3H)-yl]ethoxy}-N,N-dimethylethanamine;
1-{2-[2-(3,5-dimethylpiperazin-1-yl)ethoxy]ethyl}-3-(2-fluorophenyl)-1,3-dihydro-2,1,3-benzothiadiazole2,2-dioxide;
1-[5-(3,5-dimethylpiperazin-1-yl)pentyl]-3-(2-fluorophenyl)-1,3-dihydro-2,1,3-benzothiadiazole2,2-dioxide;
(2R)-3-[3-(2-fluorophenyl)-2,2-dioxido-2,1,3-benzothiadiazol-1(3H)-yl]-2-methylpropan-1-amine;
(2S)-3-[3-(2-fluorophenyl)-2,2-dioxido-2,1,3-benzothiadiazol-1(3H)-yl]-2-methylpropan-1-amine;
4-[3-(2-fluorophenyl)-2,2-dioxido-2,1,3-benzothiadiazol-1(3H)-yl]butan-2-amine;
3-[3-(2-fluorophenyl)-2,2-dioxido-2,1,3-benzothiadiazol-1(3H)-yl]-N-methylbutan-1-amine;
4-[3-(2-fluorophenyl)-2,2-dioxido-2,1,3-benzothiadiazol-1(3H)-yl]-N-methylbutan-2-amine;
(2R)-3-[3-(2-fluorophenyl)-2,2-dioxido-2,1,3-benzothiadiazol-1(3H)-yl]-N,2-dimethylpropan-1-amine;
(2S)-3-[3-(2-fluorophenyl)-2,2-dioxido-2,1,3-benzothiadiazol-1(3H)-yl]-N,2-dimethylpropan-1-amine;
3-[3-(2-fluorophenyl)-2,2-dioxido-2,1,3-benzothiadiazol-1(3H)-yl]butan-1-amine;
1-Phenyl-3-(piperidin-4-ylmethyl)-1,3-dihydro-2,1,3-benzothiadiazole2,2-dioxide;
1-(2,6-Difluorophenyl)-3-(morpholin-2-ylmethyl)-1,3-dihydro-2,1,3-benzothiadiazole2,2-dioxide;
1-(2,6-Difluorophenyl)-3-[(2R)-morpholin-2-ylmethyl]-1,3-dihydro-2,1,3-benzothiadiazole2,2-dioxide;
1-(2,6-Difluorophenyl)-3-[(2S)-morpholin-2-ylmethyl]-1,3-dihydro-2,1,3-benzothiadiazole2,2-dioxide;
1-(2,3-Difluorophenyl)-3-(morpholin-2-ylmethyl)-1,3-dihydro-2,1,3-benzothiadiazole2,2-dioxide;
1-(Morpholin-2-ylmethyl)-3-[2-(trifluoromethoxy)phenyl]-1,3-dihydro-2,1,3-benzothiadiazole2,2-dioxide;
1-Phenyl-3-(2-piperidin-4-ylethyl)-1,3-dihydro-2,1,3-benzothiadiazole2,2-dioxide
1-Phenyl-3-(2-piperazin-1-ylethyl)-1,3-dihydro-2,1,3-benzothiadiazole-2,2-dioxide;
4-Fluoro-3-phenyl-1-(piperidin-4-ylmethyl)-1,3-dihydro-2,1,3-benzothiadiazole-2,2-dioxide;
4-Fluoro-3-phenyl-1-(2-piperidin-4-ylethyl)-1,3-dihydro-2,1,3-benzothiadiazole-2,2-dioxide;
4-Fluoro-3-phenyl-1-(2-piperazin-1-ylethyl)-1,3-dihydro-2,1,3-benzothiadiazole-2,2-dioxide;
4-Fluoro-3-(morpholin-2-ylmethyl)-1-phenyl-1,3-dihydro-2,1,3-benzothiadiazole-2,2-dioxide;
1-Phenyl-3-(3-piperidin-4-ylpropyl)-1,3-dihydro-2,1,3-benzothiadiazole-2,2-dioxide;
1-Phenyl-3-(2-piperidin-2-ylethyl)-1,3-dihydro-2,1,3-benzothiadiazole-2,2-dioxide
1-(2,6-Difluorophenyl)-3-(2-piperidin-4-ylethyl)-1,3-dihydro-2,1,3-benzothiadiazole-2,2-dioxide;
1-(2,6-Difluorophenyl)-3-(2-piperazin-1-ylethyl)-1,3-dihydro-2,1,3-benzothiadiazole2,2-dioxide;
1-Phenyl-3-(piperidin-3-ylmethyl)-1,3-dihydro-2,1,3-benzothiadiazole-2,2-dioxide;
1-Phenyl-3-[(3R)-piperidin-3-ylmethyl]-1,3-dihydro-2,1,3-benzothiadiazole-2,2-dioxide;
1-Phenyl-3-[(3S)-piperidin-3-ylmethyl]-1,3-dihydro-2,1,3-benzothiadiazole-2,2-dioxide;
1-Phenyl-3-(2-piperidin-3-ylethyl)-1,3-dihydro-2,1,3-benzothiadiazole-2,2-dioxide;
1-Phenyl-3-{2-[(3S)-piperidin-3-yl]ethyl}-1,3-dihydro-2,1,3-benzothiadiazole-2,2-dioxide;
1-Phenyl-3-{2-[(3R)-piperidin-3-yl]ethyl}-1,3-dihydro-2,1,3-benzothiadiazole-2,2-dioxide;
1-(2,3-Difluorophenyl)-3-(2-piperidin-4-ylethyl)-1,3-dihydro-2,1,3-benzothiadiazole-2,2-dioxide;
1-(2,5-Difluorophenyl)-3-(2-piperidin-4-ylethyl)-1,3-dihydro-2,1,3-benzothiadiazole-2,2-dioxide;
1-(2,3-Difluorophenyl)-3-(2-piperazin-1-ylethyl)-1,3-dihydro-2,1,3-benzothiadiazole-2,2-dioxide;
1-(2,5-Difluorophenyl)-3-(2-piperazin-1-ylethyl)-1,3-dihydro-2,1,3-benzothiadiazole-2,2-dioxide;
1-[2-(cis-3,5-Dimethylpiperazin-1-yl)ethyl]-3-phenyl-1,3-dihydro-2,1,3-benzothiadiazole-2,2-dioxide;
1-(2-Fluorophenyl)-3-(2-piperazin-1-ylethyl)-1,3-dihydro-2,1,3-benzothiadiazole-2,2-dioxide;
1-[2-(cis-3,5-Dimethylpiperazin-1-yl)ethyl]-3-(2-fluorophenyl)-1,3-dihydro-2,1,3-benzothiadiazole-2,2-dioxide;
1-[3-(cis-3,5-Dimethylpiperazin-1-yl)propyl]-3-phenyl-1,3-dihydro-2,1,3-benzothiadiazole2,2-dioxide;
1-(2,6-Difluorophenyl)-3-[2-(cis-3,5-dimethylpiperazin-1-yl)ethyl]-1,3-dihydro-2,1,3-benzothiadiazole-2,2-dioxide;
1-(2-piperazin-1-ylethyl)-3-(2,4,6-trifluorophenyl)-1,3-dihydro-2,1,3-benzothiadiazole-2,2-dioxide;
1-[2-(cis-3,5-Dimethylpiperazin-1-yl)ethyl]-3-(2,4,6-trifluorophenyl)-1,3-dihydro-2,1,3-benzothiadiazole-2,2-dioxide;
1-Phenyl-3-(3-piperazin-1-ylpropyl)-1,3-dihydro-2,1,3-benzothiadiazole-2,2-dioxide;
1-(4-Fluorophenyl)-3-(2-piperazin-1-ylethyl)-1,3-dihydro-2,1,3-benzothiadiazole-2,2-dioxide;
1-[2-(cis-3,5-Dimethylpiperazin-1-yl)ethyl]-3-(4-fluorophenyl)-1,3-dihydro-2,1,3-benzothiadiazole-2,2-dioxide;
1-(2,4-difluorophenyl)-3-(2-piperazin-1-ylethyl)-1,3-dihydro-2,1,3-benzothiadiazole2,2-dioxide;
1-(2,4-difluorophenyl)-3-[2-(3,5-dimethylpiperazin-1-yl)ethyl]-1,3-dihydro-2,1,3-benzothiadiazole-2,2-dioxide;
1-[2-(3,5-dimethylpiperazin-1-yl)ethyl]-4-fluoro-3-(2-fluorophenyl)-1,3-dihydro-2,1,3-benzothiadiazole2,2-dioxide;

1-(2-{[3-(2,3-difluorophenyl)-2,2-dioxido-2,1,3-benzothiadiazol-1(3H)-yl]methyl}phenyl)-N-methylmethanamine;
3-[3-(2,3-difluorophenyl)-2,2-dioxido-2,1,3-benzothiadiazol-1(3H)-yl]-N-methyl-1-phenylpropan-1-amine;
3-[3-(2-fluorophenyl)-2,2-dioxido-2,1,3-benzothiadiazol-1(3H)-yl]-N-methyl-1-phenylpropan-1-amine;
4-[3-(2-fluorophenyl)-2,2-dioxido-2,1,3-benzothiadiazol-1(3H)-yl]-N-methylbut-2-yn-1-amine;
4-[3-(2-fluorophenyl)-2,2-dioxido-2,1,3-benzothiadiazol-1(3H)-yl]-N,N-dimethylbut-2-yn-1-amine;
(2E)-4-[3-(2-fluorophenyl)-2,2-dioxido-2,1,3-benzothiadiazol-1(3H)-yl]-N-methylbut-2-en-1-amine;
(2E)-4-[3-(2-fluorophenyl)-2,2-dioxido-2,1,3-benzothiadiazol-1(3H)-yl]-N,N-dimethylbut-2-en-1-amine;
3-{2-[(3R,5S)-3,5-dimethylpiperazin-1-yl]ethyl}-4-fluoro-1-(2-fluorophenyl)-1,3-dihydro-2,1,3-benzothiadiazole2,2-dioxide;
2,2-difluoro-3-[3-(2-fluorophenyl)-2,2-dioxido-2,1,3-benzothiadiazol-1(3H)-yl]-N-methylpropan-1-amine;
1-(2-Fluorophenyl)-3-(2-piperidin-4-ylethyl)-1,3-dihydro-2,1,3-benzothiadiazole2,2-dioxide;
1-[2-(1,4-Diazepan-1-yl)ethyl]-3-phenyl-1,3-dihydro-2,1,3-benzothiadiazole-2,2-dioxide;
1-(2,4-Difluorophenyl)-4-fluoro-3-(2-piperazin-1-ylethyl)-1,3-dihydro-2,1,3-benzothiadiazole-2,2-dioxide;
3-(2,4-Difluorophenyl)-4-fluoro-1-(2-piperazin-1-ylethyl)-1,3-dihydro-2,1,3-benzothiadiazole-2,2-dioxide
1-[2-(1,4-Diazepan-1-yl)ethyl]-3-(2,4,6-trifluorophenyl)-1,3-dihydro-2,1,3-benzothiadiazole-2,2-dioxide
1-{2-[(1S,4S)-2,5-Diazabicyclo[2.2.1]hept-2-yl]ethyl}-3-(2,4,6-trifluorophenyl)-1,3-dihydro-2,1,3-benzothiadiazole-2,2-dioxide;
3-[2-(1,4-Diazepan-1-yl)ethyl]-1-(2,4-difluorophenyl)-4-fluoro-1,3-dihydro-2,1,3-benzothiadiazole2,2-dioxide;
1-[2-(1,4-Diazepan-1-yl)ethyl]-3-(2-fluorophenyl)-1,3-dihydro-2,1,3-benzothiadiazole2,2-dioxide;
1-{2-[(1S,4S)-2,5-diazabicyclo[2.2.1]hept-2-yl]ethyl}-3-(2-fluorophenyl)-1,3-dihydro-2,1,3-benzothiadiazole2,2-dioxide;
1-Phenyl-3-(2-piperidin-1-ylethyl)-1,3-dihydro-2,1,3-benzothiadiazole-2,2-dioxide;
1-(2,4-Difluorophenyl)-3-[2-(cis-3,5-dimethylpiperazin-1-yl)ethyl]-4-fluoro-1,3-dihydro-2,1,3-benzothiadiazole2,2-dioxide;
1-[3-(1,4-Diazepan-1-yl)propyl]-3-phenyl-1,3-dihydro-2,1,3-benzothiadiazole-2,2-dioxide;
1-[2-(1,4-Diazepan-1-yl)ethyl]-3-(2,6-difluorophenyl)-1,3-dihydro-2,1,3-benzothiadiazole-2,2-dioxide;
1-[2-(1,4-Diazepan-1-yl)ethyl]-3-(2,4-difluorophenyl)-1,3-dihydro-2,1,3-benzothiadiazole-2,2-dioxide;
1-{2-[(1S,4S)-2,5-Diazabicyclo[2.2.1]hept-2-yl]ethyl}-3-(2,4-difluorophenyl)-1,3-dihydro-2,1,3-benzothiadiazole-2,2-dioxide;
1-(2,4-Difluorophenyl)-3-(2-piperidin-4-ylethyl)-1,3-dihydro-2,1,3-benzothiadiazole-2,2-dioxide;
1-(2,4-Difluorophenyl)-3-[2-(4-methylpiperazin-1-yl)ethyl]-1,3-dihydro-2,1,3-benzothiadiazole2,2-dioxide;
1-(2,4-Difluorophenyl)-4-fluoro-3-[2-(4-methylpiperazin-1-yl)ethyl]-1,3-dihydro-2,1,3-benzothiadiazole2,2-dioxide;
1-(2,4-Difluorophenyl)-3-[2-(4-methyl-1,4-diazepan-1-yl)ethyl]-1,3-dihydro-2,1,3-benzothiadiazole2,2-dioxide;
1-[2-(4-Methyl-1,4-diazepan-1-yl)ethyl]-3-(2,4,6-trifluorophenyl)-1,3-dihydro-2,1,3-benzothiadiazole2,2-dioxide;
N-{2-[3-(2-Fluorophenyl)-2,2-dioxido-2,1,3-benzothiadiazol-1(3H)-yl]ethyl}-N,N'-dimethylethane-1,2-diamine;
N-{2-[3-(2,4-Difluorophenyl)-2,2-dioxido-2,1,3-benzothiadiazol-1(3H)-yl]ethyl}-N,N'-dimethylethane-1,2-diamine;
N-{2-[2,2-Dioxido-3-(2,4,6-trifluorophenyl)-2,1,3-benzothiadiazol-1(3H)-yl]ethyl}-N,N'-dimethylethane-1,2-diamine;
1-{3-[3-(2-fluorophenyl)-2,2-dioxido-2,1,3-benzothiadiazol-1(3H)-yl]propyl}piperidin-4-amine;
1-[3-(2,2-dioxido-3-phenyl-2,1,3-benzothiadiazol-1(3H)-yl)propyl]piperidin-4-amine;
1-{2-[3-(2-fluorophenyl)-2,2-dioxido-2,1,3-benzothiadiazol-1(3H)-yl]ethyl}piperidin-4-amine;
1-{2-[3-(2-fluorophenyl)-2,2-dioxido-2,1,3-benzothiadiazol-1(3H)-yl]ethyl}-N-methylpiperidin-4-amine;
1-{2-[3-phenyl-2,2-dioxido-2,1,3-benzothiadiazol-1(3H)-yl]ethyl}piperidin-4-amine;
1-{2-[3-phenyl-2,2-dioxido-2,1,3-benzothiadiazol-1(3H)-yl]ethyl}-N-methylpiperidin-4-amine;
1-{1-[2-(2,2-dioxido-3-phenyl-2,1,3-benzothiadiazol-1(3H)-yl)ethyl]pyrrolidin-3-yl}methanamine;
1-phenyl-3-[2-(4-pyrrolidin-1-ylpiperidin-1-yl)ethyl]-1,3-dihydro-2,1,3-benzothiadiazole2,2-dioxide;
2-{2-[3-(2-chloro-4-fluorophenyl)-2,2-dioxido-2,1,3-benzothiadiazol-1(3H)-yl]ethoxy}-N-methylethanamine;
2-{2-[3-(2-chloro-4-fluorophenyl)-2,2-dioxido-2,1,3-benzothiadiazol-1(3H)-yl]ethoxy}-N,N-dimethylethanamine;
1-(4-chloro-2-fluorophenyl)-3-(2-piperazin-1-yl-ethyl)-1,3-dihydro-2,1,3-benzothiadiazole2,2-dioxide;
1-(4-chloro-2-fluorophenyl)-3-{2-[(3R,5S)-3,5-dimethylpiperazin-1-yl]ethyl}-1,3-dihydro-2,1,3-benzothiadiazole2,2-dioxide;
1-(4-chloro-2-fluorophenyl)-3-(2-piperidin-4-ylethyl)-1,3-dihydro-2,1,3-benzothiadiazole2,2-dioxide;
1-(4-chloro-2-methylphenyl)-3-{2-[(3R,5S)-3,5-dimethylpiperazin-1-yl]ethyl}-1,3-dihydro-2,1,3-benzothiadiazole2,2-dioxide;
1-(4-chloro-2-methylphenyl)-3-(2-piperazin-1-ylethyl)-1,3-dihydro-2,1,3-benzothiadiazole2,2-dioxide;
1-(tert-butylamino)-4-(2,2-dioxido-3-phenyl-2,1,3-benzothiadiazol-1(3H)-yl)butan-2-one;
4-(2,2-dioxido-3-phenyl-2,1,3-benzothiadiazol-1(3H)-yl)-1-(isopropylamino)butan-2-one;
1-(cyclopropylamino)-4-(2,2-dioxido-3-phenyl-2,1,3-benzothiadiazol-1(3H)-yl)butan-2-one;
4-(2,2-dioxido-3-phenyl-2,1,3-benzothiadiazol-1(3H)-yl)-1-(methylamino)butan-2-one;
4-[3-(2-fluorophenyl)-2,2-dioxido-2,1,3-benzothiadiazol-1(3H)-yl]-1-(methylamino)butan-2-one;
(2Z)-4-(2,2-dioxido-3-phenyl-2,1,3-benzothiadiazol-1(3H)-yl)-1-(methylamino)butan-2-one oxime;
(2S)-4-[3-(2-fluorophenyl)-2,2-dioxido-2,1,3-benzothiadiazol-1(3H)-yl]-2-methoxy-N-methylbutan-1-amine;
(2S)-2-methoxy-N-methyl-4-[3-(2-methylphenyl)-2,2-dioxido-2,1,3-benzothiadiazol-1(3H)-yl]butan-1-amine;
(2S)-2-methoxy-4-[3-(3-methoxyphenyl)-2,2-dioxido-2,1,3-benzothiadiazol-1(3H)-yl]-N-methylbutan-1-amine;
4-(2,2-dioxido-3-phenyl-2,1,3-benzothiadiazol-1(3H)-yl)-2-methoxy-N-methylbutan-1-amine;
(2R)-4-(2,2-dioxido-3-phenyl-2,1,3-benzothiadiazol-1(3H)-yl)-2-methoxy-N-methylbutan-1-amine;
(2S)-4-(2,2-dioxido-3-phenyl-2,1,3-benzothiadiazol-1(3H)-yl)-2-methoxy-N-methylbutan-1-amine;
N-{(2S)-4-[3-(2-fluorophenyl)-2,2-dioxido-2,1,3-benzothiadiazol-1(3H)-yl]-2-methoxybutyl}cyclopropanamine;

N-{(2S)-2-methoxy-4-[3-(2-methylphenyl)-2,2-dioxido-2,1,3-benzothiadiazol-1(3H)-yl]butyl}cyclopropanamine;
N-{(2S)-2-methoxy-4-[3-(3-methoxyphenyl)-2,2-dioxido-2,1,3-benzothiadiazol-1(3H)-yl]butyl}cyclopropanamine;
N-{(2S)-4-[3-(2,4-difluorophenyl)-2,2-dioxido-2,1,3-benzothiadiazol-1(3H)-yl]-2-methoxybutyl}cyclopropanamine;
N-{(2S)-4-[3-(2,5-difluorophenyl)-2,2-dioxido-2,1,3-benzothiadiazol-1(3H)-yl]-2-methoxybutyl}cyclopropanamine;
N-{(2S)-4-[3-(2,6-difluorophenyl)-2,2-dioxido-2,1,3-benzothiadiazol-1(3H)-yl]-2-methoxybutyl}cyclopropanamine;
2S)-4-[3-(2,6-difluorophenyl)-2,2-dioxido-2,1,3-benzothiadiazol-1(3H)-yl]-2-methoxy-N-methylbutan-1-amine;
(2S)-4-[3-(2,4-difluorophenyl)-2,2-dioxido-2,1,3-benzothiadiazol-1(3H)-yl]-2-methoxy-N-methylbutan-1-amine;
1-(2-morpholin-2-ylethyl)-3-phenyl-1,3-dihydro-2,1,3-benzothiadiazole2,2-dioxide;
1-{2-[(2S)-morpholin-2-yl]ethyl}-3-phenyl-1,3-dihydro-2,1,3-benzothiadiazole2,2-dioxide;
1-{2-[(2R)-morpholin-2-yl]ethyl}-3-phenyl-1,3-dihydro-2,1,3-benzothiadiazole2,2-dioxide;
1-(4-fluorophenyl)-3-(2-morpholin-2-ylethyl)-1,3-dihydro-2,1,3-benzothiadiazole2,2-dioxide;
1-(4-fluorophenyl)-3-{2-[(2S)-morpholin-2-yl]ethyl}-1,3-dihydro-2,1,3-benzothiadiazole2,2-dioxide;
1-(4-fluorophenyl)-3-{2-[(2R)-morpholin-2-yl]ethyl}-1,3-dihydro-2,1,3-benzothiadiazole2,2-dioxide;
1-(2,4-difluorophenyl)-3-(2-morpholin-2-ylethyl)-1,3-dihydro-2,1,3-benzothiadiazole2,2-dioxide;
1-(2,4-difluorophenyl)-3-{2-[(2S)-morpholin-2-yl]ethyl}-1,3-dihydro-2,1,3-benzothiadiazole2,2-dioxide;
1-(2,4-difluorophenyl)-3-{2-[(2R)-morpholin-2-yl]ethyl}-1,3-dihydro-2,1,3-benzothiadiazole2,2-dioxide;
1-(2-morpholin-2-ylethyl)-3-(2,4,6-trifluorophenyl)-1,3-dihydro-2,1,3-benzothiadiazole2,2-dioxide;
1-2-[(2S)-morpholin-2-yl]ethyl-3-(2,4,6-trifluorophenyl)-1,3-dihydro-2,1,3-benzothiadiazole2,2-dioxide;
1-{2-[(2R)-morpholin-2-yl]ethyl}-3-(2,4,6-trifluorophenyl)-1,3-dihydro-2,1,3-benzothiadiazole2,2-dioxide;
1-(3-methoxyphenyl)-3-{2-[(2S)-morpholin-2-yl]ethyl}-1,3-dihydro-2,1,3-benzothiadiazole2,2-dioxide;
1-(3-methoxyphenyl)-3-{2-[(2R)-morpholin-2-yl]ethyl}-1,3-dihydro-2,1,3-benzothiadiazole2,2-dioxide;
1-(2-fluorophenyl)-3-{2-[(2S)-morpholin-2-yl]ethyl}-1,3-dihydro-2,1,3-benzothiadiazole2,2-dioxide;
1-(2-fluorophenyl)-3-{2-[(2R)-morpholin-2-yl]ethyl}-1,3-dihydro-2,1,3-benzothiadiazole2,2-dioxide;
1-(2,6-difluorophenyl)-3-{2-[(2S)-morpholin-2-yl]ethyl}-1,3-dihydro-2,1,3-benzothiadiazole2,2-dioxide;
1-(3-{[3-(2-fluorophenyl)-2,2-dioxido-2,1,3benzothiadiazol-1(3H)-yl]methyl}phenyl)-N-methylmethanamine;
1-(3-{[3-(2-fluorophenyl)-2,2-dioxido-2,1,3-benzothiadiazol-1(3H)-yl]methyl}phenyl)methanamine;
1-(3-{[3-(2-fluorophenyl)-2,2-dioxido-2,1,3-benzothiadiazol-1(3H)-yl]methyl}phenyl)-N,N-dimethylmethanamine;
1-(4-{[3-(2-fluorophenyl)-2,2-dioxido-2,1,3-benzothiadiazol-1(3H)-yl]methyl}phenyl)-N,N-dimethylmethanamine;
1-(4-{[3-(2-fluorophenyl)-2,2-dioxido-2,1,3-benzothiadiazol-1(3H)-yl]methyl}phenyl)methanamine;
1-(4-{[3-(2-fluorophenyl)-2,2-dioxido-2,1,3-benzothiadiazol-1(3H)-yl]methyl}phenyl)-N-methylmethanamine;

(2Z)-4-[3-(2-fluoro-4-methylphenyl)-2,2-dioxido-2,1,3-benzothiadiazol-1(3H)-yl]-N-methylbut-2-en-1-amine;
(2Z)-4-[3-(2-fluoro-4-methylphenyl)-2,2-dioxido-2,1,3-benzothiadiazol-1(3H)-yl]but-2-en-1-amine;
(2Z)-4-[3-(2-fluoro-4-methylphenyl)-2,2-dioxido-2,1,3-benzothiadiazol-1(3H)-yl]-N,N-dimethylbut-2-en-1-amine;
(2Z)-N-ethyl-4-[3-(2-fluoro-4-methylphenyl)-2,2-dioxido-2,1,3-benzothiadiazol-1(3H)-yl]but-2-en-1-amine;
1-(3,4-difluorophenyl)-3-(2-piperazin-1-ylethyl)-1,3-dihydro-2,1,3-benzothiadiazole2,2-dioxide;
1-(3,4-difluorophenyl)-3-(3-piperazin-1-ylpropyl)-1,3-dihydro-2,1,3-benzothiadiazole2,2-dioxide;
1-(3,4-difluorophenyl)-3-[3-(3,5-dimethylpiperazin-1-yl)propyl]-1,3-dihydro-2,1,3-benzothiadiazole2,2-dioxide;
2-{2-[3-(3,4-difluorophenyl)-2,2-dioxido-2,1,3-benzothiadiazol-1(3H)-yl]ethoxy}-N-methylethanamine;
1-(2-piperazin-1-ylethyl)-3-(2,3,4-trifluorophenyl)-1,3-dihydro-2,1,3-benzothiadiazole2,2-dioxide;
1-(2-methylphenyl)-3-(2-piperazin-1-ylethyl)-1,3-dihydro-2,1,3-benzothiadiazole2,2-dioxide;
1-(2-chlorophenyl)-3-(2-piperazin-1-ylethyl)-1,3-dihydro-2,1,3-benzothiadiazole2,2-dioxide;
2-{2-[3-(2,4-difluorophenyl)-2,2-dioxido-2,1,3-benzothiadiazol-1(3H)-yl]ethoxy}-N-methylethanamine;
2-{2-[3-(2,4-difluorophenyl)-2,2-dioxido-2,1,3-benzothiadiazol-1(3H)-yl]ethoxy}ethanamine;
2-{2-[3-(2,4-difluorophenyl)-2,2-dioxido-2,1,3-benzothiadiazol-1(3H)-yl]ethoxy}-N,N-dimethylethanamine;
(2E)-4-[3-(2,4-difluorophenyl)-2,2-dioxido-2,1,3-benzothiadiazol-1(3H)-yl]-N-methylbut-2-en-1-amine;
(2E)-4-[3-(2,4-difluorophenyl)-2,2-dioxido-2,1,3-benzothiadiazol-1(3H)-yl]-N,N-dimethylbut-2-en-1-amine;
(2E)-4-[3-(2,4-difluorophenyl)-2,2-dioxido-2,1,3-benzothiadiazol-1(3H)-yl]but-2-en-1-amine;
N-(2-{2-[3-(2,6-difluorophenyl)-2,2-dioxido-2,1,3-benzothiadiazol-1(3H)-yl]ethoxy}ethyl)cyclopropanamine;
N-(2-{2-[3-(2,6-difluorophenyl)-2,2-dioxido-2,1,3-benzothiadiazol-1(3H)-yl]ethoxy}ethyl)cyclobutanamine;
N-(2-{2-[3-(2,6-difluorophenyl)-2,2-dioxido-2,1,3-benzothiadiazol-1(3H)-yl]ethoxy}ethyl)cyclopentanamine;
2-{2-[3-(2,6-difluorophenyl)-2,2-dioxido-2,1,3-benzothiadiazol-1(3H)-yl]ethoxy}-N-methylethanamine;
2-{2-[3-(2,6-difluorophenyl)-2,2-dioxido-2,1,3-benzothiadiazol-1(3H)-yl]ethoxy}-N-ethylethanamine;
N-(2-{2-[3-(2,6-difluorophenyl)-2,2-dioxido-2,1,3-benzothiadiazol-1(3H)-yl]ethoxy}ethyl)propan-2-amine;
1-(4-chlorophenyl)-3-(4-morpholin-4-ylbutyl)-1,3-dihydro-2,1,3-benzothiadiazole2,2-dioxide;
1-(2-Fluorophenyl)-4-fluoro-3-{2-[(2R)-morpholin-2-yl]ethyl}-1,3-dihydro-2,1,3-benzothiadiazole2,2-dioxide;
1-(2-Fluorophenyl)-4-fluoro-3-{2-[(2S)-morpholin-2-yl]ethyl}-1,3-dihydro-2,1,3-benzothiadiazole2,2-dioxide;
1-(2-Fluorophenyl)-5-fluoro-3-{2-[(2R)-morpholin-2-yl]ethyl}-1,3-dihydro-2,1,3-benzothiadiazole2,2-dioxide;
1-(2-Fluorophenyl)-5-fluoro-3-{2-[(2S)-morpholin-2-yl]ethyl}-1,3-dihydro-2,1,3-benzothiadiazole2,2-dioxide;
1-(2-Fluorophenyl)-6-fluoro-3-{2-[(2R)-morpholin-2-yl]ethyl}-1,3-dihydro-2,1,3-benzothiadiazole2,2-dioxide;
1-(2-Fluorophenyl)-6-fluoro-3-{2-[(2S)-morpholin-2-yl]ethyl}-1,3-dihydro-2,1,3-benzothiadiazole2,2-dioxide;
1-(2-Fluorophenyl)-7-fluoro-3-{2-[(2R)-morpholin-2-yl]ethyl}-1,3-dihydro-2,1,3-benzothiadiazole2,2-dioxide;
1-(2-Fluorophenyl)-7-fluoro-3-{2-[(2S)-morpholin-2-yl]ethyl}-1,3-dihydro-2,1,3-benzothiadiazole2,2-dioxide;
1-(2,6-Difluorophenyl)-4-fluoro-3-{2-[(2R)-morpholin-2-yl]ethyl}-1,3-dihydro-2,1,3-benzothiadiazole2,2-dioxide;

1-(2,6-Difluorophenyl)-4-fluoro-3-{2-[(2S)-morpholin-2-yl]ethyl}-1,3-dihydro-2,1,3-benzothiadiazole2,2-dioxide;
1-(2,6-Difluorophenyl)-5-fluoro-3-{2-[(2R)-morpholin-2-yl]ethyl}-1,3-dihydro-2,1,3-benzothiadiazole2,2-dioxide;
1-(2,6-Difluorophenyl)-5-fluoro-3-{2-[(2S)-morpholin-2-yl]ethyl}-1,3-dihydro-2,1,3-benzothiadiazole2,2-dioxide;
1-(2,6-Difluorophenyl)-6-fluoro-3-{2-[(2R)-morpholin-2-yl]ethyl}-1,3-dihydro-2,1,3-benzothiadiazole2,2-dioxide;
1-(2,6-Difluorophenyl)-6-fluoro-3-{2-[(2S)-morpholin-2-yl]ethyl}-1,3-dihydro-2,1,3-benzothiadiazole2,2-dioxide;
1-(2,6-Difluorophenyl)-7-fluoro-3-{2-[(2R)-morpholin-2-yl]ethyl}-1,3-dihydro-2,1,3-benzothiadiazole2,2-dioxide;
1-(2,6-Difluorophenyl)-7-fluoro-3-{2-[(2S)-morpholin-2-yl]ethyl}-1,3-dihydro-2,1,3-benzothiadiazole2,2-dioxide; and
pharmaceutically acceptable salts thereof.

Another aspect of the invention provides a compound of formula II:

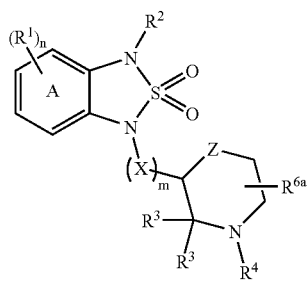

II or a pharmaceutically acceptable salt, stereoisomer or tautomer thereof;
wherein:
n is an integer from 0 to 4;
m is an integer from 1 to 6;
X is, independently at each occurrence, $C(R^7)_2$, $N(R^3)$, O, S, S(=O), or S(=O)$_2$;
Z is O, $N(R^3)$, S, or $C(R^7)_2$;
$R^1$ is, independently at each occurrence, H, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;
$R^2$ is aryl substituted with 0-3 $R^9$ or heteroaryl substituted with 0-3 $R^9$;
$R^3$ is, independently at each occurrence, H, $C_1$-$C_4$ alkyl, aryl substituted with 0-3 $R^{12}$, or heteroaryl substituted with 0-3 $R^{12}$;
$R^4$ is H, $C_1$-$C_6$ alkyl, arylalkyl substituted with 0-3 $R^{13}$ or heteroarylmethyl substituted with 0-3 $R^{13}$;
$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;
$R^{6a}$ is H, $C_1$-$C_4$ alkyl, $C_1$-$C_6$ alkoxy, halo, aryl substituted with 0-3 $R^1$, heteroaryl substituted with 0-3 $R^1$, —$N(R^3)_2$, —$S(R^3)$, or —$R^8$—O—$R^3$;
$R^7$ is, independently at each occurrence, H, hydroxy, $C_1$-$C_6$ alkoxy, or $C_1$-$C_4$ alkyl;
$R^8$ is, independently at each occurrence, straight or branched $C_1$-$C_6$ alkylenyl;
or
one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl;
$R^9$ is, independently at each occurrence, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide, alkylamido, or arylamido;
$R^{10}$ is, independently at each occurrence, alkyl, alkoxy, halo, $CF_3$, $OCF_3$, hydroxy, alkanoyloxy, nitro, nitrile, alkenyl, or alkynyl;
$R^{11}$ is, independently at each occurrence, alkyl, alkoxy, halo, $CF_3$, $OCF_3$, hydroxy, alkanoyloxy, nitro, nitrile, alkenyl, or alkynyl;
$R^{12}$ and $R^{13}$ are each, independently at each occurrence, alkyl, alkoxy, halo, $CF_3$, $OCF_3$, hydroxyalkyl, aminoalkyl, a heterocyclic ring, alkanoyloxy, nitro, nitrile, alkenyl, or alkynyl; and
wherein 1-3 carbon atoms in ring A may optionally be replaced with N.

In another embodiment, Z is O.
In another embodiment, Z is $N(R^3)$.
In another embodiment, X is $CH_2$ and m is 2 to 4.
In another embodiment:
ring A is composed of all carbon atoms;
$R^1$ is H;
$R^2$ is phenyl substituted with one to three fluoro (F) atoms;
each $R^3$ is H;
$R^4$ is H; and
$R^{6a}$ is H.
In another embodiment, the compound is:

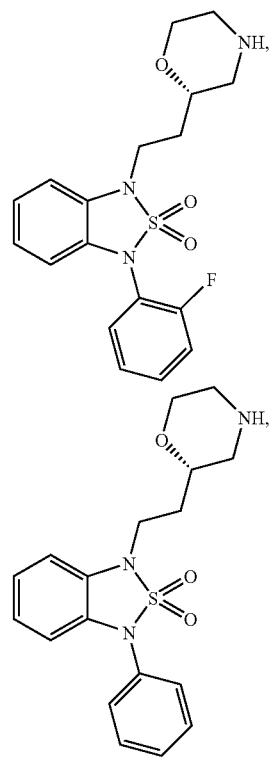

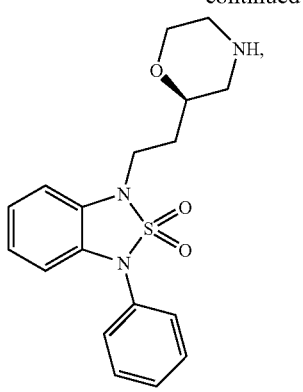
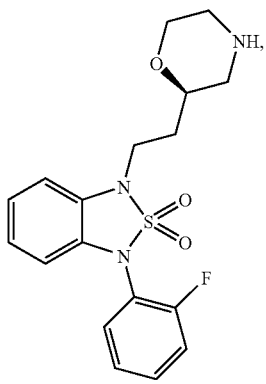
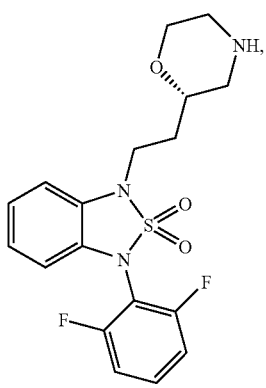
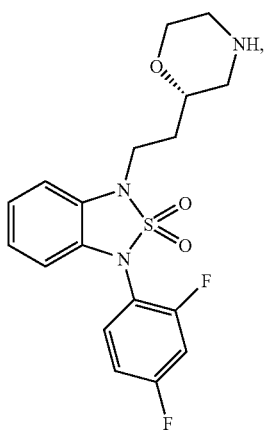
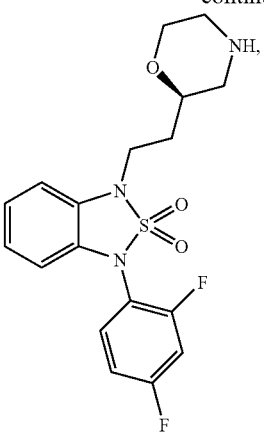
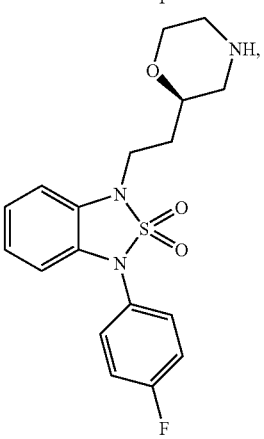
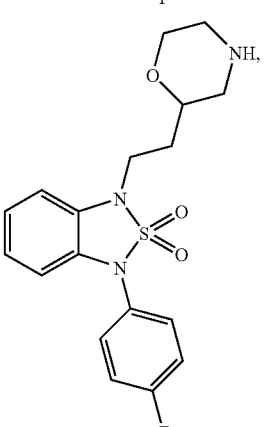
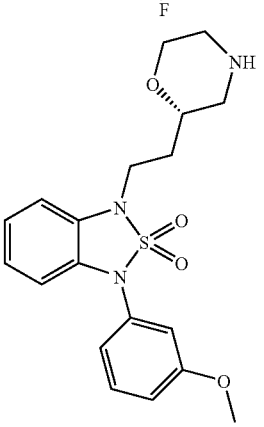
or -continued

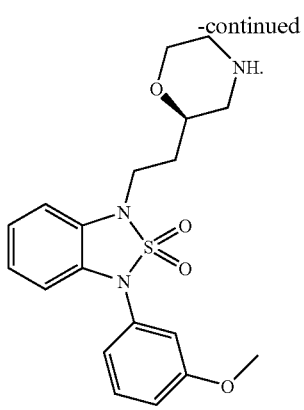

Another aspect of the invention provides a compound selected from the group consisting of:
1-(morpholin-2-ylmethyl)-3-phenyl-1,3-dihydro-2,1,3-benzothiadiazole2,2-dioxide;
1-[(2R)-morpholin-2-ylmethyl]-3-phenyl-1,3-dihydro-2,1,3-benzothiadiazole 2,2-dioxide;
1-[(2S)-morpholin-2-ylmethyl]-3-phenyl-1,3-dihydro-2,1,3-benzothiadiazole 2,2-dioxide;
1-[(4-methylmorpholin-2-yl)methyl]-3-phenyl-1,3-dihydro-2,1,3-benzothiadiazole2,2-dioxide;
1-(2-chloro-4-fluorophenyl)-3-{2-[(3R,5S)-3,5-dimethylpiperazin-1-yl]ethyl}-1,3-dihydro-2,1,3-benzothiadiazole-2,2-dioxide;
1-(2-chloro-4-fluorophenyl)-3-{2-piperazin-1-ylethyl}-1,3-dihydro-2,1,3-benzothiadiazole-2,2-dioxide;
1-(4-fluoro-2-methylphenyl)-3-{2-piperazin-1-ylethyl}-1,3-dihydro-2,1,3-benzothiadiazole-2,2-dioxide;
1-(4-fluoro-2-methylphenyl)-3-{2-[(3R,5S)-3,5-dimethylpiperazin-1-yl]ethyl}-1,3-dihydro-2,1,3-benzothiadiazole-2,2-dioxide;
1-(4-fluoro-2-methoxyphenyl)-3-{2-piperazin-1-ylethyl}-1,3-dihydro-2,1,3-benzothiadiazole-2,2-dioxide;
1-[2-(2,5-diazabicyclo[2.2.1]hept-2-yl)ethyl]-3-phenyl-1,3-dihydro-2,1,3-benzothiadiazole2,2-dioxide;
2-{2-[3-(2-fluorophenyl)-2,2-dioxido-2,1,3-benzothiadiazol-1(3H)-yl]ethoxy}ethanamine;
2-{2-[3-(2-fluorophenyl)-2,2-dioxido-2,1,3-benzothiadiazol-1(3H)-yl]ethoxy}-N-methylethanamine;
2-{2-[3-(2-fluorophenyl)-2,2-dioxido-2,1,3-benzothiadiazol-1(3H)-yl]ethoxy}-N,N-dimethylethanamine;
1-{2-[2-(3,5-dimethylpiperazin-1-yl)ethoxy]ethyl}-3-(2-fluorophenyl)-1,3-dihydro-2,1,3-benzothiadiazole2,2-dioxide;
1-[5-(3,5-dimethylpiperazin-1-yl)pentyl]-3-(2-fluorophenyl)-1,3-dihydro-2,1,3-benzothiadiazole2,2-dioxide;
(2R)-3-[3-(2-fluorophenyl)-2,2-dioxido-2,1,3-benzothiadiazol-1(3H)-yl]-2-methylpropan-1-amine;
(2S)-3-[3-(2-fluorophenyl)-2,2-dioxido-2,1,3-benzothiadiazol-1(3H)-yl]-2-methylpropan-1-amine;
4-[3-(2-fluorophenyl)-2,2-dioxido-2,1,3-benzothiadiazol-1(3H)-yl]butan-2-amine;
3-[3-(2-fluorophenyl)-2,2-dioxido-2,1,3-benzothiadiazol-1(3H)-yl]-N-methylbutan-1-amine;
4-[3-(2-fluorophenyl)-2,2-dioxido-2,1,3-benzothiadiazol-1(3H)-yl]-N-methylbutan-2-amine;
(2R)-3-[3-(2-fluorophenyl)-2,2-dioxido-2,1,3-benzothiadiazol-1(3H)-yl]-N,2-dimethylpropan-1-amine;
(2S)-3-[3-(2-fluorophenyl)-2,2-dioxido-2,1,3-benzothiadiazol-1(3H)-yl]-N,2-dimethylpropan-1-amine;
3-[3-(2-fluorophenyl)-2,2-dioxido-2,1,3-benzothiadiazol-1(3H)-yl]butan-1-amine;
1-Phenyl-3-(piperidin-4-ylmethyl)-1,3-dihydro-2,1,3-benzothiadiazole2,2-dioxide;
1-(2,6-Difluorophenyl)-3-(morpholin-2-ylmethyl)-1,3-dihydro-2,1,3-benzothiadiazole2,2-dioxide;
1-(2,6-Difluorophenyl)-3-[(2R)-morpholin-2-ylmethyl]-1,3-dihydro-2,1,3-benzothiadiazole2,2-dioxide;
1-(2,6-Difluorophenyl)-3-[(2S)-morpholin-2-ylmethyl]-1,3-dihydro-2,1,3-benzothiadiazole2,2-dioxide;
1-(2,3-Difluorophenyl)-3-(morpholin-2-ylmethyl)-1,3-dihydro-2,1,3-benzothiadiazole2,2-dioxide;
1-(Morpholin-2-ylmethyl)-3-[2-(trifluoromethoxy)phenyl]-1,3-dihydro-2,1,3-benzothiadiazole2,2-dioxide;
1-Phenyl-3-(2-piperidin-4-ylethyl)-1,3-dihydro-2,1,3-benzothiadiazole-2,2-dioxide
1-Phenyl-3-(2-piperazin-1-ylethyl)-1,3-dihydro-2,1,3-benzothiadiazole-2,2-dioxide;
4-Fluoro-3-phenyl-1-(piperidin-4-ylmethyl)-1,3-dihydro-2,1,3-benzothiadiazole-2,2-dioxide;
4-Fluoro-3-phenyl-1-(2-piperidin-4-ylethyl)-1,3-dihydro-2,1,3-benzothiadiazole2,2-dioxide;
4-Fluoro-3-phenyl-1-(2-piperazin-1-ylethyl)-1,3-dihydro-2,1,3-benzothiadiazole-2,2-dioxide;
4-Fluoro-3-(morpholin-2-ylmethyl)-1-phenyl-2,1,3-benzothiadiazole-2,2-dioxide;
1-Phenyl-3-(3-piperidin-4-ylpropyl)-1,3-dihydro-2,1,3-benzothiadiazole-2,2-dioxide;
1-Phenyl-3-(2-piperidin-2-ylethyl)-1,3-dihydro-2,1,3-benzothiadiazole-2,2-dioxide
1-(2,6-Difluorophenyl)-3-(2-piperidin-4-ylethyl)-1,3-dihydro-2,1,3-benzothiadiazole-2,2-dioxide;
1-(2,6-Difluorophenyl)-3-(2-piperazin-1-ylethyl)-1,3-dihydro-2,1,3-benzothiadiazole2,2-dioxide;
1-Phenyl-3-(piperidin-3-ylmethyl)-1,3-dihydro-2,1,3-benzothiadiazole-2,2-dioxide;
1-Phenyl-3-[(3R)-piperidin-3-ylmethyl]-1,3-dihydro-2,1,3-benzothiadiazole-2,2-dioxide;
1-Phenyl-3-[(3S)-piperidin-3-ylmethyl]-1,3-dihydro-2,1,3-benzothiadiazole-2,2-dioxide;
1-Phenyl-3-(2-piperidin-3-ylethyl)-1,3-dihydro-2,1,3-benzothiadiazole-2,2-dioxide;
1-Phenyl-3-{2-[(3S)-piperidin-3-yl]ethyl}-1,3-dihydro-2,1,3-benzothiadiazole-2,2-dioxide;
1-Phenyl-3-{2-[(3R)-piperidin-3-yl]ethyl}-1,3-dihydro-2,1,3-benzothiadiazole-2,2-dioxide;
1-(2,3-Difluorophenyl)-3-(2-piperidin-4-ylethyl)-1,3-dihydro-2,1,3-benzothiadiazole-2,2-dioxide;
1-(2,5-Difluorophenyl)-3-(2-piperidin-4-ylethyl)-1,3-dihydro-2,1,3-benzothiadiazole-2,2-dioxide;
1-(2,3-Difluorophenyl)-3-(2-piperazin-1-ylethyl)-1,3-dihydro-2,1,3-benzothiadiazole-2,2-dioxide;
1-(2,5-Difluorophenyl)-3-(2-piperazin-1-ylethyl)-1,3-dihydro-2,1,3-benzothiadiazole-2,2-dioxide;
1-[2-(cis-3,5-Dimethylpiperazin-1-yl)ethyl]-3-phenyl-1,3-dihydro-2,1,3-benzothiadiazole-2,2-dioxide;
1-(2-Fluorophenyl)-3-(2-piperazin-1-ylethyl)-1,3-dihydro-2,1,3-benzothiadiazole-2,2-dioxide;
1-[2-(cis-3,5-Dimethylpiperazin-1-yl)ethyl]-3-(2-fluorophenyl)-1,3-dihydro-2,1,3-benzothiadiazole-2,2-dioxide;
1-[3-(cis-3,5-Dimethylpiperazin-1-yl)propyl]-3-phenyl-1,3-dihydro-2,1,3-benzothiadiazole2,2-dioxide;
1-(2,6-Difluorophenyl)-3-[2-(cis-3,5-dimethylpiperazin-1-yl)ethyl]-1,3-dihydro-2,1,3-benzothiadiazole-2,2-dioxide;

1-(2-piperazin-1-ylethyl)-3-(2,4,6-trifluorophenyl)-1,3-dihydro-2,1,3-benzothiadiazole-2,2-dioxide;

1-[2-(cis-3,5-Dimethylpiperazin-1-yl)ethyl]-3-(2,4,6-trifluorophenyl)-1,3-dihydro-2,1,3-benzothiadiazole-2,2-dioxide;

1-Phenyl-3-(3-piperazin-1-ylpropyl)-1,3-dihydro-2,1,3-benzothiadiazole-2,2-dioxide;

1-(4-Fluorophenyl)-3-(2-piperazin-1-ylethyl)-1,3-dihydro-2,1,3-benzothiadiazole-2,2-dioxide;

1-[2-(cis-3,5-Dimethylpiperazin-1-yl)ethyl]-3-(4-fluorophenyl)-1,3-dihydro-2,1,3-benzothiadiazole-2,2-dioxide;

1-(2,4-difluorophenyl)-3-(2-piperazin-1-ylethyl)-1,3-dihydro-2,1,3-benzothiadiazole2,2-dioxide;

1-(2,4-difluorophenyl)-3-[2-(3,5-dimethylpiperazin-1-yl)ethyl]-1,3-dihydro-2,1,3-benzothiadiazole-2,2-dioxide;

1-[2-(3,5-dimethylpiperazin-1-yl)ethyl]-4-fluoro-3-(2-fluorophenyl)-1,3-dihydro-2,1,3-benzothiadiazole2,2-dioxide;

1-(2-{[3-(2,3-difluorophenyl)-2,2-dioxido-2,1,3-benzothiadiazol-1(3H)-yl]methyl}phenyl)-N-methylmethanamine;

3-[3-(2,3-difluorophenyl)-2,2-dioxido-2,1,3-benzothiadiazol-1(3H)-yl]-N-methyl-1-phenylpropan-1-amine;

3-[3-(2-fluorophenyl)-2,2-dioxido-2,1,3-benzothiadiazol-1(3H)-yl]-N-methyl-1-phenylpropan-1-amine;

4-[3-(2-fluorophenyl)-2,2-dioxido-2,1,3-benzothiadiazol-1(3H)-yl]-N-methylbut-2-yn-1-amine;

4-[3-(2-fluorophenyl)-2,2-dioxido-2,1,3-benzothiadiazol-1(3H)-yl]-N,N-dimethylbut-2-yn-1-amine;

(2E)-4-[3-(2-fluorophenyl)-2,2-dioxido-2,1,3-benzothiadiazol-1(3H)-yl]-N-methylbut-2-en-1-amine;

(2E)-4-[3-(2-fluorophenyl)-2,2-dioxido-2,1,3-benzothiadiazol-1(3H)-yl]-N,N-dimethylbut-2-en-1-amine;

3-{2-[(3R,5S)-3,5-dimethylpiperazin-1-yl]ethyl}-4-fluoro-1-(2-fluorophenyl)-1,3-dihydro-2,1,3-benzothiadiazole2,2-dioxide;

2,2-difluoro-3-[3-(2-fluorophenyl)-2,2-dioxido-2,1,3-benzothiadiazol-1(3H)-yl]-N-methylpropan-1-amine;

1-(2-Fluorophenyl)-3-(2-piperidin-4-ylethyl)-1,3-dihydro-2,1,3-benzothiadiazole2,2-dioxide;

1-[2-(1,4-Diazepan-1-yl)ethyl]-3-phenyl-1,3-dihydro-2,1,3-benzothiadiazole-2,2-dioxide;

1-(2,4-Difluorophenyl)-4-fluoro-3-(2-piperazin-1-ylethyl)-1,3-dihydro-2,1,3-benzothiadiazole-2,2-dioxide;

3-(2,4-Difluorophenyl)-4-fluoro-1-(2-piperazin-1-ylethyl)-1,3-dihydro-2,1,3-benzothiadiazole-2,2-dioxide 1-[2-(1,4-Diazepan-1-yl)ethyl]-3-(2,4,6-trifluorophenyl)-1,3-dihydro-2,1,3-benzothiadiazole-2,2-dioxide 1-{2-[(1S,4S)-2,5-Diazabicyclo[2.2.1]hept-2-yl]ethyl}-3-(2,4,6-trifluorophenyl)-1,3-dihydro-2,1,3-benzothiadiazole-2,2-dioxide;

3-[2-(1,4-Diazepan-1-yl)ethyl]-1-(2,4-difluorophenyl)-4-fluoro-1,3-dihydro-2,1,3-benzothiadiazole2,2-dioxide;

1-[2-(1,4-Diazepan-1-yl)ethyl]-3-(2-fluorophenyl)-1,3-dihydro-2,1,3-benzothiadiazole2,2-dioxide;

1-{2-[(1S,4S)-2,5-diazabicyclo[2.2.1]hept-2-yl]ethyl}-3-(2-fluorophenyl)-1,3-dihydro-2,1,3-benzothiadiazole2,2-dioxide;

1-Phenyl-3-(2-piperidin-1-ylethyl)-1,3-dihydro-2,1,3-benzothiadiazole-2,2-dioxide;

1-(2,4-Difluorophenyl)-3-[2-(cis-3,5-dimethylpiperazin-1-yl)ethyl]-4-fluoro-1,3-dihydro-2,1,3-benzothiadiazole2,2-dioxide;

1-[3-(1,4-Diazepan-1-yl)propyl]-3-phenyl-1,3-dihydro-2,1,3-benzothiadiazole-2,2-dioxide;

1-[2-(1,4-Diazepan-1-yl)ethyl]-3-(2,6-difluorophenyl)-1,3-dihydro-2,1,3-benzothiadiazole-2,2-dioxide;

1-[2-(1,4-Diazepan-1-yl)ethyl]-3-(2,4-difluorophenyl)-1,3-dihydro-2,1,3-benzothiadiazole-2,2-dioxide;

1-{2-[(1S,4S)-2,5-Diazabicyclo[2.2.1]hept-2-yl]ethyl}-3-(2,4-difluorophenyl)-1,3-dihydro-2,1,3-benzothiadiazole-2,2-dioxide;

1-(2,4-Difluorophenyl)-3-(2-piperidin-4-ylethyl)-1,3-dihydro-2,1,3-benzothiadiazole-2,2-dioxide;

1-(2,4-Difluorophenyl)-3-[2-(4-methylpiperazin-1-yl)ethyl]-1,3-dihydro-2,1,3-benzothiadiazole2,2-dioxide;

1-(2,4-Difluorophenyl)-4-fluoro-3-[2-(4-methylpiperazin-1-yl)ethyl]-1,3-dihydro-2,1,3-benzothiadiazole2,2-dioxide;

1-(2,4-Difluorophenyl)-3-[2-(4-methyl-1,4-diazepan-1-yl)ethyl]-1,3-dihydro-2,1,3-benzothiadiazole2,2-dioxide;

1-[2-(4-Methyl-1,4-diazepan-1-yl)ethyl]-3-(2,4,6-trifluorophenyl)-1,3-dihydro-2,1,3-benzothiadiazole2,2-dioxide;

N-{2-[3-(2-Fluorophenyl)-2,2-dioxido-2,1,3-benzothiadiazol-1(3H)-yl]ethyl}-N,N'-dimethylethane-1,2-diamine;

N-{2-[3-(2,4-Difluorophenyl)-2,2-dioxido-2,1,3-benzothiadiazol-1(3H)-yl]ethyl}-N,N'-dimethylethane-1,2-diamine;

N-{2-[2,2-Dioxido-3-(2,4,6-trifluorophenyl)-2,1,3-benzothiadiazol-1(3H)-yl]ethyl}-N,N'-dimethylethane-1,2-diamine;

1-{3-[3-(2-fluorophenyl)-2,2-dioxido-2,1,3-benzothiadiazol-1(3H)-yl]propyl}piperidin-4-amine;

1-[3-(2,2-dioxido-3-phenyl-2,1,3-benzothiadiazol-1(3H)-yl)propyl]piperidin-4-amine;

1-{2-[3-(2-fluorophenyl)-2,2-dioxido-2,1,3-benzothiadiazol-1(3H)-yl]ethyl}piperidin-4-amine;

1-{2-[3-(2-fluorophenyl)-2,2-dioxido-2,1,3-benzothiadiazol-1(3H)-yl]ethyl}-N-methylpiperidin-4-amine;

1-{2-[3-phenyl-2,2-dioxido-2,1,3-benzothiadiazol-1(3H)-yl]ethyl}piperidin-4-amine;

1-{2-[3-phenyl-2,2-dioxido-2,1,3-benzothiadiazol-1(3H)-yl]ethyl}-N-methylpiperidin-4-amine;

1-{1-[2-(2,2-dioxido-3-phenyl-2,1,3-benzothiadiazol-1(3H)-yl)ethyl]pyrrolidin-3-yl}methanamine;

1-phenyl-3-[2-(4-pyrrolidin-1-ylpiperidin-1-yl)ethyl]-1,3-dihydro-2,1,3-benzothiadiazole2,2-dioxide;

2-{2-[3-(2-chloro-4-fluorophenyl)-2,2-dioxido-2,1,3-benzothiadiazol-1(3H)-yl]ethoxy}-N-methylethanamine;

2-{2-[3-(2-chloro-4-fluorophenyl)-2,2-dioxido-2,1,3-benzothiadiazol-1(3H)-yl]ethoxy}-N,N-dimethylethanamine;

1-(4-chloro-2-fluorophenyl)-3-(2-piperazin-1-yl-ethyl)-1,3-dihydro-2,1,3-benzothiadiazole2,2-dioxide;

1-(4-chloro-2-fluorophenyl)-3-{2-[(3R,5S)-3,5-dimethylpiperazin-1-yl]ethyl}-1,3-dihydro-2,1,3-benzothiadiazole2,2-dioxide;

1-(4-chloro-2-fluorophenyl)-3-(2-piperidin-4-ylethyl)-1,3-dihydro-2,1,3-benzothiadiazole2,2-dioxide;

1-(4-chloro-2-methylphenyl)-3-{2-[(3R,5S)-3,5-dimethylpiperazin-1-yl]ethyl}-1,3-dihydro-2,1,3-benzothiadiazole2,2-dioxide;

1-(4-chloro-2-methylphenyl)-3-(2-piperazin-1-ylethyl)-1,3-dihydro-2,1,3-benzothiadiazole2,2-dioxide;

1-(tert-butylamino)-4-(2,2-dioxido-3-phenyl-2,1,3-benzothiadiazol-1(3H)-yl)butan-2-one;

4-(2,2-dioxido-3-phenyl-2,1,3-benzothiadiazol-1(3H)-yl)-1-(isopropylamino)butan-2-one;

1-(cyclopropylamino)-4-(2,2-dioxido-3-phenyl-2,1,3-benzothiadiazol-1(3H)-yl)butan-2-one;

4-(2,2-dioxido-3-phenyl-2,1,3-benzothiadiazol-1(3H)-yl)-1-(methylamino)butan-2-one;

4-[3-(2-fluorophenyl)-2,2-dioxido-2,1,3-benzothiadiazol-1(3H)-yl]-1-(methylamino)butan-2-one;

(2Z)-4-(2,2-dioxido-3-phenyl-2,1,3-benzothiadiazol-1(3H)-yl)-1-(methylamino)butan-2-one oxime;
(2S)-4-[3-(2-fluorophenyl)-2,2-dioxido-2,1,3-benzothiadiazol-1(3H)-yl]-2-methoxy-N-methylmethanamine;
(2S)-2-methoxy-N-methyl-4-[3-(2-methylphenyl)-2,2-dioxido-2,1,3-benzothiadiazol-1(3H)-yl]butan-1-amine;
(2S)-2-methoxy-4-[3-(3-methoxyphenyl)-2,2-dioxido-2,1,3-benzothiadiazol-1(3H)-yl]-N-methylbutan-1-amine;
4-(2,2-dioxido-3-phenyl-2,1,3-benzothiadiazol-1(3H)-yl)-2-methoxy-N-methylbutan-1-amine;
(2R)-4-(2,2-dioxido-3-phenyl-2,1,3-benzothiadiazol-1(3H)-yl)-2-methoxy-N-methylbutan-1-amine;
(2S)-4-(2,2-dioxido-3-phenyl-2,1,3-benzothiadiazol-1(3H)-yl)-2-methoxy-N-methylbutan-1-amine;
N-{(2S)-4-[3-(2-fluorophenyl)-2,2-dioxido-2,1,3-benzothiadiazol-1(3H)-yl]-2-methoxybutyl}cyclopropanamine;
N-{(2S)-2-methoxy-4-[3-(2-methylphenyl)-2,2-dioxido-2,1,3-benzothiadiazol-1(3H)-yl]butyl}cyclopropanamine;
N-{(2S)-2-methoxy-4-[3-(3-methoxyphenyl)-2,2-dioxido-2,1,3-benzothiadiazol-1(3H)-yl]butyl}cyclopropanamine;
N-{(2S)-4-[3-(2,4-difluorophenyl)-2,2-dioxido-2,1,3-benzothiadiazol-1(3H)-yl]-2-methoxybutyl}cyclopropanamine;
N-{(2S)-4-[3-(2,5-difluorophenyl)-2,2-dioxido-2,1,3-benzothiadiazol-1(3H)-yl]-2-methoxybutyl}cyclopropanamine;
N-{(2S)-4-[3-(2,6-difluorophenyl)-2,2-dioxido-2,1,3-benzothiadiazol-1(3H)-yl]-2-methoxybutyl}cyclopropanamine;
2S)-4-[3-(2,6-difluorophenyl)-2,2-dioxido-2,1,3-benzothiadiazol-1(3H)-yl]-2-methoxy-N-methylbutan-1-amine;
(2S)-4-[3-(2,4-difluorophenyl)-2,2-dioxido-2,1,3-benzothiadiazol-1(3H)-yl]-2-methoxy-N-methylbutan-1-amine;
1-(2-morpholin-2-ylethyl)-3-phenyl-1,3-dihydro-2,1,3-benzothiadiazole2,2-dioxide;
1-{2-[(2S)-morpholin-2-yl]ethyl}-3-phenyl-1,3-dihydro-2,1,3-benzothiadiazole2,2-dioxide;
1-{2-[(2R)-morpholin-2-yl]ethyl}-3-phenyl-1,3-dihydro-2,1,3-benzothiadiazole2,2-dioxide;
1-(4-fluorophenyl)-3-(2-morpholin-2-ylethyl)-1,3-dihydro-2,1,3-benzothiadiazole2,2-dioxide;
1-(4-fluorophenyl)-3-{2-[(2S)-morpholin-2-yl]ethyl}-1,3-dihydro-2,1,3-benzothiadiazole2,2-dioxide;
1-(4-fluorophenyl)-3-{2-[(2R)-morpholin-2-yl]ethyl}-1,3-dihydro-2,1,3-benzothiadiazole2,2-dioxide;
1-(2,4-difluorophenyl)-3-(2-morpholin-2-ylethyl)-1,3-dihydro-2,1,3-benzothiadiazole2,2-dioxide;
1-(2,4-difluorophenyl)-3-{2-[(2S)-morpholin-2-yl]ethyl}-1,3-dihydro-2,1,3-benzothiadiazole2,2-dioxide;
1-(2,4-difluorophenyl)-3-{2-[(2R)-morpholin-2-yl]ethyl}-1,3-dihydro-2,1,3-benzothiadiazole2,2-dioxide;
1-(2-morpholin-2-ylethyl)-3-(2,4,6-trifluorophenyl)-1,3-dihydro-2,1,3-benzothiadiazole2,2-dioxide;
1-2-[(2S)-morpholin-2-yl]ethyl-3-(2,4,6-trifluorophenyl)-1,3-dihydro-2,1,3-benzothiadiazole2,2-dioxide;
1-{2-[(2R)-morpholin-2-yl]ethyl}-3-(2,4,6-trifluorophenyl)-1,3-dihydro-2,1,3-benzothiadiazole2,2-dioxide;
1-(3-methoxyphenyl)-3-{2-[(2S)-morpholin-2-yl]ethyl}-1,3-dihydro-2,1,3-benzothiadiazole2,2-dioxide;
1-(3-methoxyphenyl)-3-{2-[(2R)-morpholin-2-yl]ethyl}-1,3-dihydro-2,1,3-benzothiadiazole2,2-dioxide;
1-(2-fluorophenyl)-3-{2-[(2S)-morpholin-2-yl]ethyl}-1,3-dihydro-2,1,3-benzothiadiazole2,2-dioxide;
1-(2-fluorophenyl)-3-{2-[(2R)-morpholin-2-yl]ethyl}-1,3-dihydro-2,1,3-benzothiadiazole2,2-dioxide;
1-(2,6-difluorophenyl)-3-{2-[(2S)-morpholin-2-yl]ethyl}-1,3-dihydro-2,1,3-benzothiadiazole2,2-dioxide;
1-(3-{[3-(2-fluorophenyl)-2,2-dioxido-2,1,3benzothiadiazol-1(3H)-yl]methyl}phenyl)-N-methylmethanamine;
1-(3-{[3-(2-fluorophenyl)-2,2-dioxido-2,1,3-benzothiadiazol-1(3H)-yl]methyl}phenyl)methanamine;
1-(3-{[3-(2-fluorophenyl)-2,2-dioxido-2,1,3-benzothiadiazol-1(3H)-yl]methyl}phenyl)-N,N-dimethylmethanamine;
1-(4-{[3-(2-fluorophenyl)-2,2-dioxido-2,1,3-benzothiadiazol-1(3H)-yl]methyl}phenyl)-N,N-dimethylmethanamine;
1-(4-{[3-(2-fluorophenyl)-2,2-dioxido-2,1,3-benzothiadiazol-1(3H)-yl]methyl}phenyl)methanamine;
1-(4-{[3-(2-fluorophenyl)-2,2-dioxido-2,1,3-benzothiadiazol-1(3H)-yl]methyl}phenyl)-N-methylmethanamine;
(2Z)-4-[3-(2-fluoro-4-methylphenyl)-2,2-dioxido-2,1,3-benzothiadiazol-1(3H)-yl]-N-methylbut-2-en-1-amine;
(2Z)-4-[3-(2-fluoro-4-methylphenyl)-2,2-dioxido-2,1,3-benzothiadiazol-1(3H)-yl]but-2-en-1-amine;
(2Z)-4-[3-(2-fluoro-4-methylphenyl)-2,2-dioxido-2,1,3-benzothiadiazol-1(3H)-yl]-N,N-dimethylbut-2-en-1-amine;
(2Z)-N-ethyl-4-[3-(2-fluoro-4-methylphenyl)-2,2-dioxido-2,1,3-benzothiadiazol-1(3H)-yl]but-2-en-1-amine;
1-(3,4-difluorophenyl)-3-(2-piperazin-1-ylethyl)-1,3-dihydro-2,1,3-benzothiadiazole2,2-dioxide;
1-(3,4-difluorophenyl)-3-(3-piperazin-1-ylpropyl)-1,3-dihydro-2,1,3-benzothiadiazole2,2-dioxide;
1-(3,4-difluorophenyl)-3-[3-(3,5-dimethylpiperazin-1-yl)propyl]-1,3-dihydro-2,1,3-benzothiadiazole2,2-dioxide;
2-{2-[3-(3,4-difluorophenyl)-2,2-dioxido-2,1,3-benzothiadiazol-1(3H)-yl]ethoxy}-N-methylethanamine;
1-(2-piperazin-1-ylethyl)-3-(2,3,4-trifluorophenyl)-1,3-dihydro-2,1,3-benzothiadiazole2,2-dioxide;
1-(2-methylphenyl)-3-(2-piperazin-1-ylethyl)-1,3-dihydro-2,1,3-benzothiadiazole2,2-dioxide;
1-(2-chlorophenyl)-3-(2-piperazin-1-ylethyl)-1,3-dihydro-2,1,3-benzothiadiazole2,2-dioxide;
2-{2-[3-(2,4-difluorophenyl)-2,2-dioxido-2,1,3-benzothiadiazol-1(3H)-yl]ethoxy}-N-methylethanamine;
2-{2-[3-(2,4-difluorophenyl)-2,2-dioxido-2,1,3-benzothiadiazol-1(3H)-yl]ethoxy}ethanamine;
2-{2-[3-(2,4-difluorophenyl)-2,2-dioxido-2,1,3-benzothiadiazol-1(3H)-yl]ethoxy}-N,N-dimethylethanamine;
(2E)-4-[3-(2,4-difluorophenyl)-2,2-dioxido-2,1,3-benzothiadiazol-1(3H)-yl]-N-methylbut-2-en-1-amine;
(2E)-4-[3-(2,4-difluorophenyl)-2,2-dioxido-2,1,3-benzothiadiazol-1(3H)-yl]-N,N-dimethylbut-2-en-1-amine;
(2E)-4-[3-(2,4-difluorophenyl)-2,2-dioxido-2,1,3-benzothiadiazol-1(3H)-yl]but-2-en-1-amine;
N-(2-{2-[3-(2,6-difluorophenyl)-2,2-dioxido-2,1,3-benzothiadiazol-1(3H)-yl]ethoxy}ethyl)cyclopropanamine;
N-(2-{2-[3-(2,6-difluorophenyl)-2,2-dioxido-2,1,3-benzothiadiazol-1(3H)-yl]ethoxy}ethyl)cyclobutanamine;
N-(2-{2-[3-(2,6-difluorophenyl)-2,2-dioxido-2,1,3-benzothiadiazol-1(3H)-yl]ethoxy}ethyl)cyclopentanamine;
2-{2-[3-(2,6-difluorophenyl)-2,2-dioxido-2,1,3-benzothiadiazol-1(3H)-yl]ethoxy}-N-methylethanamine;
2-{2-[3-(2,6-difluorophenyl)-2,2-dioxido-2,1,3-benzothiadiazol-1(3H)-yl]ethoxy}-N-ethylethanamine;
N-(2-{2-[3-(2,6-difluorophenyl)-2,2-dioxido-2,1,3-benzothiadiazol-1(3H)-yl]ethoxy}ethyl)propan-2-amine;
1-(4-chlorophenyl)-3-(4-morpholin-4-ylbutyl)-1,3-dihydro-2,1,3-benzothiadiazole2,2-dioxide;
1-(2-Fluorophenyl)-4-fluoro-3-{2-[(2R)-morpholin-2-yl]ethyl}-1,3-dihydro-2,1,3-benzothiadiazole2,2-dioxide;

1-(2-Fluorophenyl)-4-fluoro-3-{2-[(2S)-morpholin-2-yl]ethyl}-1,3-dihydro-2,1,3-benzothiadiazole2,2-dioxide;
1-(2-Fluorophenyl)-5-fluoro-3-{2-[(2R)-morpholin-2-yl]ethyl}-1,3-dihydro-2,1,3-benzothiadiazole2,2-dioxide;
1-(2-Fluorophenyl)-5-fluoro-3-{2-[(2S)-morpholin-2-yl]ethyl}-1,3-dihydro-2,1,3-benzothiadiazole2,2-dioxide;
1-(2-Fluorophenyl)-6-fluoro-3-{2-[(2R)-morpholin-2-yl]ethyl}-1,3-dihydro-2,1,3-benzothiadiazole2,2-dioxide;
1-(2-Fluorophenyl)-6-fluoro-3-{2-[(2S)-morpholin-2-yl]ethyl}-1,3-dihydro-2,1,3-benzothiadiazole2,2-dioxide;
1-(2-Fluorophenyl)-7-fluoro-3-{2-[(2R)-morpholin-2-yl]ethyl}-1,3-dihydro-2,1,3-benzothiadiazole2,2-dioxide;
1-(2-Fluorophenyl)-7-fluoro-3-{2-[(2S)-morpholin-2-yl]ethyl}-1,3-dihydro-2,1,3-benzothiadiazole2,2-dioxide;
1-(2,6-Difluorophenyl)-4-fluoro-3-{2-[(2R)-morpholin-2-yl]ethyl}-1,3-dihydro-2,1,3-benzothiadiazole2,2-dioxide;
1-(2,6-Difluorophenyl)-4-fluoro-3-{2-[(2S)-morpholin-2-yl]ethyl}-1,3-dihydro-2,1,3-benzothiadiazole2,2-dioxide;
1-(2,6-Difluorophenyl)-5-fluoro-3-{2-[(2R)-morpholin-2-yl]ethyl}-1,3-dihydro-2,1,3-benzothiadiazole2,2-dioxide;
1-(2,6-Difluorophenyl)-5-fluoro-3-{2-[(2S)-morpholin-2-yl]ethyl}-1,3-dihydro-2,1,3-benzothiadiazole2,2-dioxide;
1-(2,6-Difluorophenyl)-6-fluoro-3-{2-[(2R)-morpholin-2-yl]ethyl}-1,3-dihydro-2,1,3-benzothiadiazole2,2-dioxide;
1-(2,6-Difluorophenyl)-6-fluoro-3-{2-[(2S)-morpholin-2-yl]ethyl}-1,3-dihydro-2,1,3-benzothiadiazole2,2-dioxide;
1-(2,6-Difluorophenyl)-7-fluoro-3-{2-[(2R)-morpholin-2-yl]ethyl}-1,3-dihydro-2,1,3-benzothiadiazole2,2-dioxide;
1-(2,6-Difluorophenyl)-7-fluoro-3-{2-[(2S)-morpholin-2-yl]ethyl}-1,3-dihydro-2,1,3-benzothiadiazole2,2-dioxide; and pharmaceutically acceptable salts thereof.

Another aspect of the invention provides a composition, comprising:
a. at least one compound of formula I or formula II; and
b. at least one pharmaceutically acceptable carrier.

Another aspect of the invention provides a method for treating or preventing a condition selected from the group consisting of a vasomotor symptom, sexual dysfunction, gastrointestinal disorder, genitourinary disorder, chronic fatigue syndrome, fibromyalgia syndrome, depression disorder, diabetic neuropathy, endogenous behavioral disorder, cognitive disorder, pain, and combinations thereof in a subject in need thereof, comprising the step of:
administering to said subject an effective amount of a compound of formula I or formula II.

In certain embodiments, the vasomotor symptom is hot flush.

In certain embodiments, the sexual dysfunction is desire-related or arousal-related.

In certain embodiments, the gastrointestinal disorder or the genitourinary disorder is stress incontinence or urge incontinence.

In certain embodiments, the condition is chronic fatigue syndrome.

In certain embodiments, the condition is fibromyalgia syndrome.

In certain embodiments, the condition is a depression disorder selected from the group consisting of major depressive disorder, generalized anxiety disorder, panic disorder, attention deficit disorder with or without hyperactivity, sleep disturbance, social phobia, and combinations thereof.

In certain embodiments, the disorder is an endogenous behavioral disorder or a cognitive disorder.

In certain embodiments, the condition is diabetic neuropathy.

In certain embodiments, the condition is pain.

In certain embodiments, the pain is acute centralized pain, acute peripheral pain, or a combination thereof.

In certain embodiments, the pain is chronic centralized pain, chronic peripheral pain, or a combination thereof.

In certain embodiments, the pain is neuropathic pain, visceral pain, musculoskeletal pain, bony pain, cancer pain, inflammatory pain, or a combination thereof.

In certain embodiments, the neuropathic pain is associated with diabetes, post traumatic pain of amputation, lower back pain, cancer, chemical injury, toxins, major surgery, peripheral nerve damage due to traumatic injury compression, postherpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, viral infection, bacterial infection, metastatic infiltration, adiposis dolorosa, burns, central pain conditions related to thalamic conditions, or a combination thereof.

In certain embodiments, the neuropathic pain is post-herpetic neuralgia.

In certain embodiments, the visceral pain is associated with ulcerative colitis, irritable bowel syndrome, irritable bladder, Crohn's disease, rheumatologic (arthralgias), tumors, gastritis, pancreatitis, infections of the organs, biliary tract disorders, or a combination thereof.

In certain embodiments, the pain is female-specific pain.

The present invention provides a treatment for vasomotor symptoms by methods of recovering the reduced activity of norepinephrine. Without wishing to be bound by any theory, norepinephrine activity in the hypothalamus or in the brainstem can be elevated by (i) blocking the activity of the NE transporter, (ii) blocking the activity of the presynaptic adrenergic$_{\alpha 2}$ receptor with an antagonist, or (iii) blocking the activity of 5-HT on NE neurons with a 5-HT$_{2a}$ antagonist.

The compounds of the invention are also useful to prevent and treat pain. The pain may be, for example, acute pain or chronic pain. The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromyalgia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns, or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pain associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

Another aspect of the invention provides a process for the preparation of a compound of formula I:
the process comprising:
(d) reacting a compound of formula IA:

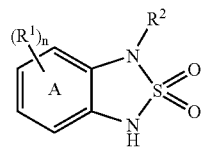

with a compound of formula IB:

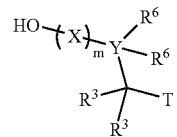

wherein,

T is an —N(R$^4$)$_2$ or an activating group;

wherein, if T is —N(R$^4$)$_2$, then the compound of formula I is formed; or if T is an activating group, then a compound of formula IC is formed:

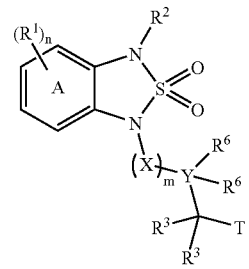

and the process further comprises:
(e) reacting the compound formula IC with —N(R$^4$)R$^P$ to form a compound of formula ID:

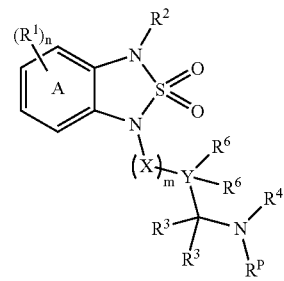

wherein,

R$^P$ is R$^4$ or a protecting group;

wherein, if R$^P$ is R$^4$, the compound of formula I is formed; or if R$^P$ is a protecting group, the process further comprises:

(f) deprotecting the compound of formula ID to form a deprotected compound; and (g) reacting the deprotected compound with an activated-R$^4$ group, provided that R$^4$ in the activated-R$^4$ group is not H;

wherein the compound of formula I is formed.

In another embodiment, step (d) further comprises contacting the compound of formula IA and IB with dialkyl azodicarboxylate and triphenylphosphine.

In another embodiment, the dialkyl azodicarboxylate is diisopropyl azodicarboxylate.

In another embodiment, the activating group is selected from the group consisting of halo, tosylate, mesylate, triflate, and oxo.

In another embodiment, the activating group is Br.

In another embodiment, the protecting group is selected from the group consisting of BOC, benzyl, acetyl, PMB, alkyl, Fmoc, Cbz, trifluoroacetyl, tosyl and triphenylmethyl.

In another embodiment, the protecting group is BOC.

In another embodiment, the deprotecting step is performed in the presence of at least one agent selected from hydrochloric acid (HCl), tin(II)chloride, ammonium chloride, zinc, trifluoroacetic acid (TFA), tosic acid, a halotrimethylsilane, or aluminum chloride.

In another embodiment, any one of steps (d)-(g) is performed at or above 30° C. or any one of steps (d)-(g) includes a purification step comprising at least one of: filtration, extraction, chromatography, trituration, or recrystallization.

In another embodiment, the activated-$R^4$ group is halo-$R^4$ or O=$R^4$.

In another aspect of the invention, the compound of formula IA is prepared by:

(a) reacting a compound of formula IE:

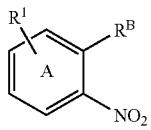

IE wherein $R^B$ is F or Cl;

with $R^2$—$NH_2$ to form a compound of formula IF:

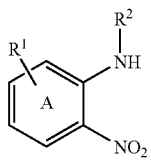

IF (b) hydrogenating the compound of formula IF to form a compound of formula IG:

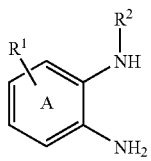

IG and (c) reacting the compound of formula IG with sulfamide in diglyme to form the compound of formula IA.

In another embodiment, the hydrogenating step is performed in the presence of hydrogen ($H_2$) and Pd/C.

In another embodiment, any one of steps (a)-(c) is performed at or above 30° C.

In another embodiment, any one of steps (a)-(c) includes a purification step comprising at least one of: filtration, extraction, chromatography, trituration, or recrystallization.

Another aspect of the invention provides a process for the preparation of a compound of formula I:

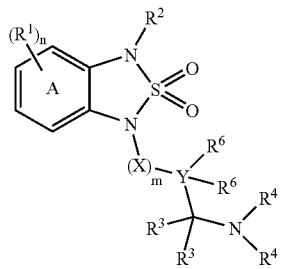

I or a pharmaceutically acceptable salt, stereoisomer or tautomer thereof;

wherein:

n is an integer from 0 to 4;

m is an integer from 0 to 6;

X is, independently at each occurrence, $C(R^7)_2$, $N(R^3)$, O, S, S(=O), or S(=O)$_2$;

Y is C; or

Y and an adjacent X together form —$CR^7$=$CR^7$—, —C≡C—, or arylenyl substituted with 0-3 $R^{10}$;

$R^1$ is, independently at each occurrence, H, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;

$R^2$ is aryl substituted with 0-3 $R^9$ or heteroaryl substituted with 0-3 $R^9$;

$R^3$ is, independently at each occurrence, H, halo, hydroxy, alkyl substituted with 0-3 $R^{13}$, a heterocyclic ring, aryl substituted with 0-3 $R^{12}$, or heteroaryl substituted with 0-3 $R^{12}$;

$R^4$ is, independently at each occurrence, H, alkyl substituted with 0-3 $R^{13}$, arylalkyl substituted with 0-3 $R^{13}$ or heteroarylmethyl substituted with 0-3 $R^{13}$;

$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;

$R^6$ is, independently at each occurrence, H, hydroxy, $C_1$-$C_4$ alkyl, $C_1$-$C_6$ alkoxy, halo, aryl substituted with 0-3 $R^1$, heteroaryl substituted with 0-3 $R^1$, —$N(R^3)_2$, —$S(R^3)$, or —$R^8$—O—$R^3$; or both $R^6$ groups form a cycloalkyl, a heterocyclic ring, =O or =N—OH;

provided that if each $R^3$ is H, each X is $CH_2$, and either each $R^6$ is H or one $R^6$ is hydroxy; then, both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, or a heterocyclic ring, F, or $CF_3$; and where any additional N atom may be optionally substituted with $C_1$-$C_4$ alkyl;

$R^7$ is, independently at each occurrence, H, hydroxy, alkoxy, or $C_1$-$C_4$ alkyl;

$R^8$ is, independently at each occurrence, straight or branched alkylenyl;

or one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, F, or $CF_3$; and where any additional N atom may be optionally substituted with alkyl;

or both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, a heterocyclic ring, F, or $CF_3$; and where any additional N atom may be optionally substituted with alkyl;

or one of said $R^6$ or one of said $R^7$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl; provided that $R^4$ and $R^7$, taken together, do not form a piperidinyl ring;

$R^9$ is, independently at each occurrence, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide, alkylamido, or arylamido;

$R^{10}$ is, independently at each occurrence, alkyl, alkoxy, halo, $CF_3$, $OCF_3$, hydroxy, alkanoyloxy, nitro, nitrile, alkenyl, or alkynyl;

$R^{11}$ is, independently at each occurrence, alkyl, alkoxy, halo, $CF_3$, $OCF_3$, hydroxy, alkanoyloxy, nitro, nitrile, alkenyl, or alkynyl;

$R^{12}$ and $R^{13}$ are each, independently at each occurrence, alkyl, alkoxy, halo, $CF_3$, $OCF_3$, hydroxy, hydroxyalkyl, aminoalkyl, a heterocyclic ring, alkanoyloxy, nitro, nitrile, alkenyl, or alkynyl; and wherein 1-3 carbon atoms in ring A may optionally be replaced with N;

the process comprising:

(d) reacting $R^2(BOH)_2$ and a transitional metal salt with a compound of formula IH:

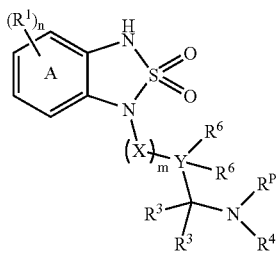

IH wherein, $R^P$ is $R^4$ or a protecting group; and if $R^P$ is $R^4$, the compound of formula I is formed; or if $R^P$ is a protecting group, the process further comprises:

(e) deprotecting the compound of formula IH to form a deprotected compound; and (g) reacting the deprotected compound with an activated-$R^4$ group, provided that $R^4$ group in the activated-$R^4$ group is not H;

wherein the compound of formula I is formed.

In another embodiment, the transitional metal salt is copper (II)acetate.

In another embodiment, the activated-$R^4$ group is halo-$R^4$ or O=$R^4$.

In another embodiment, the protecting group is selected from the group consisting of BOC, benzyl, acetyl, PMB, alkyl, Fmoc, Cbz, trifluoroacetyl, tosyl and triphenylmethyl.

In another embodiment, the protecting group is BOC.

In another embodiment, the deprotecting step is performed in the presence of at least one agent selected from hydrochloric acid (HCl), tin(II)chloride, ammonium chloride, zinc, trifluoroacetic acid (TFA), tosic acid, a halotrimethylsilane, or aluminum chloride.

In another embodiment, any one of steps (d)-(g) is performed at or above 30° C. or any one of steps (d)-(g) includes a purification step comprising at least one of: filtration, extraction, chromatography, trituration, or recrystallization.

In another embodiment, the compound of formula IH is prepared by:

(a) reacting a compound of formula IJ:

IJ wherein $R^B$ is F or Cl;

with a compound of formula IK:

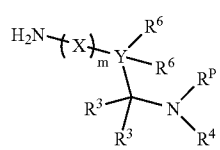

IK to form a compound of formula IL:

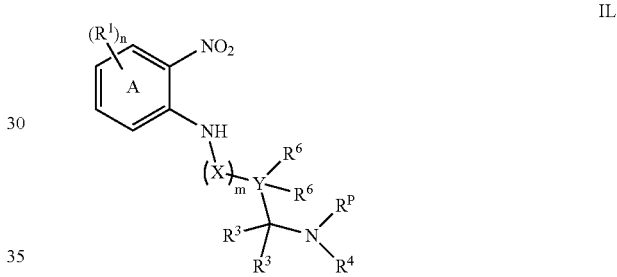

IL (b) hydrogenating the compound of formula IL to form a compound of formula IM:

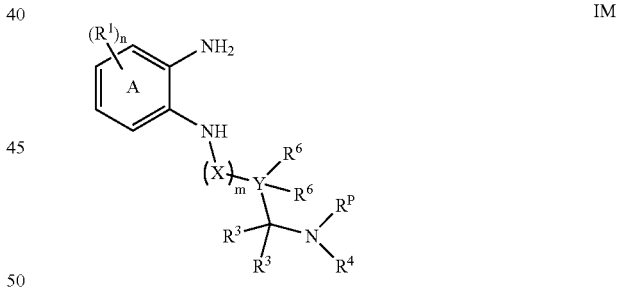

IM and (c) reacting the compound of formula IM with sulfamide and diglyme to form the compound of formula IH.

In another embodiment, the hydrogenating step is performed in the presence of hydrogen ($H_2$) and Pd/C.

In another embodiment, any one of steps (a)-(c) is performed at or above 30° C.

In another embodiment, any one of steps (a)-(c) includes a purification step comprising at least one of: filtration, extraction, chromatography, trituration, or recrystallization.

Some of the compounds of the present invention may contain chiral centers and such compounds may exist in the form of stereoisomers (i.e. enantiomers or diastereomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron*, 33:2725 (1977); Eliel, E. L. *Stereochemistry of Carbon Compounds*, (McGraw-Hill, New York, 1962); Wilen, S. H. *Tables of Resolving Agents and Optical Resolutions*, p. 268 (E. L. Eliel, Ed., University of Notre Dame Press, Notre Dame, Ind. 1972), the entire disclosures of which are herein incorporated by reference.

The present invention includes prodrugs of the compounds of formula I. "Prodrug," as used herein, means a compound which is convertible in vivo by chemical or metabolic means (e.g. by hydrolysis) to a compound of formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews*, 1992, 8:1-38, Bundgaard, *J. of Pharmaceutical Sciences*, 1988, 77:285 et seq.; and Higuchi and Stella (eds.) *Prodrugs as Novel Drug Delivery Systems*, American Chemical Society (1975), the entire disclosures of which are herein incorporated by reference.

Further, the compounds of formula I may exist in unsolvated as well as in solvated forms with pharmaceutically acceptable solvents such as water, ethanol, and the like. In general, the solvated forms are considered equivalent to the unsolvated forms for the purpose of the present invention.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991, the entire disclosure of which is herein incorporated by reference.

Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature. In accordance with this invention, compounds of formula I may be produced by the following reaction schemes (Schemes 1 and 2).

The compounds of this invention contain chiral centers, providing for various stereoisomeric forms such as diastereomeric mixtures, enantiomeric mixtures as well as optical isomers. The individual optical isomers can be prepared directly through asymmetric and/or stereospecific synthesis or by conventional chiral separation of optical isomers from the enantiomeric mixture.

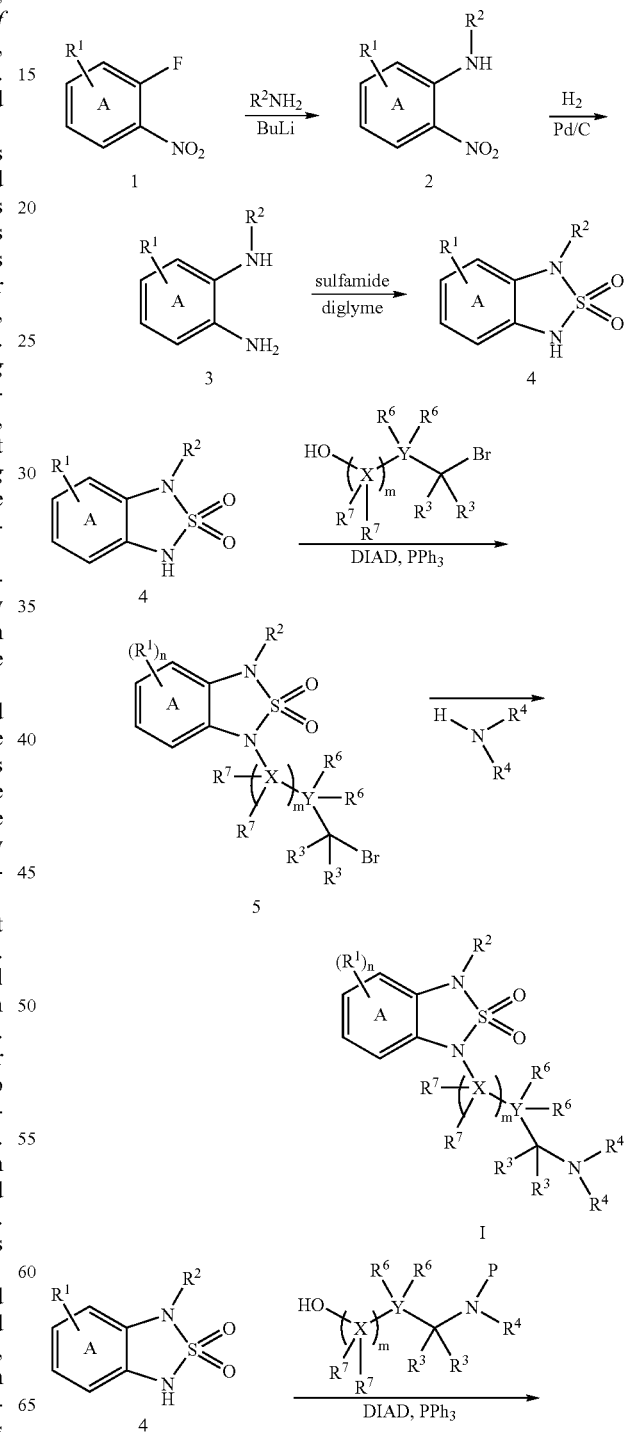

Scheme 1

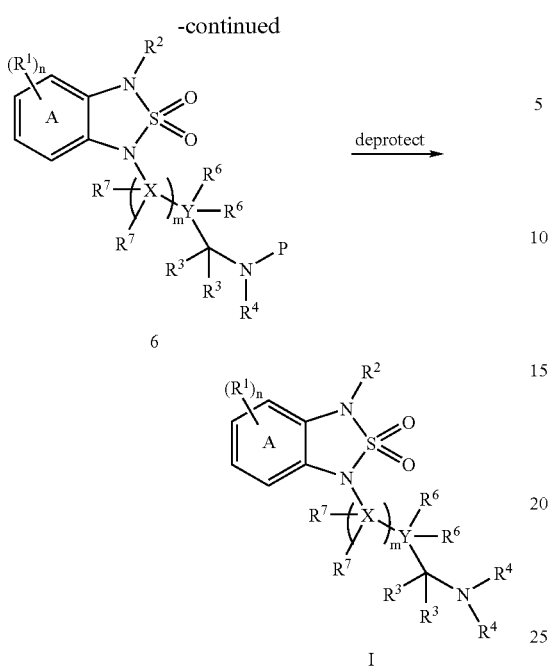

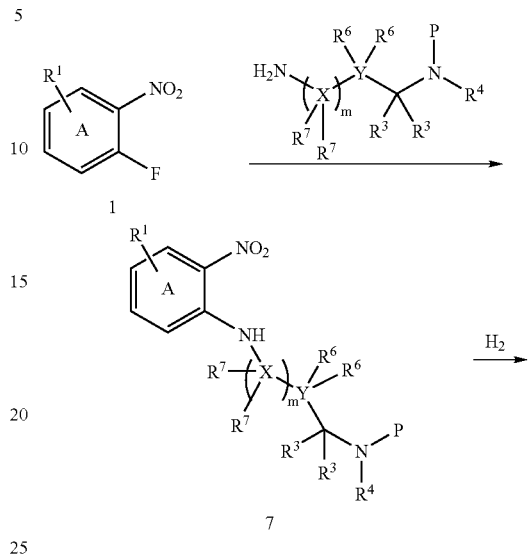

be used. The protecting group is then removed, in the case of t-butoxycarbonyl using an acid such as hydrochloric acid, to give compounds of formula I.

Scheme 2

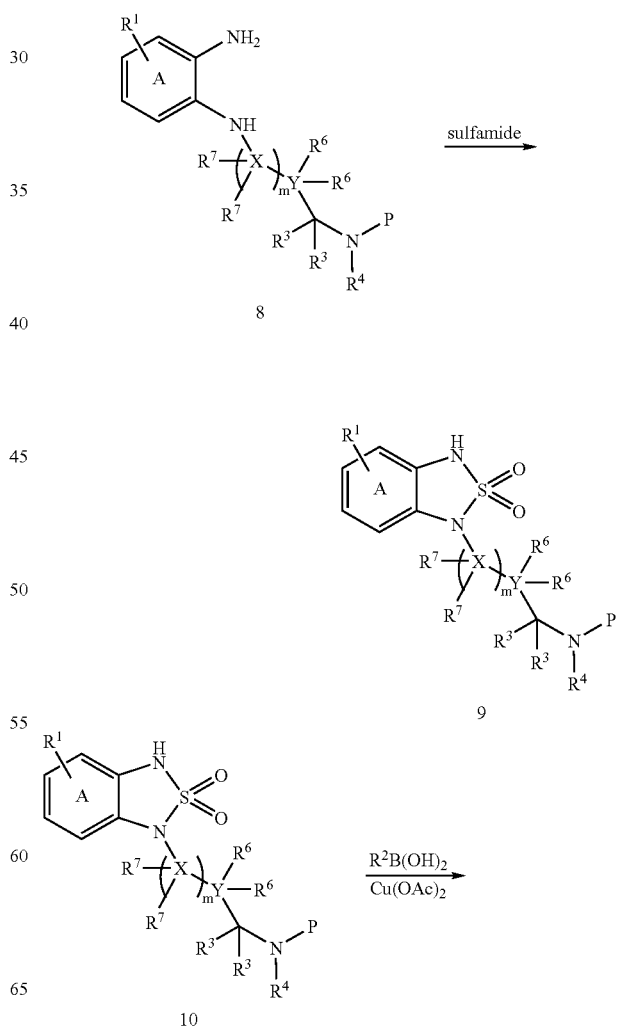

Following Scheme 1, an appropriate fluoronitroarene 1 may be substituted with an aryl amine using a base under standard conditions to provide an aminonitroarene 2. Typically conditions for this reaction a base such as sodium hydride in DMF or an organometallic base such as butyllithium in THF. Reduction of the nitro group in structure 2 is accomplished under standard conditions using hydrogen and a suitable catalyst such as palladium or Raney nickel to provide a dianiline 3. Nitro reduction is a common transformation and one could employ a number of alternative procedures including reduction conditions using metal salts such as aqueous HCl with tin(II)chloride or aqueous ammonium chloride with zinc metal. The dianiline 3 is then treated a suitable sulfate containing reagent to form arylsulfamide of structure 4. In a typical example, 3 was heated with sulfamide in diglyme to provide the cyclized product 4. The acidic nitrogen is then combined with a suitably substituted side chain providing products 5 or 6 defending on the structure of the desired side chain. An effective method for attaching the side chain to sulfamide 4 is the Mitsunobu reaction in which an alcohol is activated and displaced by treating with a phosphine and an activating reagent. In accordance with the embodiment of the invention, typical conditions for effecting the attachment of the sulfamide to the alcohol containing side chain were treatment with diisopropyl azodicarboxylate and triphenylphosphine in THF. Another suitable method for accomplishing side chain attachment is direct nucleophilic substitution of a leaving group containing side chain with the sulfamide and can be facilitated by addition of a base in a suitable solvent. Typically compounds of structure 5 with a bromine containing side chain were treated with an excess of the desired amine to provide the desired compounds of formula I. An alternative method for the synthesis of compounds of formula I is possible from 6 where the side chain is attached with the amine present in protected form (the protecting group is represented by the letter P). Any suitable amine protecting group, t-butoxycarbonyl in a typical example, may

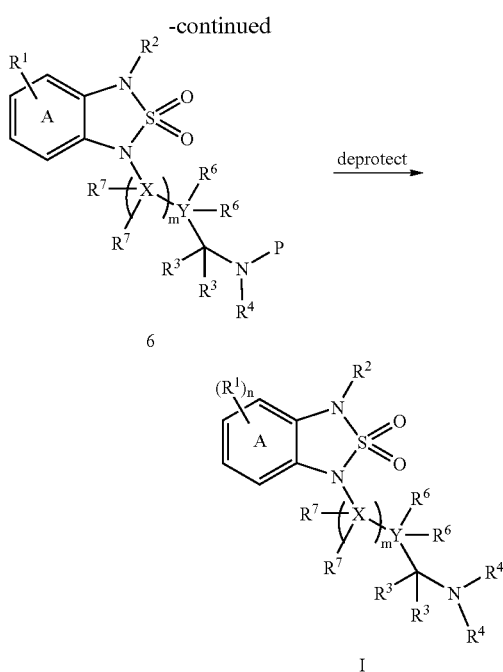

An additional method for the synthesis of compounds of formula I is described in Scheme 2. An appropriate fluoronitroarene is substituted with an amine bearing the desired side chain to give compounds of structure 7. Reduction of the nitro group under conditions described in Scheme 1 provides 8. Compounds of structure 8 can be converted to arylsulfamide of structure 9 by treatment with a suitable sulfate containing reagent. In a typical example, 8 was heated with sulfamide in diglyme to provide the cyclized product 9. An aryl group may then be attached to the sulfamide 9 using conventional methods for formation of an aryl-nitrogen bond. In a typical example an aryl boronic acid forms an aryl-nitrogen bond in the presence of a transition metal salt such as copper(II) acetate to provide 6. Subsequent deprotection of the protecting group P in 6 affords compounds of formula I. As described in Scheme 1, the protecting group t-butoxycarbonyl was useful for this purpose and is readily removed using an acid such as hydrochloric acid to give compounds of formula I.

In other embodiments, the invention is directed to pharmaceutical compositions, comprising:
a. at least one compound of formula I, or pharmaceutically acceptable salt thereof; and
b. at least one pharmaceutically acceptable carrier.

Generally, the compound of formula I, or a pharmaceutically acceptable salt thereof, will be present at a level of from about 0.1%, by weight, to about 90% by weight, based on the total weight of the pharmaceutical composition, based on the total weight of the pharmaceutical composition. Preferably, the compound of formula I, or a pharmaceutically acceptable salt thereof, will be present at a level of at least about 1%, by weight, based on the total weight of the pharmaceutical composition. More preferably, the compound of formula I, or a pharmaceutically acceptable salt thereof, will be present at a level of at least about 5%, by weight, based on the total weight of the pharmaceutical composition. Even more preferably, the compound of formula I, or a pharmaceutically acceptable salt thereof will be present at a level of at least about 10%, by weight, based on the total weight of the pharmaceutical composition. Yet even more preferably, the compound of formula I, or a pharmaceutically acceptable salt thereof, will be present at a level of at least about 25%, by weight, based on the total weight of the pharmaceutical composition.

Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985), the entire disclosure of which is herein incorporated by reference. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to about 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions for parenteral administration, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The term "combination therapy" refers to the administration of two or more therapeutic agents or compounds to treat a therapeutic condition or disorder described in the present disclosure, for example hot flush, sweating, thermoregulatory-related condition or disorder, or other condition or disorder. Such administration includes use of each type of therapeutic agent in a concurrent manner. In either case, the treatment regimen will provide beneficial effects of the drug combination in treating the conditions or disorders described herein.

The route of administration may be any enteral or parenteral route which effectively transports the active compound of formula I, or a pharmaceutically acceptable salt thereof, to the appropriate or desired site of action; such as oral, nasal, pulmonary, transdermal, such as passive or iontophoretic delivery, or parenteral, e.g. rectal, depot, subcutaneous, intravenous, intraurethral, intramuscular, intrathecal, intra-articular, intranasal, ophthalmic solution or an ointment. Furthermore, the administration of compound of formula I, or pharmaceutically acceptable salt thereof, with other active ingredients may be separate, consecutive or simultaneous.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

General Procedures

General Procedure I: Synthesis of 1-aryl-1,3-dihydro-2,1,3-benzothiadiazole2,2-dioxide core

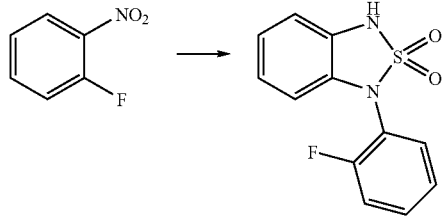

Step 1: 2-Fluoroaniline (1.45 mL, 15 mmol) was dissolved in DMF (10 mL) and sodium hydride (0.58 g, 15 mmol) was added and the mixture was stirred for 30 minutes. 2-Fluoronitrobenzene (1.05 mL, 10 mmol) was added and the mixture was stirred for 16 hours. The mixture was quenched with saturated NH$_4$Cl and diluted with ether. The mixture was washed with water, brine, dried over anhydrous magnesium sulfate, and concentrated. The crude product was purified via Isco chromatography (Redisep, silica, gradient 5-30% ethyl acetate in hexane) to afford 1.4 g 2-fluoro-N-(2-nitrophenyl) aniline that was carried on directly to the next step. MS (ES) m/z 232.9.

Step 2: 2-fluoro-N-(2-nitrophenyl)aniline (1.4 g, 6.0 mmol) was dissolved in ethyl acetate (20 mL) and 10% palladium on activated carbon (150 mg) was added. The mixture was shaken under a hydrogen atmosphere (40 psi) for 2 hours. The mixture was filtered through a pad of Celite and concentrated to give N-(2-fluorophenyl)benzene-1,2-diamine (1.2 g) that was carried on directly to the next step.

MS (ES) m/z 203.0.

Step 3: Dry diglyme (10 mL) was added to a flask equipped with a dropping funnel under a nitrogen atmosphere and brought to a vigorous reflux N-(2-fluorophenyl)benzene-1,2-diamine (1.2 g, 6.0 mmol) and sulfamide (0.69 g, 7.2 mmol) were dissolved in 5 mL of diglyme and placed in the dropping funnel. The mixture was added dropwise to the flask over 15 minutes and then refluxing was continued for an additional 15 minutes. The mixture was cooled to ambient temperature and diluted with ether, washed with water, 2N HCl, water, brine, dried over anhydrous magnesium sulfate, and concentrated. The crude product was purified via Isco chromatography (Redisep, silica, gradient 5-50% (ethyl acetate containing 2% formic acid) in hexane) to afford 1-(2-fluorophenyl)-1,3-dihydro-2,1,3-benzothiadiazole 2,2-dioxide (0.37 g).

MS (ES) m/z 263.0; HPLC purity 100.0% at 210-370 nm, 8.9 minutes Xterra RP18, 3.5 u, 150×4.6 mm column, 1.2 mL/min, 85/15-5/95 (ammonium formate buffer pH=3.5, acetonitrile/MeOH) for 10 minutes, hold 4 minutes.

General Procedure II, Installation of Boc-Protected Side-Chain and Deprotection 1-(2-morpholin-2-ylethyl)-3-phenyl-1,3-dihydro-2,1,3-benzothiadiazole 2,2-dioxide

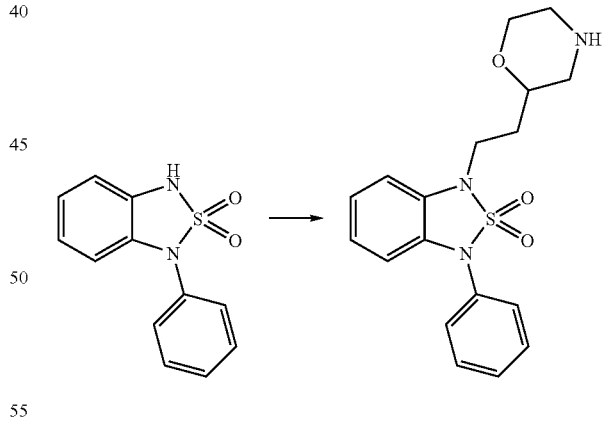

Step 1: To a solution of 1-phenyl-1,3-dihydro-2,1,3-benzothiadiazole 2,2-dioxide (made analogously as in general procedure I, 0.2 g, 0.8 mmol) in THF (10 mL) was added triphenylphosphine (0.26 g, 1 mmol), tert-butyl 2-(2-hydroxyethyl)morpholine-4-carboxylate (0.2 g, 0.9 mmol) and DIAD (0.2 g, 1 mmol) at 0° C. The mixture was allowed to warm to ambient temperature overnight then concentrated and chromatographed on silica gel (0 to 40% EtOAc in hexane).

Step 2: The resulting mostly pure carbamate was dissolved in dichloromethane (10 mL) and treated with HCl (4 mL, 4M in dioxane). The resulting salt was chromatographed on silica (0 to 100% of (7N NH₃/MeOH) in dichloromethane) giving the desired product as a clear oil (0.23 g, 80%). HRMS: calcd for C18H21N3O3S+H+, 360.1376; found (ESI, [M+H]+), 360.1377. HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

General Procedure III: Resolution of Racemic Agents

1-{2-[(2S)-morpholin-2-yl]ethyl}-3-phenyl-1,3-dihydro-2,1,3-benzothiadiazole 2,2-dioxide

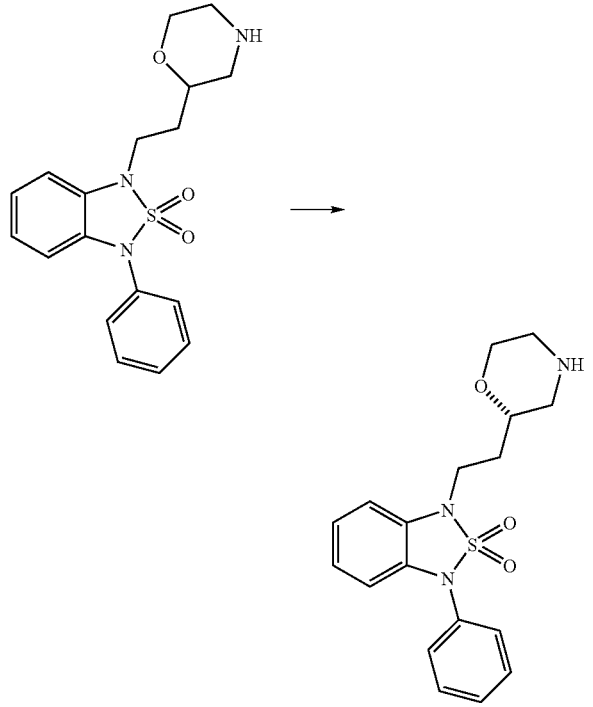

1-(2-morpholin-2-ylethyl)-3-phenyl-1,3-dihydro-2,1,3-benzothiadiazole-2,2-dioxide was dissolved in methanol. 200 uL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AS-H 5□m, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

| | |
|---|---|
| SFC Instrument: | Berger MultiGram Prep SFC (Berger Instruments, Inc. Newark, DE) |
| Column: | Chiralpak AS-H; 5□m; 250 mm L × 20 mm ID (Chiral Technologies, Inc, Exton, PA) |
| Column temperature: | 35° C. |
| SFC Modifier: | 18% MeOH w 0.2% DMEA |
| Flow rate: | 50 mL/min |
| Outlet Pressure: | 100 bar |
| Detector: | UV at 220 nm. |

HRMS: calcd for C18H21N3O3S+H+, 360.1376; found (ESI, [M+H]+), 360.1378. HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

General Procedure IV: Installation of Bromo-substituted Side-chain by Alkylation

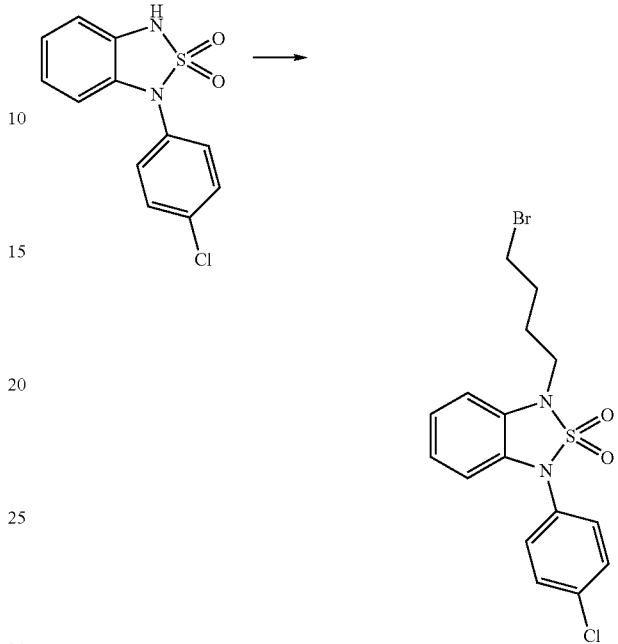

Cesium carbonate (0.29 g, 0.9 mmol) was added to a solution of 1-(4-chlorophenyl)-1,3-dihydro-2,1,3-benzothiadiazole 2,2-dioxide (Made analogously as in general procedure I, 0.25 g, 0.9 mmol), and 1,4-dibromobutane (0.42 mL, 3.6 mmol) in dry DMF (5.0 mL) under nitrogen. After 3 h, the reaction mixture was diluted with diethyl ether and washed with water and brine. The ether layer was dried over magnesium sulfate, filtered and concentrated in vacuo to give 0.41 g of crude product. The crude product was pre-adsorbed onto Celite and purified via Isco chromatography (Redisep, silica, gradient 5-30% ethyl acetate in hexane) to afford 0.22 g (59%) of 1-(4-bromobutyl)-3-(4-chlorophenyl)-1,3-dihydro-2,1,3-benzothiadiazole 2,2-dioxide.

General Procedure V: Substitution of Bromo-substituted Side-chain with an Amine 1-(4-chlorophenyl)-3-(4-morpholin-4-ylbutyl)-1,3-dihydro-2,1,3-benzothiadiazole 2,2-dioxide

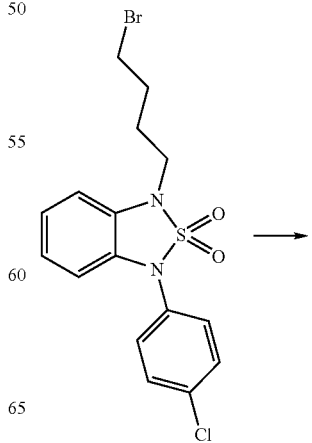

-continued

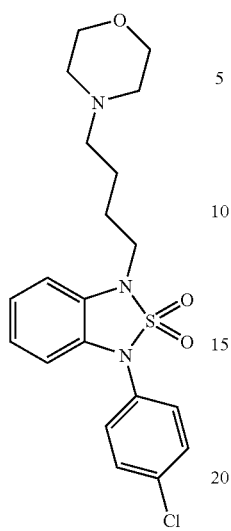

Morpholine (2 mL, 23 mmol) was added to a round bottom flask containing (50 mg, 0.12 mmol) of 1-(4-bromobutyl)-3-(4-chlorophenyl)-1,3-dihydro-2,1,3-benzothiadiazole 2,2-dioxide (made in general procedure IV). The reaction flask was covered with a septum and stirred overnight at room temperature. The reaction solution was concentrated in vacuo and the crude product was pre-adsorbed onto Celite and purified via Isco chromatography (Redisep, silica, gradient 1-8% methanol in dichloromethane with ammonia) to afford 29 mg (78%) of 1-(4-chlorophenyl)-3-(4-morpholin-4-ylbutyl)-1,3-dihydro-2,1,3-benzothiadiazole 2,2-dioxide. HPLC purity 100.0% at 210-370 nm, 8.2 minutes Xterra RP18, 3.5 u, 150×4.6 mm column, 1.2 mL/min, 85/15-5/95 (ammonium formate buffer pH=3.5, acetonitrile/MeOH) for 10 minutes, hold 4 minutes.

HRMS: calculated for $C_{20}H_{24}ClN_3O_3S+H^+$, 422.12996; found (ESI, $[M+H]^+$), 422.1296.

General Procedure VI: Installation of Bromo-substituted Side-chain by Mitsunobu

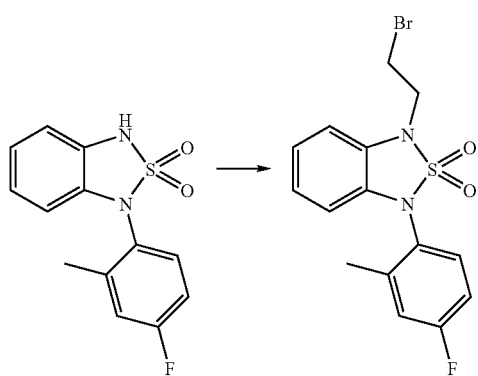

1-(4-fluoro-2-methylphenyl)-1,3-dihydro-2,1,3-benzothiadiazole 2,2-dioxide (prepared analogously as described in general procedure I, 0.35 g, 1.3 mmol) was treated with triphenylphosphine (0.46 g, 1.5 mmol), 2-bromoethanol (0.21 g, 1.4 mmol) and diisopropylazodicarboxylate (0.35 g, 1.7 mmol) to provide 0.32 g of 1-(2-bromoethyl)-3-(4-fluoro-2-methylphenyl)-1,3-dihydro-2,1,3-benzothiadiazole 2,2-dioxide. HRMS: calculated for $C15H_{14}BrFN_2O_2S$, 383.99434; found (EI, M+), 383.9958

EXAMPLES

Example 1

1-(morpholin-2-ylmethyl)-3-phenyl-1,3-dihydro-2,1,3-benzothiadiazole 2,2-dioxide hydrochloride

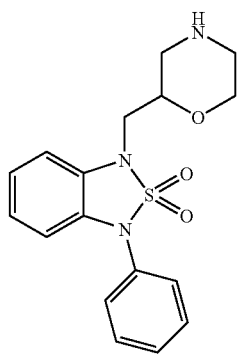

Step 1: A mixture of 1-phenyl-1,3-dihydro-2,1,3-benzothiadiazole 2,2-dioxide (prepared analogously as in general procedure I, 246 mg, 1.00 mmol), tert-butyl 2-(hydroxymethyl)morpholine-4-carboxylate (228 mg, 1.05 mmol, 1.05 equiv.) and triphenylphosphine (289 mg, 1.10 mmol, 1.1 equiv.) in tetrahydrofuran (5 mL) was cooled to 0° C. in an ice bath. Diispropyl azodicarboxylate (0.22 mL, 1.1 mmol, 1.1 equiv.) was added dropwise via a syringe. The reaction mixture was stirred overnight while warming to room temperature. Solvent was removed under reduced pressure and the residue was purified by Isco flash column chromatography (silica gel, 3-30% ethyl acetate/hexane) to give 398 mg (89%) of tert-butyl 2-[(2,2-dioxido-3-phenyl-2,1,3-benzothiadiazol-1(3H)-yl)methyl]morpholine-4-carboxylate as a white foam. MS (ESI) m/z 445.9 ($[M+H]^+$).

Step 2: To a solution of tert-butyl 2-[(2,2-dioxido-3-phenyl-2,1,3-benzothiadiazol-1(3H)-yl)methyl]morpholine-4-carboxylate (385 mg, 0.864 mmol) in methanol (5 mL) was added slowly an ethereal solution of hydrochloric acid (1M, 10 mL). The mixture was swirled for 20 minutes. All volatiles were removed under reduced pressure. The white precipitate was redissolved in minutesimal amount of methanol (~1 mL). Isopropyl ether was added until the solution became slightly cloudy. The mixture was cooled to −30° C. in a freezer. The white solid formed was collected by decantation, washed with hexane and dried in vacuo to give 327 mg (99%) of 1-(morpholin-2-ylmethyl)-3-phenyl-1,3-dihydro-2,1,3-benzothiadiazole 2,2-dioxide hydrochloride as a white powder. MS (ESI) m/z 345.9 ($[M+H]^+$).

Example 2

1-[(2R)-morpholin-2-ylmethyl]-3-phenyl-1,3-dihydro-2,1,3-benzothiadiazole 2,2-dioxide hydrochloride

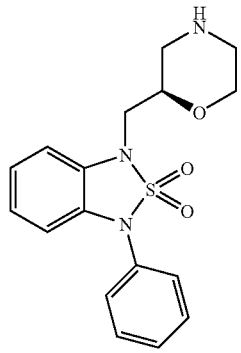

Step 1: Racemic 1-(morpholin-2-ylmethyl)-3-phenyl-1,3-dihydro-2,1,3-benzothiadiazole 2,2-dioxide hydrochloride (Example 1, 164 mg, 0.429 mmol) was dissolved in methanol (4 mL). 500 µL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralcel OJ-H 5 u, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

| | |
|---|---|
| SFC Instrument: | Berger MultiGram Prep SFC (Berger Instruments, Inc. Newark, DE. |
| Column: | Chiralcel OJ-H; 5 u; 250 mm L × 20 mm ID (Chiral Technologies, Inc, Exton, PA, USA) |
| Column temperature: | 35° C. |
| SFC Modifier: | 15% MeOH/85% CO$_2$ with 0.2% DEA |
| Flow rate: | 50 mL/min |
| Outlet Pressure: | 100 bar |
| Detector: | UV at 220 nm |

Step 2: A solution of 1-[(2R)-morpholin-2-ylmethyl]-3-phenyl-1,3-dihydro-2,1,3-benzothiadiazole 2,2-dioxide, isolated as Peak 1 of the above chiral HPLC separation, in dichloromethane (3 mL) was treated with an ethereal solution of hydrochloric acid (1 M, 0.2 mL, 0.2 mmol). To the resulting solution was added hexane until white powder formed, which was collected, washed with hexane, and dried in vacuo to yield 44 mg (27%) of 1-[(2R)-morpholin-2-ylmethyl]-3-phenyl-1,3-dihydro-2,1,3-benzothiadiazole 2,2-dioxide hydrochloride. Absolute stereochemistry was arbitrarily assigned. MS (ESI) m/z 346.2 ([M+H]$^+$).

Example 3

1-[(2S)-morpholin-2-ylmethyl]-3-phenyl-1,3-dihydro-2,1,3-benzothiadiazole 2,2-dioxide hydrochloride

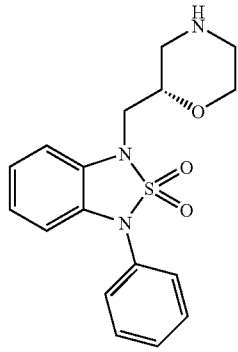

In an analogous manner to Example 2, 1-[(2S)-morpholin-2-ylmethyl]-3-phenyl-1,3-dihydro-2,1,3-benzothiadiazole 2,2-dioxide hydrochloride was prepared as a white powder from racemic 1-(morpholin-2-ylmethyl)-3-phenyl-1,3-dihydro-2,1,3-benzothiadiazole 2,2-dioxide hydrochloride (Example 1), which was isolated as peak 2 of the chiral HPLC separation (Example 2, Step 1). Absolute stereochemistry was arbitrarily assigned. MS (ESI) m/z 346.2 ([M+H]$^+$).

Example 4

1-[(4-methylmorpholin-2-yl)methyl]-3-phenyl-1,3-dihydro-2,1,3-benzothiadiazole 2,2-dioxide hydrochloride

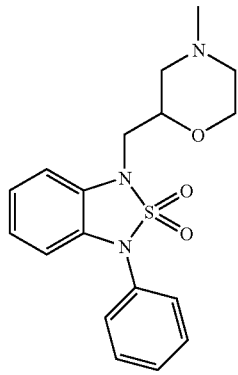

To a solution of 1-(morpholin-2-ylmethyl)-3-phenyl-1,3-dihydro-2,1,3-benzothiadiazole 2,2-dioxide hydrochloride (Example 1, 76 mg, 0.20 mmol) in methanol (2 mL) was added a solution of formaldehyde (37% in water, 0.15 mL) and the mixture was stirred for 30 minutes. Sodium cyanoborohydride (38 mg, 0.60 mmol, 3 equiv.) was added portionwise and the mixture was stirred for an additional 3 hours. Saturated aqueous sodium bicarbonate (5 mL) was added slowly followed by the addition of water (5 mL). The reaction mixture was extracted with ethyl acetate (2×15 mL). The combined organic extracts were washed with brine, dried (anhydrous sodium sulfate), and concentrated. The crude liquid residue was purified by Isco flash column chromatography (silica gel, 0-10% methanol/dichloromethane) to give 70 mg (98%) of 1-[(4-methylmorpholin-2-yl)methyl]-3-phenyl-1,3-dihydro-2,1,3-benzothiadiazole 2,2-dioxide as viscous colorless liquid. This free base was dissolved in dichloromethane (3 mL) and was treated with an ethereal solution of hydrochloric acid (1 M, 0.3 mL, 0.3 mmol). To the resulting solution was added hexane until white powder formed, which was collected, washed with hexane, and dried in vacuo to yield 76 mg (96%) of 1-[(4-methylmorpholin-2-yl)methyl]-3-phenyl-1,3-dihydro-2,1,3-benzothiadiazole 2,2-dioxide hydrochloride. MS (ESI) m/z 360.2 ([M+H]$^+$).

Example 5

1-(2-chloro-4-fluorophenyl)-3-{2-[(3R,5S)-3,5-dimethylpiperazin-1-yl]ethyl}-1,3-dihydro-2,1,3-benzothiadiazole-2,2-dioxide

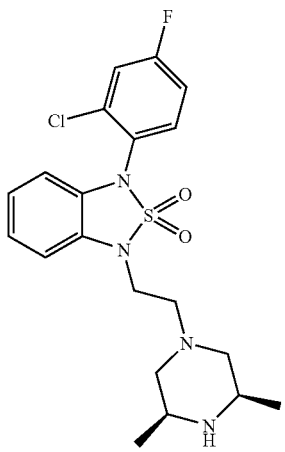

Step 1: 1-(2-chloro-4-fluorophenyl)-1,3-dihydro-2,1,3-benzothiadiazole 2,2-dioxide (made analogously as in general procedure I, 0.33 g, 1.1 mmol) was treated with triphenylphosphine (0.36 g, 1.4 mmol), 2-bromo ethanol (0.16 g, 1.4 mmol), and diisopropylazodicarboxylate (0.28 g, 1.4 mmol) to provide 0.30 g of 1-(2-bromoethyl)-3-(2-chloro-4-fluorophenyl)-1,3-dihydro-2,1,3-benzothiadiazole 2,2-dioxide. HRMS: calculated for C14H11BrClFN2O2S, 403.93971; found (EI, M+), 403.9386

Step 2 0.20 g (0.5 mmol) of 1-(2-bromoethyl)-3-(2-chloro-4-fluorophenyl)-1,3-dihydro-2,1,3-benzothiadiazole 2,2-dioxide, 0.09 g (0.75 mmol) of cis-2,6-dimethyl piperazine and 0.35 g (1 mmol) of cesium carbonate were dissolved in ethanol and heated to 90° C. for 30 hr. At the end of this time the solution was concentrated and the residue placed on a pad of silica gel eluting first with 20% ethyl acetate:hexane then 90% chloroform:methanol. The chloroform eluent was concentrated and the residue dissolved in ethanol, whereupon 2 mL of 2N HCl in ether added. The solution was concentrated to a smaller volume and triturated with ether and the solid removed by filtration to provide 0.11 g of 1-(2-chloro-4-fluorophenyl)-3-{2-[(3R,5S)-3,5-dimethylpiperazin-1-yl]ethyl}-1,3-dihydro-2,1,3-benzothiadiazole-2,2-dioxide dihydrochloride.

HPLC purity 95.9% at 210-370 nm, 9.6 minutes; Xterra RP18, 3.5 u, 150×4.6 mm column, 1.2 mL/minutes 85/15-5/95 (Ammon. Bicarb Buff. pH=9.5/ACN+MeOH) for 10 minutes hold 4 minutes HRMS: calculated for C$_{20}$H$_{24}$ClFN$_4$O$_2$S+H+, 439.13653; found (ESI, [M+H]$^+$), 439.1368.

Example 6

1-(2-chloro-4-fluorophenyl)-3-{2-piperazin-1-ylethyl}-1,3-dihydro-2,1,3-benzothiadiazole-2,2-dioxide

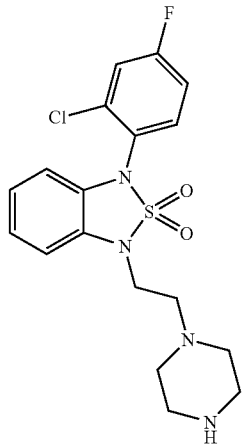

Step 1: 1-(2-chloro-4-fluorophenyl)-1,3-dihydro-2,1,3-benzothiadiazole 2,2-dioxide (made analogously as in general procedure I, 0.35 g, 1.2 mmol) was treated with triphenylphosphine (0.46 g, 1.5 mmol), t-butyl 4-(2-hydroxyethyl)piperazine-1-carboxylate (0.33 g, 1.4 mmol), and diisopropylazodicarboxylate (0.32 g, 1.5 mmol) to provide 0.30 g of an oil, which was used as is in the next step.

Step 2: The residue isolated from Step 1 (0.3 g) was dissolved in ether:methanol (10:1) and 2 mL of 2N HCl in ether added. The solution was allowed to stand for 16 hours whereupon the solid was collected by filtration to 0.29 g of 1-(2-chloro-4-fluorophenyl)-3-{2-piperazin-1-ylethyl}-1,3-dihydro-2,1,3-benzothiadiazole-2,2-dioxide dihydrochloride.

MS (ES) m/z 410.9; HPLC purity 98.8% at 210-370 nm, 9.0 minutes; Xterra RP18, 3.5 u, 150×4.6 mm column, 1.2 mL/minutes 85/15-5/95 (Ammon. Bicarb Buff. pH=9.5/ACN+MeOH) for 10 minutes hold 4 minutes; HRMS: calculated for C$_{18}$H$_{20}$ClFN$_4$O$_2$S+H+, 411.10523; found (ESI, [M+H]$^+$), 411.1066.

Example 7

1-(4-fluoro-2-methylphenyl)-3-{2-piperazin-1-ylethyl}-1,3-dihydro-2,1,3-benzothiadiazole-2,2-dioxide

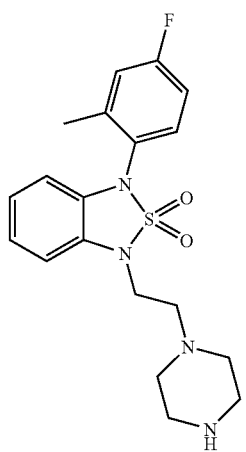

Step 1: In an analogous manner to general procedure II, 1-(4-fluoro-2-methylphenyl)-1,3-dihydro-2,1,3-benzothiadiazole 2,2-dioxide (0.35 g, 1.3 mmol) was treated with triphenylphosphine (0.46 g, 1.5 mmol), t-butyl 4-(2-hydroxyethyl)piperazine-1-carboxylate (0.33 g, 1.4 mmol), and diisopropylazodicarboxylate (0.32 g, 1.5 mmol) to provide 0.31 g of an oil, which was treated with HCl to provide 0.29 g of 1-(4-fluoro-2-methylphenyl)-3-{2-piperazin-1-ylethyl}-1,3-dihydro-2,1,3-benzothiadiazole-2,2-dioxide dihydrochloride.

MS (ES) m/z 391.0;

HPLC purity 98.6% at 210-370 nm, 9.2 minutes; Xterra RP18, 3.5 u, 150×4.6 mm column, 1.2 mL/minutes 85/15-5/95 (Ammon. Bicarb Buff.

pH=9.5/ACN+MeOH) for 10 minutes hold 4 minutes

HRMS: calculated for $C_{19}H_{23}FN_4O_2S+H+$, 391.15985; found (ESI, $[M+H]^+$), 391.1604.

Example 8

1-(4-fluoro-2-methylphenyl)-3-{2-[(3R,5S)-3,5-dimethylpiperazin-1-yl]ethyl}-1,3-dihydro-2,1,3-benzothiadiazole-2,2-dioxide

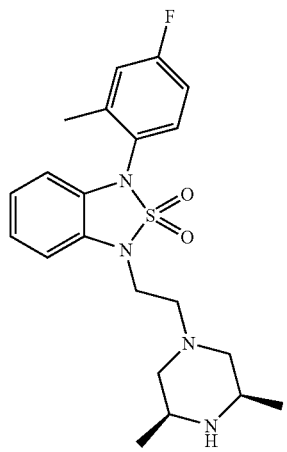

0.19 g (0.5 mmol) of 1-(2-bromoethyl)-3-(4-fluoro-2-methylphenyl)-1,3-dihydro-2,1,3-benzothiadiazole 2,2-dioxide (prepared as described in general procedure I), 0.09 g (0.75 mmol) of cis-2,6-dimethyl piperazine and 0.35 g (1 mmol) of cesium carbonate were dissolved in ethanol and heated to 90° C. for 30 hr. At the end of this time the solution was concentrated and the residue placed on a pad of silica gel eluting first with 20% ethyl acetate:hexane then 90% chloroform:methanol. The chloroform eluent was concentrated and the residue dissolved in ethanol, whereupon 2 mL of 2N HCl in ether added. The solution was concentrated to a smaller volume and triturated with ether and the solid removed by filtration to provide 0.11 g of 1-(4-fluoro-2-methylphenyl)-3-{2-[(3R,5S)-3,5-dimethylpiperazin-1-yl]ethyl}-1,3-dihydro-2,1,3-benzothiadiazole-2,2-dioxide dihydrochloride.

MS (ES) m/z 419.2;

HPLC purity 93.4% at 210-370 nm, 9.8 minutes; Xterra RP18, 3.5 u, 150×4.6 mm column, 1.2 mL/minutes 85/15-5/95 (Ammon. Bicarb Buff.

pH=9.5/ACN+MeOH) for 10 minutes hold 4 minutes

HRMS: calculated for $C_{21}H_{27}FN_4O_2S+H+$, 419.19115; found (ESI, $[M+H]^+$), 419.1921.

Example 9

1-(4-fluoro-2-methoxyphenyl)-3-{2-piperazin-1-ylethyl}-1,3-dihydro-2,1,3-benzothiadiazole-2,2-dioxide

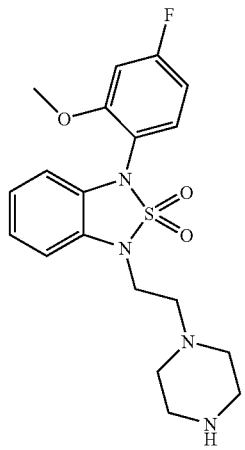

Step 1: In an analogous manner as in general procedure II, 1-(4-fluoro-2-methoxyphenyl)-1,3-dihydro-2,1,3-benzothiadiazole 2,2-dioxide (prepared analogously as described in general procedure I, 0.41 g, 1.4 mmol) was treated with triphenylphosphine (0.46 g, 1.5 mmol), t-butyl 4-(2-hydroxyethyl)piperazine-1-carboxylate (0.33 g, 1.4 mmol), and diisopropylazodicarboxylate (0.32 g, 1.5 mmol) to provide 0.32 g of an oil, which was used as is in the next step.

Step 2: 0.3 g of the product from Step 1 was converted to 0.30 g of 1-(4-fluoro-2-methoxyphenyl)-3-[2-piperazin-1-ylethyl]-1,3-dihydro-2,1,3-benzothiadiazole-2,2-dioxide dihydrochloride:

HPLC purity 100.0% at 210-370 nm, 7.2 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes. HRMS: calculated for $C_{19}H_{23}FN_4O_3S+H+$, 407.15476; found (ESI, $[M+H]^+$), 407.1552.

Example 10

1-[2-(2,5-diazabicyclo[2.2.1]hept-2-yl)ethyl]-3-phenyl-1,3-dihydro-2,1,3-benzothiadiazole 2,2-dioxide

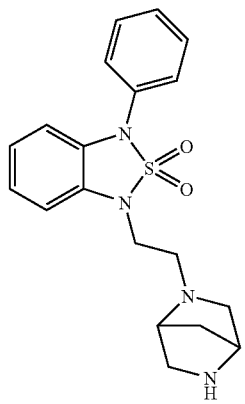

Step 1 In an analogous manner as described in general procedure V, 0.051 g of tert-butyl-1-[2-(2,5-diazabicyclo[2.2.1]hept-2-yl)ethyl]-3-phenyl-1,3-dihydro-2,1,3-benzothiadiazole 2,2-dioxide-4-carboxylate was prepared from 0.15 g (0.42 mmol) of 1-(2-bromoethyl)-3-phenyl-1,3-dihydro-2,1,3-benzothiadiazole 2,2-dioxide (see Example 50, Step 1) and 0.125 g (0.63 mmol) of tert-butyl (1-S,4S-(−)-2,5-diazabicyclo[2.2.1]heptane-2-carboxylate as an oil an used in the next step.

Step 2 In an analogous manner as described in general procedure II, step 2, 1-[2-(2,5-diazabicyclo[2.2.1]hept-2-yl)ethyl]-3-phenyl-1,3-dihydro-2,1,3-benzothiadiazole 2,2-dioxide dihydrochloride was prepared from tert-butyl-1-[2-(2,5-diazabicyclo[2.2.1]hept-2-yl)ethyl]-3-phenyl-1,3-dihydro-2,1,3-benzothiadiazole 2,2-dioxide-4-carboxylate. MS (ES) m/z 371.2; HPLC purity 100.0% at 210-370 nm, 7.0 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Example 11

Preparation of 2-{2-[3-(2-fluorophenyl)-2,2-dioxido-2,1,3-benzothiadiazol-1(3H)-yl]ethoxy}ethanamine

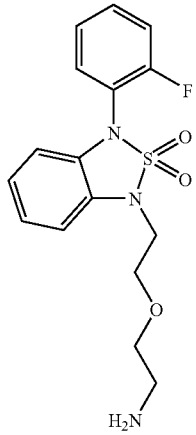

Step 1: In an analogous manner to general procedure I, step 3, N-(2-fluorophenyl)benzene-1,2-diamine (1.0 g, 5.0 mmol) was treated with sulfamide (0.58 g, 6.0 mmol) to provide 0.52 g (40%) of 1-(2-fluorophenyl)-1,3-dihydro-2,1,3-benzothiadiazole 2,2-dioxide. HRMS: calculated for $C_{12}H_9FN_2O_2S+Na^+$, 287.02609; found (ESI, [M+Na]$^+$), 287.0263; HPLC purity 100.0% at 210-370 nm, 8.4 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Step 2: In an analogous manner as described in general procedure IV, 1-(2-fluorophenyl)-1,3-dihydro-2,1,3-benzothiadiazole 2,2-dioxide (0.22 g, 0.83 mmol) was treated with cesium carbonate (0.27 g, 0.83 mmol) and 1-Bromo-2-(2-bromo-ethoxy)-ethane (0.03 mL, 3.3 mmol) to provide 0.23 g (67%) of 1-[2-(2-bromoethoxy)ethyl]-3-(2-fluorophenyl)-1,3-dihydro-2,1,3-benzothiadiazole 2,2-dioxide. HRMS: calculated for $C_{16}H_{16}BrFN_2O_3S+H^+$, 415.01218; found (ESI, [M+H]$^+$), 415.0127; HPLC purity 100.0% at 210-370 nm, 10.1 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Step 3: In an analogous manner as described in general procedure V, 1-[2-(2-bromoethoxy)ethyl]-3-(2-fluorophenyl)-1,3-dihydro-2,1,3-benzothiadiazole 2,2-dioxide (0.07 g, 0.16 mmol) was treated with ammonia (10 mL) to prepare 0.04 g (71%) of 2-{2-[3-(2-fluorophenyl)-2,2-dioxido-2,1,3-benzothiadiazol-1(3H)-yl]ethoxy}ethanamine. MS (ES) m/z 351.9; HRMS: calculated for $C_{16}H_{18}FN_3O_3S+H^+$, 352.11257; found (ESI, [M+H]$^+$), 352.1128; HPLC purity 100.0% at 210-370 nm, 8.1 minutes; Xterra RP18, 3.5 u, 150×4.6 mm column, 1.2 mL/minutes 85/15-5/95 (Ammon. Bicarb Buff. pH=9.5/ACN+MeOH) for 10 minutes hold 4 minutes.

Example 12

Preparation of 2-{2-[3-(2-fluorophenyl)-2,2-dioxido-2,1,3-benzothiadiazol-1(3H)-yl]ethoxy}-N-methylethanamine

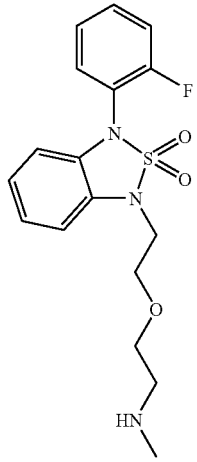

In an analogous manner as described in general procedure V, 1-[2-(2-bromoethoxy)ethyl]-3-(2-fluorophenyl)-1,3-dihydro-2,1,3-benzothiadiazole 2,2-dioxide (0.07 g, 0.16 mmol) was treated with methylamine (10 mL) to provide 0.05 g (95%) of 2-{2-[3-(2-fluorophenyl)-2,2-dioxido-2,1,3-benzothiadiazol-1(3H)-yl]ethoxy}-N-methylethanamine. MS (ES) m/z 366.0; HRMS: calculated for $C_{17}H_{20}FN_3O_3S+H^+$, 366.12822; found (ESI, [M+H]$^+$), 366.1285; HPLC purity 100.0% at 210-370 nm, 8.4 minutes; Xterra RP18, 3.5 u, 150×4.6 mm column, 1.2 mL/minutes 85/15-5/95 (Ammon. Bicarb Buff. pH=9.5/ACN+MeOH) for 10 minutes hold 4 minutes.

Example 13

Preparation of 2-{2-[3-(2-fluorophenyl)-2,2-dioxido-2,1,3-benzothiadiazol-1(3H)-yl]ethoxy}-N,N-dimethylethanamine

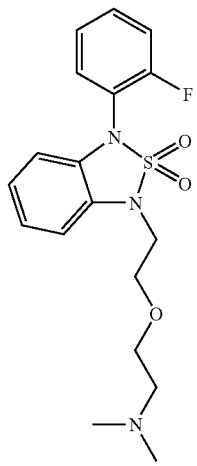

In an analogous manner as described in general procedure V, 1-[2-(2-bromoethoxy)ethyl]-3-(2-fluorophenyl)-1,3-dihydro-2,1,3-benzothiadiazole 2,2-dioxide (0.07 g, 0.16 mmol)

was treated with dimethylamine (10 mL) to provide 0.05 g (95%) of 2-{2-[3-(2-fluorophenyl)-2,2-dioxido-2,1,3-benzothiadiazol-1(3H)-yl]ethoxy}-N,N-dimethylethanamine. MS (ES) m/z 380.0; HRMS: calculated for $C_{18}H_{22}FN_3O_3S+H^+$, 380.14387; found (ESI, [M+H]$^+$), 380.1443; HPLC purity 98.1% at 210-370 nm, 9.1 minutes; Xterra RP18, 3.5 u, 150×4.6 mm column, 1.2 mL/minutes 85/15-5195 (Ammon. Bicarb Buff. pH=9.5/ACN+MeOH) for 10 minutes hold 4 minutes.

Example 14

Preparation of 1-{2-[2-(3,5-dimethylpiperazin-1-yl)ethoxy]ethyl}-3-(2-fluorophenyl)-1,3-dihydro-2,1,3-benzothiadiazole 2,2-dioxide In an analogous manner as described in general procedure V, 1-[2-(2-bromoethoxy)ethyl]-3-(2-fluorophenyl)-1,3-dihydro-2,1,3-benzothiadiazole 2,2-dioxide (0.07 g, 0.18 mmol) was treated with 2,6-Dimethyl-piperazine (0.06 g, 0.54 mmol) to provide 0.07 g (92%) of 1-{2-[2-(3,5-dimethylpiperazin-1-yl)ethoxy]ethyl}-3-(2-fluorophenyl)-1,3-dihydro-2,1,3-benzothiadiazole 2,2-dioxide.

MS (ES) m/z 449.0; HRMS: calculated for $C_{22}H_{29}FN_4O_3S+H^+$, 449.20171; found (ESI, [M+H]$^+$), 449.202; HPLC purity 98.4% at 210-370 nm, 7.1 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Example 15

Preparation of 1-[5-(3,5-dimethylpiperazin-1-yl)pentyl]-3-(2-fluorophenyl)-1,3-dihydro-2,1,3-benzothiadiazole 2,2-dioxide

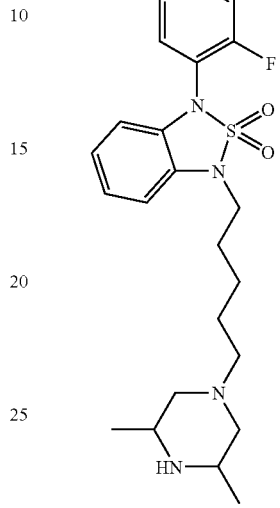

In an analogous manner as described in general procedure V, 1-(5-bromopentyl)-3-(2-fluorophenyl)-1,3-dihydro-2,1,3-benzothiadiazole 2,2-dioxide (0.07 g, 0.18 mmol) was treated with 2,6-Dimethyl-piperazine (0.06 g, 0.54 mmol) to provide 0.08 g (88%) of 1-[5-(3,5-dimethylpiperazin-1-yl)pentyl]-3-(2-fluorophenyl)-1,3-dihydro-2,1,3-benzothiadiazole 2,2-dioxide. MS (ES) m/z 447.0;

HRMS: calculated for $C_{23}H_{31}FN_4O_2S+H^+$, 447.22245; found (ESI, [M+H]$^+$), 447.2234 and HPLC purity 100.0% at 210-370 nm, 7.9 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Example 16

(2R)-3-[3-(2-fluorophenyl)-2,2-dioxido-2,1,3-benzothiadiazol-1(3H)-yl]-2-methylpropan-1-amine

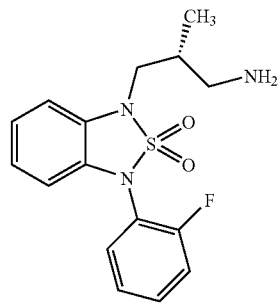

In an analogous manner to Example 23, (2R)-3-[3-(2-fluorophenyl)-2,2-dioxido-2,1,3-benzothiadiazol-1(3H)-yl]-2-methylpropan-1-amine was prepared from 1-[(2S)-3-bromo-2-methylpropyl]-3-(2-fluorophenyl)-1,3-dihydro-2,1,3-benzothiadiazole 2,2-dioxide, potassium phthalimide and methyl hydrazine giving the desired product.

HRMS: calculated for C17H15FN2O+H+, 336.1182; found (ESI, [M+H]+), 336.1178.

HPLC purity 99.1% at 210-370 nm, 7.0 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Example 17

(2S)-3-[3-(2-fluorophenyl)-2,2-dioxido-2,1,3-benzothiadiazol-1(3H)-yl]-2-methylpropan-1-amine

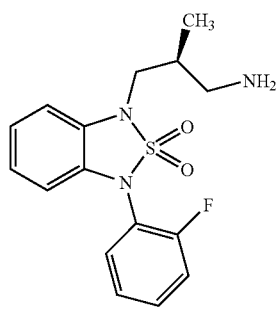

In an analogous manner to Example 23, (2S)-3-[3-(2-fluorophenyl)-2,2-dioxido-2,1,3-benzothiadiazol-1(3H)-yl]-2-methylpropan-1-amine was prepared from 1-[(2R)-3-bromo-2-methylpropyl]-3-(2-fluorophenyl)-1,3-dihydro-2,1,3-benzothiadiazole 2,2-dioxide, potassium phthalimide and methyl hydrazine giving the desired product. HRMS: calculated for C17H15FN2O+H+, 336.1182; found (ESI, [M+H]+), 336.1177. HPLC purity 100% at 210-370 nm, 7.0 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Example 18

4-[3-(2-fluorophenyl)-2,2-dioxido-2,1,3-benzothiadiazol-1(3H)-yl]butan-2-amine

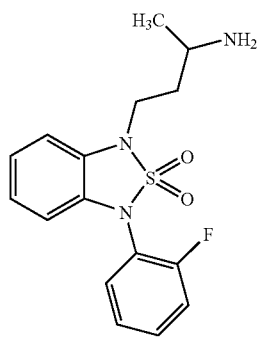

In an analogous manner to Example 23, 4-[3-(2-fluorophenyl)-2,2-dioxido-2,1,3-benzothiadiazol-1(3H)-yl]butan-2-amine was prepared from 1-(3-bromobutyl)-3-(2-fluorophenyl)-1,3-dihydro-2,1,3-benzothiadiazole 2,2-dioxide, potassium phthalimide and methyl hydrazine giving the desired product. HRMS: calculated for C17H15FN2O+H+, 336.1182; found (ESI, [M+H]+), 336.118.

HPLC purity 91.2% at 210-370 nm, 7.0 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Example 19

3-[3-(2-fluorophenyl)-2,2-dioxido-2,1,3-benzothiadiazol-1(3H)-yl]-N-methylbutan-1-amine

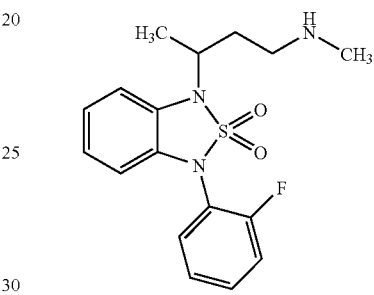

Step 1: 1-(2-fluorophenyl)-1,3-dihydro-2,1,3-benzothiadiazole 2,2-dioxide (general procedure 10.2 g, 0.8 mmol) was dissolved in tetrahydrofuran (10 mL) and triphenylphosphine (0.54 g, 0.9 mmol) was added followed by 4-bromobutan-2-ol (0.14 g, 0.9 mmol) and diisopropyl azodicarboxylate (0.18 g, 0.9 mmol). The mixture was stirred for 18 hours at 23° C. The mixture was concentrated and purified via Isco chromatography (Redisep, silica, gradient 0-50% ethyl acetate in hexane) to afford 0.22 g of 1-(3-bromo-1-methylpropyl)-3-(2-fluorophenyl)-1,3-dihydro-2,1,3-benzothiadiazole 2,2-dioxide.

HRMS: calculated for C17H15FN2O, Exact Mass: 398.0100; found (ESI, [M+], 398.0102.

HPLC purity 96.4% at 210-370 nm, 10.6 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Step 2: 1-(3-bromo-1-methylpropyl)-3-(2-fluorophenyl)-1,3-dihydro-2,1,3-benzothiadiazole 2,2-dioxide (0.04 g, 0.09 mmol) was dissolved in 2 mL of MeNH2 solution (8M in EtOH). The solution was irradiated in a microwave cuvette at 100° C. for 3 minutes. The reaction mixture was concentrated then loaded directly onto silica gel and purified via Isco chromatography (Redisep, silica, gradient 0-10% 7M ammonia/MeOH solution in dichloromethane) to afford 44 mg of 3-[3-(2-fluorophenyl)-2,2-dioxido-2,1,3-benzothiadiazol-1(3H)-yl]-N-methylbutan-1-amine.

HRMS: calculated for C17H15FN2O+H+, 350.1339; found (ESI, [M+H]+), 350.1335.

HPLC purity 97% at 210-370 nm, 7.2 minutes; Xterra RP18, 3.5 u, 150×4.6 mm column, 1.2 mL/minutes 85/15-5195 (Ammonium formate buffer pH=3.5/ACN+MeOH) for 10 minutes hold 4 minutes.

Example 20

4-[3-(2-fluorophenyl)-2,2-dioxido-2,1,3-benzothiadiazol-1(3H)-yl]-N-methylbutan-2-amine

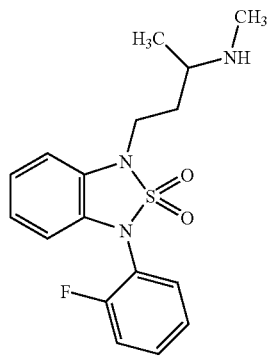

Step 1: In an analogous manner to Example 19, step 1, 1-(3-bromobutyl)-3-(2-fluorophenyl)-1,3-dihydro-2,1,3-benzothiadiazole 2,2-dioxide was prepared from 1-(2-fluorophenyl)-1,3-dihydro-2,1,3-benzothiadiazole 2,2-dioxide and 3-bromobutan-1-ol giving 0.27 g of the desired product.

HRMS: calculated for C17H15FN2O, Exact Mass: 398.0100; found (ESI, [M+], 398.0106.

HPLC purity 93.6% at 210-370 nm, 10.7 minutes; Xterra RP18, 3.5 u, 150×4.6 mm column, 1.2 mL/minutes 85/15-5195 (Ammonium formate buffer pH=3.5/ACN+MeOH) for 10 minutes hold 4 minutes.

Step 2: In an analogous manner to Example 19, step 2, 4-[3-(2-fluorophenyl)-2,2-dioxido-2,1,3-benzothiadiazol-1(3H)-yl]-N-methylbutan-2-amine was prepared from 1-(3-bromobutyl)-3-(2-fluorophenyl)-1,3-dihydro-2,1,3-benzothiadiazole 2,2-dioxide and MeNH$_2$ solution (8M in EtOH) giving 51 mg of the desired product.

HRMS: calculated for C17H15FN2O+H+, 350.1339; found (ESI, [M+H]+), 350.1338.

HPLC purity 100% at 210-370 nm, 7.1 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Example 21

(2R)-3-[3-(2-fluorophenyl)-2,2-dioxido-2,1,3-benzothiadiazol-1(3H)-yl]-N,2-dimethylpropan-1-amine

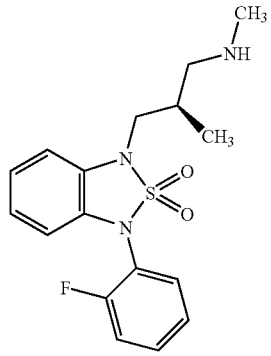

Step 1: In an analogous manner to Example 19, step 1, 1-[(2S)-3-bromo-2-methylpropyl]-3-(2-fluorophenyl)-1,3-dihydro-2,1,3-benzothiadiazole 2,2-dioxide was prepared from 1-(2-fluorophenyl)-1,3-dihydro-2,1,3-benzothiadiazole 2,2-dioxide and (S)-3-bromo-2-methylpropan-1-ol giving 0.26 g of the desired product.

HRMS: calculated for C17H15FN2O, Exact Mass: 398.0100; found (ESI, [M+], 398.0111.

HPLC purity 100% at 210-370 nm, 10.7 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Step 2: In an analogous manner to Example 19, step 2, (2R)-3-[3-(2-fluorophenyl)-2,2-dioxido-2,1,3-benzothiadiazol-1(3H)-yl]-N,2-dimethylpropan-1-amine was prepared from 1-[(2S)-3-bromo-2-methylpropyl]-3-(2-fluorophenyl)-1,3-dihydro-2,1,3-benzothiadiazole 2,2-dioxide and MeNH$_2$ solution (8M in EtOH) giving 65 mg of the desired product.

HRMS: calculated for C17H15FN2O+H+, 350.1339; found (ESI, [M+H]+), 350.1335.

HPLC purity 97.6% at 210-370 nm, 7.1 minutes; Xterra RP18, 3.5 u, 150×4.6 mm column, 1.2 mL/minutes 85/15-5195 (Ammonium formate buffer pH=3.5/ACN+MeOH) for 10 minutes hold 4 minutes.

Example 22

(2S)-3-[3-(2-fluorophenyl)-2,2-dioxido-2,1,3-benzothiadiazol-1(3H)-yl]-N,2-dimethylpropan-1-amine

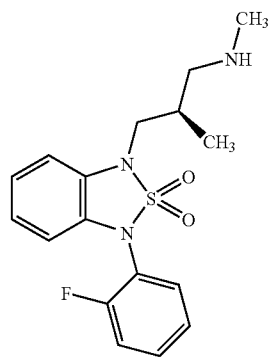

Step 1: In an analogous manner to Example 19, step 1, 1-[(2R)-3-bromo-2-methylpropyl]-3-(2-fluorophenyl)-1,3-dihydro-2,1,3-benzothiadiazole 2,2-dioxide was prepared from 1-(2-fluorophenyl)-1,3-dihydro-2,1,3-benzothiadiazole 2,2-dioxide and (R)-3-bromo-2-methylpropan-1-ol giving 0.27 g of the desired product.

HRMS: calculated for C17H15FN2O, Exact Mass: 398.0100; found (ESI, [M+], 398.0103.

HPLC purity 100% at 210-370 nm, 10.7 minutes; Xterra RP18, 3.5 u, 150×4.6 mm column, 1.2 mL/minutes 85/15-5195 (Ammonium formate buffer pH=3.5/ACN+MeOH) for 10 minutes hold 4 minutes.

Step 2: In an analogous manner to Example 19, step 2, (2S)-3-[3-(2-fluorophenyl)-2,2-dioxido-2,1,3-benzothiadiazol-1(3H)-yl]-N,2-dimethylpropan-1-amine was prepared from 1-[(2R)-3-bromo-2-methylpropyl]-3-(2-fluorophenyl)-1,3-dihydro-2,1,3-benzothiadiazole 2,2-dioxide and MeNH$_2$ solution (8M in EtOH) giving 65 mg of the desired product.

HRMS: calculated for C17H15FN2O+H+, 350.1339; found (ESI, [M+H]+), 350.1337.

HPLC purity 98.1% at 210-370 nm, 7.1 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Example 23

3-[3-(2-fluorophenyl)-2,2-dioxido-2,1,3-benzothiadiazol-1(3H)-yl]butan-1-amine

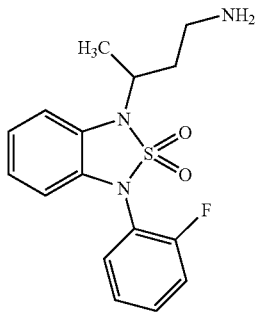

1-(3-bromo-1-methylpropyl)-3-(2-fluorophenyl)-1,3-dihydro-2,1,3-benzothiadiazole 2,2-dioxide (0.1 g, 0.25 mmol) was dissolved in dimethylformamide (2 mL) in a microwave cuvette and potassium phthalimide (0.06 g, 0.3 mmol) was added. The mixture was irradiated at 100° C. for 3 minutes. Upon cooling the mixture was diluted with EtOAc and washed with water and brine then dried with Na$_2$SO$_4$. Upon concentration, the residue was dissolved in MeOH (5 mL), methyl hydrazine (0.06 g, 1.25 mmol) was added and the mixture heated to reflux for 5 hours. Upon cooling the reaction was concentrated and water (10 ml) added followed by acetic acid (to pH 4). After 1 hour the mixture was filtered and basified to pH 14 with NaOH then extracted with dichloromethane. The organic extracts were washed with water, dried with Na$_2$SO$_4$ and purified via Isco chromatography (Redisep, silica, gradient 0-10% 7M ammonia/MeOH solution in dichloromethane) to afford 32 mg of 3-[3-(2-fluorophenyl)-2,2-dioxido-2,1,3-benzothiadiazol-1(3H)-yl]-N-methylbutan-1-amine.

HRMS: calculated for C17H15FN2O+H+, 336.1182; found (ESI, [M+H]+), 336.1182.

HPLC purity 100% at 210-370 nm, 7.1 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Example 24

1-Phenyl-3-(piperidin-4-ylmethyl)-1,3-dihydro-2,1,3-benzothiadiazole 2,2-dioxide hydrochloride

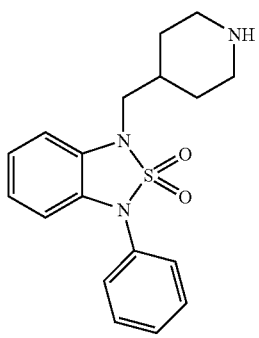

In an analogous manner as described in general procedure II, 1-phenyl-3-(piperidin-4-ylmethyl)-1,3-dihydro-2,1,3-benzothiadiazole 2,2-dioxide hydrochloride was prepared from 1-phenyl-1,3-dihydro-2,1,3-benzothiadiazole 2,2-dioxide (prepared in an analogous manner as described in general procedure I) and N-Boc-4-piperidinemethanol as a light yellow powder. MS (ESI) m/z 343.8 ([M+H]+).

Example 25

1-(2,6-Difluorophenyl)-3-(morpholin-2-ylmethyl)-1,3-dihydro-2,1,3-benzothiadiazole 2,2-dioxide hydrochloride

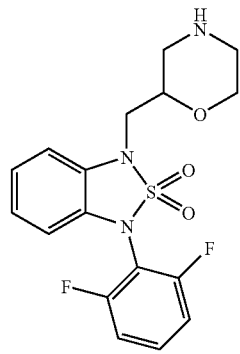

In an analogous manner as described in general procedure II, 1-(2,6-difluorophenyl)-3-(morpholin-2-ylmethyl)-1,3-dihydro-2,1,3-benzothiadiazole 2,2-dioxide hydrochloride was prepared from 1-(2,6-difluorophenyl)-1,3-dihydro-2,1,3-benzothiadiazole 2,2-dioxide (prepared in an analogous manner as described in general procedure I) and tert-butyl 2-(hydroxymethyl)morpholine-4-carboxylate as a light yellow powder. MS (ESI) m/z 382.1 ([M+H]+).

Example 26

1-(2,6-Difluorophenyl)-3-[(2R)-morpholin-2-ylmethyl]-1,3-dihydro-2,1,3-benzothiadiazole 2,2-dioxide hydrochloride

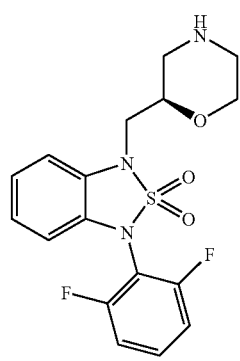

Step 1: Racemic tert-butyl 2-{[3-(2,6-difluorophenyl)-2,2-dioxido-2,1,3-benzothiadiazol-1(3H)-yl]methyl}morpholine-4-carboxylate (Example 25, step 1, 119 mg, 0.247 mmol) was dissolved in methanol (3 mL). 300 μL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H, 5 u, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure. Absolute stereochemistry of the two enantiomers was arbitrarily assigned.

| SFC Instrument: | Berger MultiGram Prep SFC (Berger Instruments, Inc. Newark, DE. |
| --- | --- |
| Column: | Chiralpak AD-H; 5 u; 250 mm L × 20 mm ID (Chiral Technologies, Inc, Exton, PA, USA) |
| Column temperature: | 35° C. |
| SFC Modifier: | 10% MeOH/90% $CO_2$ |
| Flow rate: | 50 mL/min |
| Outlet Pressure: | 100 bar |
| Detector: | UV at 220 nm |

Step 2 In an analogous manner as described in general procedure II, step 2, 1-(2,6-difluorophenyl)-3-[(2R)-morpholin-2-ylmethyl]-1,3-dihydro-2,1,3-benzothiadiazole 2,2-dioxide hydrochloride was prepared as a light yellow powder from tert-butyl (2R)-2-{[3-(2,6-difluorophenyl)-2,2-dioxido-2,1,3-benzothiadiazol-1(3H)-yl]methyl}morpholine-4-carboxylate (absolute stereochemistry was arbitrarily assigned) which was isolated as Peak 1 of the above chiral HPLC separation (step 1). MS (ESI) m/z 382.1 ([M+H]$^+$).

Example 27

1-(2,6-Difluorophenyl)-3-[(2S)-morpholin-2-ylmethyl]-1,3-dihydro-2,1,3-benzothiadiazole 2,2-dioxide hydrochloride

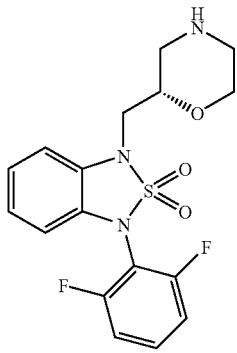

In an analogous manner as described in general procedure II, step 2, 1-(2,6-difluorophenyl)-3-[(2S)-morpholin-2-ylmethyl]-1,3-dihydro-2,1,3-benzothiadiazole 2,2-dioxide hydrochloride was prepared as a light yellow powder from tert-butyl (2S)-2-{[3-(2,6-difluorophenyl)-2,2-dioxido-2,1,3-benzothiadiazol-1(3H)-yl]methyl}morpholine-4-carboxylate (absolute stereochemistry was arbitrarily assigned) which was isolated as Peak 2 the chiral HPLC separation of Example 26, step 1. MS (ESI) m/z 382.1 ([M+H]$^+$).

Example 28

1-(2,3-Difluorophenyl)-3-(morpholin-2-ylmethyl)-1,3-dihydro-2,1,3-benzothiadiazole 2,2-dioxide hydrochloride

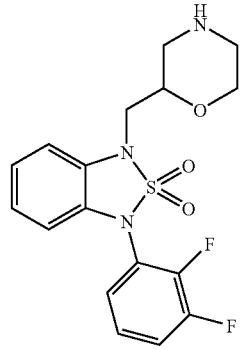

In an analogous manner as described in general procedure II, 1-(2,3-difluorophenyl)-3-(morpholin-2-ylmethyl)-1,3-dihydro-2,1,3-benzothiadiazole 2,2-dioxide hydrochloride was prepared from 1-(2,3-difluorophenyl)-1,3-dihydro-2,1,3-benzothiadiazole 2,2-dioxide (Prepared in an analogous manner as described in general procedure V) and tert-butyl 2-(hydroxymethyl)morpholine-4-carboxylate as a white powder. MS (ESI) m/z 382.1 ([M+H]$^+$).

Example 29

1-(Morpholin-2-ylmethyl)-3-[2-(trifluoromethoxy)phenyl]-1,3-dihydro-2,1,3-benzothiadiazole 2,2-dioxide hydrochloride

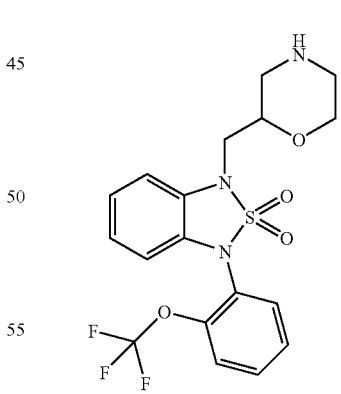

In an analogous manner as described in general procedure II, 1-(morpholin-2-ylmethyl)-3-[2-(trifluoromethoxy)phenyl]-1,3-dihydro-2,1,3-benzothiadiazole 2,2-dioxide hydrochloride was prepared from 1-[2-(trifluoromethoxy)phenyl]-1,3-dihydro-2,1,3-benzothiadiazole 2,2-dioxide (Prepared in an analogous manner as described in general procedure V) and tert-butyl 2-(hydroxymethyl)morpholine-4-carboxylate as a tan powder. MS (ESI) m/z 430.1 ([M+H]$^+$).

Example 30

1-Phenyl-3-(2-piperidin-4-ylethyl)-1,3-dihydro-2,1,3-benzothiadiazole 2,2-dioxide hydrochloride

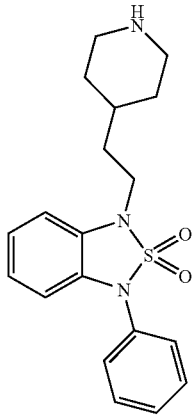

In an analogous manner as described in general procedure II, 1-phenyl-3-(2-piperidin-4-ylethyl)-1,3-dihydro-2,1,3-benzothiadiazole 2,2-dioxide hydrochloride was prepared from 1-phenyl-1,3-dihydro-2,1,3-benzothiadiazole 2,2-dioxide (Prepared in an analogous manner as described in general procedure I) and N-Boc-4-piperidineethanol as a white powder. MS (ESI) m/z 358.0 ([M+H]$^+$).

Example 31

1-Phenyl-3-(2-piperazin-1-ylethyl)-1,3-dihydro-2,1,3-benzothiadiazole 2,2-dioxide dihydrochloride

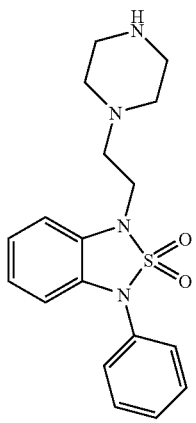

In an analogous manner as described in general procedure II, 1-phenyl-3-(2-piperazin-1-ylethyl)-1,3-dihydro-2,1,3-benzothiadiazole 2,2-dioxide dihydrochloride was prepared from 1-phenyl-1,3-dihydro-2,1,3-benzothiadiazole 2,2-dioxide (Prepared in an analogous manner as described in general procedure I) and tert-butyl 4-(2-hydroxyethyl)piperazine-1-carboxylate as a off-white solid.

MS (ESI) m/z 359.2 ([M+H]$^+$).

Example 32

4-Fluoro-3-phenyl-1-(piperidin-4-ylmethyl)-1,3-dihydro-2,1,3-benzothiadiazole 2,2-dioxide hydrochloride

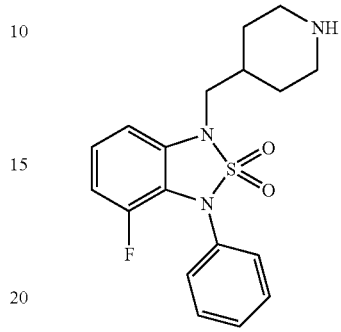

In an analogous manner as described in general procedure II, 4-fluoro-3-phenyl-1-(piperidin-4-ylmethyl)-1,3-dihydro-2,1,3-benzothiadiazole 2,2-dioxide hydrochloride was prepared from 7-fluoro-1-phenyl-1,3-dihydro-2,1,3-benzothiadiazole 2,2-dioxide (Prepared in an analogous manner as described in general procedure I) and N-Boc-4-piperidinemethanol as white crystals. MS (ESI) m/z 361.9 ([M+H]$^+$). MS (ESI) m/z 361.9 ([M+H-Boc]$^+$).

Example 33

4-Fluoro-3-phenyl-1-(2-piperidin-4-ylethyl)-1,3-dihydro-2,1,3-benzothiadiazole 2,2-dioxide hydrochloride

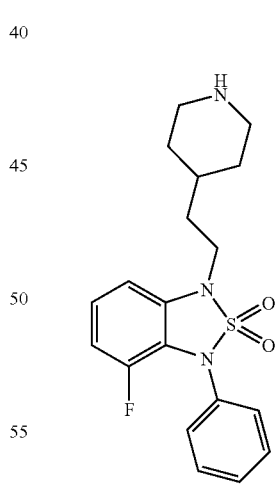

In an analogous manner as described in general procedure II, 4-fluoro-3-phenyl-1-(2-piperidin-4-ylethyl)-1,3-dihydro-2,1,3-benzothiadiazole 2,2-dioxide hydrochloride was prepared from 7-fluoro-1-phenyl-1,3-dihydro-2,1,3-benzothiadiazole 2,2-dioxide (prepared in an analogous manner as described in general procedure I) and N-Boc-4-piperidineethanol as gray crystals. MS (ESI) m/z 375.8 ([M+H]$^+$).

Example 34

4-Fluoro-3-phenyl-1-(2-piperazin-1-ylethyl)-1,3-dihydro-2,1,3-benzothiadiazole 2,2-dioxide dihydrochloride

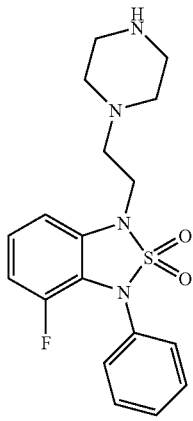

In an analogous manner as described in general procedure II, 4-fluoro-3-phenyl-1-(2-piperazin-1-ylethyl)-1,3-dihydro-2,1,3-benzothiadiazole 2,2-dioxide dihydrochloride was prepared from 7-fluoro-1-phenyl-1,3-dihydro-2,1,3-benzothiadiazole 2,2-dioxide (prepared in an analogous manner as described in general procedure I) and tert-butyl 4-(2-hydroxyethyl)piperazine-1-carboxylate as an off-white solid. MS (ESI) m/z 377.2 ([M+H]$^+$).

Example 35

4-Fluoro-3-(morpholin-2-ylmethyl)-1-phenyl-1,3-dihydro-2,1,3-benzothiadiazole 2,2-dioxide hydrochloride

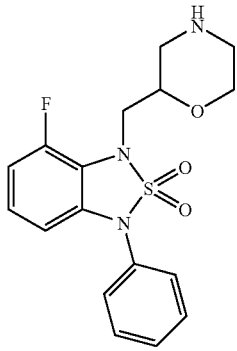

In an analogous manner as described in general procedure II, 4-fluoro-3-(morpholin-2-ylmethyl)-1-phenyl-1,3-dihydro-2,1,3-benzothiadiazole 2,2-dioxide hydrochloride was prepared from 4-fluoro-1-phenyl-1,3-dihydro-2,1,3-benzothiadiazole 2,2-dioxide (prepared in an analogous manner as described in general procedure I) and tert-butyl 2-(hydroxymethyl)morpholine-4-carboxylate as a white powder. MS (ESI) m/z 364.1 ([M+H]$^+$).

Example 36

1-Phenyl-3-(3-piperidin-4-ylpropyl)-1,3-dihydro-2,1,3-benzothiadiazole 2,2-dioxide hydrochloride

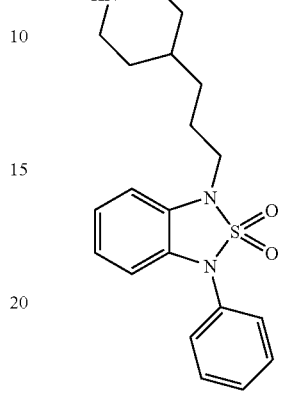

In an analogous manner as described in general procedure II, 1-phenyl-3-(3-piperidin-4-ylpropyl)-1,3-dihydro-2,1,3-benzothiadiazole 2,2-dioxide hydrochloride was prepared from 1-phenyl-1,3-dihydro-2,1,3-benzothiadiazole 2,2-dioxide (prepared in an analogous manner as described in general procedure I) and tert-butyl 4-(3-hydroxypropyl)tetrahydro-1(2H)-pyridinecarboxylate as a tan powder. MS (ESI) m/z 371.9 ([M+H]$^+$).

Example 37

1-Phenyl-3-(2-piperidin-2-ylethyl)-1,3-dihydro-2,1,3-benzothiadiazole 2,2-dioxide hydrochloride

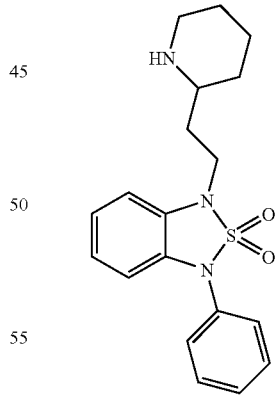

In an analogous manner as described in general procedure II, 1-phenyl-3-(2-piperidin-2-ylethyl)-1,3-dihydro-2,1,3-benzothiadiazole 2,2-dioxide hydrochloride was prepared from 1-phenyl-1,3-dihydro-2,1,3-benzothiadiazole 2,2-dioxide (prepared in an analogous manner as described in general procedure I) and Boc-2-(2-piperidyl)ethanol as an ivory solid. HRMS: calculated for $C_{19}H_{23}N_3O_2S+H^+$, 358.1584; found (ESI, [M+H]$^+$), 358.1588.

Example 38

1-(2,6-Difluorophenyl)-3-(2-piperidin-4-ylethyl)-1,3-dihydro-2,1,3-benzothiadiazole 2,2-dioxide hydrochloride

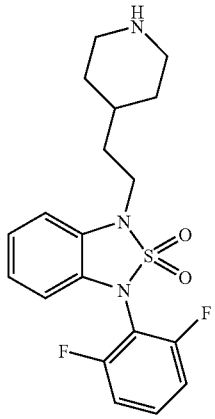

In an analogous manner as described in general procedure II, 1-(2,6-difluorophenyl)-3-(2-piperidin-4-ylethyl)-1,3-dihydro-2,1,3-benzothiadiazole 2,2-dioxide hydrochloride was prepared from 1-(2,6-difluorophenyl)-1,3-dihydro-2,1,3-benzothiadiazole 2,2-dioxide (prepared in an analogous manner as described in general procedure I) and N-Boc-4-piperidineethanol as white crystals. MS (ESI) m/z 394.3 ([M+H]$^+$). HRMS: calculated for $C_{19}H_{21}F_2N_3O_2S+H^+$, 394.1395; found (ESI, [M+H]$^+$), 394.1382.

Example 39

1-(2,6-Difluorophenyl)-3-(2-piperazin-1-ylethyl)-1,3-dihydro-2,1,3-benzothiadiazole 2,2-dioxide dihydrochloride

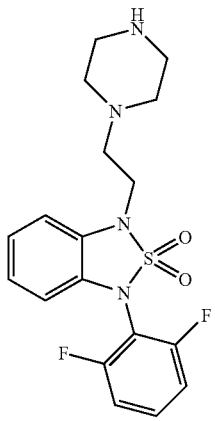

In an analogous manner as described in general procedure II, 1-(2,6-Difluorophenyl)-3-(2-piperazin-1-ylethyl)-1,3-dihydro-2,1,3-benzothiadiazole 2,2-dioxide dihydrochloride was prepared from 1-(2,6-difluorophenyl)-1,3-dihydro-2,1,3-benzothiadiazole 2,2-dioxide (prepared in an analogous manner as described in general procedure I) and tert-butyl 4-(2-hydroxyethyl)piperazine-1-carboxylate as a tan solid. MS (ESI) m/z 394.6 ([M+H]$^+$). HRMS: calculated for $C_{18}H_{20}F_2N_4O_2S+H^+$, 395.1348; found (ESI, [M+H]$^+$), 395.1362.

Example 40

1-Phenyl-3-(piperidin-3-ylmethyl)-1,3-dihydro-2,1,3-benzothiadiazole 2,2-dioxide hydrochloride

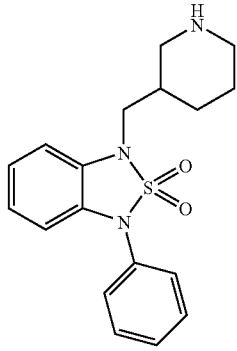

In an analogous manner as described in general procedure II, 1-phenyl-3-(piperidin-3-ylmethyl)-1,3-dihydro-2,1,3-benzothiadiazole 2,2-dioxide hydrochloride was prepared from 1-phenyl-1,3-dihydro-2,1,3-benzothiadiazole 2,2-dioxide (prepared in an analogous manner as described in general procedure I) and 3-hydroxymethyl-1-N-Boc-piperidine as white crystals. MS (ESI) m/z 344.0 ([M+H]$^+$). HRMS: calculated for $C_{18}H_{21}N_3O_2S+H^+$, 344.1427; found (ESI, [M+H]$^+$), 344.1425.

Example 41

1-Phenyl-3-[(3R)-piperidin-3-ylmethyl]-1,3-dihydro-2,1,3-benzothiadiazole 2,2-dioxide hydrochloride

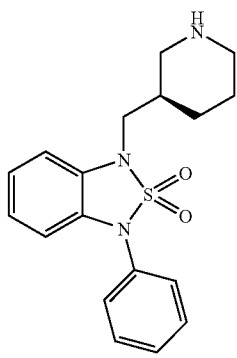

Step 1: Racemic tert-butyl 3-[(2,2-dioxido-3-phenyl-2,1,3-benzothiadiazol-1(3H)-yl)methyl]piperidine-1-carboxylate (Example 40, step 1, 163 mg, 0.367 mmol) was dissolved in methanol (4 mL). 300 µL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H, 5u, 250 mm×4.6 mm ID column at 2.0 mL/min flow rate using Analytical Supercritical Fluid Chromatography (Berger Instruments, Inc. Newark, Del.). Both enantiomers were found to be >99.7% enantiomerically pure. Absolute stereochemistry of the two enantiomers was arbitrarily assigned.

| | |
|---|---|
| SFC Instrument: | Berger MultiGram Prep SFC (Berger Instruments, Inc. Newark, DE. |
| Column: | Chiralpak AD-H; 5 u; 250 mm L × 20 mm ID (Chiral Technologies, Inc, Exton, PA, USA) |
| Column temperature: | 35° C. |
| SFC Modifier: | 10% MeOH/90% $CO_2$ |
| Flow rate: | 50 mL/min |
| Outlet Pressure: | 100 bar |
| Detector: | UV at 220 nm |

Step 2: In an analogous manner as described in general procedure II, step 2, 1-phenyl-3-[(3R)-piperidin-3-ylmethyl]-1,3-dihydro-2,1,3-benzothiadiazole 2,2-dioxide hydrochloride was prepared as a tan solid from tert-butyl (3R)-3-[(2,2-dioxido-3-phenyl-2,1,3-benzothiadiazol-1(3H)-yl)methyl]piperidine-1-carboxylate (absolute stereochemistry was arbitrarily assigned) which was isolated as Peak 1 of the above chiral HPLC separation (step 1). HRMS: calculated for $C_{18}H_{21}N_3O_2S+H^+$, 344.1427; found (ESI, [M+H]$^+$), 344.1437.

Example 42

1-Phenyl-3-[(3S)-piperidin-3-ylmethyl]-1,3-dihydro-2,1,3-benzothiadiazole 2,2-dioxide hydrochloride

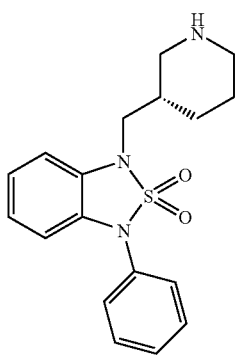

In an analogous manner as described in general procedure II, step 2, 1-phenyl-3-[(3S)-piperidin-3-ylmethyl]-1,3-dihydro-2,1,3-benzothiadiazole 2,2-dioxide hydrochloride was prepared as a tan solid from tert-butyl (3S)-3-[(2,2-dioxido-3-phenyl-2,1,3-benzothiadiazol-1(3H)-yl)methyl]piperidine-1-carboxylate (absolute stereochemistry was arbitrarily assigned) which was isolated as Peak 2 the chiral HPLC separation of Example 41, step 1. HRMS: calculated for $C_{18}H_{21}N_3O_2S+H^+$, 344.1427; found (ESI, [M+H]$^+$), 344.1442.

Example 43

1-Phenyl-3-(2-piperidin-3-ylethyl)-1,3-dihydro-2,1,3-benzothiadiazole 2,2-dioxide hydrochloride

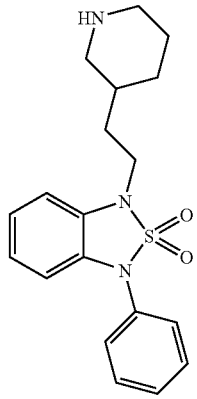

Step 1: In an analogous manner as described in general procedure II, 1-phenyl-3-(2-piperidin-3-ylethyl)-1,3-dihydro-2,1,3-benzothiadiazole 2,2-dioxide hydrochloride was prepared from 1-phenyl-1,3-dihydro-2,1,3-benzothiadiazole 2,2-dioxide (prepared in an analogous manner as described in general procedure I) and 1-N-Boc-piperidine-3-ethanol as white crystals. MS (ESI) m/z 358.1 ([M+H]$^+$). HRMS: calculated for $C_{19}H_{23}N_3O_2S+H^+$, 358.1584; found (ESI, [M+H]$^+$), 358.1587.

Example 44

1-Phenyl-3-{2-[(3S)-piperidin-3-yl]ethyl}-1,3-dihydro-2,1,3-benzothiadiazole 2,2-dioxide hydrochloride

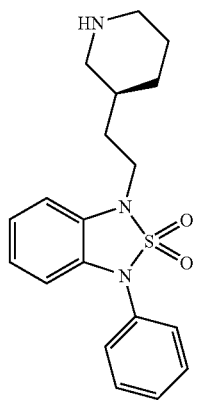

Step 1: Racemic tert-butyl 3-[2-(2,2-dioxido-3-phenyl-2,1,3-benzothiadiazol-1(3H)-yl)ethyl]piperidine-1-carboxylate (Example 43, step 1, 164 mg, 0.358 mmol) was dissolved in methanol (4 mL). 300 μL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H, 5 u, 250 mm×4.6 mm ID column at 2.0 mL/min flow rate using Analytical Supercritical Fluid Chromatography (Berger Instruments, Inc. Newark, Del.). One enantiomer (Peak 1) was found to be 99.5% enantiomerically pure, and the other enantiomer (Peak 2) was found to be 98.1% enantiomerically pure. Absolute stereochemistry of the two enantiomers was arbitrarily assigned.

| | |
|---|---|
| SFC Instrument: | Berger MultiGram Prep SFC (Berger Instruments, Inc. Newark, DE. |
| Column: | Chiralpak AD-H; 5 u; 250 mm L × 20 mm ID (Chiral Technologies, Inc, Exton, PA, USA) |
| Column temperature: | 35° C. |
| SFC Modifier: | 10% MeOH/90% $CO_2$ |
| Flow rate: | 50 mL/min |
| Outlet Pressure: | 100 bar |
| Detector: | UV at 220 nm |

Step 2: In an analogous manner as described in general procedure II, step 2, 1-phenyl-3-{2-[(3S)-piperidin-3-yl]ethyl}-1,3-dihydro-2,1,3-benzothiadiazole 2,2-dioxide hydrochloride was prepared as a white powder from tert-butyl (3S)-3-[2-(2,2-dioxido-3-phenyl-2,1,3-benzothiadiazol-1 (3H)-yl)ethyl]piperidine-1-carboxylate (absolute stereochemistry was arbitrarily assigned) which was isolated as Peak 1 of the above chiral HPLC separation (step 1). HRMS: calculated for $C_{19}H_{23}N_3O_2S+H^+$, 358.1584; found (ESI, [M+H]$^+$), 358.1595.

Example 45

1-Phenyl-3-{2-[(3R)-piperidin-3-yl]ethyl}-1,3-dihydro-2,1,3-benzothiadiazole 2,2-dioxide hydrochloride

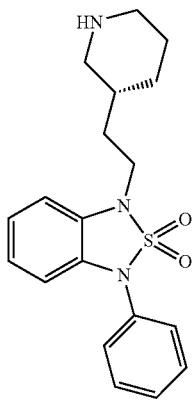

In an analogous manner as described in general procedure II, step 2, 1-phenyl-3-{2-[(3R)-piperidin-3-yl]ethyl}-1,3-dihydro-2,1,3-benzothiadiazole 2,2-dioxide hydrochloride was prepared as a light pink powder from tert-butyl (3R)-3-[2-(2,2-dioxido-3-phenyl-2,1,3-benzothiadiazol-1(3H)-yl)ethyl]piperidine-1-carboxylate (absolute stereochemistry was arbitrarily assigned) which was isolated as Peak 2 the chiral HPLC separation of Example 44, step 1. HRMS: calculated for $C_{19}H_{23}N_3O_2S+H^+$, 358.1584; found (ESI, [M+H]$^+$), 358.1594.

Example 46

1-(2,3-Difluorophenyl)-3-(2-piperidin-4-ylethyl)-1,3-dihydro-2,1,3-benzothiadiazole 2,2-dioxide hydrochloride

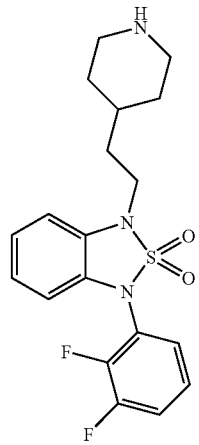

In an analogous manner as described in general procedure II, 1-(2,3-difluorophenyl)-3-(2-piperidin-4-ylethyl)-1,3-dihydro-2,1,3-benzothiadiazole 2,2-dioxide hydrochloride was prepared from 1-(2,3-difluorophenyl)-1,3-dihydro-2,1,3-benzothiadiazole 2,2-dioxide (prepared in an analogous manner as described in general procedure I) and N-Boc-4-piperidineethanol as white crystals. MS (ESI) m/z 394.1 ([M+H]$^+$). HRMS: calculated for $C_{19}H_{21}F_2N_3O_2S+H^+$, 394.1395; found (ESI, [M+H]$^+$), 394.1403.

Example 47

1-(2,5-Difluorophenyl)-3-(2-piperidin-4-ylethyl)-1,3-dihydro-2,1,3-benzothiadiazole 2,2-dioxide hydrochloride

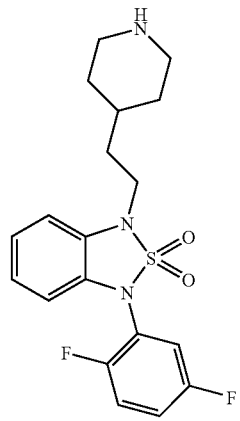

In an analogous manner as described in general procedure II, 1-(2,5-difluorophenyl)-3-(2-piperidin-4-ylethyl)-1,3-dihydro-2,1,3-benzothiadiazole 2,2-dioxide hydrochloride was prepared from 1-(2,5-difluorophenyl)-1,3-dihydro-2,1,3-benzothiadiazole 2,2-dioxide (prepared in an analogous manner as described in general procedure I) and N-Boc-4-piperidineethanol as a gray solid.

HRMS: calculated for $C_{19}H_{21}F_2N_3O_2S+H^+$, 394.1395; found (ESI, [M+H]$^+$), 394.1396.

Example 48

1-(2,3-Difluorophenyl)-3-(2-piperazin-1-ylethyl)-1,3-dihydro-2,1,3-benzothiadiazole 2,2-dioxide dihydrochloride

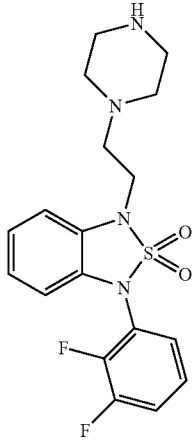

In an analogous manner as described in general procedure II, 1-(2,3-difluorophenyl)-3-(2-piperazin-1-ylethyl)-1,3-dihydro-2,1,3-benzothiadiazole 2,2-dioxide dihydrochloride was prepared from 1-(2,3-difluorophenyl)-1,3-dihydro-2,1,3-benzothiadiazole 2,2-dioxide (prepared in an analogous manner as described in general procedure I) and tert-butyl 4-(2-hydroxyethyl)piperazine-1-carboxylate as a gray solid. HRMS: calculated for $C_{18}H_{20}F_2N_4O_2S+H^+$, 395.1348; found (ESI, [M+H]$^+$), 395.1353.

Example 49

1-(2,5-Difluorophenyl)-3-(2-piperazin-1-ylethyl)-1,3-dihydro-2,1,3-benzothiadiazole 2,2-dioxide dihydrochloride

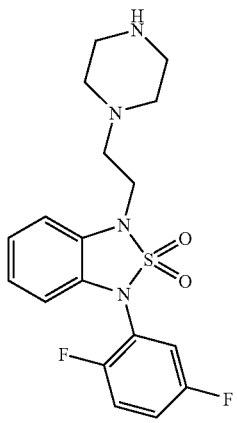

In an analogous manner as described in general procedure II, 1-(2,5-difluorophenyl)-3-(2-piperazin-1-ylethyl)-1,3-dihydro-2,1,3-benzothiadiazole 2,2-dioxide dihydrochloride was prepared from 1-(2,5-difluorophenyl)-1,3-dihydro-2,1,3-benzothiadiazole 2,2-dioxide (prepared in an analogous manner as described in general procedure I) and tert-butyl 4-(2-hydroxyethyl)piperazine-1-carboxylate as a brown solid. HRMS: calculated for $C_{18}H_{20}F_2N_4O_2S+H^+$, 395.1348; found (ESI, [M+H]$^+$), 395.1347.

Example 50

1-[2-(cis-3,5-Dimethylpiperazin-1-yl)ethyl]-3-phenyl-1,3-dihydro-2,1,3-benzothiadiazole 2,2-dioxide dihydrochloride

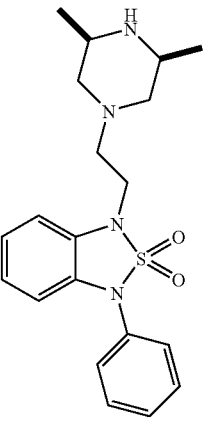

Step 1: Diisopropyl azodicarboxylate (0.47 mL, 2.4 mmol, 1.2 equiv.) was added dropwise to a solution of 1-phenyl-1,3-dihydro-2,1,3-benzothiadiazole 2,2-dioxide (prepared in an analogous manner as described in general procedure I, 493 mg, 2.00 mmol), 2-bromoethanol (275 mg, 2.20 mmol, 1.1 equiv.) and triphenylphosphine (630 mg, 2.40 mmol, 1.2 equiv.) in dry THF (10 mL) at 0° C. under nitrogen. The solution was stirred overnight while warming to room temperature. Solvent was removed and the oil residue was pre-adsorbed onto Florisil and purified via Isco flash column chromatography (40-g redisep silica gel column, 0-30% ethyl acetate/hexane) to give 706 mg (86%) of 1-(2-bromoethyl)-3-phenyl-1,3-dihydro-2,1,3-benzothiadiazole 2,2-dioxide as a viscous, colorless liquid. HRMS: calculated for $C_{14}H_{13}BrN_2O_2S+Na^+$, 374.9773; found (ESI, [M+H]$^+$), 374.9780.

Step 2: A mixture of 1-(2-bromoethyl)-3-phenyl-1,3-dihydro-2,1,3-benzothiadiazole 2,2-dioxide (212 mg, 0.600 mmol), cis-2,6-dimethylpiperazine (411 mg, 3.60 mmol, 6 equiv.) and ethanol (5 mL) in a sealed reaction vessel was heated at 90° C. for 8 h. After cooling, solvent was removed, and the residue was dissolved in ethyl acetate (15 mL). The resulting solution was washed with an aqueous potassium carbonate solution, water, dried (anhydrous sodium sulfate), and concentrated. The crude oil was pre-adsorbed onto Florisil and purified via Isco flash column chromatography (4-g redisep silica gel column, 1-18% methanol/dichloromethane, with 1% triethylamine as eluent additive) to give 162 mg (70%) of 1-[2-(cis-3,5-dimethylpiperazin-1-yl)ethyl]-3-phenyl-1,3-dihydro-2,1,3-benzothiadiazole 2,2-dioxide as a viscous, colorless liquid. This free base was dissolved in ethanol (2 mL), and was treated with an ethereal solution of hydrochloric acid (1 M, 3.0 mL, 3.0 mmol in ethyl ether). To the resulting solution was added ethyl ether until it became cloudy, then cooled to −25° C. in a freezer overnight. The white crystals formed were collected, washed with hexane, and dried in vacuo to yield 176 mg of 1-[2-(cis-3,5-dimethylpiperazin-1-yl)ethyl]-3-phenyl-1,3-dihydro-2,1,3-benzothiadiazole 2,2-dioxide dihydrochloride. HRMS: calculated for $C_{20}H_{26}N_4O_2S+H^+$, 387.1849; found (ESI, [M+H]$^+$), 387.1861.

Example 51

1-(2-Fluorophenyl)-3-(2-piperazin-1-ylethyl)-1,3-dihydro-2,1,3-benzothiadiazole 2,2-dioxide dihydrochloride

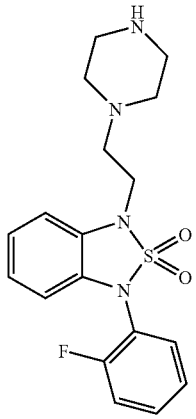

In an analogous manner as described in general procedure II, 1-(2-fluorophenyl)-3-(2-piperazin-1-ylethyl)-1,3-dihydro-2,1,3-benzothiadiazole 2,2-dioxide dihydrochloride was prepared from 1-(2-fluorophenyl)-1,3-dihydro-2,1,3-benzothiadiazole 2,2-dioxide (prepared in an analogous manner as described in general procedure I) and tert-butyl 4-(2-hydroxyethyl)piperazine-1-carboxylate as white crystals. MS (ESI) m/z 377.1 ([M+H]$^+$).

Example 52

1-[2-(cis-3,5-Dimethylpiperazin-1-yl)ethyl]-3-(2-fluorophenyl)-1,3-dihydro-2,1,3-benzothiadiazole 2,2-dioxide dihydrochloride

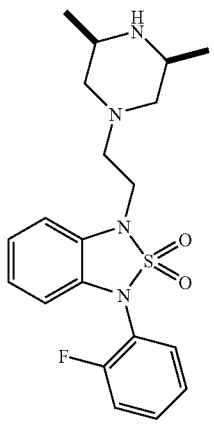

In an analogous manner as described in general procedure VI, 1-(2-bromoethyl)-3-(2-fluorophenyl)-1,3-benzothiadiazole 2,2-dioxide was prepared from 1-(2-fluorophenyl)-1,3-dihydro-2,1,3-benzothiadiazole 2,2-dioxide (prepared in an analogous manner as described in general procedure I) and 2-bromoethanol as a viscous, colorless liquid. MS (ESI) m/z 370.8 ([M+H]$^+$).

HRMS: calculated for $C_{14}H_{12}BrFN_2O_2S+H^+$, 370.9860; found (ESI, [M+H]$^+$), 370.9863.

In an analogous manner as described in general procedure V, 1-[2-(cis-3,5-dimethylpiperazin-1-yl)ethyl]-3-(2-fluorophenyl)-1,3-dihydro-2,1,3-benzothiadiazole 2,2-dioxide dihydrochloride was prepared from 1-(2-bromoethyl)-3-(2-fluorophenyl)-1,3-dihydro-2,1,3-benzothiadiazole 2,2-dioxide as a white powder. MS (ESI) m/z 405.2 ([M+H]$^+$).

Example 53

1-[3-(cis-3,5-Dimethylpiperazin-1-yl)propyl]-3-phenyl-1,3-dihydro-2,1,3-benzothiadiazole 2,2-dioxide dihydrochloride

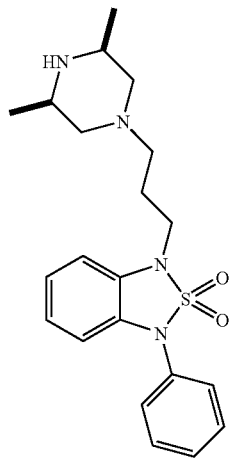

In an analogous manner as described in general procedure V, 1-[3-(cis-3,5-dimethylpiperazin-1-yl)propyl]-3-phenyl-1,3-dihydro-2,1,3-benzothiadiazole 2,2-dioxide dihydrochloride was prepared from 1-(3-bromopropyl)-3-phenyl-1,3-dihydro-2,1,3-benzothiadiazole 2,2-dioxide (prepared in an analogous manner as described in general procedure VI) as a white powder. MS (ESI) m/z 401.2 ([M+H]$^+$).

Example 54

1-(2,6-Difluorophenyl)-3-[2-(cis-3,5-dimethylpiperazin-1-yl)ethyl]-1,3-dihydro-2,1,3-benzothiadiazole 2,2-dioxide dihydrochloride

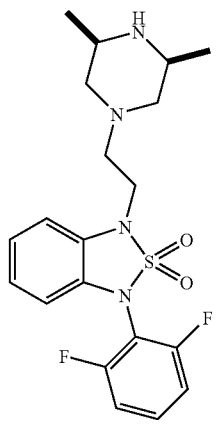

In an analogous manner as described in general procedure VI, 1-(2-bromoethyl)-3-(2,6-difluorophenyl)-1,3-dihydro-2,1,3-benzothiadiazole 2,2-dioxide was prepared from 1-(2,6-difluorophenyl)-1,3-dihydro-2,1,3-benzothiadiazole 2,2-dioxide (prepared in an analogous manner as described in general procedure I) and 2-bromoethanol as a white solid.

HRMS: calculated for $C_{14}H_{11}BrF_2N_2O_2S+H^+$, 388.9765; found (ESI, [M+H]$^+$), 388.9772.

In an analogous manner as described in general procedure V, 1-(2,6-difluorophenyl)-3-[2-(cis-3,5-dimethylpiperazin-1-yl)ethyl]-1,3-dihydro-2,1,3-benzothiadiazole 2,2-dioxide dihydrochloride was prepared from 1-(2-bromoethyl)-3-(2,6-difluorophenyl)-1,3-dihydro-2,1,3-benzothiadiazole 2,2-dioxide as a white powder. MS (ESI) m/z 423.0 ([M+H]$^+$). HRMS: calculated for $C_{20}H_{24}F_2N_4O_2S+H^+$, 423.1661; found (ESI, [M+H]$^+$), 423.1662.

Example 55

1-(2-Piperazin-1-ylethyl)-3-(2,4,6-trifluorophenyl)-1,3-dihydro-2,1,3-benzothiadiazole 2,2-dioxide dihydrochloride

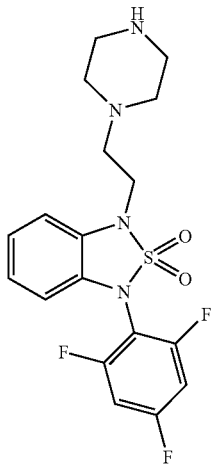

Step 1: In an analogous manner to general procedure I, step 1, 2,4,6-trifluoro-N-(2-nitrophenyl)aniline was prepared from 2,4,6-trifluoroaniline and 1-fluoro-2-nitrobenzene as a bright yellow solid. MS (ESI) m/z 269.0 ([M+H]$^+$).

Step 2: In an analogous manner to general procedure I, step 2, N-(2,4,6-trifluorophenyl)benzene-1,2-diamine was prepared from 2,4,6-trifluoro-N-(2-nitrophenyl)aniline as a gray solid. MS (ESI) m/z 239.1 ([M+H]$^+$).

Step 3: In an analogous manner to general procedure I, step 3, 1-(2,4,6-trifluorophenyl)-1,3-dihydro-2,1,3-benzothiadiazole 2,2-dioxide was prepared from N-(2,4,6-trifluorophenyl)benzene-1,2-diamine as a white solid. MS (ESI) m/z 298.8 ([M-H]$^-$). HRMS: calculated for $C_{12}H_7F_3N_2O_2S$, 300.0180; found (EI, M$^{+\cdot}$), 300.0186.

Step 4: In an analogous manner as described in general procedure II, 1-(2-piperazin-1-ylethyl)-3-(2,4,6-trifluorophenyl)-1,3-dihydro-2,1,3-benzothiadiazole 2,2-dioxide dihydrochloride was prepared from 1-(2,4,6-trifluorophenyl)-1,3-dihydro-2,1,3-benzothiadiazole 2,2-dioxide and tert-butyl 4-(2-hydroxyethyl)piperazine-1-carboxylate as a white solid. MS (ESI) m/z 413.0 ([M+H]$^+$). HRMS: calculated for $C_{18}H_{19}F_3N_4O_2S+H^+$, 413.1254; found (ESI, [M+H]$^+$), 413.1266.

Example 56

1-[2-(cis-3,5-Dimethylpiperazin-1-yl)ethyl]-3-(2,4,6-trifluorophenyl)-1,3-dihydro-2,1,3-benzothiadiazole 2,2-dioxide dihydrochloride

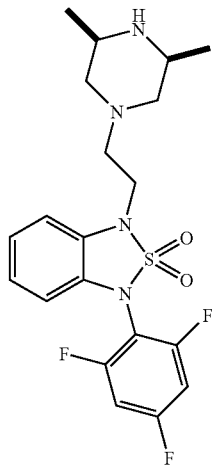

In an analogous manner as described in general procedure VI, 1-(2-bromoethyl)-3-(2,4,6-trifluorophenyl)-1,3-dihydro-2,1,3-benzothiadiazole 2,2-dioxide was prepared from 1-(2,4,6-trifluorophenyl)-1,3-dihydro-2,1,3-benzothiadiazole 2,2-dioxide (prepared in an analogous manner as described in general procedure I) and 2-bromoethanol as white needles. HRMS: calculated for $C_{14}H_{10}BrF_3N_2O_2S$, 405.9598; found (EI, M$^{+\cdot}$), 405.9602.

In an analogous manner as described in general procedure V, 1-[2-(cis-3,5-dimethylpiperazin-1-yl)ethyl]-3-(2,4,6-trifluorophenyl)-1,3-dihydro-2,1,3-benzothiadiazole 2,2-dioxide dihydrochloride was prepared from 1-(2-bromoethyl)-3-(2,4,6-trifluorophenyl)-1,3-dihydro-2,1,3-benzothiadiazole 2,2-dioxide as a white powder. MS (ESI) m/z 441.0 ([M+H]$^+$). HRMS: calculated for $C_{20}H_{23}F_3N_4O_2S+H^+$, 441.1567; found (ESI, [M+H]$^+$), 441.1582.

Example 57

1-Phenyl-3-(3-piperazin-1-ylpropyl)-1,3-dihydro-2,1,3-benzothiadiazole 2,2-dioxide dihydrochloride

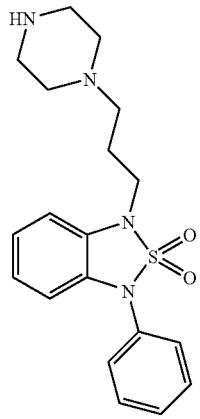

Step 1: A mixture of 1-(3-bromopropyl)-3-phenyl-1,3-dihydro-2,1,3-benzothiadiazole 2,2-dioxide (prepared in an analogous manner as described in general procedure V), 1-Boc-piperazine (624 mg, 3.35 mmol, 6 equiv.), sodium carbonate (granular, 355 mg, 3.35 mmol, 6 equiv.), and ethanol (5 mL) in a sealed reaction vessel was heated at 90° C. for 8 h. After cooling, solid sodium carbonate was removed by decantation, and the supernatant was concentrated and re-dissolved in ethyl acetate (15 mL). The resulting solution was washed with water, dried (anhydrous sodium sulfate), and concentrated. The crude oil was pre-adsorbed onto Florisil and purified via Isco flash column chromatography (4-g redisep silica gel column, 5-60% ethyl acetate/hexane) to give 252 mg (96%) of tert-butyl 4-[3-(2,2-dioxido-3-phenyl-2,1,3-benzothiadiazol-1(3H)-yl)propyl]piperazine-1-carboxylate as a viscous, brown liquid. MS (ESI) m/z 473.1 ([M+H]$^+$).

Step 2: In an analogous manner as described in general procedure II, step 2, 1-phenyl-3-(3-piperazin-1-ylpropyl)-1,3-dihydro-2,1,3-benzothiadiazole 2,2-dioxide dihydrochloride was prepared from tert-butyl 4-[3-(2,2-dioxido-3-phenyl-2,1,3-benzothiadiazol-1(3H)-yl)propyl]piperazine-1-carboxylate as a light pink solid. MS (ESI) m/z 372.9 ([M+H]$^+$). HRMS: calculated for $C_{19}H_{24}N_4O_2S+H^+$, 373.1693; found (ESI, [M+H]$^+$), 373.1694.

Example 58

1-(4-Fluorophenyl)-3-(2-piperazin-1-ylethyl)-1,3-dihydro-2,1,3-benzothiadiazole 2,2-dioxide dihydrochloride

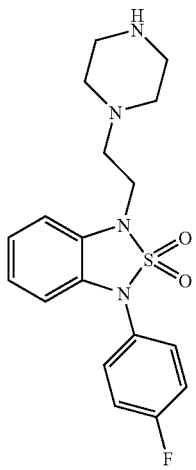

In an analogous manner as described in general procedure II, 1-(4-fluorophenyl)-3-(2-piperazin-1-ylethyl)-1,3-dihydro-2,1,3-benzothiadiazole 2,2-dioxide dihydrochloride was prepared from 1-(4-fluorophenyl)-1,3-dihydro-2,1,3-benzothiadiazole 2,2-dioxide (prepared in an analogous manner as described in general procedure I) and tert-butyl 4-(2-hydroxyethyl)piperazine-1-carboxylate as a white powder. HRMS: calculated for $C_{18}H_{21}FN_4O_2S+H^+$, 377.1442; found (ESI, [M+H]$^+$), 377.1443.

Example 59

1-[2-(cis-3,5-Dimethylpiperazin-1-yl)ethyl]-3-(4-fluorophenyl)-1,3-dihydro-2,1,3-benzothiadiazole 2,2-dioxide dihydrochloride

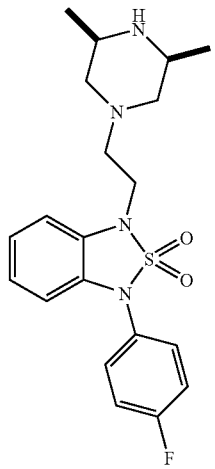

In an analogous manner as described in general procedure VI, 1-(2-bromoethyl)-3-(4-fluorophenyl)-1,3-dihydro-2,1,3-benzothiadiazole 2,2-dioxide was prepared from 1-(4-fluorophenyl)-1,3-dihydro-2,1,3-benzothiadiazole 2,2-dioxide (prepared in an analogous manner as described in general procedure I) and 2-bromoethanol as a white solid. HRMS: calculated for $C_{14}H_{12}BrFN_2O_2S+Na^+$, 392.9679; found (ESI, [M+Na]$^+$), 392.9680.

In an analogous manner as described in general procedure V, 1-[2-(cis-3,5-dimethylpiperazin-1-yl)ethyl]-3-(4-fluorophenyl)-1,3-dihydro-2,1,3-benzothiadiazole 2,2-dioxide was prepared from 1-(2-bromoethyl)-3-(4-fluorophenyl)-1,3-dihydro-2,1,3-benzothiadiazole 2,2-dioxide as a white powder. MS (ESI) m/z 404.9 ([M+H]$^+$). HRMS: calculated for $C_{20}H_{25}FN_4O_2S+H^+$, 405.1755; found (ESI, [M+H]$^+$), 405.1756.

Example 60

1-(2,4-difluorophenyl)-3-(2-piperazin-1-ylethyl)-1,3-dihydro-2,1,3-benzothiadiazole 2,2-dioxide hydrochloride

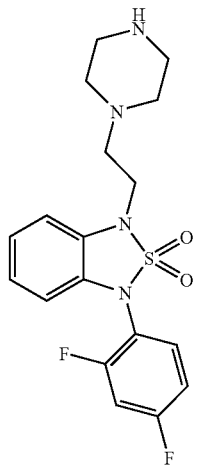

In an analogous manner to General procedure II, step 3, 1-(2,4-difluorophenyl)-1,3-dihydro-2,1,3-benzothiadiazole 2,2-dioxide was prepared from N-(2,4-difluorophenyl)benzene-1,2-diamine and sulfamide as a white solid. MS (ES) m/z 280.8.

In an analogous manner as described in general procedure II, 1-(2,4-difluorophenyl)-3-(2-piperazin-1-ylethyl)-1,3-dihydro-2,1,3-benzothiadiazole 2,2-dioxide hydrochloride was prepared from 1-(2,4-difluorophenyl)-1,3-dihydro-2,1,3-benzothiadiazole 2,2-dioxide and tert-butyl 4-(2-hydroxyethyl)piperazine-1-carboxylate as an off-white solid. MS (ES) m/z 394.9; HRMS: calculated for $C_{18}H_{20}F_2N_4O_2S+H^+$, 395.13478; found (ESI, $[M+H]^+$), 395.1356.

Example 61

1-(2,4-difluorophenyl)-3-[2-(3,5-dimethylpiperazin-1-yl)ethyl]-1,3-dihydro-2,1,3-benzothiadiazole 2,2-dioxide hydrochloride

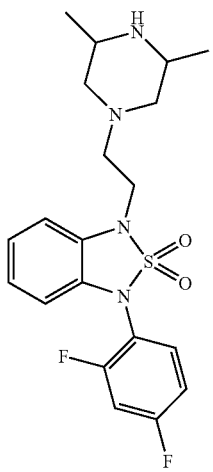

In an analogous manner to General procedure VI, 1-(2-bromoethyl)-3-(2,4-difluorophenyl)-1,3-dihydro-2,1,3-benzothiadiazole 2,2-dioxide was prepared from 1-(2,4-difluorophenyl)-1,3-dihydro-2,1,3-benzothiadiazole 2,2-dioxide (prepared in an analogous manner as described in general procedure I) and 2-bromo-ethanol as a oil. MS (ES) m/z $[M+H]^+$ 388.9.

In an analogous manner to general procedure V, 1-(2,4-difluorophenyl)-3-[2-(3,5-dimethylpiperazin-1-yl)ethyl]-1,3-dihydro-2,1,3-benzothiadiazole 2,2-dioxide hydrochloride was prepared from 1-(2-bromoethyl)-3-(2,4-difluorophenyl)-1,3-dihydro-2,1,3-benzothiadiazole 2,2-dioxide and 2,6-dimethylpiperazine as grey solid. MS (ES) m/z 423.1; HRMS: calculated for $C_{20}H_{24}F_2N_4O_2S+H^+$, 423.16608; found (ESI, $[M+H]^+$), 423.1665.

Example 62

1-[2-(3,5-dimethylpiperazin-1-yl)ethyl]-4-fluoro-3-(2-fluorophenyl)-1,3-dihydro-2,1,3-benzothiadiazole 2,2-dioxide hydrochloride

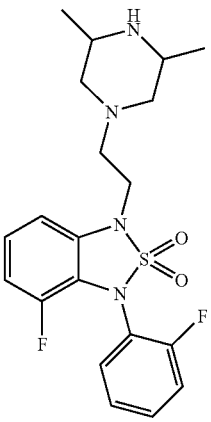

In an analogous manner to General procedure VI, 1-(2-bromoethyl)-4-fluoro-3-(2-fluorophenyl)-1,3-dihydro-2,1,3-benzothiadiazole 2,2-dioxide was prepared from 7-fluoro-1-(2-fluorophenyl)-1,3-dihydro-2,1,3-benzothiadiazole 2,2-dioxide (prepared in an analogous manner as described in general procedure I) and 2-bromo-1-ethanol as a brown oil. MS (ES) m/z 388.8.

In an analogous manner to General procedure VI, 1-[2-(3,5-dimethylpiperazin-1-yl)ethyl]-4-fluoro-3-(2-fluorophenyl)-1,3-dihydro-2,1,3-benzothiadiazole 2,2-dioxide hydrochloride was prepared from 1-(2-bromoethyl)-4-fluoro-3-(2-fluorophenyl)-1,3-dihydro-2,1,3-benzothiadiazole 2,2-dioxide as a white solid. HRMS: calculated for $C_{20}H_{24}F_2N_4O_2S+H^+$, 423.16608; found (ESI, $[M+H]^+$), 434.1786.

Example 63

1-(2-{[3-(2,3-difluorophenyl)-2,2-dioxido-2,1,3-benzothiadiazol-1(3H)-yl]methyl}phenyl)-N-methyl-methanamine

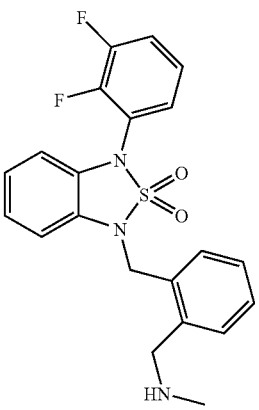

Step 1: In an analogous manner to general procedure IV, 1-(2,3-difluorophenyl)-1,3-dihydro-2,1,3-benzothiadiazole 2,2-dioxide (prepared in an analogous manner as described in general procedure I, 75 mg, 0.27 mmol) was treated with cesium carbonate (132 mg, 0.4 mmol) and α,α-dibromoortho-xylene (346 mg, 1.32 mmol) to give 68 mg of 1-[2-(bromomethyl)benzyl]-3-(2,3-difluorophenyl)-1,3-dihydro-2,1,3-benzothiadiazole 2,2-dioxide.

HPLC purity 88.5% at 210-370 nm, 11.1 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

HRMS: calculated for $C_{20}H_{15}BrF_2N_2O_2S$, 464.00056; found (EI, M$^+$. —SO$_2$), 400.0129.

Step 2: In an analogous manner to general procedure V, 1-[2-(bromomethyl)benzyl]-3-(2,3-difluorophenyl)-1,3-dihydro-2,1,3-benzothiadiazole 2,2-dioxide (38 mg, 0.082 mmol) was treated with methyl amine to give 1-(2-{[3-(2,3-difluorophenyl)-2,2-dioxido-2,1,3-benzothiadiazol-1(3H)-yl]methyl}phenyl)-N-methylmethanamine hydrochloride (18 mg, 48%) after treatment with HCl.

HPLC purity 97.5% at 210-370 nm, 8.1 minutes; Xterra RP18, 3.5 u, 150×4.6 mm column, 1.2 mL/minutes 85/15-5195 (Ammonium formate buffer pH=3.5/ACN+MeOH) for 10 minutes hold 4 minutes.

HRMS: calculated for $C_{21}H_{19}F_2N_3O_2S+H^+$, 416.12388; found (ESI, [M+H]$^+$), 416.1225.

Example 64

3-[3-(2,3-difluorophenyl)-2,2-dioxido-2,1,3-benzothiadiazol-1(3H)-yl]-N-methyl-1-phenylpropan-1-amine Step 1: A solution of 3-(methylamino)-3-phenylpropan-1-ol (800 mg, 4.85 mmol) in THF was treated with Boc-anhydride (1M in THF, 6 mL, 6 mmol) and stirred for 16 h. The mixture was concentrated and the crude product was purified via Isco chromatography (Redisep, silica, gradient 5-75% ethyl acetate in hexane) to afford 0.74 g of tert-butyl (3-hydroxy-1-phenylpropyl)methylcarbamate.

HPLC purity 100.0% at 210-370 nm, 8.7 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

HRMS: calculated for $C_{15}H_{23}NO_3+Na^+$, 288.15701; found (ESI, [M+Na]$^+$), 288.1575.

Step 2: In an analogous manner to general procedure II, 1-(2,3-difluorophenyl)-1,3-dihydro-2,1,3-benzothiadiazole 2,2-dioxide (prepared in an analogous manner as described in general procedure I, 115 mg, 0.41 mmol) was treated with triphenylphosphine (0.13 g, 0.49 mmol), tert-butyl (3-hydroxy-1-phenylpropyl)methylcarbamate (0.12 g, 0.45 mmol), and diisopropylazodicarboxylate (0.095 mL, 0.49 mmol) to provide 0.12 g tert-butyl {3-[3-(2,3-difluorophenyl)-2,2-dioxido-2,1,3-benzothiadiazol-1(3H)-yl]-1-phenylpropyl}methylcarbamate.

HPLC purity 97.8% at 210-370 nm, 11.4 minutes Xterra RP18, 3.5 u, 150×4.6 mm column, 1.2 mL/minutes 85/15-5195 (Ammonium formate buffer pH=3.5/ACN+MeOH) for 10 minutes hold 4 minutes.

HRMS: calculated for $C_{27}H_{29}F_2N_3O_4S+Na^+$, 552.17390; found (ESI, [M+Na]$^+$), 552.1733.

Step 3: tert-butyl {3-[3-(2,3-difluorophenyl)-2,2-dioxido-2,1,3-benzothiadiazol-1(3H)-yl]-1-phenylpropyl}methylcarbamate (0.10 g, 0.19 mmol) was treated with an excess of 2N HCl in ether. The precipitated amine salt was collected to give 65 mg of 3-[3-(2,3-difluorophenyl)-2,2-dioxido-2,1,3-benzothiadiazol-1(3H)-yl]-N-methyl-1-phenylpropan-1-amine.

HPLC purity 98.8% at 210-370 nm, 8.5 minutes; Xterra RP18, 3.5 u, 150×4.6 mm column, 1.2 mL/minutes 85/15-5195 (Ammonium formate buffer pH=3.5/ACN+MeOH) for 10 minutes hold 4 minutes.

HRMS: calculated for $C_{22}H_{21}F_2N_3O_2S+H^+$, 430.13953; found (ESI, [M+H]$^+$), 430.1394.

Example 65

3-[3-(2-fluorophenyl)-2,2-dioxido-2,1,3-benzothiadiazol-1(3H)-yl]-N-methyl-1-phenylpropan-1-amine Step 1: In an analogous manner to general procedure II, 1-(2-fluorophenyl)-1,3-dihydro-2,1,3-benzothiadiazole 2,2-dioxide (prepared in an analogous manner as described in general procedure I, 108 mg, 0.41 mmol) was treated with triphenylphosphine (0.13 g, 0.49 mmol), tert-butyl (3-hydroxy-1-phenylpropyl)methylcarbamate (0.12 g, 0.45 mmol), and diisopropylazodicarboxylate (0.095 mL, 0.49 mmol) to provide 0.13 g tert-butyl {3-[3-(2-fluorophenyl)-2,2-dioxido-2,1,3-benzothiadiazol-1(3H)-yl]-1-phenylpropyl}methylcarbamate.

HPLC purity 100.0% at 210-370 nm, 11.3 minutes; Xterra RP18, 3.5 u, 150×4.6 mm column, 1.2 mL/minutes 85/15-5195 (Ammonium formate buffer pH=3.5/ACN+MeOH) for 10 minutes hold 4 minutes.

HRMS: calculated for $C_{27}H_{30}FN_3O_4S+Na^+$, 534.18332; found (ESI, [M+Na]$^+$), 534.1827.

Step 2: tert-butyl {3-[3-(2-fluorophenyl)-2,2-dioxido-2,1,3-benzothiadiazol-1(3H)-yl]-1-phenylpropyl}methylcarbamate (0.11 g, 0.22 mmol) was treated with an excess of 2N HCl in ether. The precipitated amine salt was collected to give 55 mg of 3-[3-(2-fluorophenyl)-2,2-dioxido-2,1,3-benzothiadiazol-1(3H)-yl]-N-methyl-1-phenylpropan-1-amine.

HPLC purity 100.0% at 210-370 nm, 8.3 minutes; Xterra RP18, 3.5 u, 150×4.6 mm column, 1.2 mL/minutes 85/15-5195 (Ammonium formate buffer pH=3.5/ACN+MeOH) for 10 minutes hold 4 minutes.

HRMS: calculated for $C_{22}H_{22}FN_3O_2S+H^+$, 412.14895; found (ESI, [M+H]$^+$), 412.1493.

Example 66

4-[3-(2-fluorophenyl)-2,2-dioxido-2,1,3-benzothiadiazol-1(3H)-yl]-N-methylbut-2-yn-1-amine Step 1: In an analogous manner to general procedure IV, 1-(2-fluorophenyl)-1,3-dihydro-2,1,3-benzothiadiazole 2,2-dioxide (prepared in an analogous manner as described in general procedure I, 0.79 g, 3.0 mmol) was treated with cesium carbonate (1.46 g, 4.5 mmol) and but-2-yne-1,4-diyl dimethane-sulfonate (3.63 g, 15.0 mmol) to give 0.55 g of 4-[3-(2-fluorophenyl)-2,2-dioxido-2,1,3-benzothiadiazol-1(3H)-yl]but-2-yn-1-yl methanesulfonate.

MS (ES) m/z 410.8;

HPLC purity 95.2% at 210-370 nm, 9.1 minutes; Xterra RP18, 3.5 u, 150×4.6 mm column, 1.2 mL/minutes 85/15-5195 (Ammonium formate buffer pH=3.5/ACN+MeOH) for 10 minutes hold 4 minutes.

Step 2: In an analogous manner to general procedure V, 4-[3-(2-fluorophenyl)-2,2-dioxido-2,1,3-benzothiadiazol-1(3H)-yl]but-2-yn-1-yl methanesulfonate (0.25 g, 0.60 mmol) was treated with methyl amine to give 4-[3-(2-fluorophenyl)-2,2-dioxido-2,1,3-benzothiadiazol-1(3H)-yl]-N-methylbut-2-yn-1-amine hydrochloride (78 mg) after treatment with HCl.

HPLC purity 100.0% at 210-370 nm, 8.7 minutes; Xterra RP18, 3.5 u, 150×4.6 mm column, 1.2 mL/minutes 85/15-5195 (Ammon. Bicarb Buff. pH=9.5/ACN+MeOH) for 10 minutes hold 4 minutes.

HRMS: calculated for $C_{17}H_{16}FN_3O_2S+H^+$, 346.10200; found (ESI, [M+H]$^+$), 346.1027.

Example 67

4-[3-(2-fluorophenyl)-2,2-dioxido-2,1,3-benzothiadiazol-1(3H)-yl]-N,N-dimethylbut-2-yn-1-amine In an analogous manner to General Procedure V, 4-[3-(2-fluorophenyl)-2,2-dioxido-2,1,3-benzothiadiazol-1(3H)-yl] but-2-yn-1-yl methanesulfonate (0.25 g, 0.60 mmol) was treated with dimethyl amine to 4-[3-(2-fluorophenyl)-2,2-dioxido-2,1,3-benzothiadiazol-1(3H)-yl]-N,N-dimethylbut-2-yn-1-amine hydrochloride (48 mg) after treatment with HCl.

HPLC purity 100.0% at 210-370 nm, 9.2 minutes; Xterra RP18, 3.5 u, 150×4.6 mm column, 1.2 mL/minutes 85/15-5195 (Ammon. Bicarb Buff. pH=9.5/ACN+MeOH) for 10 minutes hold 4 minutes.

HRMS: calculated for $C_{18}H_{18}FN_3O_2S+H^+$, 360.11765; found (ESI, [M+H]$^+$), 360.118.

Example 68

(2E)-4-[3-(2-fluorophenyl)-2,2-dioxido-2,1,3-benzothiadiazol-1(3H)-yl]-N-methylbut-2-en-1-amine Step 1: In an analogous manner to general procedure IV, 1-(2-fluorophenyl)-1,3-dihydro-2,1,3-benzothiadiazole 2,2-dioxide (prepared in an analogous manner as described in general procedure I, 0.264 g, 1.0 mmol) was treated with cesium carbonate (0.49 g, 1.5 mmol) and (E)-1,4-dibromobut-2-ene (1.07 g, 5.0 mmol) to give 0.26 g of 1-[(2E)-4-bromobut-2-en-1-yl]-3-(2-fluorophenyl)-1,3-dihydro-2,1,3-benzothiadiazole 2,2-dioxide.

HPLC purity 100.0% at 210-370 nm, 10.3 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

HRMS: calculated for $C_{16}H_{14}BrFN_2O_2S+H^+$, 397.00161; found (ESI, [M+H]$^+$), 397.0025.

Step 2: In an analogous manner to general procedure V, 1-[(2E)-4-bromobut-2-en-1-yl]-3-(2-fluorophenyl)-1,3-dihydro-2,1,3-benzothiadiazole 2,2-dioxide (0.13 g, 0.33 mmol) was treated with methyl amine to give (2E)-4-[3-(2-fluorophenyl)-2,2-dioxido-2,1,3-benzothiadiazol-1(3H)-yl]-N-methylbut-2-en-1-amine (105 mg) after treatment with HCl.

HPLC purity 100.0% at 210-370 nm, 8.7 minutes; Xterra RP18, 3.5 u, 150×4.6 mm column, 1.2 mL/minutes 85/15-5/95 (Ammon. Bicarb Buff.

pH=9.5/ACN+MeOH) for 10 minutes hold 4 minutes.

HRMS: calculated for $C_{17}H_{18}FN_3O_2S+H^+$, 348.11765; found (ESI, [M+H]$^+$), 348.1181.

Example 69

(2E)-4-[3-(2-fluorophenyl)-2,2-dioxido-2,1,3-benzothiadiazol-1(3H)-yl]-N,N-dimethylbut-2-en-1-amine Step 1: In an analogous manner to general procedure V, 1-[(2E)-4-bromobut-2-en-1-yl]-3-(2-fluorophenyl)-1,3-dihydro-2,1,3-benzothiadiazole 2,2-dioxide (0.13 g, 0.33 mmol) was treated with dimethyl amine to give (2E)-4-[3-(2-fluorophenyl)-2,2-dioxido-2,1,3-benzothiadiazol-1(3H)-yl]-N,N-dimethylbut-2-en-1-amine (90 mg) after treatment with HCl.

HPLC purity 100.0% at 210-370 nm, 9.4 minutes; Xterra RP18, 3.5 u, 150×4.6 mm column, 1.2 mL/minutes 85/15-5/95 (Ammon. Bicarb Buff. pH=9.5/ACN+MeOH) for 10 minutes hold 4 minutes.

HRMS: calculated for $C_{18}H_{20}FN_3O_2S+H^+$, 362.13330; found (ESI, [M+H]$^+$), 362.135.

Example 70

3-{2-[(3R,5S)-3,5-dimethylpiperazin-1-yl]ethyl}-4-fluoro-1-(2-fluorophenyl)-1,3-dihydro-2,1,3-benzothiadiazole 2,2-dioxide Step 1: In an analogous manner to general procedure VI, 4-fluoro-1-(2-fluorophenyl)-1,3-dihydro-2,1,3-benzothiadiazole 2,2-dioxide (prepared in an analogous manner as described in general procedure I, 0.5 g, 1.77 mmol), was treated with triphenylphosphine (0.56 g, 2.13 mmol), 3-bromoethanol (0.125 mL, 1.77 mmol), and diisopropylazodicarboxylate (0.41 mL, 2.13 mmol) to provide 0.51 g 3-(2-bromoethyl)-4-fluoro-1-(2-fluorophenyl)-1,3-dihydro-2,1,3-benzothiadiazole 2,2-dioxide.

HPLC purity 95.2% at 210-370 nm, 10.4 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

Step 2: In an analogous manner to general procedure V, Step 3, 3-(2-bromoethyl)-4-fluoro-1-(2-fluorophenyl)-1,3-dihydro-2,1,3-benzothiadiazole 2,2-dioxide (0.50 g, 1.29 mmol) was treated with 2,6-dimethylpiperazine (0.44 g, 3.85 mL) in DMF (5 mL) to provide 3-{2-[(3R,5S)-3,5-dimethylpiperazin-1-yl]ethyl}-4-fluoro-1-(2-fluorophenyl)-1,3-dihydro-2,1,3-benzothiadiazole 2,2-dioxide dihydrochloride (0.23 g) after treatment with HCl.

HPLC purity 100.0% at 210-370 nm, 7.8 minutes; Xterra RP18, 3.5 u, 150×4.6 mm column, 1.2 mL/minutes 85/15-5/95 (Ammonium formate buffer pH=3.5/ACN+MeOH) for 10 minutes hold 4 minutes.

HRMS: calculated for $C_{20}H_{24}F_2N_4O_2S+H^+$, 423.16608; found (ESI, [M+H]$^+$), 423.1662.

Example 71

2,2-difluoro-3-[3-(2-fluorophenyl)-2,2-dioxido-2,1,3-benzothiadiazol-1(3H)-yl]-N-methylpropan-1-amine hydrochloride

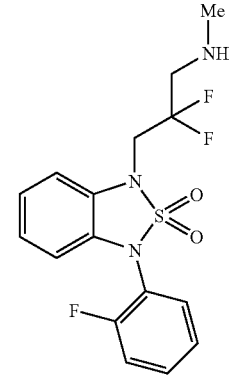

To a solution of methylamine in methanol (33% wt, 10 mL) was added methyl 2,2-difluoro-3-hydroxypropanoate (1.0 g, 7.1 mmol) and the mixture stirred at room temperature overnight. After evaporation the residue was recrystallized from diethyl ether/hexanes to afford 2,2-difluoro-3-hydroxy-N-methylpropanamide.

In an analogous manner as described in general procedure VI, 2,2-difluoro-3-[3-(2-fluorophenyl)-2,2-dioxido-2,1,3-benzothiadiazol-1(3H)-yl]-N-methylpropanamide was prepared from 1-(2-fluorophenyl)-1,3-dihydro-2,1,3-benzothiadiazole 2,2-dioxide and 2,2-difluoro-3-hydroxy-N-methylpropanamide to afford the product as an impure solid.

To a stirred solution of 2,2-difluoro-3-[3-(2-fluorophenyl)-2,2-dioxido-2,1,3-benzothiadiazol-1(3H)-yl]-N-methylpropanamide (ca. 1 mmol) at 0° C., was added borane-tetrahydrofuran complex (1 M in THF, 3 mL, 3 mmol). After stirring for 2 h, the mixture was quenched with dilute hydrochloric acid, basified (2 N NaOH) and extracted with ethylacetate. The organic layer was washed with water, dried (MgSO$_4$) and evaporated. The residue was purified by silica gel column chromatography (hexanes: ethylacetate, gradient elution) to afford the crude product which was further purified by reverse phase hplc (Xterra RP18 19×150 mm, 5 u, 55% MeOH 45% H2O w/0.05% NH4OH, 20 mL/min). The residue obtained was dissolved in diethyl ether, treated with excess ethereal HCl and lyophilized to afford 2,2-difluoro-3-[3-(2-fluorophenyl)-2,2-dioxido-2,1,3-benzothiadiazol-1(3H)-yl]-N-methylpropan-1-amine hydrochloride as a white solid.

MS (ESI) m/z 372; HPLC purity 100.0% at 210-370 nm, 6.9 minutes; Xterra RP18, 3.5 u, 150×4.6 mm column, 1.2 mL/minutes 85/15-5/95 (ammonium formate buffer pH=3.5/ACN+MeOH) for 10 minutes hold 4 minutes.

HRMS: calculated for $C_{16}H_{16}F_3N_3O_2S+H^+$, 372.09881; found (ESI, [M+H]$^+$), 372.0982.

Example 72

1-(2-Fluorophenyl)-3-(2-piperidin-4-ylethyl)-1,3-dihydro-2,1,3-benzothiadiazole 2,2-dioxide hydrochloride

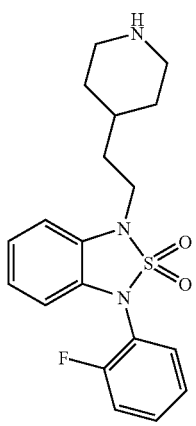

In an analogous manner as described in general procedure II, tert-butyl 4-{2-[3-(2-fluorophenyl)-2,2-dioxido-2,1,3-benzothiadiazol-1(3H)-yl]ethyl}piperidine-1-carboxylate was prepared from 1-(2-fluorophenyl)-1,3-dihydro-2,1,3-benzothiadiazole 2,2-dioxide (general procedure I) and N-boc-4-piperidineethanol as a viscous, colorless liquid. MS (ESI) m/z 475.9 ([M+H]$^+$).

HRMS: calcd for $C_{24}H_{30}FN_3O_4S+H^+$, 476.2014; found (ESI, [M+H]$^+$), 476.2016.

HPLC purity 93.9% at 210-370 nm, 11.1 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

In an analogous manner as described in general procedure II, step 2, 1-(2-fluorophenyl)-3-(2-piperidin-4-ylethyl)-1,3-dihydro-2,1,3-benzothiadiazole 2,2-dioxide hydrochloride was prepared from tert-butyl 4-{2-[3-(2-fluorophenyl)-2,2-dioxido-2,1,3-benzothiadiazol-1(3H)-yl]ethyl}piperidine-1-carboxylate as a white powder. MS (ESI) m/z 376.2 ([M+H]$^+$). HPLC purity 95.2% at 210-370 nm, 7.4 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 73

1-[2-(1,4-Diazepan-1-yl)ethyl]-3-phenyl-1,3-dihydro-2,1,3-benzothiadiazole 2,2-dioxide dihydrochloride

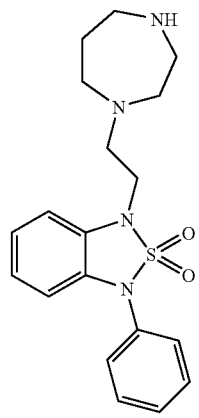

Step 1: A mixture of 1-(2-bromoethyl)-3-phenyl-1,3-dihydro-2,1,3-benzothiadiazole 2,2-dioxide (prepared in an analogous manner as described in general procedure VI, 112 mg, 0.317 mmol), tert-butyl 1-homopiperazinecarboxylate (381 mg, 1.90 mmol, 6 equiv.), sodium carbonate (202 mg, 1.90 mmol, 6 equiv.) and ethanol (4 mL) in a sealed reaction vessel was heated at 90° C. for 8 h. After cooling, solvent was removed, and the residue was dissolved in ethyl acetate (15 mL). The resulting solution was washed with an aqueous potassium carbonate solution, water, dried (anhydrous sodium sulfate), and concentrated. The crude liquid was preadsorbed onto Florisil and purified via Isco flash column chromatography (4-g redisep silica gel column, 10-60% ethyl acetate/hexane) to give tert-butyl 4-[2-(2,2-dioxido-3-phenyl-2,1,3-benzothiadiazol-1(3H)-yl)ethyl]-1,4-diazepane-1-carboxylate as a viscous, colorless liquid. Yield: 121 mg (81%). MS (ESI) m/z 473.0 ([M+H]$^+$). HPLC purity 100.0% at 210-370 nm, 9.7 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 2: In an analogous manner as described in general procedure II, step 2, 1-[2-(1,4-Diazepan-1-yl)ethyl]-3-phenyl-1,3-dihydro-2,1,3-benzothiadiazole 2,2-dioxide dihydrochloride was prepared from tert-butyl 4-[2-(2,2-dioxido-3-phenyl-2,1,3-benzothiadiazol-1(3H)-yl)ethyl]-1,4-diazepane-1-carboxylate as a white powder. MS (ESI) m/z 372.9 ([M+H]$^+$). HPLC purity 100.0% at 210-370 nm, 7.4

Example 74

1-(2,4-Difluorophenyl)-4-fluoro-3-(2-piperazin-1-ylethyl)-1,3-dihydro-2,1,3-benzothiadiazole 2,2-dioxide dihydrochloride

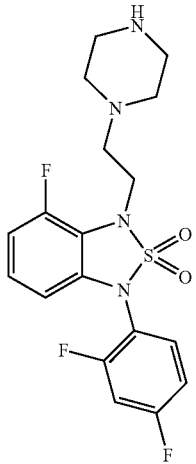

Step 1: In an analogous manner to general procedure I, step 1, N-(2,4-difluorophenyl)-3-fluoro-2-nitroaniline was prepared from 2,4-difluoroaniline and 2,6-difluoronitrobenzene as a white powder. MS (ESI) m/z 268.8 ([M+H]$^+$). HPLC purity 97.9% at 210-370 nm, 10.1 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 2: In an analogous manner to general procedure I, step 2, N1-(2,4-difluorophenyl)-3-fluorobenzene-1,2-diamine was prepared from N-(2,4-difluorophenyl)-3-fluoro-2-nitroaniline as a dark solid. MS (ESI) m/z 238.9 ([M+H]$^+$). HPLC purity 96.7% at 210-370 nm, 9.6 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 3: In an analogous manner to general procedure I, step 3, 1-(2,4-difluorophenyl)-4-fluoro-1,3-dihydro-2,1,3-benzothiadiazole 2,2-dioxide was prepared from N1-(2,4-difluorophenyl)-3-fluorobenzene-1,2-diamine as a white solid. MS (ESI) m/z 298.7 ([M−H]$^−$).

Step 4: In an analogous manner as described in general procedure II, tert-butyl 4-{2-[3-(2,4-difluorophenyl)-7-fluoro-2,2-dioxido-2,1,3-benzothiadiazol-1(3H)-yl]ethyl}piperazine-1-carboxylate was t prepared from 1-(2,4-difluorophenyl)-4-fluoro-1,3-dihydro-2,1,3-benzothiadiazole 2,2-dioxide and tert-butyl 4-(2-hydroxyethyl)piperazine-1-carboxylate as a viscous, colorless liquid.

MS (ESI) m/z 512.9 ([M+H]$^+$). HPLC purity 100.0% at 210-370 nm, 10.8 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 5: In an analogous manner as described in general procedure II, step 2, 1-(2,4-difluorophenyl)-4-fluoro-3-(2-piperazin-1-ylethyl)-1,3-dihydro-2,1,3-benzothiadiazole 2,2-dioxide dihydrochloride was prepared from tert-butyl 4-{2-[3-(2,4-difluorophenyl)-7-fluoro-2,2-dioxido-2,1,3-benzothiadiazol-1(3H)-yl]ethyl}piperazine-1-carboxylate as a white powder. MS (ESI) m/z 412.8 ([M+H]$^+$). HRMS: calcd for $C_{18}H_{19}F_3N_4O_2S+H^+$, 413.1254; found (ESI, [M+H]$^+$), 413.1261. HPLC purity 99.2% at 210-370 nm, 8.6 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 75

3-(2,4-Difluorophenyl)-4-fluoro-1-(2-piperazin-1-ylethyl)-1,3-dihydro-2,1,3-benzothiadiazole 2,2-dioxide dihydrochloride

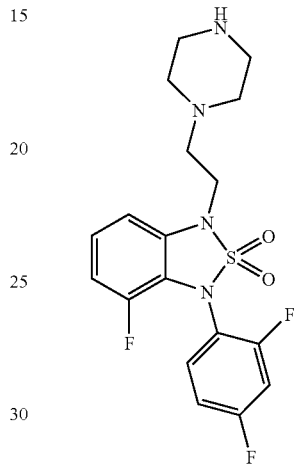

Step 1: In an analogous manner to general procedure I, step 1,2,4-difluoro-N-(2-fluoro-6-nitrophenyl)aniline was prepared from 2,4-difluoroaniline and 2,3-difluoronitrobenzene as orange needles. MS (ESI) m/z 268.8 ([M+H]$^+$).

HPLC purity 97.1% at 210-370 nm, 10.1 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 2: In an analogous manner to General procedure I, step 2, N2-(2,4-difluorophenyl)-3-fluorobenzene-1,2-diamine was prepared from 2,4-difluoro-N-(2-fluoro-6-nitrophenyl)aniline as a white solid. MS (ESI) m/z 238.9 ([M+H]$^+$).

HPLC purity 99.7% at 210-370 nm, 9.3 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 3: In an analogous manner to general procedure I, step 3, 1-(2,4-difluorophenyl)-7-fluoro-1,3-dihydro-2,1,3-benzothiadiazole 2,2-dioxide was prepared from N2-(2,4-difluorophenyl)-3-fluorobenzene-1,2-diamine as a white solid. MS (ESI) m/z 298.7 ([M−H]$^−$).

Step 4: In an analogous manner as described in general procedure II, tert-butyl 4-{2-[3-(2,4-difluorophenyl)-4-fluoro-2,2-dioxido-2,1,3-benzothiadiazol-1(3H)-yl]ethyl}piperazine-1-carboxylate was prepared from 1-(2,4-difluorophenyl)-7-fluoro-1,3-dihydro-2,1,3-benzothiadiazole 2,2-dioxide and tert-butyl 4-(2-hydroxyethyl)piperazine-1-carboxylate as a viscous, colorless liquid. MS (ESI) m/z 512.8 ([M+H]$^+$). HRMS: calcd for $C_{23}H_{27}F_3N_4O_4S+H^+$, 513.1778; found (ESI, [M+H]$^+$), 513.1776. HPLC purity 96.4% at 210-370 nm, 10.7 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 5: In an analogous manner as described in general procedure II, step 2, 3-(2,4-difluorophenyl)-4-fluoro-1-(2-piperazin-1-ylethyl)-1,3-dihydro-2,1,3-benzothiadiazole 2,2-dioxide dihydrochloride was prepared from tert-butyl 4-{2-[3-(2,4-difluorophenyl)-4-fluoro-2,2-dioxido-2,1,3-benzothiadiazol-1(3H)-yl]ethyl}piperazine-1-carboxylate as a white powder. MS (ESI) m/z 412.8 ([M+H]$^+$). HRMS: calcd for $C_{18}H_{19}F_3N_4O_2S+H^+$, 413.1254; found (ESI, [M+H]$^+$), 413.1259. HPLC purity 98.2% at 210-370 nm, 7.7 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

HPLC purity 96.5% at 210-370 nm, 7.2 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 77

1-{2-[(1S,4S)-2,5-Diazabicyclo[2.2.1]hept-2-yl]ethyl}-3-(2,4,6-trifluorophenyl)-1,3-dihydro-2,1,3-benzothiadiazole 2,2-dioxide dihydrochloride

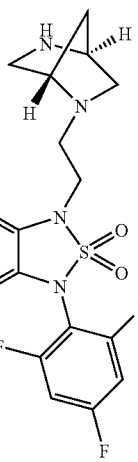

Example 76

1-[2-(1,4-Diazepan-1-yl)ethyl]-3-(2,4,6-trifluorophenyl)-1,3-dihydro-2,1,3-benzothiadiazole 2,2-dioxide dihydrochloride

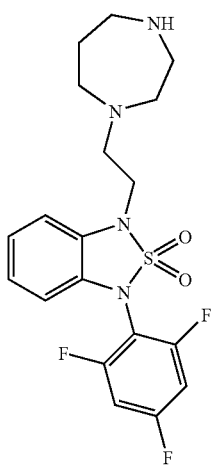

Step 1: In an analogous manner as described in general procedure V, step tert-butyl 4-{2-[2,2-dioxido-3-(2,4,6-trifluorophenyl)-2,1,3-benzothiadiazol-1(3H)-yl]ethyl}-1,4-diazepane-1-carboxylate 1, was prepared from 1-(2-bromoethyl)-3-(2,4,6-trifluorophenyl)-1,3-dihydro-2,1,3-benzothiadiazole 2,2-dioxide a viscous, colorless liquid. MS (ESI) m/z 527.0 ([M+H]$^+$). HRMS: calcd for $C_{24}H_{29}F_3N_4O_4S+H^+$, 527.1934; found (ESI, [M+H]$^+$), 527.1935. HPLC purity 95.5% at 210-370 nm, 9.1 min.; Xterra RP18, 3.5 u, 150×4.6 mm column, 1.2 mL/min, 85/15-5195 (Ammon. Form. Buff. pH=3.5/ACN+MeOH) for 10 min, hold 4 min.

Step 2: In an analogous manner as described in general procedure II, step 2, 1-[2-(1,4-diazepan-1-yl)ethyl]-3-(2,4,6-trifluorophenyl)-1,3-dihydro-2,1,3-benzothiadiazole 2,2-dioxide dihydrochloride was prepared from tert-butyl 4-{2-[2,2-dioxido-3-(2,4,6-trifluorophenyl)-2,1,3-benzothiadiazol-1(3H)-yl]ethyl}-1,4-diazepane-1-carboxylate as a white powder. MS (ESI) m/z 426.9 ([M+H]$^+$).

HRMS: calcd for $C_{19}H_{21}F_3N_4O_2S+H^+$, 427.1410; found (ESI, [M+H]$^+$), 427.1421.

Step 1: In an analogous manner as described in general procedure V, tert-butyl (1S,4S)-5-{2-[2,2-dioxido-3-(2,4,6-trifluorophenyl)-2,1,3-benzothiadiazol-1(3H)-yl]ethyl}-2,5-diazabicyclo[2.2.1]heptane-2-carboxylate was prepared as a white foam from 1-(2-bromoethyl)-3-(2,4,6-trifluorophenyl)-1,3-dihydro-2,1,3-benzothiadiazole 2,2-dioxide and 2 equiv. of tert-butyl (1-S,4S-(−)-2,5-diazabicyclo[2.2.1]heptane-2-carboxylate using 3 equiv. of sodium carbonate.

MS (ESI) m/z 524.9 ([M+H]$^+$). HRMS: calcd for $C_{24}H_{27}F_3N_4O_4S+H^+$, 525.1778; found (ESI, [M+H]$^+$), 525.1785. HPLC purity 100.0% at 210-370 nm, 8.5 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 2: In an analogous manner as described in general procedure II, step 2, 1-{2-[(1S,4S)-2,5-diazabicyclo[2.2.1]hept-2-yl]ethyl}-3-(2,4,6-trifluorophenyl)-1,3-dihydro-2,1,3-benzothiadiazole 2,2-dioxide dihydrochloride was prepared from tert-butyl (1S,4S)-5-{2-[2,2-dioxido-3-(2,4,6-trifluorophenyl)-2,1,3-benzothiadiazol-1(3H)-yl]ethyl}-2,5-diazabicyclo[2.2.1]heptane-2-carboxylate MS (ES I) m/z 424.8 ([M+H]$^+$). HRMS: calcd for $C_{19}H_{19}F_3N_4O_2S+H^+$, 425.1254; found (ESI, [M+H]$^+$), 425.1260.

Example 78

3-[2-(1,4-Diazepan-1-yl)ethyl]-1-(2,4-difluorophenyl)-4-fluoro-1,3-dihydro-2,1,3-benzothiadiazole 2,2-dioxide dihydrochloride

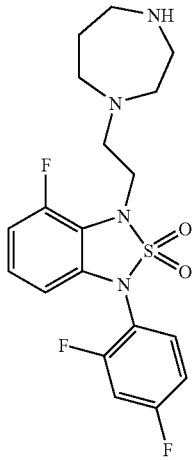

Step 1: In an analogous manner as described in general procedure VI, 3-(2-bromoethyl)-1-(2,4-difluorophenyl)-4-fluoro-1,3-dihydro-2,1,3-benzothiadiazole 2,2-dioxide was prepared from 1-(2,4-difluorophenyl)-4-fluoro-1,3-dihydro-2,1,3-benzothiadiazole 2,2-dioxide and 2-bromoethanol as a viscous, colorless liquid.

HPLC purity 97.5% at 210-370 nm, 10.4 min.; Xterra RP18, 3.5 u, 150×4.6 mm column, 1.2 mL/min, 85/15-5/95 (Ammon. Form. Buff pH=3.5/ACN+MeOH) for 10 min, hold 4 min.

Step 2: In an analogous manner as described in general procedure V, tert-butyl 4-{2-[3-(2,4-difluorophenyl)-7-fluoro-2,2-dioxido-2,1,3-benzothiadiazol-1(3H)-yl]ethyl}-1,4-diazepane-1-carboxylate was prepared from 3-(2-bromoethyl)-1-(2,4-difluorophenyl)-4-fluoro-1,3-dihydro-2,1,3-benzothiadiazole 2,2-dioxide a viscous, colorless liquid. HPLC purity 96.2% at 210-370 nm, 9.3 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 3: In an analogous manner as described in general procedure II, step 2, 3-[2-(1,4-diazepan-1-yl)ethyl]-1-(214-difluorophenyl)-4-fluoro-1,3-dihydro-2,1,3-benzothiadiazole 2,2-dioxide dihydrochloride was prepared from tert-butyl 4-{2-[3-(2,4-difluorophenyl)-7-fluoro-2,2-dioxido-2,1,3-benzothiadiazol-1(3H)-yl]ethyl}-1,4-diazepane-1-carboxylate as a white powder. HRMS: calcd for $C_{19}H_{21}F_3N_4O_2S+H^+$, 427.1410; found (ESI, [M+H]$^+$), 427.1420. HPLC purity 100.0% at 210-370 nm, 7.6 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 79

1-[2-(1,4-Diazepan-1-yl)ethyl]-3-(2-fluorophenyl)-1,3-dihydro-2,1,3-benzothiadiazole 2,2-dioxide dihydrochloride

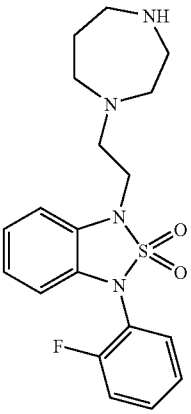

In an analogous manner as described in general procedure V, tert-butyl 4-{2-[3-(2-fluorophenyl)-2,2-dioxido-2,1,3-benzothiadiazol-1(3H)-yl]ethyl}-1,4-diazepane-1-carboxylate was prepared from 1-(2-bromoethyl)-3-(2-fluorophenyl)-1,3-dihydro-2,1,3-benzothiadiazole 2,2-dioxide (prepared in an analogous manner as described in general procedure VI) a viscous, colorless liquid. MS (ESI) m/z 490.9 ([M+H]$^+$). HRMS: calcd for $C_{24}H_{31}FN_4O_4S+H^+$, 491.2123; found (ESI, [M+H]$^+$), 491.2119. HPLC purity 95.9% at 210-370 nm, 8.9 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

In an analogous manner as described in general procedure II, step 2, 1-[2-(1,4-diazepan-1-yl)ethyl]-3-(2-fluorophenyl)-1,3-dihydro-2,1,3-benzothiadiazole 2,2-dioxide dihydrochloride was prepared from tert-butyl 4-{2-[3-(2-fluorophenyl)-2,2-dioxido-2,1,3-benzothiadiazol-1(3H)-yl]ethyl}-1,4-diazepane-1-carboxylate as a white powder. MS (ESI) m/z 390.9 ([M+H]$^+$). HRMS: calcd for $C_{19}H_{23}FN_4O_2S+H^+$, 391.1599; found (ESI, [M+H]$^+$), 391.1599. HPLC purity 98.4% at 210-370 nm, 7.0 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 80

1-{2-[(1S,4S)-2,5-diazabicyclo[2.2.1]hept-2-yl]ethyl}-3-(2-fluorophenyl)-1,3-dihydro-2,1,3-benzothiadiazole 2,2-dioxide dihydrochloride

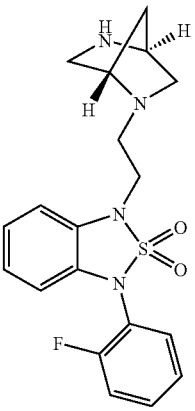

In an analogous manner as described in general procedure V, tert-butyl (1S,4S)-5-{2-[3-(2-fluorophenyl)-2,2-dioxido- 2,1,3-benzothiadiazol-1(3H)-yl]ethyl}-2,5-diazabicyclo[2.2.1]heptane-2-carboxylate was prepared as a viscous, colorless liquid from 1-(2-bromoethyl)-3-(2-fluorophenyl)-1,3-dihydro-2,1,3-benzothiadiazole 2,2-dioxide (prepared in an analogous manner as described in general procedure VI) and 2 equiv. of tert-butyl (1-S,4S-(−)-2,5-diazabicyclo[2.2.1]heptane-2-carboxylate using 3 equiv. of sodium carbonate. MS (ESI) m/z 488.9 ([M+H]$^+$). HRMS: calcd for $C_{24}H_{29}FN_4O_4S+H^+$, 489.1966; found (ESI, [M+H]$^+$), 489.1969.

In an analogous manner as described in general procedure II, step 2, 1-{2-[(1S,4S)-2,5-diazabicyclo[2.2.1]hept-2-yl]ethyl}-3-(2-fluorophenyl)-1,3-dihydro-2,1,3-benzothiadiazole 2,2-dioxide dihydrochloride was prepared from tert-butyl (1S,4S)-5-{2-[3-(2-fluorophenyl)-2,2-dioxido-2,1,3-benzothiadiazol-1(3H)-yl]ethyl}-2,5-diazabicyclo[2.2.1]heptane-2-carboxylate as a white powder. MS (ESI) m/z 388.8 ([M+H]$^+$). HRMS: calcd for $C_{19}H_{21}FN_4O_2S+H^+$, 389.1442; found (ESI, [M+H]$^+$), 389.1450.

Example 81

1-Phenyl-3-(2-piperidin-1-ylethyl)-1,3-dihydro-2,1,3-benzothiadiazole 2,2-dioxide hydrochloride

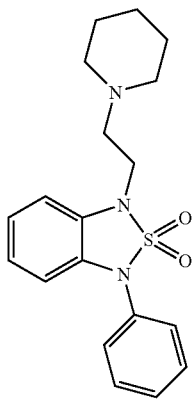

In an analogous manner as described in general procedure V, 1-phenyl-3-(2-piperidin-1-ylethyl)-1,3-dihydro-2,1,3-benzothiadiazole 2,2-dioxide hydrochloride was prepared from 1-(2-bromoethyl)-3-phenyl-1,3-dihydro-2,1,3-benzothiadiazole 2,2-dioxide (prepared in an analogous manner as described in general procedure VI) and piperidine as a white powder. MS (ESI) m/z 358.2 ([M+H]$^+$). HPLC purity 100.0% at 210-370 nm, 7.2 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 82

1-(2,4-Difluorophenyl)-3-[2-(cis-3,5-dimethylpiperazin-1-yl)ethyl]-4-fluoro-1,3-dihydro-2,1,3-benzothiadiazole 2,2-dioxide dihydrochloride

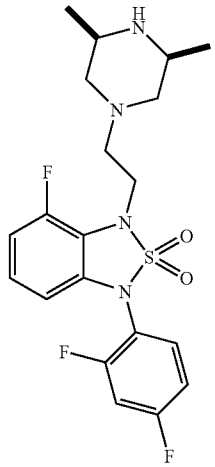

In an analogous manner as described in general procedure V, 1-(2,4-difluorophenyl)-3-[2-(cis-3,5-dimethylpiperazin-1-yl)ethyl]-4-fluoro-1,3-dihydro-2,1,3-benzothiadiazole 2,2-dioxide dihydrochloride was prepared from 3-(2-bromoethyl)-1-(2,4-difluorophenyl)-4-fluoro-1,3-dihydro-2,1,3-benzothiadiazole 2,2-dioxide (prepared in an analogous manner as described in general procedure VI) and cis-2,6-dimethylpiperazine as a white powder. MS (ESI) m/z 440.9 ([M+H]$^+$). HRMS: calcd for $C_{20}H_{23}F_3N_4O_2S+H^+$, 441.1567; found (ESI, [M+H]$^+$), 441.1566. HPLC purity 100.0% at 210-370 nm, 8.0 min.; Xterra RP18, 3.5 u, 150×4.6 mm column, 1.2 mL/min, 85/15-5195 (Ammon. Form. Buff. pH=3.5/ACN+MeOH) for 10 min, hold 4 min.

Example 83

1-[3-(1,4-Diazepan-1-yl)propyl]-3-phenyl-1,3-dihydro-2,1,3-benzothiadiazole 2,2-dioxide dihydrochloride

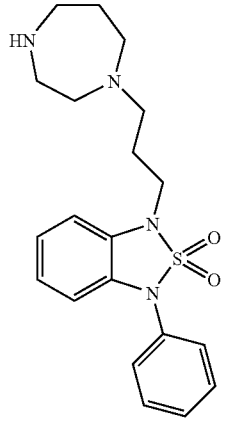

In an analogous manner as described in general procedure V, tert-butyl 4-[3-(2,2-dioxido-3-phenyl-2,1,3-benzothiadiazol-1(3H)-yl)propyl]-1,4-diazepane-1-carboxylate was prepared from 1-(3-bromopropyl)-3-phenyl-1,3-dihydro-2,1,3- benzothiadiazole 2,2-dioxide (prepared in an analogous manner as described in general procedure VI) as a viscous, colorless liquid. MS (ESI) m/z 486.9 ([M+H]$^+$). HRMS: calcd for $C_{25}H_{34}N_4O_4S+H^+$, 487.2373; found (ESI, [M+H]$^+$), 487.2375. HPLC purity 99.3% at 210-370 nm, 8.5 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

In an analogous manner as described in general procedure II, step 2, 1-[3-(1,4-diazepan-1-yl)propyl]-3-phenyl-1,3-dihydro-2,1,3-benzothiadiazole 2,2-dioxide dihydrochloride was prepared from tert-butyl 4-[3-(2,2-dioxido-3-phenyl-2,1,3-benzothiadiazol-1(3H)-yl)propyl]-1,4-diazepane-1-carboxylate as a white powder. MS (ESI) m/z 386.8 ([M+H]$^+$). HRMS: calcd for $C_{20}H_{26}N_4O_2S+H^+$, 387.1849; found (ESI, [M+H]$^+$), 387.1852. HPLC purity 100.0% at 210-370 nm, 6.0 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 84

1-[2-(1,4-Diazepan-1-yl)ethyl]-3-(2,6-difluorophenyl)-1,3-dihydro-2,1,3-benzothiadiazole 2,2-dioxide dihydrochloride

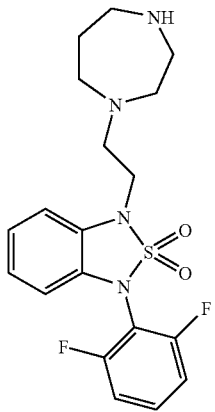

In an analogous manner as described in general procedure V, tert-butyl 4-{2-[3-(2,6-difluorophenyl)-2,2-dioxido-2,1,3-benzothiadiazol-1(3H)-yl]ethyl}-1,4-diazepane-1-carboxylate was prepared from 1-(2-bromoethyl)-3-(2,6-difluorophenyl)-1,3-dihydro-2,1,3-benzothiadiazole 2,2-dioxide (prepared in an analogous manner as described in general procedure VI) as a viscous, colorless liquid. MS (ESI) m/z 508.9 ([M+H]$^+$). HRMS: calcd for $C_{24}H_{30}F_2N_4O_4S+H^+$, 509.2029; found (ESI, [M+H]$^+$), 509.2033. HPLC purity 100.0% at 210-370 nm, 8.5 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

In an analogous manner as described in general procedure II, step 2, 1-[2-(1,4-diazepan-1-yl)ethyl]-3-(2,6-difluorophenyl)-1,3-dihydro-2,1,3-benzothiadiazole 2,2-dioxide dihydrochloride was prepared from tert-butyl 4-{2-[3-(2,6-difluorophenyl)-2,2-dioxido-2,1,3-benzothiadiazol-1(3H)-yl]ethyl}-1,4-diazepane-1-carboxylate as a white powder. MS (ESI) m/z 408.9 ([M+H]$^+$).

HRMS: calcd for $C_{19}H_{22}F_2N_4O_2S+H^+$, 409.1504; found (ESI, [M+H]$^+$), 409.1510.

HPLC purity 98.7% at 210-370 nm, 6.8 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 85

1-[2-(1,4-Diazepan-1-yl)ethyl]-3-(2,4-difluorophenyl)-1,3-dihydro-2,1,3-benzothiadiazole 2,2-dioxide dihydrochloride

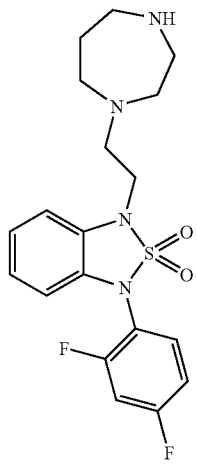

Step 1: In an analogous manner as described in general procedure V, tert-butyl 4-{2-[3-(2,4-difluorophenyl)-2,2-dioxido-2,1,3-benzothiadiazol-1(3H)-yl]ethyl}-1,4-diazepane-1-carboxylate was prepared from 1-(2-bromoethyl)-3-(2,4-difluorophenyl)-1,3-dihydro-2,1,3-benzothiadiazole 2,2-dioxide (prepared in an analogous manner as described in general procedure VI) as a viscous, colorless liquid. MS (ESI) m/z 508.9 ([M+H]$^+$). HRMS: calcd for $C_{24}H_{30}F_2N_4O_4S+H^+$, 509.2029; found (ESI, [M+H]$^+$), 509.2031. HPLC purity 98.3% at 210-370 nm, 9.0 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 2: In an analogous manner as described in general procedure II, step 2, 1-[2-(1,4-diazepan-1-yl)ethyl]-3-(2,4-difluorophenyl)-1,3-dihydro-2,1,3-benzothiadiazole 2,2-dioxide dihydrochloride was prepared from tert-butyl 4-{2-[3-(2,4-difluorophenyl)-2,2-dioxido-2,1,3-benzothiadiazol-1(3H)-yl]ethyl}-1,4-diazepane-1-carboxylate as a white powder. MS (ESI) m/z 408.9 ([M+H]$^+$).

HRMS: calcd for $C_{19}H_{22}F_2N_4O_2S+H^+$, 409.1504; found (ESI, [M+H]$^+$), 409.1509.

HPLC purity 100.0% at 210-370 nm, 7.3 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 86

1-{2-[(1S,4S)-2,5-Diazabicyclo[2.2.1]hept-2-yl]ethyl}-3-(2,4-difluorophenyl)-1,3-dihydro-2,1,3-benzothiadiazole 2,2-dioxide dihydrochloride

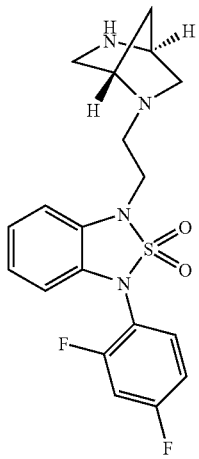

In an analogous manner as described in general procedure V, tert-butyl (1S,4S)-5-{2-[3-(2-fluorophenyl)-2,2-dioxido-2,1,3-benzothiadiazol-1(3H)-yl]ethyl}-2,5-diazabicyclo[2.2.1]heptane-2-carboxylate was prepared as a white solid from 1-(2-bromoethyl)-3-(2,4-difluorophenyl)-1,3-dihydro-2,1,3-benzothiadiazole 2,2-dioxide (prepared in an analogous manner as described in general procedure VI) and 2 equiv. of tert-butyl (1-S,4S-(−)-2,5-diazabicyclo[2.2.1]heptane-2-carboxylate using 3 equiv. of sodium carbonate. MS (ESI) m/z 507.0 ([M+H]$^+$). HRMS: calcd for $C_{24}H_{28}F_2N_4O_4S+H^+$, 507.1872; found (ESI, [M+H]$^+$), 507.1878. HPLC purity 97.6% at 210-370 nm, 9.2 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

In an analogous manner as described in general procedure II, step 2, 1-{2-[(1S,4S)-2,5-diazabicyclo[2.2.1]hept-2-yl]ethyl}-3-(2,4-difluorophenyl)-1,3-dihydro-2,1,3-benzothiadiazole 2,2-dioxide dihydrochloride was prepared from tert-butyl (1S,4S)-5-{2-[3-(2-fluorophenyl)-2,2-dioxido-2,1,3-benzothiadiazol-1(3H)-yl]ethyl}-2,5-diazabicyclo[2.2.1]heptane-2-carboxylate as a white powder.

HRMS: calcd for $C_{19}H_{20}F_2N_4O_2S+H^+$, 407.1348; found (ESI, [M+H]$^+$), 407.1349.

HPLC purity 98.9% at 210-370 nm, 7.2 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 87

1-(2,4-Difluorophenyl)-3-(2-piperidin-4-ylethyl)-1,3-dihydro-2,1,3-benzothiadiazole 2,2-dioxide hydrochloride

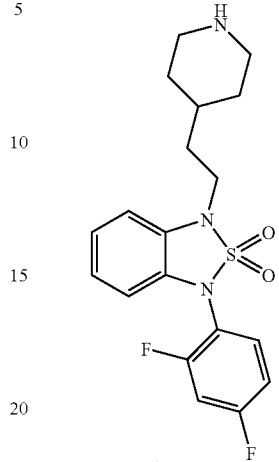

In an analogous manner as described in general procedure II, tert-butyl 4-{2-[3-(2,4-difluorophenyl)-2,2-dioxido-2,1,3-benzothiadiazol-1(3H)-yl]ethyl}piperidine-1-carboxylate was prepared from 1-(2,4-difluorophenyl)-1,3-dihydro-2,1,3-benzothiadiazole 2,2-dioxide and N-boc-4-piperidineethanol as a white foam. MS (ESI) m/z 493.8 ([M+H]$^+$). HRMS: calcd for $C_{24}H_{29}F_2N_3O_4S+H^+$, 494.1920; found (ESI, [M+H]$^+$), 494.1925. HPLC purity 100.0% at 210-370 nm, 11.1 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

In an analogous manner as described in general procedure II, step 2, 1-(2,4-difluorophenyl)-3-(2-piperidin-4-ylethyl)-1,3-dihydro-2,1,3-benzothiadiazole 2,2-dioxide hydrochloride was prepared from tert-butyl 4-{2-[3-(2,4-difluorophenyl)-2,2-dioxido-2,1,3-benzothiadiazol-1(3H)-yl]ethyl}piperidine-1-carboxylate as a white powder. HRMS: calcd for $C_{19}H_{21}F_2N_3O_2S+H^+$, 394.1395; found (ESI, [M+H]$^+$), 394.1397. HPLC purity 96.1% at 210-370 nm, 7.6 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 88

1-(2,4-Difluorophenyl)-3-[2-(4-methylpiperazin-1-yl)ethyl]-1,3-dihydro-2,1,3-benzothiadiazole 2,2-dioxide dihydrochloride

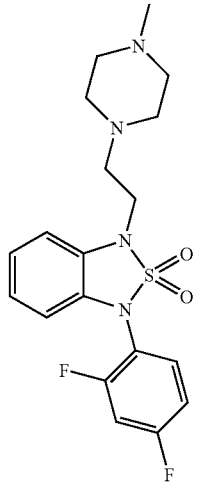

In an analogous manner to Example 4, 1-(2,4-difluorophenyl)-3-[2-(4-methylpiperazin-1-yl)ethyl]-1,3-dihydro-2,1,3- benzothiadiazole 2,2-dioxide dihydrochloride was prepared from 1-(2,4-difluorophenyl)-3-(2-piperazin-1-ylethyl)-1,3-dihydro-2,1,3-benzothiadiazole 2,2-dioxide dihydrochloride as a white powder. MS (ESI) m/z 409.0 ([M+H]$^+$). HRMS: calcd for $C_{19}H_{22}F_2N_4O_2S+H^+$, 409.1504; found (ESI, [M+H]$^+$), 409.1504. HPLC purity 99.5% at 210-370 nm, 7.2 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 89

1-(2,4-Difluorophenyl)-4-fluoro-3-[2-(4-methylpiperazin-1-yl)ethyl]-1,3-dihydro-2,1,3-benzothiadiazole 2,2-dioxide dihydrochloride

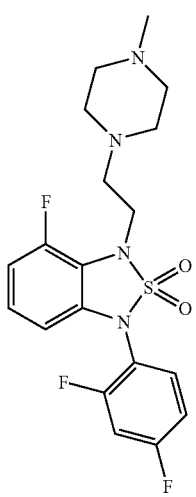

In an analogous manner to Example 4, 1-(2,4-difluorophenyl)-4-fluoro-3-[2-(4-methylpiperazin-1-yl)ethyl]-1,3-dihydro-2,1,3-benzothiadiazole 2,2-dioxide dihydrochloride was prepared from 1-(2,4-difluorophenyl)-4-fluoro-3-(2-piperazin-1-ylethyl)-1,3-dihydro-2,1,3-benzothiadiazole 2,2-dioxide dihydrochloride as a white powder. MS (ESI) m/z 427.0 ([M+H]$^+$). HRMS: calcd for $C_{19}H_{21}F_3N_4O_2S+H^+$, 427.1410; found (ESI, [M+H]$^+$), 427.1408. HPLC purity 98.2% at 210-370 nm, 7.4 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 90

1-(2,4-Difluorophenyl)-3-[2-(4-methyl-1,4-diazepan-1-yl)ethyl]-1,3-dihydro-2,1,3-benzothiadiazole 2,2-dioxide dihydrochloride

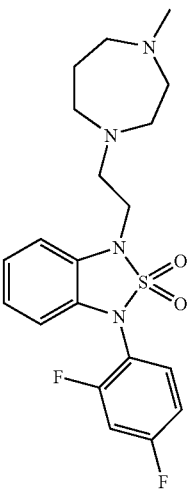

In an analogous manner to Example 4, 1-(2,4-difluorophenyl)-3-[2-(4-methyl-1,4-diazepan-1-yl)ethyl]-1,3-dihydro-2,1,3-benzothiadiazole 2,2-dioxide dihydrochloride was prepared from 1-[2-(1,4-diazepan-1-yl)ethyl]-3-(2,4-difluorophenyl)-1,3-dihydro-2,1,3-benzothiadiazole 2,2-dioxide dihydrochloride as a white powder. MS (ESI) m/z 422.8 ([M+H]$^+$). HRMS: calcd for $C_{20}H_{24}F_2N_4O_2S+H^+$, 423.1661; found (ESI, [M+H]$^+$), 423.1659. HPLC purity 99.1% at 210-370 nm, 7.5 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 91

1-[2-(4-Methyl-1,4-diazepan-1-yl)ethyl]-3-(2,4,6-trifluorophenyl)-1,3-dihydro-2,1,3-benzothiadiazole 2,2-dioxide dihydrochloride

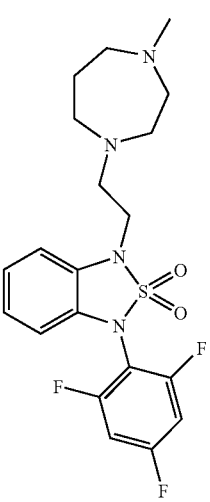

In an analogous manner to Example 4, 1-[2-(4-methyl-1,4-diazepan-1-yl)ethyl]-3-(2,4,6-trifluorophenyl)-1,3-dihydro-2,1,3-benzothiadiazole 2,2-dioxide dihydrochloride was prepared from 1-[2-(1,4-diazepan-1-yl)ethyl]-3-(2,4,6-trifluorophenyl)-1,3-dihydro-2,1,3-benzothiadiazole 2,2-dioxide dihydrochloride as a white powder. MS (ESI) m/z 440.8 ([M+H]$^+$). HRMS: calcd for $C_{20}H_{23}F_3N_4O_2S+H^+$, 441.1567; found (ESI, [M+H]$^+$), 441.1566. HPLC purity 98.6% at 210-370 nm, 7.4 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 92

N-{2-[3-(2-Fluorophenyl)-2,2-dioxido-2,1,3-benzothiadiazol-1(3H)-yl]ethyl}-N,N'-dimethylethane-1,2-diamine dihydrochloride

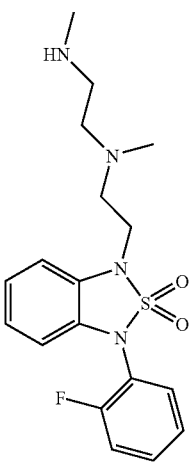

Step 1: To a solution of N,N'-dimethylethylenediamine (10.58 g, 120 mmol, 4 equiv.) in tetrahydrofuran (200 mL) at 0° C. was added dropwise over 35 min a solution of di-tert-butyl dicarbonate (6.55 g, 30.0 mmol, 1 equiv.) in tetrahydrofuran (60 mL) via an addition funnel. The reaction mixture was stirred at 0° C. for 1 h, and at room temperature overnight. All volatiles were removed under reduced pressure, and the residue was partitioned between ethyl acetate and water. The organic layer was washed with brine, dried (anhydrous sodium sulfate), filtered, and concentrated to give tert-butyl methyl[2-(methylamino)ethyl]carbamate as a colorless liquid. Yield: 4.75 g (84%).

Step 2: A mixture of 1-(2-bromoethyl)-3-(2-fluorophenyl)-1,3-dihydro-2,1,3-benzothiadiazole 2,2-dioxide (171 mg, 0.461 mmol), tert-butyl methyl[2-(methylamino)ethyl]carbamate (695 mg, 3.69 mmol, 8 equiv.), sodium carbonate (489 mg, 4.61 mmol, 10 equiv.) and N,N-dimethylformamide (5 mL) was sealed and heated at 125° C. for 5 h. After cooling, the reaction mixture was partitioned between ethyl acetate (40 mL) and water (40 mL). The organic layer was washed with brine, dried (anhydrous sodium sulfate), and concentrated. The crude liquid was pre-adsorbed onto Florisil and purified via Isco flash column chromatography (12-g redisep silica gel column, 15-70% ethyl acetate/hexane) to give tert-butyl {2-[{2-[3-(2-fluorophenyl)-2,2-dioxido-2,1,3-benzothiadiazol-1(3H)-yl]ethyl}(methyl)amino]ethyl}methylcarbamate as a viscous, colorless liquid. Yield: 142 mg (64%). MS (ESI) m/z 479.0 ([M+H]$^+$). HRMS: calcd for $C_{23}H_{31}FN_4O_4S+H^+$, 479.2123; found (ESI, [M+H]$^+$), 479.2129. HPLC purity 96.6% at 210-370 nm, 9.0 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Step 3: In an analogous manner as described in general procedure II, step 2, N-{2-[3-(2-fluorophenyl)-2,2-dioxido-2,1,3-benzothiadiazol-1(3H)-yl]ethyl}-N,N'-dimethylethane-1,2-diamine dihydrochloride was prepared from tert-butyl {2-[{2-[3-(2-fluorophenyl)-2,2-dioxido-2,1,3-benzothiadiazol-1(3H)-yl]ethyl}(methyl)amino]ethyl}methylcarbamate as a white powder. MS (ESI) m/z 379.0 ([M+H]$^+$). HRMS: calcd for $C_{18}H_{23}FN_4O_2S+H^+$, 379.1599; found (ESI, [M+H]$^+$), 379.1604. HPLC purity 95.1% at 210-370 nm, 7.1 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 93

N-{2-[3-(2,4-Difluorophenyl)-2,2-dioxido-2,1,3-benzothiadiazol-1(3H)-yl]ethyl}-N,N'-dimethylethane-1,2-diamine dihydrochloride

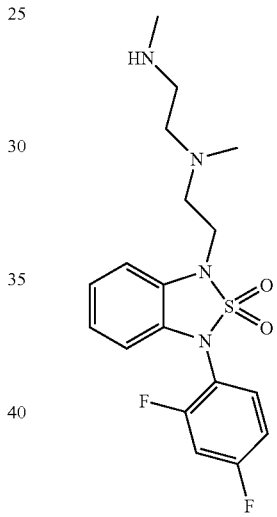

In an analogous manner to Example 92, step 2, tert-butyl {2-[{2-[3-(2,4-difluorophenyl)-2,2-dioxido-2,1,3-benzothiadiazol-1(3H)-yl]ethyl}(methyl)amino]ethyl}methylcarbamate was prepared from 1-(2-bromoethyl)-3-(2,4-difluorophenyl)-1,3-dihydro-2,1,3-benzothiadiazole 2,2-dioxide as a viscous, colorless liquid. HRMS: calcd for $C_{23}H_{30}F_2N_4O_4S+H^+$, 497.2029; found (ESI, [M+H]$^+$), 497.2032. HPLC purity 98.0% at 210-370 nm, 9.5 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

In an analogous manner as described in general procedure II, step 2, N-{2-[3-(2,4-difluorophenyl)-2,2-dioxido-2,1,3-benzothiadiazol-1(3H)-yl]ethyl}-N,N'-dimethylethane-1,2-diamine dihydrochloride was prepared from tert-butyl {2-[{2-[3-(2,4-difluorophenyl)-2,2-dioxido-2,1,3-benzothiadiazol-1(3H)-yl]ethyl}(methyl)amino]ethyl}methylcarbamate as a white powder. HRMS: calcd for $C_{18}H_{22}F_2N_4O_2S+H^+$, 397.1504; found (ESI, [M+H]$^+$), 397.1512. HPLC purity 100.0% at 210-370 nm, 7.4 min.;

Xterra RP18, 3.5 u, 150×4.6 mm column, 1.2 mL/min, 85/15-5195 (Ammon. Form. Buff. pH=3.5/ACN+MeOH) for 10 min, hold 4 min.

Example 94

N-{2-[2,2-Dioxido-3-(2,4,6-trifluorophenyl)-2,1,3-benzothiadiazol-1(3H)-yl]ethyl}-N,N'-dimethyl-ethane-1,2-diamine dihydrochloride

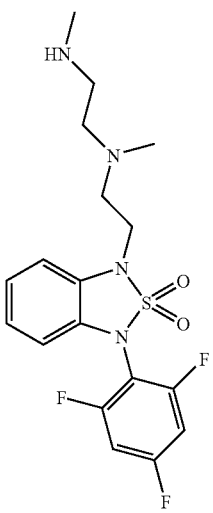

In an analogous manner to Example 92, step 2, tert-butyl {2-[{2-[2,2-dioxido-3-(2,4,6-trifluorophenyl)-2,1,3-benzothiadiazol-1(3H)-yl]ethyl}(methyl)amino]ethyl}methylcarbamate was prepared from 1-(2-bromoethyl)-3-(2,4,6-trifluorophenyl)-1,3-dihydro-2,1,3-benzothiadiazole 2,2-dioxide a viscous, colorless liquid. HRMS: calcd for $C_{23}H_{29}F_3N_4O_4S+H^+$, 515.1934; found (ESI, [M+H]$^+$), 515.1938. HPLC purity 100.0% at 210-370 nm, 9.3 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

In an analogous manner as described in general procedure II, step 2, N-{2-[2,2-dioxido-3-(2,4,6-trifluorophenyl)-2,1,3-benzothiadiazol-1(3H)-yl]ethyl}-N,N'-dimethylethane-1,2-diamine dihydrochloride was prepared from tert-butyl {2-[{2-[2,2-dioxido-3-(2,4,6-trifluorophenyl)-2,1,3-benzothiadiazol-1(3H)-yl]ethyl}(methyl)amino]ethyl}methylcarbamate as a white powder. MS (ESI) m/z 415.0 ([M+H]$^+$). HRMS: calcd for $C_{18}H_{21}F_3N_4O_2S+H^+$, 415.1410; found (ESI, [M+H]$^+$), 415.1417. HPLC purity 99.2% at 210-370 nm, 7.2 min.; Xterra RP18, 3.5 u, 150×4.6 mm column, 1.2 mL/min, 85/15-5/95 (Ammon. Form. Buff. pH=3.5/ACN+MeOH) for 10 min, hold 4 min.

Example 95

1-{3-[3-(2-fluorophenyl)-2,2-dioxido-2,1,3-benzothiadiazol-1(3H)-yl]propyl}piperidin-4-amine dihydrochloride

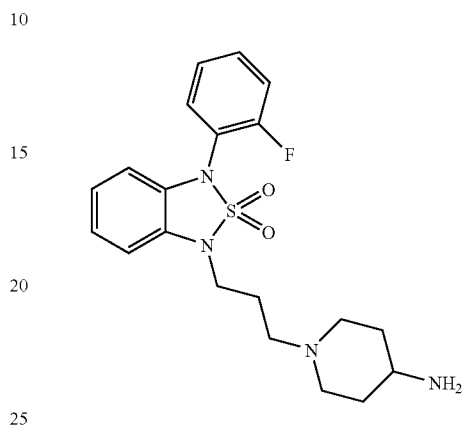

Step 1: 1-(3-bromopropyl)-3-(2-fluorophenyl)-1,3-dihydro-2,1,3-benzothiadiazole 2,2-dioxide (0.61 g, 1.56 mmol) was dissolved in 5 mL of DMF along with 430 mg (3.1 mmol) of potassium carbonate and 0.32 g (1.56 mol) of tert-butyl piperidin-4-ylcarbamate. The solution was heated to 70° C. for 16 hours then poured in water. The solution was extracted 2× with ethyl acetate and the water layer discarded. The combined organic phase was washed 3 times with brine, then dried (MgSO$_4$) and concentrated. The residue was subjected to Biotage chromatography (10-50% ethyl acetate-hexane) to afford 0.45 g (55%) of tert-butyl (1-{3-[3-(2-fluorophenyl)-2,2-dioxido-2,1,3-benzothiadiazol-1(3H)-yl]propyl}piperidin-4-yl)carbamate. MS (ES) m/z 505.1; HPLC purity 97.9% at 210-370 nm, 10.5 min.; Xterra RP18, 3.5 u, 150×4.6 mm column, 1.2 mL/min, 85/15-5/95 (Ammon. Bicarb Buff.Ph=9.5/ACN+MeOH) for 10 min, hold 4 min.

HRMS: calcd for $C_{25}H_{33}FN_4O_4S+H+$, 505.22793; found (ESI, [M+H]+Obs'd), 505.2283.

Step 2: tert-butyl (1-{3-[3-(2-fluorophenyl)-2,2-dioxido-2,1,3-benzothiadiazol-1(3H)-yl]propyl}piperidin-4-yl)carbamate (0.40 g, 0.80 mmol) was dissolved in ether:methanol (9:1) and 2 mL of 2N HCl in ether added. The solution was allowed to stand for 16 hr whereupon a colorless solid had formed. The solid was removed by filtration and washed with ether to afford 0.33 g (87%) 1-{3-[3-(2-fluorophenyl)-2,2-dioxido-2,1,3-benzothiadiazol-1(3H)-yl]propyl}piperidin-4-amine dihydrochloride. HPLC purity 98.7% at 210-370 nm, 5.5 min.; Xterra RP18, 3.5 u, 150×4.6 mm column, 1.2 mL/min, 85/15-5/95 (Ammon. Form. Buff.Ph=3.5/ACN+MeOH) for 10 min, hold 4 min. HRMS: calcd for C20H25FN4O2S+H+, 405.17550; found (ESI, [M+H]+Obs'd), 405.1768.

Example 97

1-[3-(2,2-dioxido-3-phenyl-2,1,3-benzothiadiazol-1(3H)-yl)propyl]piperidin-4-amine dihydrochloride

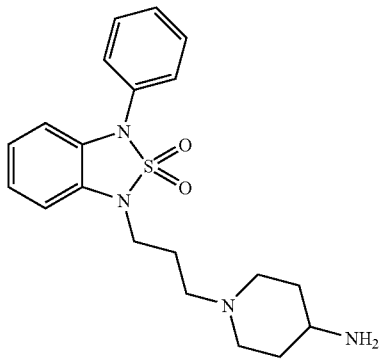

Step 1: In an analogous manner to Example 95, step 1, 1-(3-bromopropyl)-3-phenyl-1,3-dihydro-2,1,3-benzothiadiazole 2,2-dioxide (0.34 g, 0.92 mmol) was treated with 255 mg (1.85 mmol) of potassium carbonate and 0.32 g (1.56 mol) of tert-butyl piperidin-4-yl carbamate to afford tert-butyl (1-{3-[3-phenyl-2,2-dioxido-2,1,3-benzothiadiazol-1(3H)-yl]propyl}piperidin-4-yl)carbamate (0.26 g).

Step 2: In an analogous manner to Example 95, step 2, 1-[3-(2,2-dioxido-3-phenyl-2,1,3-benzothiadiazol-1(3H)-yl)propyl]piperidin-4-amine dihydrochloride was prepared from tert butyl N-{3-[3-phenyl-2,2-dioxido-2,1,3-benzothiadiazol-1(3H)-yl]propyl}piperidin-4-amine carbonate. MS (ES) m/z 386.9; HPLC purity 99.3% at 210-370 nm, 5.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min. HRMS: calcd for C20H26N4O2S+H+, 387.18492; found (ESI, [M+H]+Obs'd), 387.1858.

Example 98

1-{2-[3-(2-fluorophenyl)-2,2-dioxido-2,1,3-benzothiadiazol-1(3H)-yl]ethyl}piperidin-4-amine dihydrochloride

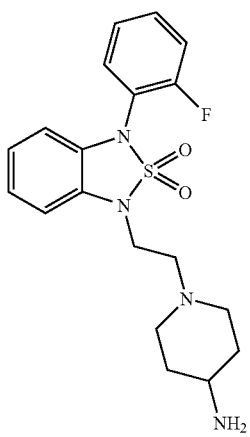

Step 1: In an analogous manner to Example 95, step 1, 1-(3-bromoethyl)-3-(2-fluorophenyl)-1,3-dihydro-2,1,3-benzothiadiazole 2,2-dioxide (0.61 g, 1.6 mmol) was treated with 255 mg (1.85 mmol) of potassium carbonate and 0.49 g (1.6 mol) of tert-butyl piperidin-4-yl carbamate to afford tert-butyl (1-{3-[3-(2-fluorophenyl)-2,2-dioxido-2,1,3-benzothiadiazol-1(3H)-yl]ethyl}piperidin-4-yl)carbamate (0.45 g).

Step 2: In an analogous manner to Example 95, step 2, 1-{2-[3-(2-fluorophenyl)-2,2-dioxido-2,1,3-benzothiadiazol-1(3H)-yl]ethyl}piperidin-4-amine dihydrochloride (0.32 g) was prepared from 0.40 g of tert-butyl (1-{3-[3-(2-fluorophenyl)-2,2-dioxido-2,1,3-benzothiadiazol-1(3H)-yl]ethyl}piperidin-4-yl)carbamate. MS (ES) m/z 390.8; HPLC purity 98.8% at 210-370 nm, 5.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min. HRMS: calcd for C19H23FN4O2S+H+, 391.15985; found (ESI, [M+H]+Obs'd), 391.1601.

Example 100

1-{2-[3-(2-fluorophenyl)-2,2-dioxido-2,1,3-benzothiadiazol-1(3H)-yl]ethyl}-N-methylpiperidin-4-amine dihydrochloride

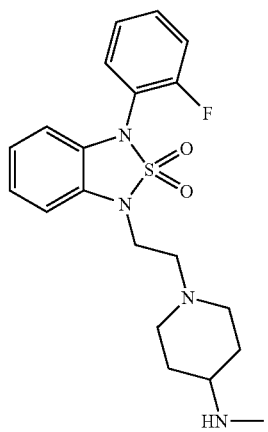

Step 1: A solution of 0.28 g (0.57 mmol) of tert-butyl (1-{3-[3-(2-fluorophenyl)-2,2-dioxido-2,1,3-benzothiadiazol-1(3H)-yl]ethyl}piperidin-4-yl)carbamate (see Example 99, step 1) in 5 mL of DMF was added dropwise to a solution of sodium hydride (0.052 g, 1.3 mmol, 60% dispersion) in 3 mL of DMF. After stirring 1/2 hr, 0.12 g (0.85 mmol) of methyl iodide was added. The solution was heated to 70° C. for 4 hr then poured in water. The solution was extracted 2× with ethyl acetate and the water layer discarded. The combined organic phase was washed 3 times with brine, then dried (MgSO4) and concentrated. The residue was subjected to Biotage chromatography (10-50% ethyl acetate-hexane) to afford 0.23 g of tert-butyl (1-{3-[3-(2-fluorophenyl)-2,2-dioxido-2,1,3-benzothiadiazol-1(3H)-yl]ethyl}-N-methylpiperidin-4-yl)carbamate used as such in the next step.

Step 2: In an analogous manner to Example 95, step 2, 1-{2-[3-(2-fluorophenyl)-2,2-dioxido-2,1,3-benzothiadiazol-1(3H)-yl]ethyl}-N-methylpiperidin-4-amine dihydrochloride (0.15 g) was prepared from 0.20 g of tert-butyl (1-{3-[3-(2-fluorophenyl)-2,2-dioxido-2,1,3-benzothiadiazol-1(3H)-yl]ethyl}-N-methylpiperidin-4-yl)carbamate. MS (ES) m/z 404.8; HPLC purity 97.7% at 210-370 nm, 6.2 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 102

1-{2-[3-phenyl-2,2-dioxido-2,1,3-benzothiadiazol-1(3H)-yl]ethyl}piperidin-4-amine dihydrochloride

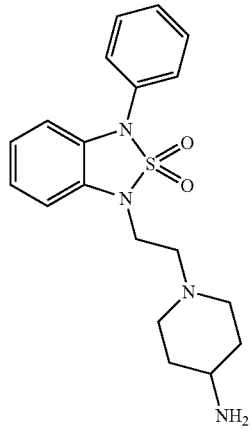

Step 1: In an analogous manner to Example 95, step 1, tert-butyl (1-{3-[3-phenyl-2,2-dioxido-2,1,3-benzothiadiazol-1(3H)-yl]ethyl}piperidin-4-yl)carbamate was prepared from 1-(3-bromoethyl)-3-phenyl-1,3-dihydro-2,1,3-benzothiadiazole and tert-butyl piperidin-4-yl carbamate.

Step 2: In an analogous manner to Example 95, step 2, 1-{2-[3-phenyl-2,2-dioxido-2,1,3-benzothiadiazol-1(3H)-yl]ethyl}piperidin-4-amine dihydrochloride was prepared from tert-butyl(1-{3-[3-phenyl-2,2-dioxido-2,1,3-benzothiadiazol-1(3H)yl]ethyl}piperidin-4-yl)carbamate. MS (ES) m/z 372.9; HPLC purity 99.4% at 210-370 nm, 5.5 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 103

1-{2-[3-phenyl-2,2-dioxido-2,1,3-benzothiadiazol-1(3H)-yl]ethyl}-N-methylpiperidin-4-amine dihydrochloride

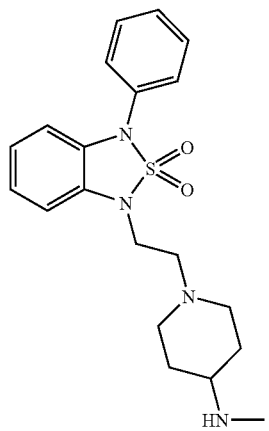

Step 1: In an analogous manner to Example 100, step 1, tert-butyl (1-{3-[3-phenyl-2,2-dioxido-2,1,3-benzothiadiazol-1(3H)-yl]ethyl}-N-methylpiperidin-4-yl)carbamate was prepared from tert-butyl (1-{3-[3-phenyl-2,2-dioxido-2,1,3-benzothiadiazol-1(3H)-yl]ethyl}piperidin-4-yl)carbamate and used in the next step.

Step 2: In an analogous manner to Example 95, step 2, 1-{2-[3-phenyl-2,2-dioxido-2,1,3-benzothiadiazol-1(3H)-yl]ethyl}-N-methylpiperidin-4-amine dihydrochloride was prepared from tert-butyl (1-{3-[3-phenyl-2,2-dioxido-2,1,3-benzothiadiazol-1(3H)-yl]ethyl}-N-methylpiperidin-4-yl) carbamate. MS (ES) m/z 386.8; HPLC purity 93.8% at 210-370 nm, 6.4 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min. HRMS: calcd for C20H26N4O2S+H+, 387.18492; found (ESI, [M+H]+ Obs'd), 387.1853.

Example 105

1-{1-[2-(2,2-dioxido-3-phenyl-2,1,3-benzothiadiazol-1(3H)-yl)ethyl]pyrrolidin-3-yl}methanamine dihydrochloride

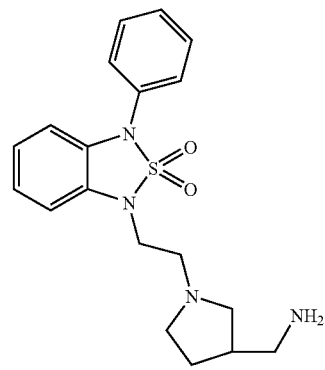

Step 1: In an analogous manner to general procedure V, tert butyl 1-{1-[2-(2,2-dioxido-3-phenyl-2,1,3-benzothiadiazol-1(3H)-yl)ethyl]pyrrolidin-3-yl}methanamine carbonate was prepared from 1-(3-bromoethyl)-3-phenyl-1,3-dihydro-2,1,3-benzothiadiazole 2,2-dioxide and tert-butyl pyrrolidin-3-ylmethylcarbamate.

Step 2: In an analogous manner to general procedure II, step 2, 1-{1-[2-(2,2-dioxido-3-phenyl-2,1,3-benzothiadiazol-1(3H)-yl)ethyl]pyrrolidin-3-yl}methanamine dihydrochloride was prepared from tert butyl 1-{1-[2-(2,2-dioxido-3-phenyl-2,1,3-benzothiadiazol-1(3H)-yl)ethyl]pyrrolidin-3-yl}methanamine carbonate. MS (ES) m/z 372.9; HPLC purity 93.1% at 210-370 nm, 7.0 min.; Xterra RP18, 3.5 u, 150×4.6 mm, 1.2 mL/min, 85/15-5/95 (Ammon. Form. Buff. Ph=3.5/ACN+MeOH) for 10 min, hold 4 min.

HRMS: calcd for C20H25FN4O2S+H+, 405.17550; found (ESI, [M+H]+Obs'd), 405.1762.

Example 106

1-phenyl-3-[2-(4-pyrrolidin-1-ylpiperidin-1-yl)ethyl]-1,3-dihydro-2,1,3-benzothiadiazole 2,2-dioxide dihydrochloride

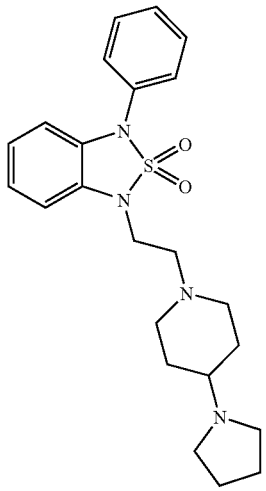

In an analogous manner to general procedure V, 1-phenyl-3-[2-(4-pyrrolidin-1-ylpiperidin-1-yl)ethyl]-1,3-dihydro-2,1,3-benzothiadiazole 2,2-dioxide dihydrochloride was prepared from 1-(3-bromoethyl)-3-phenyl-1,3-dihydro-2,1,3-benzothiadiazole 2,2-dioxide and 4-(pyrrolidin-1-yl)piperidine. The resulting product was converted to the dihydrochloride with 2N HCl in ether. MS (ES) m/z 426.9; HPLC purity 100.0% at 210-370 nm, 6.8 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 107

2-{2-[3-(2-chloro-4-fluorophenyl)-2,2-dioxido-2,1,3-benzothiadiazol-1(3H)-yl]ethoxy}-N-methylethanamine hydrochloride

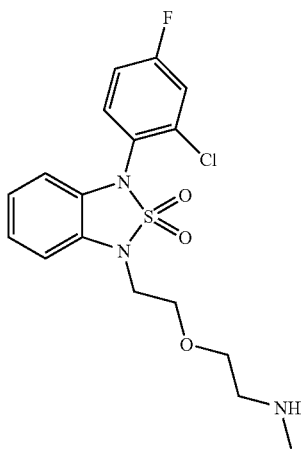

Step 1: In an analogous manner to general procedure IV, 1-[2-(2-bromoethoxy)ethyl]-3-(2-chloro-4-fluorophenyl)-1,3-dihydro-2,1,3-benzothiadiazole 2,2-dioxide was prepared from 1-(2-chloro-4-fluorophenyl)-1,3-dihydro-2,1,3-benzothiadiazole 2,2-dioxide (prepared in an analogous manner to general procedure I) and 1-bromo-2-(2-bromoethoxy)ethane. MS (ES) m/z 448.6; HPLC purity 85.1% at 210-370 nm, 10.5 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 2: In an analogous manner to general procedure V, 2-{2-[3-(2-chloro-4-fluorophenyl)-2,2-dioxido-2,1,3-benzothiadiazol-1(3H)-yl]ethoxy}-N-methylethanamine hydrochloride was prepared from 1-[2-(2-bromoethoxy)ethyl]-3-(2-chloro-4-fluorophenyl)-1,3-dihydro-2,1,3-benzothiadiazole 2,2-dioxide and methylamine (33% in ethanol). MS (ES) m/z 399.8; HPLC purity 84.9% at 210-370 nm, 7.5 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min. HRMS: calcd for C17H19ClFN3O3S+H+, 400.08924; found (ESI, [M+H]+ Obs'd), 400.0896.

Example 108

2-{2-[3-(2-chloro-4-fluorophenyl)-2,2-dioxido-2,1,3-benzothiadiazol-1(3H)-yl]ethoxy}-N N-dimethylethanamine hydrochloride

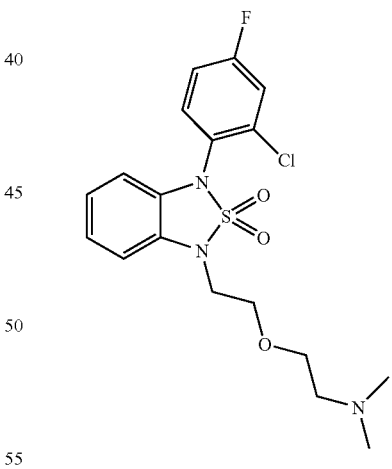

In an analogous manner to general procedure IV, 2-{2-[3-(2-chloro-4-fluorophenyl)-2,2-dioxido-2,1,3-benzothiadiazol-1(3H)-yl]ethoxy}-N,N-dimethylethanamine hydrochloride was prepared from 1-[2-(2-bromoethoxy)ethyl]-3-(2-chloro-4-fluorophenyl)-1,3-dihydro-2,1,3-benzothiadiazole 2,2-dioxide and dimethyl amine (~5.6 M in ethanol). MS (ES) m/z 413.8; HPLC purity 85.5% at 210-370 nm, 8.3 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 109

1-(4-chloro-2-fluorophenyl)-3-(2-piperazin-1-yl-ethyl)-1,3-dihydro-2,1,3-benzothiadiazole 2,2-dioxide

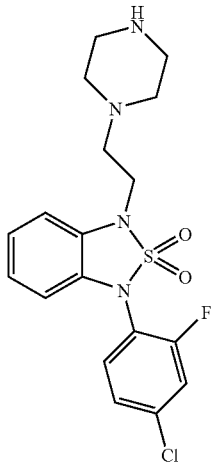

Step 1: To a stirring solution of 1-(3-bromopropyl)-3-(4-chloro-2-fluorophenyl)-1,3-dihydro-2,1,3-benzothiadiazole 2,2-dioxide (150 mg, 0.502 mmol), 2-bromoethanol (71 uL, 1.00 mmol), and triphenylphosphine (263 mg, 1.00 mmol) in anhydrous tetrahydrofuran was added diisopropylazodicarboxylate (195 uL, 1.00 mmol) and the solution stirred, capped, at room temperature for 18 hr. The reaction mixture was concentrated then loaded directly onto silica gel and purified via Isco chromatography (Redisep, silica, gradient 0-25% ethyl acetate in hexane to afford 0.07 g of 1-(2-bromoethyl)-3-(4-chloro-2-fluorophenyl)-1,3-dihydro-2,1,3-benzothiadiazole 2,2-dioxide as a white solid.

HRMS: calcd for C14H11 BrClFN2O2S+Na+, 403.94. found (ESI, [M+Na]+, 426.9293.

HPLC purity 99.3% at 210-370 nm, 10.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 2: 1-(4-chloro-2-fluorophenyl)-1,3-dihydro-2,1,3-benzothiadiazole 2,2-dioxide (50 mg, 0.123 mmol) and piperazine-1-carboxylic acid tert-butyl ester (115 mg, 0.616 mmol) were stirred in anhydrous dimethylformamide (2 mL) in a sealed vial at room temperature for 18 hr. This reaction was transferred to a separatory funnel with ethyl acetate and washed with water. The organic layer was dried (MgSO$_4$), filtered and the solvent removed. This material was dissolved in diethyl ether and 2N HCl in Et$_2$O to give a grey solid as the mono-HCl salt (24 mg, 44% Yield).

HRMS: calcd for HPLC purity 100% at 210-370 nm, 8.0 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 110

1-(4-chloro-2-fluorophenyl)-3-{2-[(3R,5S)-3,5-dimethylpiperazin-1-yl]ethyl}-1,3-dihydro-2,1,3-benzothiadiazole 2,2-dioxide

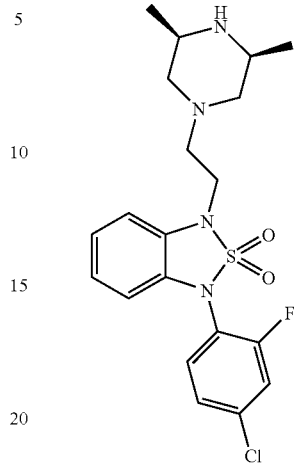

1-(2-bromoethyl)-3-(4-chloro-2-fluorophenyl)-1,3-dihydro-2,1,3-benzothiadiazole 2,2-dioxide (220 mg, 0.542 mmol) and cis-2,6-dimethyl piperazine (372 mg, 3.25 mmol) were heated in absolute ethyl alcohol (5 mL) in a sealed vial at 90° C. for 18 hr. The solvent was removed, in vacuo, and the material purified by Gilson RP-HPLC (YMC CombiPrep ProC18 50×20 mm I.D. column, S-5☐m, 12 nm. Flow rate 20 mL/min. Gradient: 10/90

Acetonitrile/Water to 100% acetonitrile over 10 minutes then hold for three minutes at 100% acetonitrile and ramp back to 10/90 acetonitrile/water over two minutes) to give a white solid. This material was dissolved in diethyl ether and methanol and 4N HCl in dioxane was added to give a white solid (119 mg, 46% Yield) as the mono-HCl salt.

HRMS: calcd for C20H24ClFN4O2S+Na+, 438.13. found (ESI, [M+Na]+, 439.1377.

HPLC purity 99.3% at 210-370 nm, 8.4 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 111

1-(4-chloro-2-fluorophenyl)-3-(2-piperidin-4-yl-ethyl)-1,3-dihydro-2,1,3-benzothiadiazole 2,2-dioxide

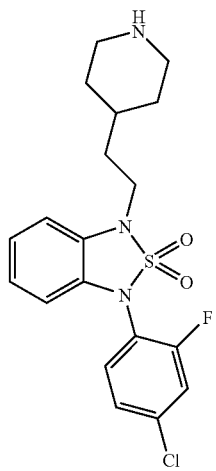

Step 1: To a stirring solution of 1-(4-chloro-2-fluorophenyl)-1,3-dihydro-2,1,3-benzothiadiazole 2,2-dioxide (100 mg, 0.335 mmol), tert-butyl 4-(2-hydroxyethyl)piperidine-1-carboxylate (147 uL, 0.67 mmol), and triphenylphosphine (176 mg, 0.67 mmol) in anhydrous tetrahydrofuran was added diisopropylazodicarboxylate (130 uL, 0.67 mmol) and the solution stirred, capped, at room temperature for 18 hr. The reaction mixture was concentrated then loaded directly onto silica gel and purified via Isco chromatography (Redisep, silica, gradient 0-35% ethyl acetate in hexane to afford 1-(4-chloro-2-fluorophenyl)-3-(2-piperidin-4-ylethyl)-1,3-dihydro-2,1,3-benzothiadiazole 2,2-dioxide carbamic acid tert-butyl ester as an orange colored wax. This material was dissolved in diethyl ether and methanol and 2N HCl in diethyl ether was added a precipitate formed. The mixture was filtered to afford impure product. This material was dissolved in DMSO and purified by Gilson RP-HPLC (YMC CombiPrep ProC18 50×20 mm I.D. column, S-5□m, 12 nm. Flow rate 20 mL/min. Gradient: 10/90 Acetonitrile/Water to 100% acetonitrile over 10 minutes then hold for three minutes at 100% acetonitrile and ramp back to 10/90 acetonitrile/water over two minutes) to give 0.089 g of 1-(4-chloro-2-fluorophenyl)-3-(2-piperidin-4-ylethyl)-1,3-dihydro-2,1,3-benzothiadiazole 2,2-dioxide as an orange solid.

HRMS: calcd for C19H21ClFN3O2S+H+, 409.10. found (ESI, [M+H]+, 410.1102.

HPLC purity 100% at 210-370 nm, 11.5 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 112

1-(4-chloro-2-methylphenyl)-3-{2-[(3R,5S)-3,5-dimethylpiperazin-1-yl]ethyl}-1,3-dihydro-2,1,3-benzothiadiazole 2,2-dioxide

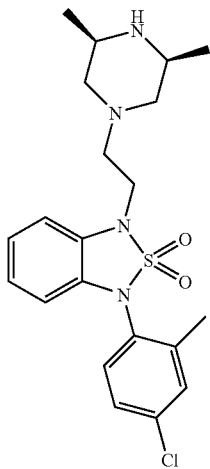

1-(4-chloro-2-methylphenyl)-3-{2-[(3R,5S)-3,5-dimethylpiperazin-1-yl]ethyl}-1,3-dihydro-2,1,3-benzothiadiazole 2,2-dioxide was prepared using 1-(2-bromoethyl)-3-(4-chloro-2-methylphenyl)-1,3-dihydro-2,1,3-benzothiadiazole2,2-dioxide and cis-2,6-dimethyl piperazine analogous to the conditions used general procedure V.

HRMS: calcd for C21H27ClN4O2S+H+, 435.1616; found (ESI, [M+H]+, 435.1625.

HPLC purity 97.7% at 210-370 nm, 8.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 113

1-(4-chloro-2-methylphenyl)-3-(2-piperazin-1-yl-ethyl)-1,3-dihydro-2,1,3-benzothiadiazole2,2-dioxide

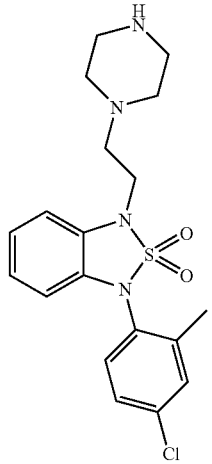

1-(4-Chloro-2-methylphenyl)-3-(2-piperazin-1-ylethyl)-1,3-dihydro-2,1,3-benzothiadiazole2,2-dioxide was prepared using 1-(4-chloro-2-methylphenyl)-1,3-dihydro-2,1,3-benzothiadiazole2,2-dioxide and tert-butyl 4-(2-hydroxyethyl)piperidine-1-carboxylate analogous to the conditions used in general procedure VI followed by removal of Boc group. HRMS: calcd for C19H23ClN4O2S+H+, 407.1303; found (ESI, [M+H]+, 407.1307; calcd for C19H22ClN4O2S+Na+, 429.1123; found (ESI, [M+H]+, 429.1123; HPLC purity 100% at 210-370 nm, 11.5 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 114

1-(tert-butylamino)-4-(2,2-dioxido-3-phenyl-2,1,3-benzothiadiazol-1(3H)-yl)butan-2-one hydrochloride

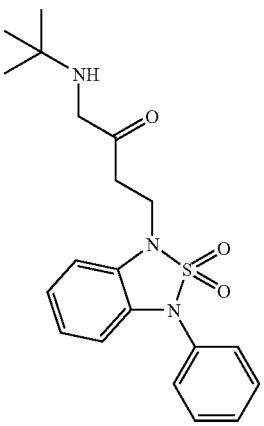

Step 1: 1-(tert-butylamino)-4-(2,2-dioxido-3-phenyl-2,1,3-benzothiadiazol-1(3H)-yl)butan-2-ol (115 mg, 0.295 mmol) and di-tert-butyl dicarbonate (71 mg, 0.325 mmol) were stirred in dichloromethane (5 mL) in a sealed vial at room temperature for 18 hr. The reaction mixture was concentrated then loaded directly onto silica gel and purified via Isco chromatography (Redisep, silica, gradient 0-50% ethyl acetate in hexane to afford 0.02 g of 1-(tert-butylamino)-4-(2,2-dioxido-3-phenyl-2,1,3-benzothiadiazol-1(3H)-yl)butan-2-ol-carbamic acid tert-butyl ester as a clear oil.

HRMS: calcd for C25H35N3O5S+H+, 490.2370; found (ESI, [M+H]+), 490.2373. HPLC purity 97.0% at 210-370 nm, 10.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 2: 1-(tert-butylamino)-4-(2,2-dioxido-3-phenyl-2,1,3-benzothiadiazol-1(3H)-yl)butan-2-ol-carbamic acid tert-butyl ester (15 mg, 0.031 mmol) and Dess Martin periodinane (20 mg, 0.046 mmol) were stirred in dichloromethane (5 mL) in a sealed vial at room temperature for 18 hr. The reaction mixture was concentrated then loaded directly onto silica gel and purified via Isco chromatography (Redisep, silica, gradient 0-50% ethyl acetate in hexane to afford 0.023 g of 1-(tert-butylamino)-4-(2,2-dioxido-3-phenyl-2,1,3-benzothiadiazol-1(3H)-yl)butan-2-one-carbamic acid tert-butyl ester as a clear oil.

HRMS: calcd for C25H33N3O5S+H+, 510.2033; found (ESI, [M+H]+), 510.2035.

HPLC purity 100% at 210-370 nm, 11.1 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 3: The clear oil, 1-(tert-butylamino)-4-(2,2-dioxido-3-phenyl-2,1,3-benzothiadiazol-1(3H)-yl)butan-2-one-carbamic acid tert-butyl ester, was dissolved in diethyl ether and methanol and 4N HCl in dioxane was added a precipitate formed. The reaction was filtered to afford 12 mg of 1-(tert-butylamino)-4-(2,2-dioxido-3-phenyl-2,1,3-benzothiadiazol-1(3H)-yl)butan-2-one hydrochloride as a white solid.

HRMS: calcd for C20H25N3O3S+H+, 388.1689; found (ESI, [M+H]+), 388.1690.

HPLC purity 97.6% at 210-370 nm, 7.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 115

4-(2,2-dioxido-3-phenyl-2,1,3-benzothiadiazol-1(3H)-yl)-1-(isopropylamino)butan-2-one hydrochloride

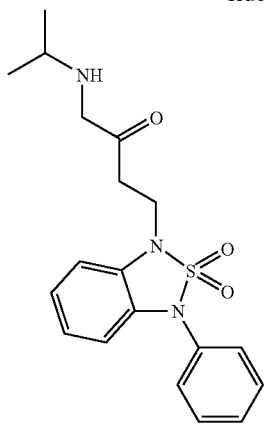

4-(2,2-Dioxido-3-phenyl-2,1,3-benzothiadiazol-1(3H)-yl)-1-(isopropylamino)butan-2-one hydrochloride was prepared using 1-(dimethylamino)-4-(2,2-dioxido-3-phenyl-2,1,3-benzothiadiazol-1(3H)-yl)butan-2-ol analogous to the conditions used in steps 2 and 3 of example 114.

HRMS: calcd for C19H23N3O3S+H+, 374.1533; found (ESI, [M+H]+), 374.1537.

HPLC purity 94.5% at 210-370 nm, 7.4 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 116

1-(cyclopropylamino)-4-(2,2-dioxido-3-phenyl-2,1,3-benzothiadiazol-1(3H)-yl)butan-2-one hydrochloride

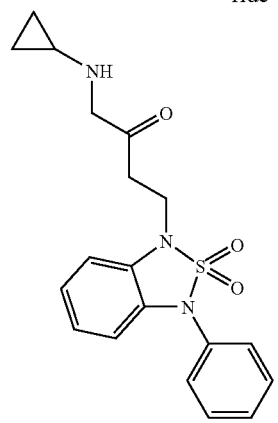

1-(Cyclopropylamino)-4-(2,2-dioxido-3-phenyl-2,1,3-benzothiadiazol-1(3H)-yl)butan-2-one hydrochloride was prepared using 1-(cyclopropylamino)-4-(2,2-dioxido-3-phenyl-2,1,3-benzothiadiazol-1(3H)-yl)butan-2-ol analogous to the conditions used in steps 2 and 3 of example 114.

HRMS: calcd for C19H21N3O3S+H+, 372.1376; found (ESI, [M+H]+), 372.1379.

HPLC purity 88.5% at 210-370 nm, 7.4 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 117

4-(2,2-dioxido-3-phenyl-2,1,3-benzothiadiazol-1(3H)-yl)-1-(methylamino)butan-2-one hydrochloride

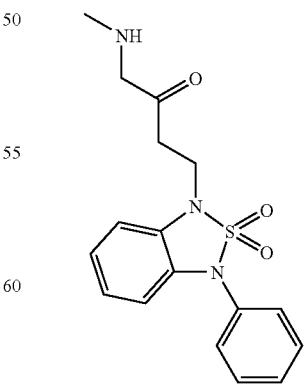

4-(2,2-Dioxido-3-phenyl-2,1,3-benzothiadiazol-1(3H)-yl)-1-(methylamino)butan-2-one hydrochloride was prepared using 4-(2,2-dioxido-3-phenyl-2,1,3-benzothiadiazol-1(3H)-yl)-1-(methylamino)butan-2-ol analogous to the conditions used in steps 2 and 3 of example 114.

HRMS: calcd for C17H19N3O3S+H+, 346.1220; found (ESI, [M+H]+), 346.1223.

HPLC purity 95.6% at 210-370 nm, 7.0 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 118
4-[3-(2-fluorophenyl)-2,2-dioxido-2,1,3-benzothiadiazol-1(3H)-yl]-1-(methylamino)butan-2-one hydrochloride

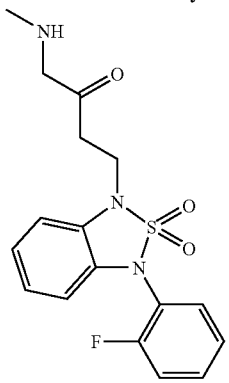

Step 1: 1-(2-fluorophenyl)-1,3-dihydro-2,1,3-benzothiadiazole2,2-dioxide (prepared using general procedure I, 0.5 g, 1.9 mmol) was dissolved in acetone (5 mL) and potassium carbonate (0.52 g, 3.8 mmol) was added followed by S(–)-4-bromo-1,2-epoxybutane (0.57 g, 3.8 mmol). The mixture was stirred for 18 hours at 50° C. in a sealed vial then diluted with EtOAc (100 mL) and washed with water (2×), brine then dried (Na2SO4). After concentration the residue was dissolved in 10 mL of MeNH2 solution (8M in EtOH). The solution was irradiated in a microwave cuvette at 100° C. for 3 minutes. The reaction mixture was concentrated then loaded directly onto silica gel and purified via Isco chromatography (Redisep, silica, gradient 0-100% of 10% 7M ammonia in MeOH/dichloromethane) to afford 387 mg of (S)-4-[3-(2-fluorophenyl)-2,2-dioxido-2,1,3-benzothiadiazol-1(3H)-yl]-1-(methylamino)butan-2-ol.

HRMS: calcd for C17H20FN3O3S+H+, 366.1288; found (ESI, [M+H]+), 366.1279.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 2: 4-[3-(2-fluorophenyl)-2,2-dioxido-2,1,3-benzothiadiazol-1(3H)-yl]-1-(methylamino)butan-2-one hydrochloride was prepared using 4-[3-(2-fluorophenyl)-2,2-dioxido-2,1,3-benzothiadiazol-1(3H)-yl]-1-(methylamino)butan-2-ol analogous to the conditions used in steps 2 and 3 of example 114.

HRMS: calcd for C17H19N3O3S+H+, 346.1220; found (ESI, [M+H]+), poor signal.

HPLC purity 92.6% at 210-370 nm, 7.0 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 119
(2Z)-4-(2,2-dioxido-3-phenyl-2,1,3-benzothiadiazol-1(3H)-yl)-1-(methylamino)butan-2-one oxime

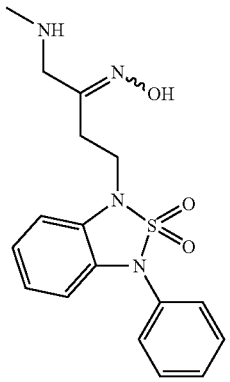

tert-butyl [4-(2,2-dioxido-3-phenyl-2,1,3-benzothiadiazol-1(3H)-yl)-2-oxobutyl]methylcarbamate (50 mg, 0.112 mmol), hydroxylamine hydrochloride (50 mg, 0.720 mmol), and pyridine (1.5 mL) were stirred in ethyl alcohol (3 mL) in a sealed vial at 70° C., for 3 hr. The reaction was allowed to cool to room temperature and transferred to a separatory funnel with dichloromethane and washed with a saturation aqueous solution of sodium bicarbonate, brine, dried (MgSO4), filtered and the solvent removed, in vacuo, to give a clear oil. This material was adsorbed onto silica gel and purified via Isco chromatography (Redisep, silica, gradient 0-50% ethyl acetate in hexane to afford a white solid. This material was dissolved in diethyl ether and methanol and 4N HCl in dioxane was added a precipitate formed. The mixture was filtered to afford 0.028 g (62% Yield) of (2Z)-4-(2,2-dioxido-3-phenyl-2,1,3-benzothiadiazol-1(3H)-yl)-1-(methylamino)butan-2-one oxime as an off white solid.

HRMS: calcd for C17H20N4O3S+H+, 361.1329; found (ESI, [M+H]+), 361.1337.

HPLC purity 96.8% at 210-370 nm, 7.3 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 120
(2S)-4-[3-(2-fluorophenyl)-2,2-dioxido-2,1,3-benzothiadiazol-1(3H)-yl]-2-methoxy-N-methylbutan-1-amine

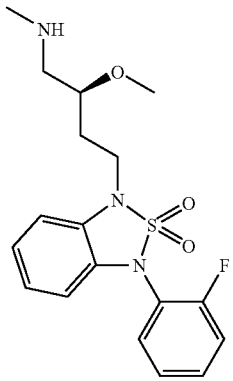

Step 1: 4-[3-(2-Fluorophenyl)-2,2-dioxido-2,1,3-benzothiadiazol-1(3H)-yl]-1-(methylamino)butan-2-ol-carbamic acid tert-butyl ester was prepared using (2S)-4-[3-(2-fluorophenyl)-2,2-dioxido-2,1,3-benzothiadiazol-1(3H)-yl]-1-(methylamino)butan-2-ol analogous to the conditions used in step 1 of example 114.

HPLC purity 93.1% at 210-370 nm, 9.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 2: 4-[3-(2-fluorophenyl)-2,2-dioxido-2,1,3-benzothiadiazol-1(3H)-yl]-1-(methylamino)butan-2-ol-carbamic acid tert-butyl ester (75 mg, 0.161 mmol), trimethyloxonium tetrafluoroborate (71 mg, 0.483 mmol), proton sponge (121 mg, 0.564 mmol) and 4A molecular sieves were stirred in dichloromethane (5 mL) in a sealed vial at room temperature for 18 hr. The reaction mixture was concentrated then loaded directly onto silica gel and purified via Isco chromatography (Redisep, silica, gradient 0-50% ethyl acetate in hexane to afford 0.065 g of (2S)-4-[3-(2-fluorophenyl)-2,2-dioxido-2,1,3-benzothiadiazol-1(3H)-yl]-2-methoxy-N-methylbutan-1-amine-carbamic acid tert-butyl ester as a clear oil. This material was dissolved in diethyl ether and methanol and 4N HCl in dioxane was added a precipitate formed. The mixture was filtered to afford 0.050 g of (2S)-4-[3-(2-fluorophenyl)-2,2-dioxido-2,1,3-benzothiadiazol-1(3H)-yl]-2-methoxy-N-methylbutan-1-amine as a brown solid.

HRMS: calcd for C18H22FN3O3S+H+, 380.1439; found (ESI, [M+H]+, 380.1438.

HPLC purity 86.0% at 210-370 nm, 7.2 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 121

(2S)-2-methoxy-N-methyl-4-[3-(2-methylphenyl)-2,2-dioxido-2,1,3-benzothiadiazol-1(3H)-yl]butan-1-amine

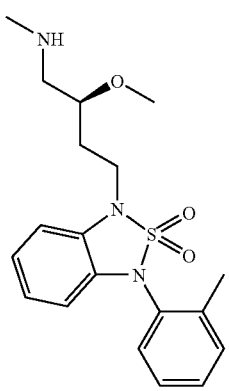

(2S)-2-methoxy-N-methyl-4-[3-(2-methylphenyl)-2,2-dioxido-2,1,3-benzothiadiazol-1(3H)-yl]butan-1-amine was prepared using (2S)-1-(methylamino)-4-[3-(2-methylphenyl)-2,2-dioxido-2,1,3-benzothiadiazol-1(3H)-yl]butan-2-ol analogous to the conditions used in step 2 of example 120.

HRMS: calcd for C19H25N3O3S+H+, 362.1533; found (ESI, [M+H]+), 362.1533.

HPLC purity 100% at 210-370 nm, 7.4 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 122

(2S)-2-methoxy-4-[3-(3-methoxyphenyl)-2,2-dioxido-2,1,3-benzothiadiazol-1(3H)-yl]-N-methylbutan-1-amine

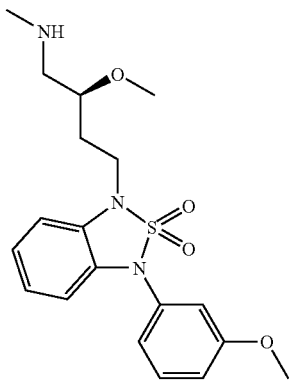

(2S)-2-Methoxy-4-[3-(3-methoxyphenyl)-2,2-dioxido-2,1,3-benzothiadiazol-1(3H)-yl]-N-methylbutan-1-amine was prepared using (2S)-4-[3-(3-methoxyphenyl)-2,2-dioxido-2,1,3-benzothiadiazol-1(3H)-yl]-1-(methylamino)butan-2-ol analogous to the conditions used in step 2 of example 120.

HRMS: calcd for C19H25N3O4S+H+, 392.1639; found (ESI, [M+H]+, 392.1638 calcd for C19H25N3O4S+Na+, 414.1458; found (ESI, [M+Na]+, 414.1455.

HPLC purity 99.3% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 123

4-(2,2-dioxido-3-phenyl-2,1,3-benzothiadiazol-1(3H)-yl)-2-methoxy-N-methylbutan-1-amine

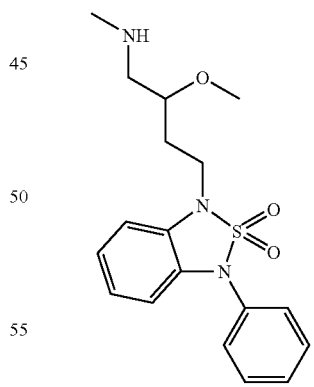

4-(2,2-dioxido-3-phenyl-2,1,3-benzothiadiazol-1(3H)-yl)-2-methoxy-N-methylbutan-1-amine was prepared using 4-[3-(3-phenyl)-2,2-dioxido-2,1,3-benzothiadiazol-1(3H)-yl]-1-(methylamino)butan-2-ol analogous to the conditions used in step 2 of example 120.

HRMS: calcd for C18H23N3O3S+H+, 362.1533; found (ESI, [M+H]+, 362.1537 calcd for C19H25N3O4S+Na+, 414.1458; found (ESI, [M+Na]+, 414.1455.

HPLC purity 97.9% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 124

(2R)-4-(2,2-dioxido-3-phenyl-2,1,3-benzothiadiazol-1(3H)-yl)-2-methoxy-N-methylbutan-1-amine

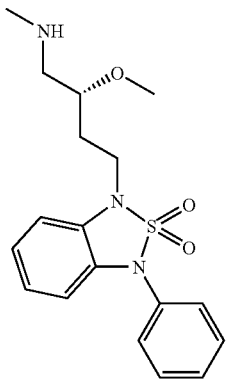

(2R)-4-(2,2-Dioxido-3-phenyl-2,1,3-benzothiadiazol-1(3H)-yl)-2-methoxy-N-methylbutan-1-amine was prepared by separating 4-(2,2-dioxido-3-phenyl-2,1,3-benzothiadiazol-1(3H)-yl)-2-methoxy-N-methylbutan-1-amine via chiral HPLC. The compound was dissolved in methanol. 200 uL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AS-H 5□m, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

| | |
|---|---|
| SFC Instrument: | Berger MultiGram Prep SFC (Berger Instruments, Inc. Newark, DE) |
| Column: | Chiralpak AS-H; 5□m; 250 mm L × 20 mm ID (Chiral Technologies, Inc, Exton, PA) |
| Column temperature: | 35° C. |
| SFC Modifier: | 18% MeOHw 0.2% DMEA |
| Flow rate: | 50 mL/min |
| Outlet Pressure: | 100 bar |
| Detector: | UV at 220 nm. |

HRMS: calcd for C18H23N3O3S+H+, 362.1533; found (ESI, [M+H]+, 362.1542 calcd for C19H25N3O4S+Na+, 414.1458; found (ESI, [M+Na]+, 414.1455.

HPLC purity 98% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 125

(2S)-4-(2,2-dioxido-3-phenyl-2,1,3-benzothiadiazol-1(3H)-yl)-2-methoxy-N-methylbutan-1-amine

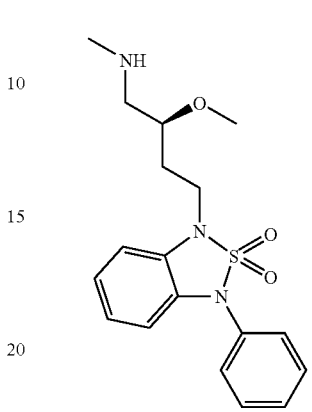

(2S)-4-(2,2-Dioxido-3-phenyl-2,1,3-benzothiadiazol-1(3H)-yl)-2-methoxy-N-methylbutan-1-amine was prepared by separating 4-(2,2-dioxido-3-phenyl-2,1,3-benzothiadiazol-1(3H)-yl)-2-methoxy-N-methylbutan-1-amine via chiral HPLC. The compound was dissolved in methanol. 200 uL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AS-H 5□m, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

| | |
|---|---|
| SFC Instrument: | Berger MultiGram Prep SFC (Berger Instruments, Inc. Newark, DE) |
| Column: | Chiralpak AS-H; 5□m; 250 mm L × 20 mm ID (Chiral Technologies, Inc, Exton, PA) |
| Column temperature: | 35° C. |
| SFC Modifier: | 18% MeOHw 0.2% DMEA |
| Flow rate: | 50 mL/min |
| Outlet Pressure: | 100 bar |
| Detector: | UV at 220 nm. |

HRMS: calcd for C18H23N3O3S+H+, 362.1533; found (ESI, [M+H]+, 362.1539 calcd for C19H25N3O4S+Na+, 414.1458; found (ESI, [M+Na]+, 414.1455.

HPLC purity 100% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 126

N-{(2S)-4-[3-(2-fluorophenyl)-2,2-dioxido-2,1,3-benzothiadiazol-1(3H)-yl]-2-methoxybutyl}cyclopropanamine

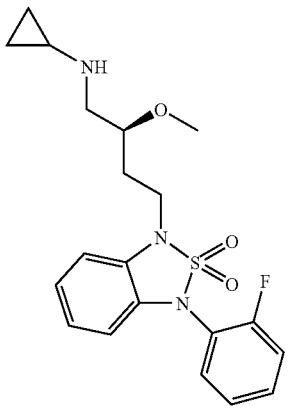

N-{(2S)-4-[3-(2-fluorophenyl)-2,2-dioxido-2,1,3-benzothiadiazol-1(3H)-yl]-2-methoxybutyl}cyclopropanamine was prepared using (2S)-1-(cyclopropylamino)-4-[3-(2-fluorophenyl)-2,2-dioxido-2,1,3-benzothiadiazol-1(3H)-yl]butan-2-ol analogous to the conditions used in step 2 of example 120.

HRMS: calcd for C20H24FN3O3S+H+, 406.1595; found (ESI, [M+H]+, 406.1594 calcd for C20H24FN3O3S+Na+, 428.1415; found (ESI, [M+Na]+, 428.1413.

HPLC purity 95.6% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 127

N-{(2S)-2-methoxy-4-[3-(2-methylphenyl)-2,2-dioxido-2,1,3-benzothiadiazol-1(3H)-yl]butyl}cyclopropanamine

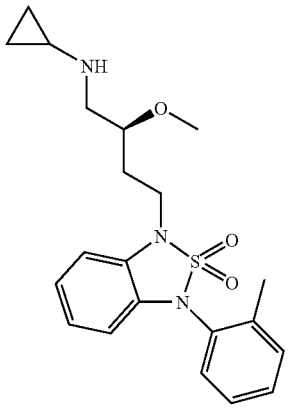

N-{(2S)-2-Methoxy-4-[3-(2-methylphenyl)-2,2-dioxido-2,1,3-benzothiadiazol-1(3H)-yl]butyl}cyclopropanamine was prepared using (2S)-1-(cyclopropylamino)-4-[3-(2-methylphenyl)-2,2-dioxido-2,1,3-benzothiadiazol-1(3H)-yl]butan-2-ol analogous to the conditions used in step 2 of example 120.

HRMS: calcd for C21H27N3O3S+H+, 402.1846; found (ESI, [M+H]+, 402.1847 calcd for C21H27N3O3S+Na+, 424.1665; found (ESI, [M+Na]+, 424.1661.

HPLC purity 100% at 210-370 nm, 8.3 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 128

N-{(2S)-2-methoxy-4-[3-(3-methoxyphenyl)-2,2-dioxido-2,1,3-benzothiadiazol-1(3H)-yl]butyl}cyclopropanamine

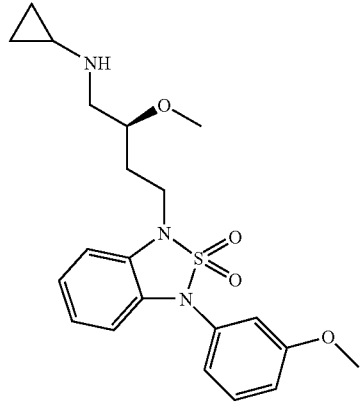

N-{(2S)-2-methoxy-4-[3-(3-methoxyphenyl)-2,2-dioxido-2,1,3-benzothiadiazol-1(3H)-yl]butyl}cyclopropanamine was prepared using (2S)-4-[3-(3-methoxyphenyl)-2,2-dioxido-2,1,3-benzothiadiazol-1(3H)-yl]-1-(methylamino)butan-2-ol analogous to the conditions used in step 2 of example 120.

HRMS: calcd for C21H27N3O4S+H+, 418.1795; found (ESI, [M+H]+, 418.1796 calcd for C21H27N3O4S+Na+, 440.1615; found (ESI, [M+Na]+, 440.1615.

HPLC purity 99.2% at 210-370 nm, 8.1 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 129

N-{(2S)-4-[3-(2,4-difluorophenyl)-2,2-dioxido-2,1,3-benzothiadiazol-1(3H)-yl]-2-methoxybutyl}cyclopropanamine

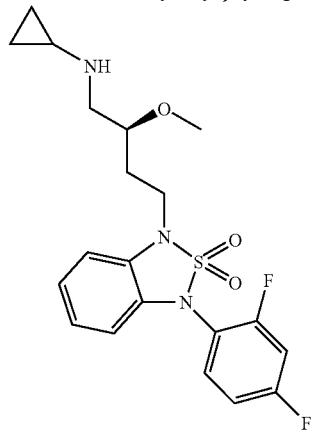

N-{(2S)-4-[3-(2,4-difluorophenyl)-2,2-dioxido-2,1,3-benzothiadiazol-1(3H)-yl]-2-methoxybutyl}cyclopropanamine was prepared using (2S)-

1-(cyclopropylamino)-4-[3-(2,4-difluorophenyl)-2,2-dioxido-2,1,3-benzothiadiazol-1(3H)-yl]butan-2-ol analogous to the conditions used in step 2 of example 120.

HRMS: calcd for C20H23F2N3O3S+H+, 424.1501; found (ESI, [M+H]+, 424.1500 calcd for C20H23F2N3O3S+Na+, 446.1320; found (ESI, [M+Na]+, 446.1320.

HPLC purity 83.5% at 210-370 nm, 8.0 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 130

N-{(2S)-4-[3-(2,5-difluorophenyl)-2,2-dioxido-2,1,3-benzothiadiazol-1(3H)-yl]-2-methoxybutyl}cyclopropanamine

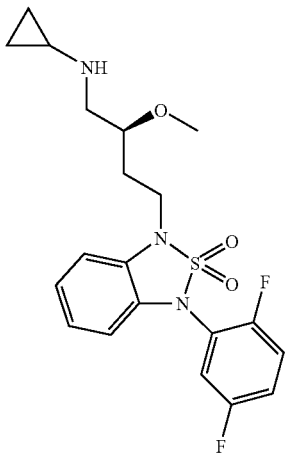

N-{(2S)-4-[3-(2,5-difluorophenyl)-2,2-dioxido-2,1,3-benzothiadiazol-1(3H)-yl]-2-methoxybutyl}cyclopropanamine was prepared using (2S)-1-(cyclopropylamino)-4-[3-(2,5-difluorophenyl)-2,2-dioxido-2,1,3-benzothiadiazol-1(3H)-yl]butan-2-ol analogous to the conditions used in step 2 of example 120.

HRMS: calcd for C20H23F2N3O3S+H+, 424.1501; found (ESI, [M+H]+, 424.1503 calcd for C20H23F2N3O3S+Na+, 446.1320; found (ESI, [M+Na]+, 446.1318.

HPLC purity 94.6% at 210-370 nm, 7.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 131

N-{(2S)-4-[3-(2,6-difluorophenyl)-2,2-dioxido-2,1,3-benzothiadiazol-1(3H)-yl]-2-methoxybutyl}cyclopropanamine

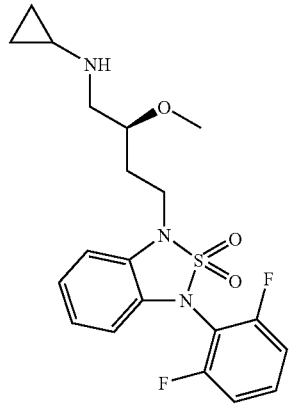

N-{(2S)-4-[3-(2,6-difluorophenyl)-2,2-dioxido-2,1,3-benzothiadiazol-1(3H)-yl]-2-methoxybutyl}cyclopropanamine was prepared using (2S)-1-(cyclopropylamino)-4-[3-(2,6-difluorophenyl)-2,2-dioxido-2,1,3-benzothiadiazol-1(3H)-yl]butan-2-ol analogous to the conditions used in step 2 of example 120.

HRMS: calcd for C20H23F2N3O3S+H+, 424.1501; found (ESI, [M+H]+, 424.1498 calcd for C20H23F2N3O3S+Na+, 446.1320; found (ESI, [M+Na]+, 446.1317.

HPLC purity 100% at 210-370 nm, 7.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 132

2S)-4-[3-(2,6-difluorophenyl)-2,2-dioxido-2,1,3-benzothiadiazol-1(3H)-yl]-2-methoxy-N-methylbutan-1-amine

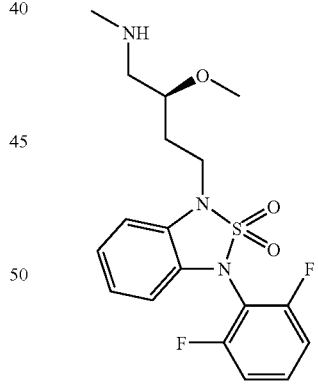

2S)-4-[3-(2,6-difluorophenyl)-2,2-dioxido-2,1,3-benzothiadiazol-1(3H)-yl]-2-methoxy-N-methylbutan-1-amine was prepared using (2S)-4-[3-(2,6-difluorophenyl)-2,2-dioxido-2,1,3-benzothiadiazol-1(3H)-yl]-1-(methylamino)butan-2-ol analogous to the conditions used in step 2 of example 120.

HRMS: calcd for C18H21F2N3O3S+H+, 398.1345; found (ESI, [M+H]+, 398.1346 calcd for C18H21F2N3O3S+Na+, 420.1164; found (ESI, [M+Na]+, 420.1165.

HPLC purity 95.6% at 210-370 nm, 7.1 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 133

(2S)-4-[3-(2,4-difluorophenyl)-2,2-dioxido-2,1,3-benzothiadiazol-1(3H)-yl]-2-methoxy-N-methylbutan-1-amine

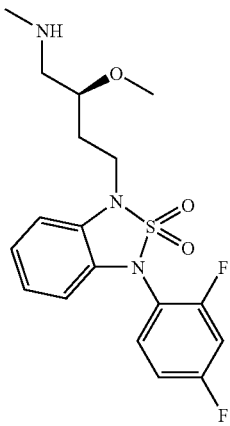

(2S)-4-[3-(2,4-difluorophenyl)-2,2-dioxido-2,1,3-benzothiadiazol-1(3H)-yl]-2-methoxy-N-methylbutan-1-amine was prepared using (2S)-4-[3-(2,4-difluorophenyl)-2,2-dioxido-2,1,3-benzothiadiazol-1(3H)-yl]-1-(methylamino)butan-2-ol analogous to the conditions used in step 2 of example 120.

HRMS: calcd for C18H21F2N3O3S+H+, 398.1345; found (ESI, [M+H]+, 398.1333 calcd for C18H21F2N3O3S+Na+, 420.1164; found (ESI, [M+Na]+, 420.1151.

HPLC purity 100% at 210-370 nm, 7.5 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 134

General Procedure II 1-(2-morpholin-2-ylethyl)-3-phenyl-1,3-dihydro-2,1,3-benzothiadiazole2,2-dioxide

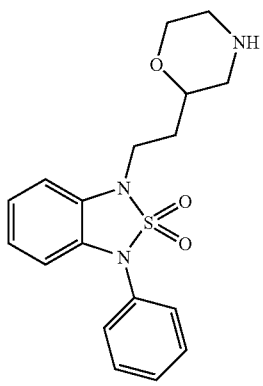

Step 1: To a solution of 1-phenyl-1,3-dihydro-2,1,3-benzothiadiazole2,2-dioxide (0.2 g, 0.8 mmol) in THF (10 mL) was added triphenylphosphine (0.26 g, 1 mmol), tert-butyl 2-(2-hydroxyethyl)morpholine-4-carboxylate (0.2 g, 0.9 mmol) and DIAD (0.2 g, 1 mmol) at 0° C. The mixture was allowed to warm to ambient temperature overnight then concentrated and chromatographed on silica gel (0 to 40% EtOAC in hexane). The resulting mostly pure carbamate was dissolved in dichloromethane (10 mL) and treated with HCL (4 mL, 4M in dioxane). The resulting salt was chromatographed on silica (0 to 100% of (7N NH3/MeOH) in dichloromethane) giving the desired product as a clear oil (0.23 g, 80%). HRMS: calcd for C18H21N3O3S+H+, 360.1376; found (ESI, [M+H]+), 360.1377.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 135

General Procedure III

1-{2-[(2S)-morpholin-2-yl]ethyl}-3-phenyl-1,3-dihydro-2,1,3-benzothiadiazole2,2-dioxide

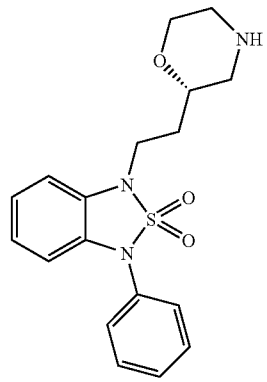

1-(2-morpholin-2-ylethyl)-3-phenyl-1,3-dihydro-2,1,3-benzothiadiazole2,2-dioxide was dissolved in methanol. 200 uL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AS-H 5 um, 250 mm×4.6 mm ID column at 2.0 mL/min flow rate using Analytical Supercritical Fluid Chromatography (Berger Instruments, Inc. Newark, Del.). Both enantiomers were found to be >99.9% enantiomerically pure.

| | |
|---|---|
| SFC Instrument: | Berger MultiGram Prep SFC (Berger Instruments, Inc. Newark, DE) |
| Column: | Chiralpak AS-H; 5 m; 250 mm L × 20 mm ID (Chiral Technologies, Inc, Exton, PA) |
| Column temperature: | 35° C. |
| SFC Modifier: | 18% MeOH w 0.2% DMEA |
| Flow rate: | 50 mL/min |
| Outlet Pressure: | 100 bar |
| Detector: | UV at 220 nm. |

HRMS: calcd for C18H21N3O3S+H+, 360.1376; found (ESI, [M+H]+), 360.1378.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 136

1-{2-[(2R)-morpholin-2-yl]ethyl}-3-phenyl-1,3-dihydro-2,1,3-benzothiadiazole2,2-dioxide

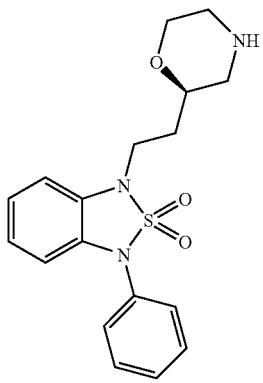

This compound was prepared from 1-(2-morpholin-2-ylethyl)-3-phenyl-1,3-dihydro-2,1,3-benzothiadiazole2,2-dioxide as described in example 135.

HRMS: calcd for C18H21N3O3S+H+, 360.1376; found (ESI, [M+H]+), 360.1379.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min

Example 137

1-(4-fluorophenyl)-3-(2-morpholin-2-ylethyl)-1,3-dihydro-2,1,3-benzothiadiazole 2,2-dioxide

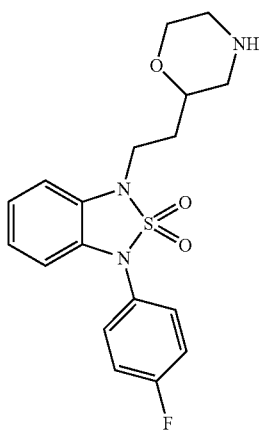

This compound was prepared using 1-(4-fluorophenyl)-1,3-dihydro-2,1,3-benzothiadiazole2,2-dioxide analogous to the conditions used in general procedure II.

HRMS: calcd for C18H20FN3O3S+H+, 378.1282; found (ESI, [M+H]+), 378.1283.

HPLC purity 99.4% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 138

1-(4-fluorophenyl)-3-{2-[(2S)-morpholin-2-yl]ethyl}-1,3-dihydro-2,1,3-benzothiadiazole2,2-dioxide

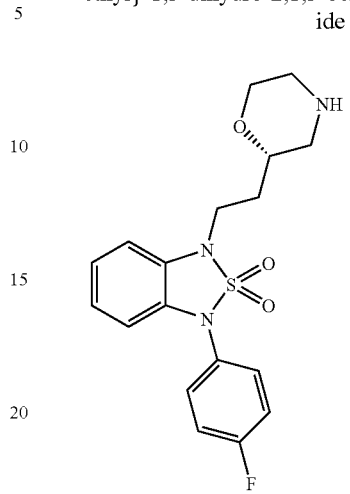

This compound was prepared using 1-(4-fluorophenyl)-3-(2-morpholin-2-ylethyl)-1,3-dihydro-2,1,3-benzothiadiazole2,2-dioxide analogous to the conditions used in general procedure III.

HRMS: calcd for C18H20FN3O3S+H+, 378.1282; found (ESI, [M+H]+), 378.1271.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 139

1-(4-fluorophenyl)-3-{2-[(2R)-morpholin-2-yl]ethyl}-1,3-dihydro-2,1,3-benzothiadiazole2,2-dioxide

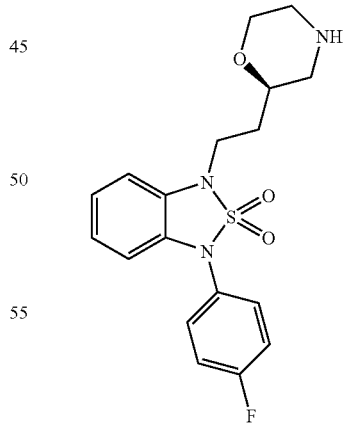

This compound was prepared using 1-(4-fluorophenyl)-3-(2-morpholin-2-ylethyl)-1,3-dihydro-2,1,3-benzothiadiazole2,2-dioxide analogous to the conditions used in general procedure II.

HRMS: calcd for C18H20FN3O3S+H+, 378.1282; found (ESI, [M+H]+), 378.1272.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 140

1-(2,4-difluorophenyl)-3-(2-morpholin-2-ylethyl)-1,3-dihydro-2,1,3-benzothiadiazole2,2-dioxide

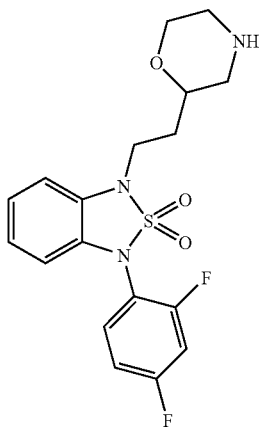

This compound was prepared using 1-(2,4-difluorophenyl)-1,3-dihydro-2,1,3-benzothiadiazole2,2-dioxide analogous to the conditions used in general procedure II.

HRMS: calcd for C18H19F2N3O3S+H+, 396.1189; found (ESI, [M+H]+), 396.1189.

HPLC purity 98.8% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 141

1-(2,4-difluorophenyl)-3-{2-[(2S)-morpholin-2-yl]ethyl}-1,3-dihydro-2,1,3-benzothiadiazole2,2-dioxide

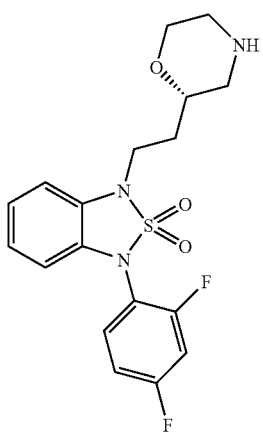

This compound was prepared using 1-(2,4-difluorophenyl)-3-(2-morpholin-2-ylethyl)-1,3-dihydro-2,1,3-benzothiadiazole2,2-dioxide analogous to the conditions used in general procedure III.

HRMS: calcd for C18H19F2N3O3S+H+, 396.1189; found (ESI, [M+H]+), 396.1178.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 142

1-(2,4-difluorophenyl)-3-{2-[(2R)-morpholin-2-yl]ethyl}-1,3-dihydro-2,1,3-benzothiadiazole2,2-dioxide

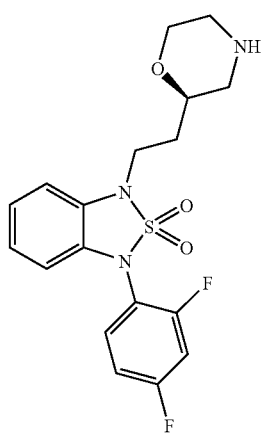

This compound was prepared using 1-(2,4-difluorophenyl)-3-(2-morpholin-2-ylethyl)-1,3-dihydro-2,1,3-benzothiadiazole2,2-dioxide analogous to the conditions used in general procedure III.

HRMS: calcd for C18H19F2N3O3S+H+, 396.1189; found (ESI, [M+H]+), 396.1178.

HPLC purity 98.6% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 143

1-(2-morpholin-2-ylethyl)-3-(2,4,6-trifluorophenyl)-1,3-dihydro-2,1,3-benzothiadiazole2,2-dioxide

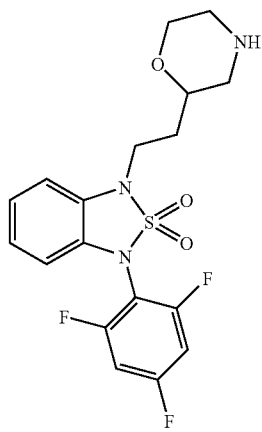

This compound was prepared using 1-(2,4,6-trifluorophenyl)-1,3-dihydro-2,1,3-benzothiadiazole2,2-dioxide analogous to the conditions used in general procedure II.

HRMS: calcd for C18H18F3N3O3S+H+, 414.1094; found (ESI, [M+H]+), 414.1096.

HPLC purity 98.8% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 144

1-{2-[(2S)-morpholin-2-yl]ethyl}-3-(2,4,6-trifluorophenyl)-1,3-dihydro-2,1,3-benzothiadiazole2,2-dioxide

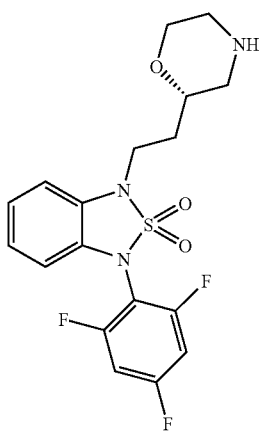

This compound was prepared using 1-(4-fluorophenyl)-3-(2-morpholin-2-ylethyl)-1,3-dihydro-2,1,3-benzothiadiazole2,2-dioxide analogous to the conditions used in general procedure III.

HRMS: calcd for C18H18F3N3O3S+H+, 414.1094; found (ESI, [M+H]+), 414.1081.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 145

1-{2-[(2R)-morpholin-2-yl]ethyl}-3-(2,4,6-trifluorophenyl)-1,3-dihydro-2,1,3-benzothiadiazole2,2-dioxide

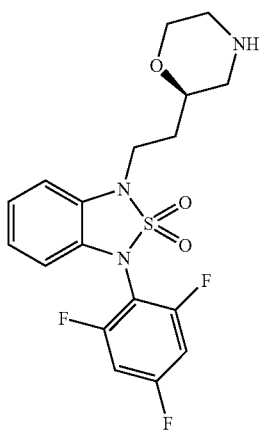

This compound was prepared using 1-(4-fluorophenyl)-3-(2-morpholin-2-ylethyl)-1,3-dihydro-2,1,3-benzothiadiazole2,2-dioxide analogous to the conditions used in general procedure III.

HRMS: calcd for C18H18F3N3O3S+H+, 414.1094; found (ESI, [M+H]+), 414.1080.

HPLC purity 95.3% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 146

1-(3-methoxyphenyl)-3-{2-[(2S)-morpholin-2-yl]ethyl}-1,3-dihydro-2,1,3-benzothiadiazole2,2-dioxide

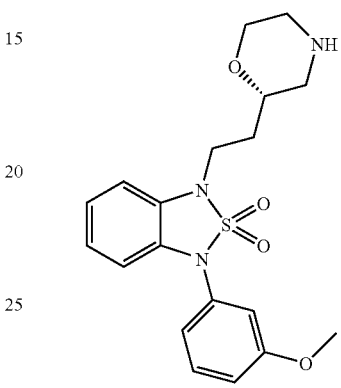

This compound was prepared using 1-(3-methoxyphenyl)-1,3-dihydro-2,1,3-benzothiadiazole2,2-dioxide analogous to the conditions used in general procedures II and III.

HRMS: calcd for C19H23N3O4S+H+, 390.1482; found (ESI, [M+H]+), 390.1472.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 147

1-(3-methoxyphenyl)-3-{2-[(2R)-morpholin-2-yl]ethyl}-1,3-dihydro-2,1,3-benzothiadiazole2,2-dioxide

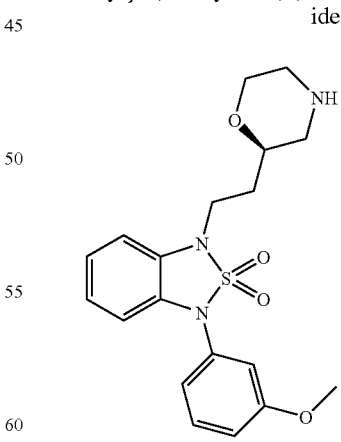

This compound was prepared using 1-(3-methoxyphenyl)-1,3-dihydro-2,1,3-benzothiadiazole2,2-dioxide analogous to the conditions used in general procedures II and III.

HRMS: calcd for C19H23N3O4S+H+, 390.1482; found (ESI, [M+H]+), 390.1472.

Example 148

1-(2-fluorophenyl)-3-{2-[(2S)-morpholin-2-yl]ethyl}-1,3-dihydro-2,1,3-benzothiadiazole2,2-dioxide

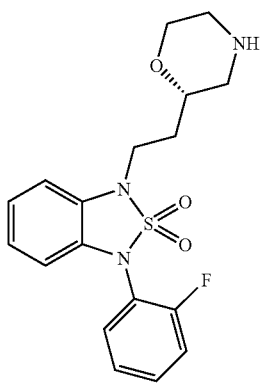

This compound was prepared using 1-(2-fluorophenyl)-1,3-dihydro-2,1,3-benzothiadiazole2,2-dioxide analogous to the conditions used in general procedure II and III.

HRMS: calcd for C18H20FN3O3S+H+, 378.1282; found (ESI, [M+H]+), 378.1272.

HPLC purity 97% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 149

1-(2-fluorophenyl)-3-{2-[(2R)-morpholin-2-yl]ethyl}-1,3-dihydro-2,1,3-benzothiadiazole2,2-dioxide

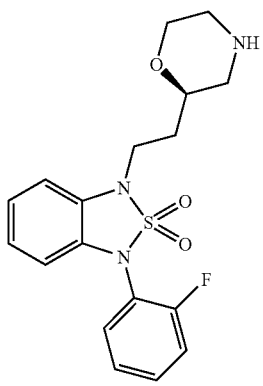

This compound was prepared using 1-(2-fluorophenyl)-1,3-dihydro-2,1,3-benzothiadiazole2,2-dioxide analogous to the conditions used in general procedure II and III.

HRMS: calcd for C18H20FN3O3S+H+, 378.1282; found (ESI, [M+H]+), 378.1273.

HPLC purity 92.9% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 150

1-(2,6-difluorophenyl)-3-{2-[(2S)-morpholin-2-yl]ethyl}-1,3-dihydro-2,1,3-benzothiadiazole2,2-dioxide

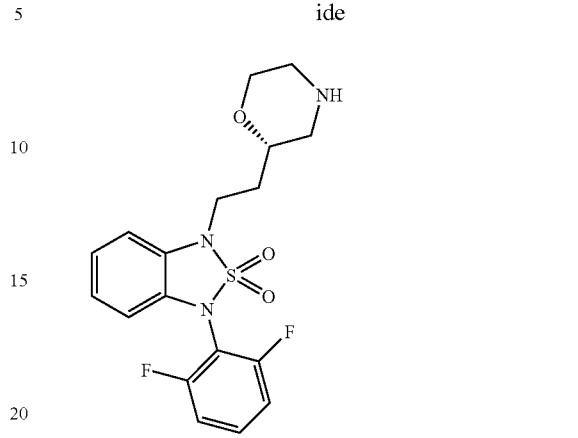

This compound was prepared using 1-(2,6-difluorophenyl)-1,3-dihydro-2,1,3-benzothiadiazole2,2-dioxide analogous to the conditions used in general procedures II and III.

HRMS: calcd for C18H19F2N3O3S+H+, 396.1188; found (ESI, [M+H]+), 396.1178.

HPLC purity 100% at 210-370 nm, 6.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 151

1-(3-{[3-(2-fluorophenyl)-2,2-dioxido-2,1,3benzothiadiazol-1(3H)-yl]methyl}Phenyl)-N-methylmethanamine

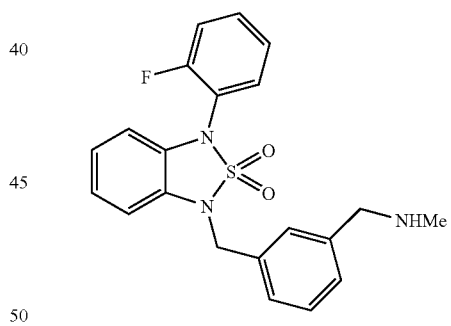

Step 1: In an analogous manner to general procedure IV, 1-(2-fluorophenyl)-1,3-dihydro-2,1,3-benzothiadiazole2,2-dioxide (0.20 g, 0.75 mmol) was treated with cesium carbonate (0.24 g, 0.75 mmol) and 1,3-bis(bromomethyl)benzene) (0.80 g, 3.00 mmol) to provide 0.23 g (70%) of 1-[3-(bromomethyl)benzyl]-3-(2-fluorophenyl)-1,3-dihydro-2,1,3-benzothiadiazole2,2-dioxide. MS (ES) m/z 446.7; HPLC purity 98.5% at 210-370 nm, 10.8 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min Step 2: In an analogous manner to general procedure V, 1-[3(bromomethyl)benzyl]-3-(2-fluorophenyl)-1,3-dihydro-2,1,3-benzothiadiazole2,2-dioxide (0.08 g, 0.18 mmol) was treated with methylamine (10 mL) to provide 0.05 g (71%) of 1-(3-{[3-(2-fluorophenyl)-2,2-dioxido-2,1,3-benzothiadiazol-1(3H)-yl]methyl}phenyl)-N-methylmethanamine.

HRMS: calcd for $C_{21}H_{20}FN_3O_2S+H+$, 398.13330; found (ESI, [M+H]+), 398.1337; HPLC purity 95.4% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 152

1-(3-{[3-(2-fluorophenyl)-2,2-dioxido-2,1,3-benzothiadiazol-1(3H)-yl]methyl}phenyl)methanamine

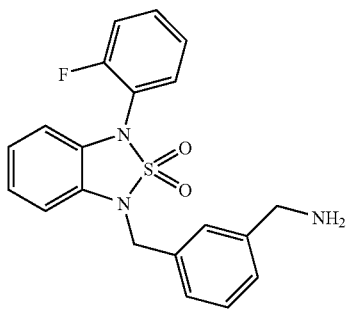

In an analogous manner to general procedure V, 1-[3-(bromomethyl)benzyl]-3-(2-fluorophenyl)-1,3-dihydro-2,1,3-benzothiadiazole2,2-dioxide (0.08 g, 0.18 mmol) was treated with ammonia (10 mL) to prepare 0.05 g (78%) of 1-(3-{[3-(2-fluorophenyl)-2,2-dioxido-2,1,3-benzothiadiazol-1(3H) yl]methyl}phenyl)methanamine. HRMS: calcd for $C_{20}H_{18}FN_3O_2S+H+$, 384.11765; found (ESI, [M+H]+), 384.1181; HPLC purity 100.0% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 153

1-(3-{[3-(2-fluorophenyl)-2,2-dioxido-2,1,3-benzothiadiazol-1(3H)-yl]methyl}phenyl)-N,N-dimethylmethanamine

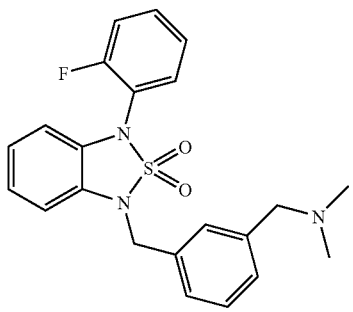

In an analogous manner to general procedure V, 1-[3-(bromomethyl)benzyl]-3-(2-fluorophenyl)-1,3-dihydro-2,1,3-benzothiadiazole2,2-dioxide (0.07 g, 0.18 mmol) was treated with dimethylamine (10 mL) to provide 0.03 g (39%) of 1-(3-{[3-(2-fluorophenyl)-2,2-dioxido-2,1,3-benzothiadiazol-1(3H)-yl]methyl}phenyl)-N,N-dimethylmethanamine. HRMS: calcd for $C_{22}H_{22}FN_3O_2S+H+$, 412.14895; found (ESI, [M+H]+), 412.1493; HPLC purity 96.3% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 154

1-(4-{[3-(2-fluorophenyl)-2,2-dioxido-2,1,3-benzothiadiazol-1(3H)-yl]methyl}phenyl)-N,N-dimethylmethanamine

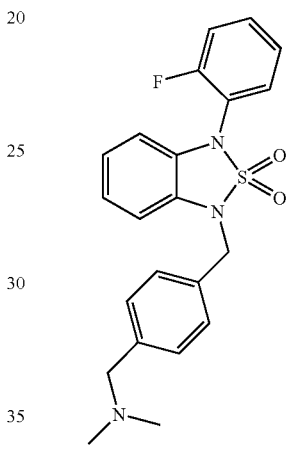

Step 1: Diisopropyl azodicarboxylate (0.34 mL, 1.77 mmol) was added to a solution of 1-(2-fluorophenyl)-1,3-dihydro-2,1,3-benzothiadiazole2,2-dioxide (0.39 g, 1.47 mmol), 4-(bromomethyl)phenyl)methanol (0.3 g, 1.47 mmol) and triphenylphosphine (0.46 g, 1.77 mmol) in dry THF (2 mL) under nitrogen. The solution was stirred overnight at room temperature. The reaction was concentrated in vacuo to provide the crude product. The crude product was pre-adsorbed onto Celite and purified via Isco chromatography (Redisep, silica gel, gradient 5-50% ethyl acetate in hexane) to afford 0.34 g (52%) of 1-[4-(bromomethyl)benzyl]-3-(2-fluorophenyl)-1,3-dihydro-2,1,3-benzothiadiazole2,2-dioxide. HRMS: calcd for $C_{20}H_{16}BrFN_2O_2S+H+$, 447.01726; found (ESI, [M+H]+), 447.0172; HPLC purity 95.2% at 210-370 nm, 10.8 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 2: In an analogous manner to general procedure V, 1-[4-(bromomethyl)benzyl]-3-(2-fluorophenyl)-1,3-dihydro-2,1,3-benzothiadiazole2,2-dioxide (0.11 g, 0.24 mmol) was treated with dimethylamine (10 mL) to provide 0.09 g, (92%) of 1-(4-{[3-(2-fluorophenyl)-2,2-dioxido-2,1,3-benzothiadiazol-1(3H)-yl]methyl}phenyl)-N,N-dimethylmethanamine. MS (ES) m/z 411.0. HPLC purity 97.3% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 155

1-(4-{[3-(2-fluorophenyl)-2,2-dioxido-2,1,3-benzothiadiazol-1(3H)-yl]methyl}phenyl)methanamine

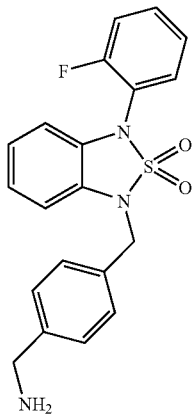

In an analogous manner to general procedure V, 1-[4-(bromomethyl)benzyl]-3-(2-fluorophenyl)-1,3-dihydro-2,1,3-benzothiadiazole2,2-dioxide (0.11 g, 0.24 mmol) was treated with ammonia (10 mL) to provide 0.09 g, (100%) of 1-(4-{[3-(2-fluorophenyl)-2,2-dioxido-2,1,3-benzothiadiazol-1(3H-yl]methyl}phenyl)methanamine. MS (ES) m/z 383.0. HPLC purity 100.0% at 210-370 nm, 7.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 156

1-(4-{[3-(2-fluorophenyl)-2,2-dioxido-2,1,3-benzothiadiazol-1(3H)-yl]methyl}phenyl)-N-methylmethanamine

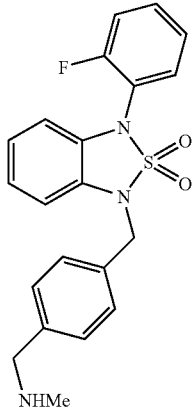

In an analogous manner to general procedure V, 1-[4-(bromomethyl)benzyl]-3-(2-fluorophenyl)-1,3-dihydro-2,1,3-benzothiadiazole2,2-dioxide (0.11 g, 0.24 mmol) was treated with methylamine (10 mL) to provide 0.09 g, (100%) of 1-(4-{[3-(2-fluorophenyl)-2,2-dioxido-2,1,3-benzothiadiazol-1(3H)-yl]methyl}phenyl)-N-methylmethanamine. MS (ES) m/z 397.0. HPLC purity 100.0% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 157

(2Z)-4-[3-(2-fluoro-4-methylphenyl)-2,2-dioxido-2,1,3-benzothiadiazol-1(3H)-yl]-N-methylbut-2-en-1-amine

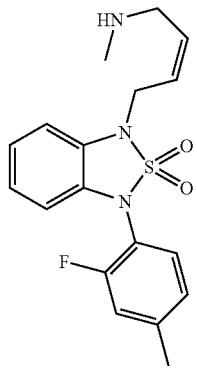

Step 1: A solution of 2-fluoro-4-methylaniline (6.8 mL, 60 mmol) in tetrahydrofuran (200 mL) was cooled to −78° C. and treated with n-butyllithium (26 mL of a 2.5 M solution in hexanes, 66 mmol) and stirred for 1 h. A solution of 2-fluoronitrobenzene (6.3 mL, 60 mmol) in tetrahydrofuran (20 mL) was added dropwise over 5 min, and the reaction mixture was stirred at −78° C. for 0.5 h, then warmed to 22° C. After 16 h, the reaction mixture was concentrated, diluted with ethyl ether (200 mL), washed with 2 M hydrochloric acid (200 mL), dried ($Na_2SO_4$), and concentrated to a black oil. A solution of this black oil in a mixture of methanol (100 mL) and ethyl acetate (100 mL) was treated with 10% palladium on carbon (1 g) and stirred under a hydrogen atmosphere at 65 psi for 2 h, and then the reaction mixture was filtered, and concentrated. Flash chromatography ($SiO_2$, 10→100% dichloromethane/hexanes) provided N-(2-fluoro-4-methylphenyl)benzene-1,2-diamine (7.0 g) as an orange solid:

HPLC purity 92.2% at 210-370 nm, 9.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C13H13FN2+H+, 217.11355; found (ESI, [M+H]+), 217.113.

Step 2: A solution of N-(2-fluoro-4-methylphenyl)benzene-1,2-diamine (3.9 g, 18 mmol) in diglyme (36 mL) was treated with sulfamide (2.1 g, 22 mmol) and added dropwise over 10 min to a refluxing solution of sulfamic acid (0.9 g, 9 mmol) in diglyme (36 mL), and the reaction mixture was kept at reflux for an additional 15 minutes, then cooled to room temperature and concentrated. The residue was dissolved in ethyl ether (300 mL), washed with 2 N hydrochloric acid (100 mL), evaporated, and flash chromatographed ($SiO_2$, 050% ethyl acetate/hexanes) provided 1-(2-fluoro-4-methylphenyl)-1,3-dihydro-2,1,3-benzothiadiazole2,2-dioxide (2.6 g) as a red solid:

HPLC purity 98.0% at 210-370 nm, 9.1 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C13H11FN2O2S+H+, 279.05980; found (ESI, [M+H]+), 301.0421.

Step 3: A solution of -(2-fluoro-4-methylphenyl)-1,3-dihydro-2,1,3-benzothiadiazole2,2-dioxide (0.5 g, 1.8 mmol) in dimethylformamide (15 mL) was treated with cesium carbonate (1.2 g, 3 mmol) and cis-1,4-dichloro-2-butene (3.2 mL, 20 mmol) and stirred at 22° C. for 14 h. The reaction mixture was diluted with ethyl ether (100 mL), washed with 2 M hydrochloric acid (100 mL) and concentrated. Flash chromatography (SiO$_2$, 10→50% ethyl acetate/hexanes) provided 1-[(2Z)-4-chlorobut-2-en-1-yl]-3-(2-fluoro-4-methylphenyl)-1,3-dihydro-2,1,3-benzothiadiazole2,2-dioxide (0.5 g) as a yellow oil:

MS (ES) m/z 366.9.

HPLC purity 98.2% at 210-370 nm, 10.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 4: A solution of 1-[(2Z)-4-chlorobut-2-en-1-yl]-3-(2-fluoro-4-methylphenyl)-1,3-dihydro-2,1,3-benzothiadiazole2,2-dioxide (0.1 g) was stirred in an 8 M methylamine-ethanol solution at 22° C. for 16 h. The reaction mixture was concentrated under reduced pressure to provide (2Z)-4-[3-(2-fluoro-4-methylphenyl)-2,2-dioxido-2,1,3-benzothiadiazol-1(3H)-yl]-N-methylbut-2-en-1-amine hydrochloride (0.12 g) as a white solid:

HPLC purity 97.7% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C18H20FN3O2S+H+, 362.13330; found (ESI, [M+H]+Obs'd), 362.1337.

Example 158

(2Z)-4-[3-(2-fluoro-4-methylphenyl)-2,2-dioxido-2,1,3-benzothiadiazol-1(3H)-yl]but-2-en-1-amine

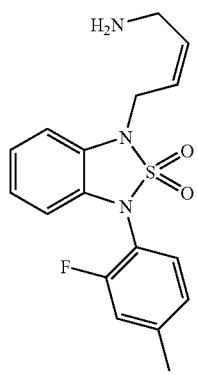

In an analogous manner to general procedure V, 1-[(2Z)-4-chlorobut-2-en-1-yl]-3-(2-fluoro-4-methylphenyl)-1,3-dihydro-2,1,3-benzothiadiazole2,2-dioxide was reacted with ammonia to provide (2Z)-4-[3-(2-fluoro-4-methylphenyl)-2,2-dioxido-2,1,3-benzothiadiazol-1(3H)-yl]but-2-en-1-amine hydrochloride:

HPLC purity 92.1% at 210-370 nm, 7.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min. HRMS: calcd for C17H18FN3O2S+H+, 348.11765; found (ESI, [M+H]+Obs'd), 348.1182.

Example 159

(2Z)-4-[3-(2-fluoro-4-methylphenyl)-2,2-dioxido-2,1,3-benzothiadiazol-1(3H)-yl]-N,N-dimethylbut-2-en-1-amine

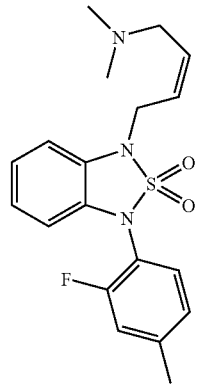

In an analogous manner to general procedure V, 1-[(2Z)-4-chlorobut-2-en-1-yl]-3-(2-fluoro-4-methylphenyl)-1,3-dihydro-2,1,3-benzothiadiazole2,2-dioxide was reacted with dimethylamine to provide (2Z)-4-[3-(2-fluoro-4-methylphenyl)-2,2-dioxido-2,1,3-benzothiadiazol-1(3H)-yl]-N,N-dimethylbut-2-en-1-amine hydrochloride:

HPLC purity 100.0% at 210-370 nm, 7.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 160

(2Z)-N-ethyl-4-[3-(2-fluoro-4-methylphenyl)-2,2-dioxido-2,1,3-benzothiadiazol-1(3H)-yl]but-2-en-1-amine

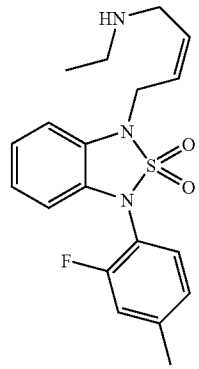

In an analogous manner to general procedure V, 1-[(2Z)-4-chlorobut-2-en-1-yl]-3-(2-fluoro-4-methylphenyl)-1,3-dihydro-2,1,3-benzothiadiazole2,2-dioxide was reacted with ethylamine to provide (2Z)-N-ethyl-4-[3-(2-fluoro-4-methylphenyl)-2,2-dioxido-2,1,3-benzothiadiazol-1(3H)-yl]but-2-en-1-amine hydrochloride:

HPLC purity 98.6% at 210-370 nm, 7.9 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C19H22FN3O2S+H+, 376.14895; found (ESI, [M+H]+Obs'd), 376.1495.

Example 161

1-(3,4-difluorophenyl)-3-(2-piperazin-1-ylethyl)-1,3-dihydro-2,1,3-benzothiadiazole2,2-dioxide

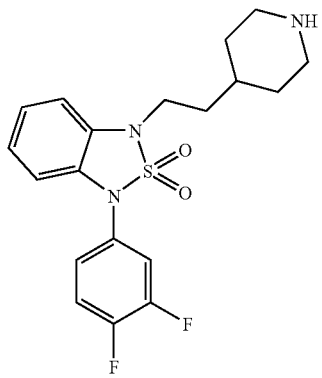

Step 1: A solution of 3,4-difluoroaniline (10.0 mL, 1.0 mol) in tetrahydrofuran (200 mL) was cooled to −78° C., treated with n-butyllithium solution (44 mL of a 2.5 M hexanes solution, 1.1 mol), stirred at −78° C. for 1 h and then warmed to 0° C. for 30 min. The reaction mixture was cooled to −78° C. and 1-fluoro-2-nitrobenzene (9.5 mL, 0.9 mol) in tetrahydrofuran (10 mL) was slowly added and the reaction, after which the reaction was warmed to room temperature. The reaction mixture was evaporated to provide 3,4-difluoro-N-(2-nitrophenyl)aniline (22.76 g, 91%) as a brown solid. The crude product was taken on to the next step.

Step 2: A solution of 3,4-difluoro-N-(2-nitrophenyl)aniline (22.76 g, 91 mmol) in 50% ethyl acetate/methanol (500 mL) was treat with palladium on carbon 10 w. % loading, matrix activated carbon support (3.07 g). The reaction mixture was placed on the Parr shaker for 3 h at 60 psi. The reaction mixture was filtered through celite and evaporated. The crude reaction product was purified by flash chromatography (SiO$_2$, 3→50% ethyl acetate/heptane) to provided N-(3,4-difluorophenyl)benzene-1,2-diamine (10.17 g, 51%) as a brown solid: HPLC purity 99.9% at 210-370 nm, 9.4 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C12H10F2N2+H+, 221.08848; found (ESI, [M+H]+), 221.0887;

Step 3: Dry diglyme (10 mL) was added to a flask equipped with a dropping funnel under a nitrogen atmosphere and brought to a vigorous reflux. N-(3,4-difluorophenyl)benzene-1,2-diamine (1.03 g, 4.7 mmol) and sulfamide (0.54 g, 5.6 mmol) were dissolved in 5 mL of diglyme and placed in the dropping funnel. The mixture was added dropwise to the flask over 15 minutes and then refluxing was continued for an additional 15 minutes. The mixture was cooled to ambient temperature and the reaction mixture was evaporated using high temperature. The crude reaction product was purified by flash chromatography (SiO$_2$, 3-50% ethyl acetate/hexane) to provide 1-(3,4-difluorophenyl)-1,3-dihydro-2,1,3-benzothiadiazole2,2-dioxide (0.62 g, 47%) as a pink solid:

MS (ES) m/z 280.8;

HPLC purity 95.7% at 210-370 nm, 9.0 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 4: A solution of 1-(3,4-difluorophenyl)-1,3-dihydro-2,1,3-benzothiadiazole2,2-dioxide (0.29 g, 1.0 mmol) in tetrahydrofuran (10 mL) was cooled to 0° C., treated with triphenylphosphine (0.41 g, 1.5 mmol), tert-Butyl 4-(2-hydroxyethyl)piperazine-1-carboxylate (0.47 g, 2.1 mmol) were added followed by diisopropylazodicarboxylate (0.3 mL, 1.5 mmol). The reaction mixture stirred for 2 hours at ambient temperature and then was evaporated. The crude reaction product was purified by flash chromatography (SiO$_2$, 3-70% ethyl acetate/hexane) to provide tert-butyl 4-{2-[3-(3,4-difluorophenyl)-2,2-dioxido-2,1,3-benzothiadiazol-1(3H)-yl]ethyl}piperazine-1-carboxylate (0.39 g, 76%) as a pink solid:

MS (ES) m/z 494.9;

HPLC purity 96.9% at 210-370 nm, 10.8 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 5: A solution of tert-butyl 4-{2-[3-(3,4-difluorophenyl)-2,2-dioxido-2,1,3-benzothiadiazol-1(3H)-yl]ethyl}piperazine-1-carboxylate (0.34 g, 0.69 mmol) in dichloromethane (5 mL) was treated with hydrogen chloride (2.0 mL of a 4 M solution in dioxane), resulting in a white precipitate that was evaporated and dried under vacuum to provided 1-(3,4-difluorophenyl)-3-(2-piperazin-1-ylethyl)-1,3-dihydro-2,1,3-benzothiadiazole2,2-dioxide (0.2 g, 74%) as a white solid:

MS (ES) m/z 394.9;

HPLC purity 99.1% at 210-370 nm, 7.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Example 162

1-(3,4-difluorophenyl)-3-(3-piperazin-1-ylpropyl)-1,3-dihydro-2,1,3-benzothiadiazole2,2-dioxide

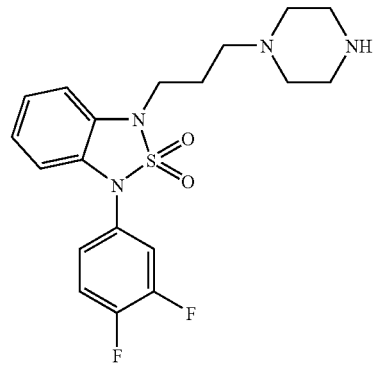

Step 1: A solution of 1-(3-bromopropyl)-3-(3,4-difluorophenyl)-1,3-dihydro-2,1,3-benzothiadiazole2,2-dioxide (0.2, 0.5 mmol) in anhydrous dimethylformamide (3 mL) was treated with tert-butyl piperazine-1-carboxylate (0.19 g, 1 mmol) and N,N-diisopropylethylamine (0.17 mL, 1 mmol). The reaction mixture stirred at ambient for 48 h. The reaction mixture was diluted with ethyl ether (10 mL) and washed with H$_2$O (2×10 mL), the organic layer was isolated, dried with MgSO$_4$ and evaporated. The crude reaction product was purified by flash chromatography (SiO$_2$, 3-50% ethyl acetate/hexane) to provided tert-butyl 4-{3-[3-(3,4-difluorophenyl)-2,2-dioxido-2,1,3-benzothiadiazol-1(3H)-yl]propyl}piperazine-1-carboxylate (0.17 g, 67%) as a white solid:

MS (ES) m/z 508.9;

HPLC purity 98.4% at 210-370 nm, 9.3 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 2: A solution of tert-butyl 4-{3-[3-(3,4-difluorophenyl)-2,2-dioxido-2,1,3-benzothiadiazol-1(3H)-yl]propyl}piperazine-1-carboxylate (0.16 g, 0.3 mmol) in dichloromethane (10 mL) was treated with hydrogen chloride (6.0 mL of a 4 M solution in dioxane), resulting in a white precipitate that was evaporated and dried under vacuum to provided 1-(3,4-difluorophenyl)-3-(3-piperazin-1-ylpropyl)-1,3-dihydro-2,1,3-benzothiadiazole2,2-dioxide (0.11 g, 81%) as a white solid:

HPLC purity 96.8% at 210-370 nm, 7.8 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C19H22F2N4O2S+H+, 409.15043; found (ESI, [M+H]+Obs'd), 409.1506;

HRMS: calcd for C19H22F2N4O2S+H+, 409.15043; found (ESI, [M+H]+ Calc'd), 409.1504.

Example 163

1-(3,4-difluorophenyl)-3-[3-(3,5-dimethylpiperazin-1-yl)propyl]-1,3-dihydro-2,1,3-benzothiadiazole2,2-dioxide

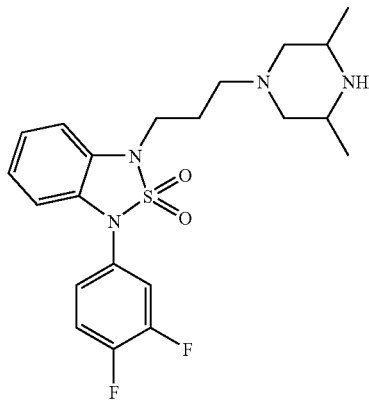

In an analogous manner as general procedure V, 1-(3-bromopropyl)-3-(3,4-difluorophenyl)-1,3-dihydro-2,1,3-benzothiadiazole2,2-dioxide (0.2, 0.51 mmol) was treated with 2,6-dimethylpiperazine (0.21 g, 1.8 mmol) to provide 1-(3,4-difluorophenyl)-3-[3-(3,5-dimethylpiperazin-1-yl)propyl]-1,3-dihydro-2,1,3-benzothiadiazole2,2-dioxide (0.19 g, 85%) as a white solid:

HPLC purity 100.0% at 210-370 nm, 8.2 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C21H26F2N4O2S+H+, 437.18173; found (ESI, [M+H]+Obs'd), 437.1829.

Example 164

2-{2-[3-(3,4-difluorophenyl)-2,2-dioxido-2,1,3-benzothiadiazol-1(3H)-yl]ethoxy}-N-methylethanamine

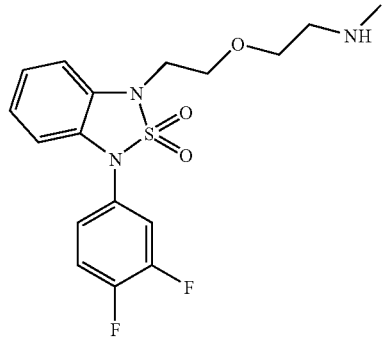

Step 1: In an analogous manner as general procedure V, 2-{2-[3-(3,4-difluorophenyl)-2,2-dioxido-2,1,3-benzothiadiazol-1(3H)-yl]ethoxy}-N-methylethanamine was prepared from 1-[2-(2-bromoethoxy)ethyl]-3-(3,4-difluorophenyl)-1,3-dihydro-2,1,3-benzothiadiazole2,2-dioxide as a white solid.

HPLC purity 98.0% at 210-370 nm, 7.6 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C17H19F2N3O3S+H+, 384.11879; found (ESI, [M+H]+Obs'd), 384.1186.

Example 165

1-(2-piperazin-1-ylethyl)-3-(2,3,4-trifluorophenyl)-1,3-dihydro-2,1,3-benzothiadiazole2,2-dioxide

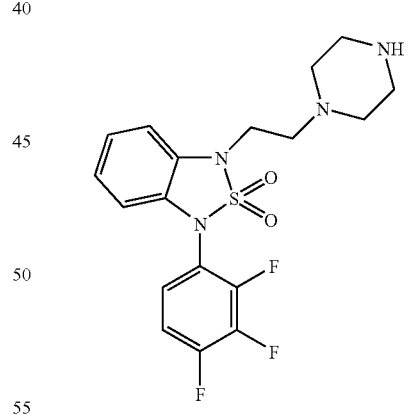

Step 1: In an analogous manner as general procedure 1,1-(2,3,4-trifluorophenyl)-1,3-dihydro-2,1,3-benzothiadiazole2,2-dioxide was prepared from 2,3,4-trifluoroaniline as a solid. MS (ES) m/z 298.7;

HPLC purity 83.7% at 210-370 nm, 9.0 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

Step 2: In an analogous manner as general VI, a solution of 1-(2,3,4-trifluorophenyl)-1,3-dihydro-2,1,3-benzothiadiazole2,2-dioxide (0.21 g, 0.7 mmol) in tetrahydrofuran (10 mL)

was cooled to 0° C., treated with triphenylphosphine (0.27 g, 1.0 mmol), tert-Butyl 4-(2-hydroxyethyl)piperazine-1-carboxylate (0.38 g, 1.4 mmol) were added followed by diisopropylazodicarboxylate (0.2 mL, 1.0 mmol to provide tert-butyl 4-{2-[2,2-dioxido-3-(2,3,4-trifluorophenyl)-2,1,3-benzothiadiazol-1(3H)-yl]ethyl}piperazine-1-carboxylate (0.22 g, 625) as white solid:

HPLC purity 95.5% at 210-370 nm, 10.5 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C23H27F3N4O4S+H+, 513.17779; found (ESI, [M+H]+Obs'd), 513.1799.

Step 3: In an analogous manner as general procedure II, step 2, a solution of tert-butyl 4-{2-[2,2-dioxido-3-(2,3,4-trifluorophenyl)-2,1,3-benzothiadiazol-1(3H)-yl]ethyl}piperazine-1-carboxylate (0.2 g, 0.39 mmol) in dichloromethane (5 mL) was treated with hydrogen chloride (2.0 mL of a 4 M solution in dioxane), resulting in a white precipitate that was evaporated and dried under vacuum to provided 3-[3-(3,4-difluorophenyl)-2,2-dioxido-2,1,3-benzothiadiazol-1(3H)-yl]-N-(2,2,2-trifluoroethyl)propan-1-amine (0.12 g, 77%) as a white solid. HPLC purity 99.5% at 210-370 nm, 7.6 min.; Xterra RP18, 3.5 u, 150×4.6 mm column, 1.2 mL/min, 85/15-5/95 (Ammon. Form. Buff.

Ph=3.5/ACN+MeOH) for 10 min, hold 4 min. HRMS: calcd for C18H19F3N4O2S+H+, 413.12536; found (ESI, [M+H]+Obs'd), 413.1259.

Example 166

1-(2-methylphenyl)-3-(2-piperazin-1-ylethyl)-1,3-dihydro-2,1,3-benzothiadiazole2,2-dioxide

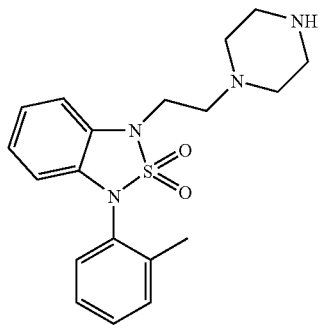

Step 1: In an analogous manner as general procedure II, step 1, a solution of 1-(2-methylphenyl)-1,3-dihydro-2,1,3-benzothiadiazole2,2-dioxide (0.2 g, 0.77 mmol) in tetrahydrofuran (10 mL) was cooled to 0° C., treated with triphenylphosphine (0.3 g, 1.2 mmol), tert-Butyl 4-(2-hydroxyethyl)piperazine-1-carboxylate (0.36 g, 1.54 mmol) were added followed by diisopropylazodicarboxylate (0.23 mL, 1.2 mmol to provide tert-butyl 4-{2-[3-(2-methylphenyl)-2,2-dioxido-2,1,3-benzothiadiazol-1(3H)-yl]ethyl}piperazine-1-carboxylate (0.25 g, 69%) as a white foam. HPLC purity 100.0% at 210-370 nm, 10.7 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min. HRMS: calcd for C24H32N4O4S+H+, 473.22170; found (ESI, [M+H]+Obs'd), 473.2229;

Step 2: In an analogous manner as general procedure II, step 2, a solution of tert-butyl 4-{2-[3-(2-methylphenyl)-2,2-dioxido-2,1,3-benzothiadiazol-1(3H)-yl]ethyl}piperazine-1-carboxylate (0.22 g, 0.47 mmol) in dichloromethane (10 mL) was treated with hydrogen chloride (3.0 mL of a 4 M solution in dioxane), resulting in a white precipitate that was evaporated and dried under vacuum to provided 1-(2-methylphenyl)-3-(2-piperazin-1-ylethyl)-1,3-dihydro-2,1,3-benzothiadiazole2,2-dioxide (0.16 g, 92%) as a white solid:

HPLC purity 99.0% at 210-370 nm, 7.5 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C19H24N4O2S+H+, 373.16927; found (ESI, [M+H]+Obs'd), 373.1692.

Example 167

1-(2-chlorophenyl)-3-(2-piperazin-1-ylethyl)-1,3-dihydro-2,1,3-benzothiadiazole 2,2-dioxide

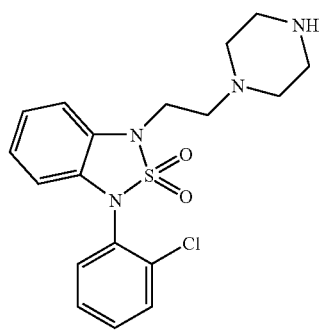

Step 1: In an analogous manner as general procedure II, step 1, a solution of 1-(2-chlorophenyl)-1,3-dihydro-2,1,3-benzothiadiazole2,2-dioxide (0.23 g, 0.8 mmol) in tetrahydrofuran (10 mL) was cooled to 0° C., treated with triphenylphosphine (0.32 g, 1.2 mmol), tert-Butyl 4-(2-hydroxyethyl)piperazine-1-carboxylate (0.37 g, 1.6 mmol) were added followed by diisopropylazodicarboxylate (0.23 mL, 1.2 mmol) to provide tert-butyl 4-{2-[3-(2-chlorophenyl)-2,2-dioxido-2,1,3-benzothiadiazol-1(3H)-yl]ethyl}piperazine-1-carboxylate (0.24 g, 61%) as a white foam:

HPLC purity 98.1% at 210-370 nm, 10.5 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C23H29ClN4O4S+H+, 493.16708; found (ESI, [M+H]+Obs'd), 493.1675.

Step 2: In an analogous manner as general procedure II, step 2, a solution of tert-butyl 4-{2-[3-(2-chlorophenyl)-2,2-dioxido-2,1,3-benzothiadiazol-1(3H)-yl]ethyl}piperazine-1-carboxylate (0.22 g, 0.45 mmol) in dichloromethane (10 mL) was treated with hydrogen chloride (3.0 mL of a 4 M solution in dioxane), resulting in a white precipitate that was evaporated and dried under vacuum to provided 1-(2-chlorophenyl)-3-(2-piperazin-1-ylethyl)-1,3-dihydro-2,1,3-benzothiadiazole2,2-dioxide (0.14 g, 81%) as a white solid:

HPLC purity 98.7% at 210-370 nm, 7.3 min.; Xterra RP18, 3.5 u, 150×4.6 mm column, 1.2 mL/min, 85/15-5/95 (Ammon. Form. Buff. Ph=3.5/ACN+MeOH) for 10 min, hold 4 min.

HRMS: calcd for C18H21ClN4O2S+H+, 393.11465; found (ESI, [M+H]+Obs'd), 393.1149.

Example 168

2-{2-[3-(2,4-difluorophenyl)-2,2-dioxido-2,1,3-benzothiadiazol-1(3H)-yl]ethoxy}-N-methylethanamine hydrochloride

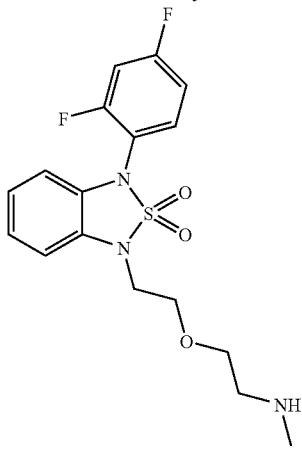

Step 1: In an analogous manner to general procedure IV, 1-(2,4-difluorophenyl)-1,3-dihydro-2,1,3-benzothiadiazole2,2-dioxide (2.07 g, 7.3 mmol) was treated with 1-bromo-2-(2-bromoethoxy)ethane (3.2 mL, 25.7 mmol) and cesium carbonate (2.4 g, 7.3 mmol) to give 1-[2-(2-bromoethoxy)ethyl]-3-(2,4-difluorophenyl)-1,3-dihydro-2,1,3-benzothiadiazole2,2-dioxide (1.72 g, 53%) as a white amorphous solid. MS (ES) m/z 368.7 [M+H—SO$_2$]$^+$.

Step 2: In an analogous manner to general procedure V, 1-[2-(2-bromoethoxy)ethyl]-3-(2,4-difluorophenyl)-1,3-dihydro-2,1,3-benzothiadiazole 2,2-dioxide (0.66 g, 1.5 mmol) was treated with 8N methylamine in methanol to give 2-{2-[3-(2,4-difluorophenyl)-2,2-dioxido-2,1,3-benzothiadiazol-1(3H)-yl]ethoxy}-N-methylethanamine which was treated with 1N hydrochloric acid in ether to afford its hydrochloride salt as a white solid (0.10 g, 16%). MS (ES) m/z 384.3 ([M+H]$^+$).

Example 169

2-{2-[3-(2,4-difluorophenyl)-2,2-dioxido-2,1,3-benzothiadiazol-1(3H)-yl]ethoxy}ethanamine hydrochloride

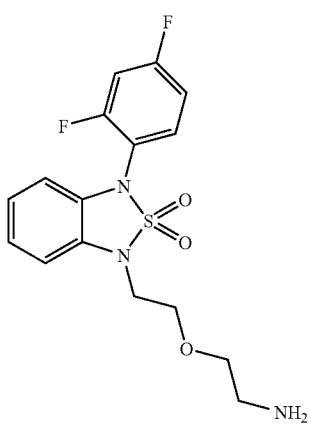

Step 1: In an analogous manner to general procedure V, 1-[2-(2-bromoethoxy)ethyl]-3-(2,4-difluorophenyl)-1,3-dihydro-2,1,3-benzothiadiazole 2,2-dioxide (0.53 g, 1.2 mmol) was treated with 7N ammonia in methanol to give 2-{2-[3-(2,4-difluorophenyl)-2,2-dioxido-2,1,3-benzothiadiazol-1(3H)-yl]ethoxy}ethanamine which was treated with 1N hydrochloric acid in ether to afford its hydrochloride salt as a white solid (0.042 g, 8.6%). MS (ES) m/z 369.9 ([M+H]$^+$).

Example 170

2-{2-[3-(2,4-difluorophenyl)-2,2-dioxido-2,1,3-benzothiadiazol-1(3H)-yl]ethoxy}-N,N-dimethylethanamine hydrochloride

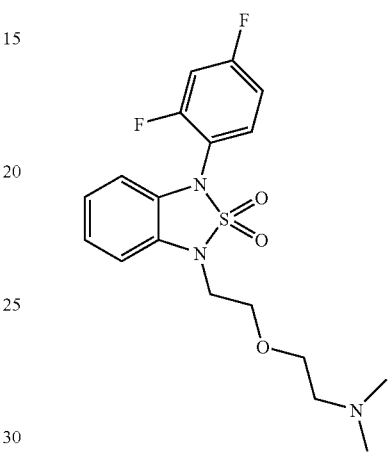

In an analogous manner to general procedure V, 1-[2-(2-bromoethoxy)ethyl]-3-(2,4-difluorophenyl)-1,3-dihydro-2,1,3-benzothiadiazole 2,2-dioxide (0.53 g, 1.2 mmol) was treated with 33% dimethylamine in ethanol to give 2-{2-[3-(2,4-difluorophenyl)-2,2-dioxido-2,1,3-benzothiadiazol-1(3H)-yl]ethoxy}-N,N-dimethylethanamine which was treated with 1N hydrochloric acid in ether to give its hydrochloride salt as a white solid (0.157 g, 30%). MS (ES) m/z 397.9 ([M+H]$^+$). HPLC retention time: 7.1 min.

Example 171

(2E)-4-[3-(2,4-difluorophenyl)-2,2-dioxido-2,1,3-benzothiadiazol-1(3H)-yl]-N-methylbut-2-en-1-amine hydrochloride

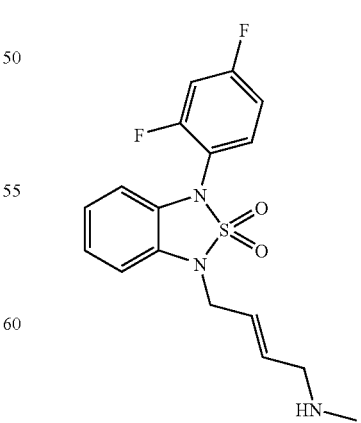

Step 1: In an analogous manner to general procedure IV, 1-(2,4-difluorophenyl)-1,3-dihydro-2,1,3-benzothiadiazole2,2-dioxide (3.37 g, 11.9 mmol) was treated with (E)-1,4-dibromobut-2-ene (8.9 g, 41.7 mmol) and cesium carbonate (3.9 g, 11.9 mmol) to give 1-[(2E)-4-bromobut-2-en-1-yl]-3-(2,4-difluorophenyl)-1,3-dihydro-2,1,3-benzothiadiazole2,2-dioxide (3.3 g, 67%) as a clear oil.

Step 2: In an analogous manner to general procedure V, 1-[(2E)-4-bromobut-2-en-1-yl]-3-(2,4-difluorophenyl)-1,3-dihydro-2,1,3-benzothiadiazole 2,2-dioxide (0.52 g, 1.2 mmol) was treated with 8N methylamine in methanol to give (2E)-4-[3-(2,4-difluorophenyl)-2,2-dioxido-2,1,3-benzothiadiazol-1(3H)-yl]-N-methylbut-2-en-1-amine which was treated with 1N hydrochloric acid in ether to give its hydrochloride salt as a white solid (0.27 g, 54%). MS (ES) m/z 365.9 ([M+H]$^+$).

Example 172

(2E)-4-[3-(2,4-difluorophenyl)-2,2-dioxido-2,1,3-benzothiadiazol-1(3H)-yl]-N,N-dimethylbut-2-en-1-amine hydrochloride

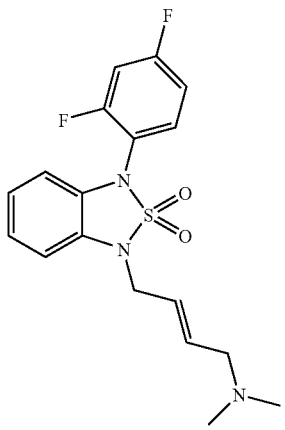

Step 1: In an analogous manner to general procedure V, 1-[(2E)-4-bromobut-2-en-1-yl]-3-(2,4-difluorophenyl)-1,3-dihydro-2,1,3-benzothiadiazole 2,2-dioxide (0.18 g, 0.43 mmol) was treated with 33% dimethylamine in ethanol to give (2E)-4-[3-(2,4-difluorophenyl)-2,2-dioxido-2,1,3-benzothiadiazol-1(3H)-yl]-N,N-dimethylbut-2-en-1-amine which was treated with 1N hydrochloric acid in ether to give its hydrochloride salt as a white solid (0.018 g, 10%). MS (ES) m/z 379.8 ([M+H]$^+$).

Example 173

(2E)-4-[3-(2,4-difluorophenyl)-2,2-dioxido-2,1,3-benzothiadiazol-1(3H)-yl]but-2-en-1-amine hydrochloride

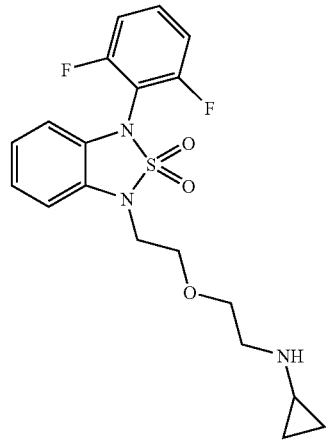

Step 1: In an analogous manner to general procedure V, 1-[(2E)-4-bromobut-2-en-1-yl]-3-(2,4-difluorophenyl)-1,3-dihydro-2,1,3-benzothiadiazole 2,2-dioxide (0.14 g, 0.33 mmol) was treated with 7N ammonia in methanol to give (2E)-4-[3-(2,4-difluorophenyl)-2,2-dioxido-2,1,3-benzothiadiazol-1(3H)-yl]but-2-en-1-amine which was treated with 1N hydrochloric acid in ether to give hydrochloride salt as a white solid (0.052 g, 40%). MS (ES) m/z 351.9 ([M+H]$^+$).

HPLC retention time: 7.0 min.

Example 174

N-(2-{2-[3-(2,6-difluorophenyl)-2,2-dioxido-2,1,3-benzothiadiazol-1(3H)-yl]ethoxy}ethyl)cyclopropanamine hydrochloride Step 1: In an analogous manner to general procedure IV, 1-(2,6-difluorophenyl)-1,3-dihydro-2,1,3-benzothiadiazole2,2-dioxide (2.69 g, 9.5 mmol) was treated with 1-bromo-2-(2-bromoethoxy)ethane (3.6 mL, 28.6 mmol) and cesium carbonate (3.1 g, 9.5 mmol) to give 1-[2-(2-bromoethoxy)ethyl]-3-(2,6-difluorophenyl)-1,3-dihydro-2,1,3-benzothiadiazole2,2-dioxide as a clear oil (3.1 g, 76%). MS (ES) m/z 432.7.

Step 2: In an analogous manner to general procedure V, 1-[2-(2-bromoethoxy)ethyl]-3-(2,6-difluorophenyl)-1,3-dihydro-2,1,3-benzothiadiazole 2,2-dioxide (0.1 g, 0.23 mmol) was treated with cyclopropylamine (0.64 mL, 9.2 mmol) in methanol to give N-(2-{2-[3-(2,6-difluorophenyl)-2,2-dioxido-2,1,3-benzothiadiazol-1(3H)-yl]ethoxy}ethyl)cyclopropanamine which was treated with 1N hydrochloric acid in ether to give its hydrochloride salt as a white solid (0.63 g, 57%). HRMS: calcd for $C_{19}H_{21}F_2N_3O_3S+H_+$, 410.13444; found (ESI, [M+H]$_+$Obs'd), 410.1341.

Example 175

N-(2-{2-[3-(2,6-difluorophenyl)-2,2-dioxido-2,1,3-benzothiadiazol-1(3H)-yl]ethoxy}ethyl)cyclobutanamine hydrochloride

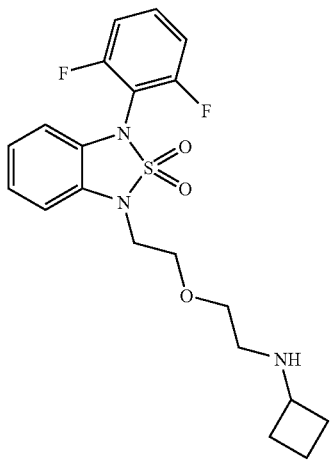

Step 1: In an analogous manner to general procedure V, 1-[2-(2-bromoethoxy)ethyl]-3-(2,6-difluorophenyl)-1,3-dihydro-2,1,3-benzothiadiazole 2,2-dioxide (0.1 g, 0.23 mmol) was treated with cyclobutylamine (0.8 mL, 9.2 mmol) in methanol to give N-(2-{2-[3-(2,6-difluorophenyl)-2,2-dioxido-2,1,3-benzothiadiazol-1(3H)-yl]ethoxy}ethyl)cyclobutanamine which was treated with 1N hydrochloric acid in ether to give its hydrochloride salt as a white solid (0.59 g, 56%). HRMS: calcd for $C_{20}H_{23}F_2N_3O_3S+H^+$, 424.15009; found (ESI, [M+H]$^+$Obs'd), 424.1497.

Example 176

N-(2-{2-[3-(2,6-difluorophenyl)-2,2-dioxido-2,1,3-benzothiadiazol-1(3H)-yl]ethoxy}ethyl)cyclopentanamine hydrochloride

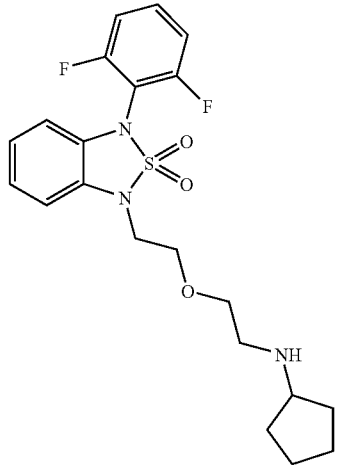

Step 1: In an analogous manner to general procedure V, 1-[2-(2-bromoethoxy)ethyl]-3-(2,6-difluorophenyl)-1,3-dihydro-2,1,3-benzothiadiazole 2,2-dioxide (0.1 g, 0.23 mmol) was treated with cyclopentylamine (2.4 mL, 9.2 mmol) in methanol to give N-(2-{2-[3-(2,6-difluorophenyl)-2,2-dioxido-2,1,3-benzothiadiazol-1(3H)-yl]ethoxy}ethyl)cyclopentanamine which was treated with 1N hydrochloric acid in ether to give its hydrochloride salt as a white soldi (0.94 g, 87%). HRMS: calcd for $C_{21}H_{25}F_2N_3O_3S+H^+$, 438.16574; found (ESI, [M+H]$^+$Obs'd), 438.1652.

Example 177

2-{2-[3-(2,6-difluorophenyl)-2,2-dioxido-2,1,3-benzothiadiazol-1(3H)-yl]ethoxy}-N-methylethanamine hydrochloride

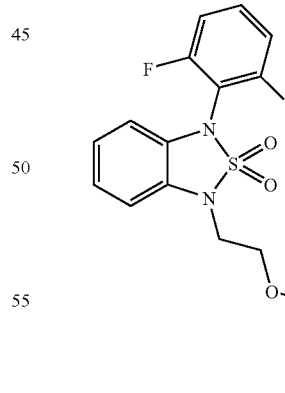

Step 1: In an analogous manner to general procedure V, 1-[2-(2-bromoethoxy)ethyl]-3-(2,6-difluorophenyl)-1,3-dihydro-2,1,3-benzothiadiazole 2,2-dioxide (0.1 g, 0.23 mmol) was treated with 8N methylamine in methanol to give 2-{2-[3-(2,6-difluorophenyl)-2,2-dioxido-2,1,3-benzothiadiazol-1(3H)-yl]ethoxy}-N-methylethanamine which was treated with 1N hydrochloric acid in ether to give its hydrochloride

Example 178

2-{2-[3-(2,6-difluorophenyl)-2,2-dioxido-2,1,3-benzothiadiazol-1(3H)-yl]ethoxy}-N-ethylethanamine hydrochloride

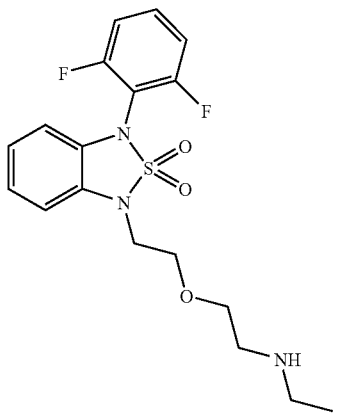

Step 1: In an analogous manner to general procedure V, 1-[2-(2-bromoethoxy)ethyl]-3-(2,6-difluorophenyl)-1,3-dihydro-2,1,3-benzothiadiazole 2,2-dioxide (0.1 g, 0.23 mmol) was treated with 30-40% ethylamine in methanol to give 2-{2-[3-(2,6-difluorophenyl)-2,2-dioxido-2,1,3-benzothiadiazol-1(3H)-yl]ethoxy}-N-ethylethanamine which was treated with 1N hydrochloric acid in ether to give its hydrochloride salt as a white solid (0.67 g, 67%). HRMS: calcd for $C_{18}H_{21}F_2N_3O_3S+H^+$, 398.13444; found (ESI, [M+H]$^+$ Obs'd), 398.1341.

Example 179

N-(2-{2-[3-(2,6-difluorophenyl)-2,2-dioxido-2,1,3-benzothiadiazol-1(3H)-yl]ethoxy}ethyl)propan-2-amine hydrochloride

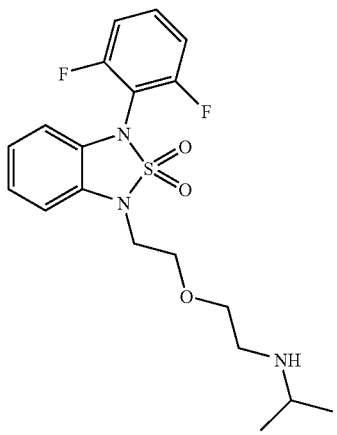

Step 1: In an analogous manner to general procedure V, 1-[2-(2-bromoethoxy)ethyl]-3-(2,6-difluorophenyl)-1,3-dihydro-2,1,3-benzothiadiazole 2,2-dioxide (0.1 g, 0.23 mmol) was treated with isopropylamine (0.8 mL, 9.2 mmol) in methanol to give N-(2-{2-[3-(2,6-difluorophenyl)-2,2-dioxido-2,1,3-benzothiadiazol-1(3H)-yl]ethoxy}ethyl)propan-2-amine which was treated with 1N hydrochloric acid in ether to give its hydrochloride salt as a white solid (0.32 g, 31%). HRMS: calcd for $C_{19}H_{23}F_2N_3O_3S+H^+$, 412.15009; found (ESI, [M+H]$^+$Obs'd), 412.1497.

Example 180

1-(4-chlorophenyl)-3-(4-morpholin-4-ylbutyl)-1,3-dihydro-2,1,3-benzothiadiazole2,2-dioxide

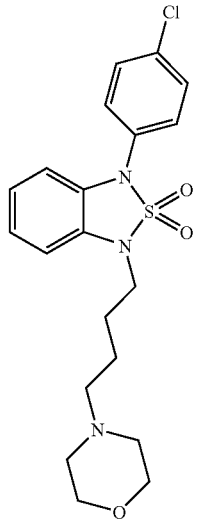

In an analogous manner to General Procedure V, morpholine (2 mL, 23 mmol) and 1-(4-bromobutyl)-3-(4-chlorophenyl)-1,3-dihydro-2,1,3-benzothiadiazole2,2-dioxide (50 mg, 0.12 mmol) were stirred overnight to prepare 29 mg (45%) of 1-(4-chlorophenyl)-3-(4-morpholin-4-ylbutyl)-1,3-dihydro-2,1,3-benzothiadiazole2,2-dioxide as the TFA salt.

HPLC purity 100.0% at 210-370 nm, 8.2 min.; Xterra RP18, 3.5 u, 150×4.6 mm column, 1.2 mL/min, 85/15-5/95 (ammonium formate buffer pH=3.5, acetonitrile/MeOH) for 10 min, hold 4 min.

HRMS: calculated for $C_{20}H_{24}ClN_3O_3S+H^+$, 422.12996; found (ESI, [M+H]$^+$), 422.1296.

Examples 181-196 are prepared as described in Examples 134 and 135.

Example 181

1-(2-Fluorophenyl)-4-fluoro-3-{2-[(2R)-morpholin-2-yl]ethyl}-1,3-dihydro-2,1,3-benzothiadiazole2,2-dioxide

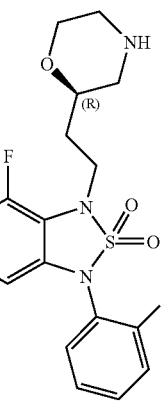

Example 182

1-(2-Fluorophenyl)-4-fluoro-3-{2-[(2S)-morpholin-2-yl]ethyl}-1,3-dihydro-2,1,3-benzothiadiazole2,2-dioxide

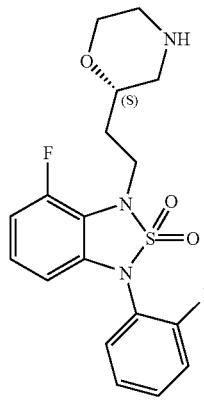

Example 183

1-(2-Fluorophenyl)-5-fluoro-3-{2-[(2R)-morpholin-2-yl]ethyl}-1,3-dihydro-2,1,3-benzothiadiazole2,2-dioxide

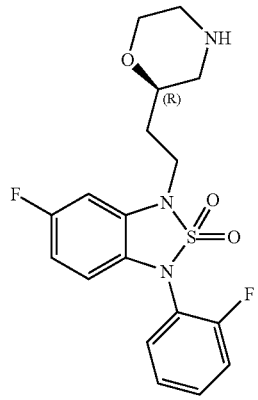

Example 184

1-(2-Fluorophenyl)-5-fluoro-3-{2-[(2S)-morpholin-2-yl]ethyl}-1,3-dihydro-2,1,3-benzothiadiazole2,2-dioxide

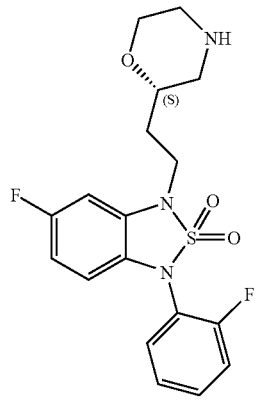

Example 185

1-(2-Fluorophenyl)-6-fluoro-3-{2-[(2R)-morpholin-2-yl]ethyl}-1,3-dihydro-2,1,3-benzothiadiazole2,2-dioxide

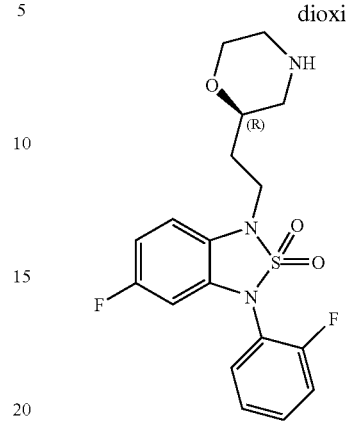

Example 186

1-(2-Fluorophenyl)-6-fluoro-3-{2-[(2S)-morpholin-2-yl]ethyl}-1,3-dihydro-2,1,3-benzothiadiazole2,2-dioxide

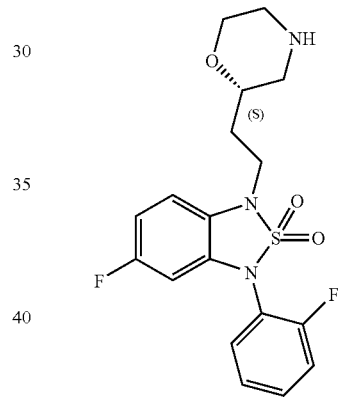

Example 187

1-(2-Fluorophenyl)-7-fluoro-3-{2-[(2R)-morpholin-2-yl]ethyl}-1,3-dihydro-2,1,3-benzothiadiazole2,2-dioxide

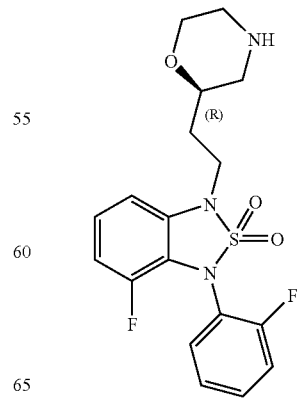

Example 188

1-(2-Fluorophenyl)-7-fluoro-3-{2-[(2S)-morpholin-2-yl]ethyl}-1,3-dihydro-2,1,3-benzothiadiazole2,2-dioxide

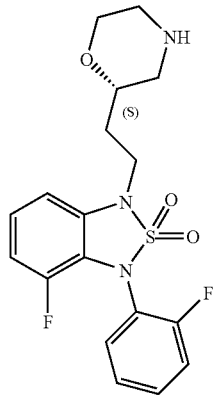

Example 189

1-(2,6-Difluorophenyl)-4-fluoro-3-{2-[(2R)-morpholin-2-yl]ethyl}-1,3-dihydro-2,1,3-benzothiadiazole2,2-dioxide

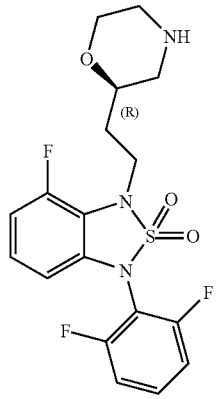

Example 190

1-(2,6-Difluorophenyl)-4-fluoro-3-{2-[(2S)-morpholin-2-yl]ethyl}-1,3-dihydro-2,1,3-benzothiadiazole2,2-dioxide

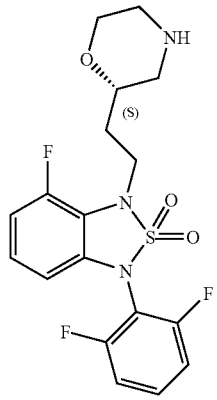

Example 191

1-(2,6-Difluorophenyl)-5-fluoro-3-{2-[(2R)-morpholin-2-yl]ethyl}-1,3-dihydro-2,1,3-benzothiadiazole2,2-dioxide

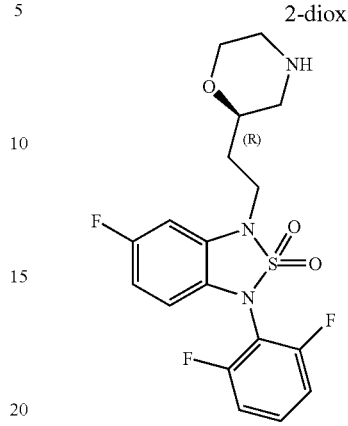

Example 192

1-(2,6-Difluorophenyl)-5-fluoro-3-{2-[(2S)-morpholin-2-yl]ethyl}-1,3-dihydro-2,1,3-benzothiadiazole2,2-dioxide

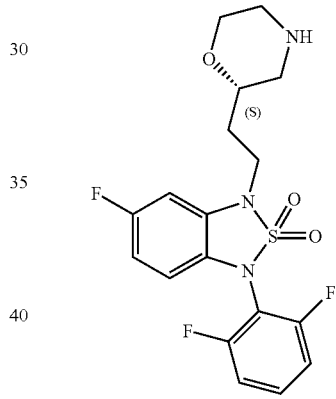

Example 193

1-(2,6-Difluorophenyl)-6-fluoro-3-{2-[(2R)-morpholin-2-yl]ethyl}-1,3-dihydro-2,1,3-benzothiadiazole2,2-dioxide

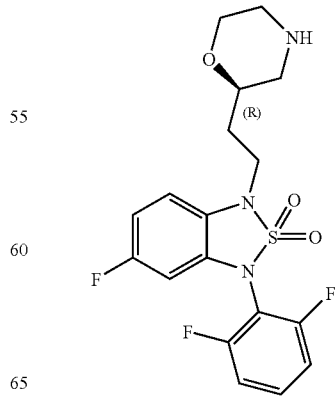

Example 194

1-(2,6-Difluorophenyl)-6-fluoro-3-{2-[(2S)-morpholin-2-yl]ethyl}-1,3-dihydro-2,1,3-benzothiadiazole2,2-dioxide

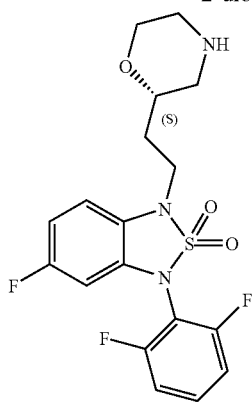

Example 195

1-(2,6-Difluorophenyl)-7-fluoro-3-{2-[(2R)-morpholin-2-yl]ethyl}-1,3-dihydro-2,1,3-benzothiadiazole2,2-dioxide

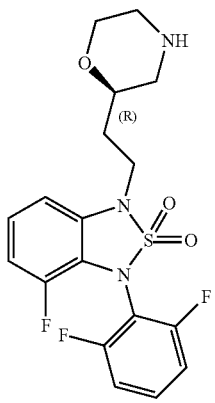

Example 196

1-(2,6-Difluorophenyl)-7-fluoro-3-{2-[(2S)-morpholin-2-yl]ethyl}-1,3-dihydro-2,1,3-benzothiadiazole2,2-dioxide

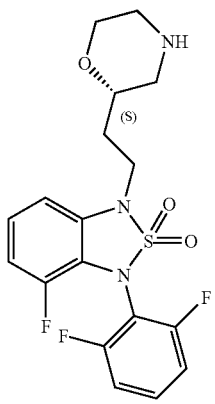

hNET Assay Procedure Protocol A: Inhibition of [$^3$H] NE Uptake into Cloned Human NE Transporters (MDCK Cells) ("hNET uptake")

The hNET uptake assay procedure was used to screen for compounds that inhibit the reuptake of norepinephrine and to determine IC$_{50}$ values for compounds identified as hNET reuptake inhibitors.

Materials and Methods:

Cell Line and Culture Reagents:

[$^3$H] NE uptake studies were performed using MDCK cells stably expressing human norepinephrine transporter (hNET) (See Pacholczyk T, Blakely R D and Amara S G (1991) Expression cloning of a cocaine- and antidepressant-sensitive human noradrenaline transporter. *Nature*. 350:350-354) cultured in growth medium containing high glucose DMEM (Gibco, Cat. No. 11995), 10% FBS (dialyzed, heat-inactivated, US Bio-Technologies, Lot FBD1129HI) and 500 µg/ml G418 (Gibco, Cat. No. 10131). Cells were seeded at 300,000/T75 flask, and split twice weekly.

Norepinephrine Uptake Assays:

All uptake experiments were performed in 96-well plates (Falcon Optilux, cat #353947) in a total volume of 250 µl/well. MDCK cells were plated at 50,000 cells/well. At the time of the assay, the media was removed, and 200 µl assay buffer (25 mM Hepes, 120 mM NaCl, 5 mM KCl, 2.5 mM CaCl$_2$, 1.2 mM MgSO$_4$.7H$_2$O, 2 mg/ml glucose, 0.2 mg/ml ascorbic acid, 1 µM pargyline, pH 7.4) was added to each well. 25 µl of each test compound was subsequently added to plates in triplicate and incubated at 37° C. for 5 minutes. All test compounds were dissolved in 100% DMSO and diluted in 4% DMSO/H$_2$O, and assayed using a 7-point dose response curve (1 nM-10 µM). Next, 25 µl of [$^3$H] NE (74.9 Ci/mmol, Perkin Elmer, Boston, Mass.) was added to all wells and incubated at 37° C. for an additional 5 minutes. Non-specific uptake was defined by 20 µM desipramine. The final concentrations of [$^3$H] NE was 16 nM, respectively. The reaction was terminated by aspiration and washed with ice cold 50 mM Tris (pH 7.4). The plates were left to air dry for roughly 30 min, and MDCK cells were lysed by the addition of 25 µl of 0.25 M NaOH. 100 µl of Microscint-20 were added to each well (Packard, Perkin Elmer, Boston, Mass.), and the plates were counted using a TopCount (Perkin Elmer, Downer's Grove, Ill.) liquid scintillation counter.

Analysis of Results:

% Inhibition of uptake=((mean cpm control wells–each cpm drug well)/(mean cpm control wells–non-specific wells)×100.

IC$_{50}$ values were calculated using a Prism® nonlinear regression program where % inhibition is plotted versus concentration of inhibitor.

See: Pacholczyk T, Blakely R D and Amara S G (1991) Expression cloning of a cocaine- and antidepressant-sensitive human noradrenaline transporter. *Nature*. 350:350-354.

See also: Ramamoorthy J D, Ramamoorthy S, Papapetropoulos A, Catravas J D, Leibach F H and Ganaphthy V (1995) Cyclic AMP-independent up-regulation of the human serotonin transporter by staurosporine in choriocarcinoma cells. *Journal of Biological Chemistry*. 270:17189-17195, the contents of which is hereby incorporated by reference.

hNET Assay Procedure Protocol B: Cell based norepinephrine (NE) reuptake assay using the recombinant human norepinephrine transporter (hNET) ("hNET uptake")

The hNET uptake assay procedure was used to screen for compounds that inhibit the reuptake of norepinephrine and to determine IC$_{50}$ values for compounds identified as hNET reuptake inhibitors.

Materials and Methods:

Compounds:

For screening, hydrochloride salts of compounds were dissolved in solution and 25 µl aliquots of compound solution at a 1 µM or 10 µM final concentration delivered directly to cells. For $IC_{50}$ determinations, stock compounds were prepared at 10 mM from powder. The stock solution was diluted according to compound testing range. Typically, the compound testing range was from 6 nM to 6 µM by half log dilutions. On the day of assay, 25 µl of compound solution at the specified concentrations was added to the plates containing cells. A DMSO stock of desipramine was prepared at 10 mM in DMSO and diluted for a final concentration of 20 µM to determine the non-specific reuptake. The radioligand in this assay is $^3$H-norepinephrine (NE) (PerkinElmer; NET678; 40-80 Ci/mmol) was delivered at approximately 16 nM final concentration for both single point testing and compound $IC_{50}$ determinations.

Tissue Culture Conditions:

MDCK-Net6 cells, stably transfected with human hNET (See Pacholczyk T, Blakely R D and Amara S G (1991) Expression cloning of a cocaine- and antidepressant-sensitive human noradrenaline transporter. Nature. 350:350-354) was maintained in growth media [high glucose DMEM (Gibco Cat. 11995), 10% FBS (dialyzed, heat-inactivated, Sigma, dialysed, heat inactivated, Lot# K0922 or equivalent) 1× Pen/Strep, and 500 µg/ml G418 (Gibco Cat. 10131)]. Cells were plated at 300,000/T75 flask and cells were split twice weekly.

Functional Reuptake Assay:

Cells were plated at 3,000 cells/well on day 1 in BD Falcon Microtest 96-well sterile cell culture plates, Optilux White/Clear Bottom TC plate (VWR; # 62406-466 or equivalent) in growth media and maintained in a cell incubator (37° C., 5% $CO_2$). On Day 2, cells were removed from the cell incubator and the growth media is replaced by 200 µl of assay buffer (25 mm HEPES 120 mM NaCL; 5 mM KCl; 2.5 mM $CaCl_2$; 1.2 mM $MgSO_4$; 2 mg/ml glucose (pH 7.4, 37° C.)) containing 0.2 mg/ml ascorbic acid and 1 µM parglyine. For screening, 25 µl of compound in 4% DMSO is added directly to each well and the plate is incubated for 5 min (37° C.). To initiate the norepinephrine reuptake, 16 nM (final concentration) of $^3$H norepinephrine (specific activity; 40-80 Ci/mmol) in assay buffer was delivered in 25 µl aliquots to each well, and the plates were incubated for 5 min at 37° C. The reaction was aspirated from the plate and the cells washed with 250 µl of 50 mM Tris Buffer (4° C.). The plates were left to dry for 1 hour. The cells were lysed using 0.25 M NaOH solution then placed on a shake table and vigorously shaken for 10 min. After cell lysis, 100 µl of Microscint 20 (PerkinElmer; #87-051101) was added to the plates and the plates were sealed with film tape and replaced on the shake table for a minimum of 10 min. The plates were counted in a TopCount counter (PerkinElmer).

Analysis of Results:

For screening single point determinations, each compound plate contained at least 3 control wells (maximum NE reuptake determinant) and 3 non-specific wells determined by adding 20 µM of desipramine (minimum NE reuptake determinant). Determination of active compounds were calculated using a Microsoft Excel spread sheet applying the following formula:

% inhibition=[1−((mean cpm test compound wells−mean cpm non-specific wells)/(mean cpm control wells−mean cpm non-specific wells))]×100

For $IC_{50}$ determination, raw cpm values were generated in a data file from the TopCount counter. The data was organized Microsoft Excel and transferred into PRIZM graphing and statistical program, which calculated the estimated $IC_{50}$ value. Calculation of $IC_{50}$ values was made using non-linear regression analysis with a sigmoidal dose response with variable slope. The statistical program used wells containing $^3$H norepinephrine only as the maximal NE reuptake determinant and wells containing $^3$H norepinephrine plus 20 µM desipramine as the minimal NE reuptake determinant (non-specific determinant). Estimation of the $IC_{50}$ value is completed on a log scale and the line is fit between the maximal and minimal NE reuptake values. In the event that the highest test concentration does not exceed 50% reuptake inhibition, data will be reported as percent maximal NE reuptake at the highest concentration tested.

See: Pacholczyk, T., Blakely, R. D., and Amara, S. G. (1991) Expression cloning of a cocaine- and antidepressant-sensitive human noradrenaline transporter. Nature, 350, 350-354, the contents of which is hereby incorporated by reference.

Results are shown in the following tables:

| Example | NE uptake (Protocol B) $IC_{50}$ (nM) |
|---|---|
| 1 | 145 |
| 2 | 207 |
| 3 | 199 |
| 4 | 4310 |
| 5 | 347 |
| 6 | 157 |
| 7 | 135 |
| 8 | 229 |
| 9 | 341 |
| 10 | 17.5 |
| 11 | 2.61 |
| 12 | 0.389 |
| 13 | 27.7 |
| 14 | 453 |
| 15 | 5473 |
| 16 | 205 |
| 17 | 207 |
| 18 | 18 |
| 19 | 6.91 |
| 20 | 71.5 |
| 21 | 305 |
| 22 | 602 |
| 23 | 6.13 |
| 24 | 548 |
| 25 | 12.9 |
| 26 | 45.3 |
| 27 | 147 |
| 28 | 8.92 |
| 29 | 6000 |
| 30 | 3.64 |
| 31 | 7.39 |
| 32 | 1133 |
| 33 | 187 |
| 34 | 900 |
| 35 | 41.1 |
| 36 | 105 |
| 37 | 736 |
| 38 | 36.6 |
| 39 | 6.72 |
| 40 | 51.9 |
| 41 | 9.4 |
| 42 | 415 |
| 43 | 32.8 |
| 44 | 61.2 |
| 45 | 43.4 |
| 46 | 16.3 |
| 47 | 40.6 |
| 48 | 4.65 |
| 49 | 3.11 |
| 50 | 29.4 |
| 51 | 5.06 |

-continued

| Example | |
|---|---|
| 52 | 5.11 |
| 53 | 1284 |
| 54 | 31.8 |
| 55 | 13.4 |
| 56 | 58.6 |
| 57 | 62.4 |
| 58 | 21.4 |
| 59 | 59.7 |
| 60 | 6.25 |
| 61 | 19 |
| 62 | 87.9 |
| 63 | 532 |
| 64 | 702 |
| 65 | 210 |
| 66 | 8.5 |
| 67 | 2.04 |
| 68 | 0.764 |
| 69 | 0.206 |
| 70 | 33.9 |
| 71 | 238 |
| 72 | 15 |
| 73 | 15 |
| 74 | 29 |
| 75 | 473 |
| 76 | 19 |
| 77 | 59 |
| 78 | 70 |
| 79 | 8 |
| 80 | 9 |
| 81 | 2114 |
| 82 | 59 |
| 83 | 348 |
| 84 | 7 |
| 85 | 27 |
| 86 | 99 |
| 87 | 430 |
| 88 | 439 |
| 89 | 430 |
| 90 | 1260 |
| 91 | 1647 |
| 92 | 154 |
| 93 | 2555 |
| 94 | 3569 |
| 95 | 522 |
| 97 | 1846 |
| 99 | 3628 |
| 100 | 3103 |
| 102 | 34 |
| 103 | 52% inhibition @ 6 uM |
| 105 | binding IC50 289 nM* |
| 106 | 1464 |
| 107 | 381 |
| 108 | 6499 |
| 109 | 559 |
| 110 | 102 |
| 111 | 7% inhibition @ 6 uM |
| 112 | 2315 |
| 113 | 422 |
| 114 | 1136 |
| 115 | 2948 |
| 116 | 352 |
| 117 | 4 |
| 118 | 5 |
| 119 | 78 |
| 120 | 21 |
| 121 | 360 |
| 122 | 175 |
| 123 | 45 |
| 124 | 27 |
| 125 | 151 |
| 126 | 103 |
| 127 | 2745 |
| 128 | 1594 |
| 129 | 3680 |
| 130 | 119 |
| 131 | 82 |
| 132 | 20 |

-continued

| Example | |
|---|---|
| 133 | 372 |
| 134 | 18 |
| 135 | 13 |
| 136 | 11 |
| 137 | 516 |
| 138 | 704 |
| 139 | 611 |
| 140 | 164 |
| 141 | 173 |
| 142 | 199 |
| 143 | 101 |
| 144 | 133 |
| 145 | 91 |
| 146 | 163 |
| 147 | 89 |
| 148 | 16 |
| 149 | 20 |
| 150 | 17 |
| 151 | 656 |
| 152 | 273 |
| 153 | 1158 |
| 154 | 2489 |
| 155 | 1003 |
| 156 | 1607 |
| 157 | 19 |
| 158 | 137 |
| 159 | 19 |
| 160 | 95 |
| 161 | 28 |
| 162 | 597 |
| 163 | 4190 |
| 164 | 84 |
| 165 | 39 |
| 166 | 35 |
| 167 | 23 |
| 168 | 18 |
| 169 | 17 |
| 170 | binding IC50 206.6 nM* |
| 171 | 7 |
| 172 | 1 |
| 173 | 71 |
| 174 | 213 |
| 175 | 157 |
| 176 | 1265 |
| 177 | 13 |
| 178 | 43.9 |
| 179 | 343 |
| | NE uptake (Protocol A) IC$_{50}$ (nM) |
| 180 | 1761 |

*For hNET binding performed according to: P. E. Mahaney et al. Bioorg. Med. Chem. 14 (2006) 8455-8466, the contents of which is hereby incorporated by reference in its entirety.

Rat Liver Microsomal Stability Assay:

DMSO stock solutions of test compounds were prepared at 0.5 mM concentration. Diluted solutions of test compounds were prepared by adding 50 uL of each DMSO stock solution to 200 uL of acetonitrile to make 0.1 mM solutions in 20% DMSO/80% acetonitrile. Rat liver microsomal solution was prepared by adding 1.582 mL of concentrated rat liver microsomes (20 mg/mL protein concentration) to 48.291 mL of pre-warmed (to 37° C.) 0.1M potassium phosphate buffer (pH 7.4) containing 127 uL of 0.5 M EDTA to make a 0.6329 mg/mL (protein) microsomal solution. 11.2 uL of each test compound diluted solution was each added directly to 885 uL of rat liver microsomal solution (allowing direct binding of drugs to microsomal proteins and lipids to minimize precipitation and non-specific binding to the plasticware). This solution was mixed and 180 uL was transferred to "Time 0" and "Time 15 min" plates (each in duplicate wells). For the Time 15 min plate, NADPH regenerating agent (45 uL) was added to each well to initiate the reaction, the plate was incubated at 37° C. for 15 min, followed by quenching of the reaction by adding 450 uL of cold acetonitrile to each well. For the Time 0 plate, 450 uL of cold acetonitrile was added to each well, followed by addition of NADPH regenerating agent (45 uL) and no incubation. All of the plates were centrifuged at 3000 rpm for 15 min and the supernatants were transferred to other well plates for analysis by LC-MS.

Dopamine Transporter (hDAT) Membrane Binding Assay

The method for this radioligand binding assay was modified from the methods supplied with hDAT membranes (catalog number RBHDATM; Perkin Elmer Life Analytical Sciences), and those modifications are listed within this method section. Frozen membrane samples from a cell line that expresses hDAT were diluted to 7.5 ml in binding buffer (50 mM Tris-HCl; pH 7.4, 100 mM NaCl), homogenized with a tissue-tearer (Polytron PT 1200C, Kinematica AG) and delivered at a volume of 75 μl to each well of a polypropylene 96-well plate. The binding reaction was run in polypropylene 96-well plates (Costar General Assay Plate, Cat. No. 3359; Lid, Cat. No. 3930). A stock solution of mazindol was prepared in DMSO (10 mM) and delivered to triplicate wells containing membrane for a final test concentration of 10 uM. Mazindol is a DA transporter inhibitor with a 50% inhibitory concentration ($IC_{50}$) value of 18.0±6.0 nM in the present assays. Data from wells containing mazindol (10 uM) were used to define non-specific (NSB) hDAT binding (minimum hDAT binding). Total binding is defined by addition of 5 μl of binding buffer alone in the presence of [$^3$H] WIN-35,428. Stock solutions of compounds to be tested were prepared in DMSO at concentrations of 10 mM to 10 uM. On the day of assay, test compounds were diluted in assay buffer according to test range (100,000 to 10 nM) ensuring a maximal DMSO concentration of less than 0.5% in the assay reaction wells. Homogenized membranes were pre-incubated with test compounds for 20 min at 4° C. before the initiation of the binding reaction. The binding reaction is initiated by addition of 25 μl of $^3$[H]-WIN 35,428 diluted in binding buffer. The final concentration of $^3$[H]-WIN 35,428 delivered was 10 nM. The $K_D$ value estimated for $^3$[H]-WIN-35,428 in hDAT membranes (Lot#296-083-A) was 6.9 nM. The radioligand concentration, [L], used in the competition binding assays is a factor difference of 1.4 compared to the $K_D$ value and was used to calculate the $K_i$ value. The plate containing the radioligand binding reactions were incubated for 2 h at 4° C. on a shaking table (Bellco, Vineland, N.J.) at 3 revolutions per minute. The MultiScreen-FB opaque 96-well filtration plates contained Millipore glass fiber filters (Millipore glass fiber B, Cat. No. MAFBNOB) were used to terminate the binding reactions and to separate bound from free radioligand. The plates were presoaked with 0.5% polyethylenimine (PEI; Sigma Cat. No. P-3143) in water for a minimum of two hours at room temperature to reduce nonspecific binding of $^3$[H]-WIN 35,428 during the harvest procedure. Before harvesting the reaction plates, the PEI solution is aspirated from the filter plates using a vacuum manifold. Aliquots of each reaction (90 μl of each 100 μl reaction well) were transferred from the reaction plates to the filter plates using a Zymark Rapid Plate-96 automated pipette station. The binding reaction is terminated by vacuum filtration through the glass fiber filters. The filter plates were aspirated at 5-10 inches of Hg, and the wells are washed 9 times with 200 μl wash buffer (50 mM Tris-HCl, 0.9% NaCl, pH 7.4; 4° C.) using a 12 channel aspiration/wash system. Plastic bottom supports are removed from the filter plates and the plates are placed in plastic liners. A 100 μl aliquot of scintillation fluid was added to each well and the top of each plate is sealed with adhesive film. The plates are vigorously shaken at 5 rpm for 10-15 minutes to ensure adequate equilibration of aqueous to solvent partitioning. The collection of raw counts per minute (cpm) data was done using a Wallac Microbeta counter (Perkin Elmer).

Evaluation of Results

For each experiment, a data stream of cpm values collected from the Wallac Microbeta counter was downloaded to a Microsoft Excel statistical application program. Calculations of $IC_{50}$ values were made using the transformed-both-sides logistic dose response program that uses mean cpm values from wells representing maximum binding (total) (assay buffer) and mean cpm values from wells representing minimum binding (NSB, 10 μM mazindol). Estimation of the $IC_{50}$ values was completed on a log scale and the line was fit between the maximum and minimum binding values. The $K_i$ value is a function of the concentration of the compound required to inhibit 50% of the radioligand ($IC_{50}$ value) divided by the free radioligand concentration [L] divided by the $K_D$ value plus one ($K_i = IC_{50}/(1+[L]/K_D)$). The $K_i$ value for these studies was determined by dividing the $IC_{50}$ value by a factor of 2.4 to account for the concentration of $^3$[H]-WIN 35,428 used in the assay.

Results are shown in the following table:

TABLE A

| Structure CHEMISTRY | hNET Function IC50 (nM) | hDAT Binding IC50 (nM) | RLM stability t1/2 (min) |
|---|---|---|---|
| 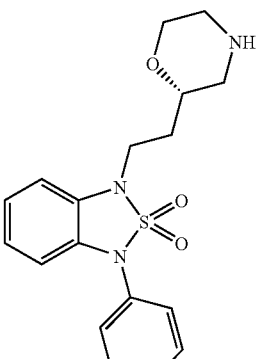 | 13.1 | 479.3 | 5 |
| 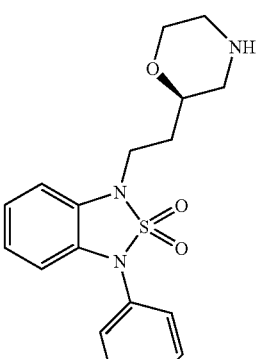 | 10.8 | 598.5 | 3 |

TABLE A-continued
| Structure CHEMISTRY | hNET Function IC50 (nM) | hDAT Binding IC50 (nM) | RLM stability t1/2 (min) |
|---|---|---|---|
| 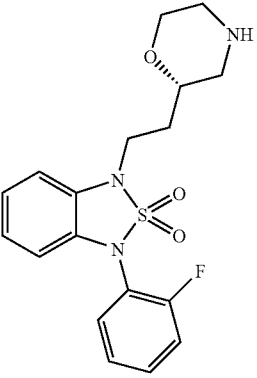 | 16.2 | 1402.3 | 4 |
| | 20.0 | 2190.4 | 5 |
| | 17.3 | | 3 |
TABLE A-continued
| Structure CHEMISTRY | hNET Function IC50 (nM) | hDAT Binding IC50 (nM) | RLM stability t1/2 (min) |
|---|---|---|---|
| | 173.0 | | 2 |
| | 199.0 | | N/A |
| | 611.0 | | 10 |

TABLE A-continued

| Structure CHEMISTRY | hNET Function IC50 (nM) | hDAT Binding IC50 (nM) | RLM stability t1/2 (min) |
|---|---|---|---|
| 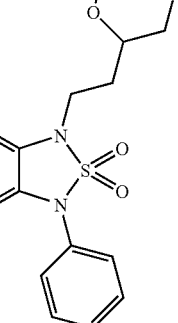 | 516.0 | | 9 |
| 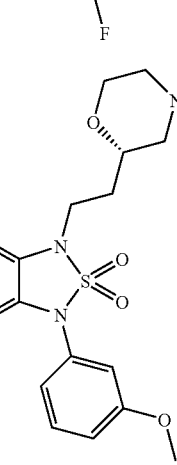 | 163.0 | | 5 |
| 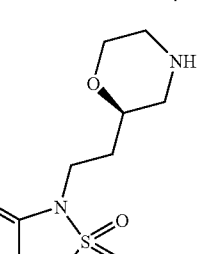 | 89.0 | | N/A |

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

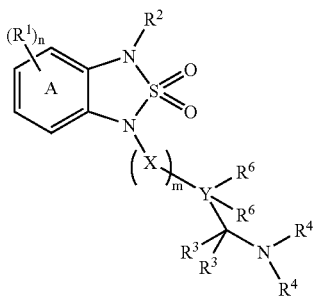

I or a pharmaceutically acceptable salt, stereoisomer or tautomer thereof;

wherein:

n is an integer from 0 to 4;

m is an integer from 0 to 6;

X is, independently at each occurrence, $C(R^7)_2$, $N(R^3)$, O, S, $S(=O)$, or $S(=O)_2$;

Y is C; or

Y and an adjacent X together form —$CR^7$=$CR^7$—, —C≡C—, or arylenyl substituted with 0-3 $R^{10}$;

$R^1$ is, independently at each occurrence, H, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;

$R^2$ is aryl substituted with 0-3 $R^9$;

$R^3$ is, independently at each occurrence, H, halo, hydroxy, alkyl substituted with 0-3 $R^{13}$, a heterocyclic ring, aryl substituted with 0-3 $R^{12}$, or heteroaryl substituted with 0-3 $R^{12}$;

$R^4$ is, independently at each occurrence, H, alkyl substituted with 0-3 $R^{13}$, arylalkyl substituted with 0-3 $R^{13}$ or heteroarylmethyl substituted with 0-3 $R^{13}$;

$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;

$R^6$ is, independently at each occurrence, H, hydroxy, $C_1$-$C_4$ alkyl, $C_1$-$C_6$ alkoxy, halo, aryl substituted with 0-3 $R^1$, heteroaryl substituted with 0-3 $R^1$, —$N(R^3)_2$, —$S(R^3)$, or —$R^8$—O—$R^3$; or both $R^6$ groups form a cycloalkyl, a heterocyclic ring, =O or =N—OH;

provided that if each $R^3$ is H, each X is $CH_2$, and either each $R^6$ is H or one $R^6$ is hydroxy; then, both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, or a heterocyclic ring, F, or $CF_3$; and where any additional N atom may be optionally substituted with $C_1$-$C_4$ alkyl;

$R^7$ is, independently at each occurrence, H, hydroxy, alkoxy, or $C_1$-$C_4$ alkyl;

$R^8$ is, independently at each occurrence, straight or branched alkylenyl;

or one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, F, or $CF_3$; and where any additional N atom may be optionally substituted with alkyl;

or both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, a heterocyclic ring, F, or $CF_3$; and where any additional N atom may be optionally substituted with alkyl;

or one of said $R^6$ or one of said $R^7$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl; provided that $R^4$ and $R^7$, taken together, do not form a piperidinyl ring;

$R^9$ is, independently at each occurrence, alkyl, alkoxy;

$R^{10}$ is, independently at each occurrence, alkyl, alkoxy, halo, $CF_3$, $OCF_3$, hydroxy, alkanoyloxy, nitro, nitrile, alkenyl, or alkynyl;

$R^{11}$ is, independently at each occurrence, alkyl, alkoxy, halo, $CF_3$, $OCF_3$, hydroxy, alkanoyloxy, nitro, nitrile, alkenyl, or alkynyl; and $R^{12}$ and $R^{13}$ are each, independently at each occurrence, alkyl, alkoxy, halo, $CF_3$, $OCF_3$, hydroxy, hydroxyalkyl, aminoalkyl, a heterocyclic ring, alkanoyloxy, nitro, nitrile, alkenyl, or alkynyl wherein ring A is a phenyl ring.

2. The compound of claim 1, wherein:
$R^4$ and $R^6$, taken together, form a morpholinyl group optionally substituted with $C_1$-$C_4$ alkyl, F, or $CF_3$.

3. The compound of claim 2, wherein:
$R^4$ and $R^6$, taken together, form morpholin-2-yl.

4. The compound of claim 3, wherein:
$R^4$ and $R^6$, taken together, form (R)-morpholin-2-yl.

5. The compound of claim 3, wherein:
$R^4$ and $R^6$, taken together, form (S)-morpholin-2-yl.

6. The compound of claim 1, wherein:
n is an integer from 0 to 2.

7. The compound of claim 1, wherein:
m is an integer from 1 to 6.

8. The compound of claim 1, wherein:
X is, independently at each occurrence, $C(R^7)_2$, $N(R^3)$, or O.

9. The compound of claim 1, wherein:
X is, independently at each occurrence, $C(R^7)_2$.

10. The compound of claim 1, wherein:
$R^1$ is, independently at each occurrence, alkyl, alkoxy, halo, $CF_3$, $OCF_3$ or nitrile.

11. The compound of claim 1, wherein:
$R^2$ is aryl substituted with 0-3 $R^9$.

12. The compound of claim 1, wherein:
$R^2$ is phenyl, fluoro-phenyl, difluoro-phenyl, trifluoro-phenyl, chloro-phenyl, fluoro-chloro-phenyl, bromo-phenyl, trifluoromethyl-phenyl trifluoromethoxy-phenyl, methyl-fluoro-phenyl, methoxy-fluoro-phenyl, or naphthyl.

13. The compound of claim 1, wherein:
$R^3$ is, independently at each occurrence, H, methyl, or phenyl.

14. The compound of claim 1, wherein:
$R^4$ is, independently at each occurrence, hydrogen, methyl, ethyl, cyclopropyl, or n-butyl.

15. The compound of claim 1, wherein:
both of said $R^4$, together with the nitrogen through which they are attached, form a heterocyclic ring of 4 to 7 atoms, where one carbon may be optionally replaced with N or O; where any carbon ring atom may be optionally substituted with one or two $C_1$-$C_4$ alkyl, F, or $CF_3$; and where any additional N atom may be optionally substituted with $C_1$-$C_4$ alkyl.

16. The compound of claim 1, wherein:
$R^5$ is, independently at each occurrence, alkyl, alkoxy, halo, or $OCF_3$.

17. The compound of claim 1, wherein:
$R^6$ is, independently at each occurrence, H methyl, or fluoro.

18. The compound of claim 1, wherein:
$R^7$ is, independently at each occurrence, H, methyl, or phenyl.

19. The compound of claim 1, wherein:
Y and an adjacent X together form —CH═CH—, —C≡C—, or phenylenyl.

20. The compound of claim 1, wherein:
m is an integer from 1 to 3;
X is, independently at each occurrence, $C(R^7)_2$, $N(R^3)$, or O;
Y is C;
$R^1$ is, independently at each occurrence, alkyl, alkoxy, halo, $CF_3$, or $OCF_3$;
$R^2$ is aryl substituted with 0-3 $R^9$;
$R^3$ is, independently at each occurrence, H or $C_1$-$C_4$ alkyl;
$R^4$ is, independently at each occurrence, H or $C_1$-$C_6$ alkyl;
$R^6$ is, independently at each occurrence, H, $C_1$-$C_4$ alkyl, or halo; and
$R^7$ is, independently at each occurrence, H or $C_1$-$C_4$ alkyl.

21. The compound of claim 1, wherein:
m is an integer from 0 to 1;
X is, independently at each occurrence, $C(R^7)_2$;
Y is C;
$R^1$ is, independently at each occurrence, alkyl, alkoxy, halo, $CF_3$, or $OCF_3$;
$R^2$ is aryl substituted with 0-3 $R^9$;
$R^3$ is, independently at each occurrence, H or $C_1$-$C_4$ alkyl;
$R^6$ is, independently at each occurrence, H, $C_1$-$C_4$ alkyl, or halo; and
$R^7$ is, independently at each occurrence, H or $C_1$-$C_4$ alkyl;

or both of said $R^4$, together with the nitrogen through which they are attached, form a heterocyclic ring of 4 to 7 atoms, where one carbon may be optionally replaced with N or O, where any carbon ring atom may be optionally substituted with one or two $C_1$-$C_4$ alkyl, F, or $CF_3$; and where any additional N atom may be optionally substituted with $C_1$-$C_4$ alkyl.

22. The compound of claim 1, wherein:
m is an integer from 0-1;
X is, independently at each occurrence, $C(R^7)_2$
Y is C
$R^1$ is, independently at each occurrence, alkyl, alkoxy, halo, $CF_3$, or $OCF_3$;

$R^2$ is aryl substituted with 0-3 $R^9$;

$R^3$ is, independently at each occurrence, H or $C_1$-$C_4$ alkyl;

$R^6$ is, independently at each occurrence, H, $C_1$-$C_4$ alkyl, or halo; and $R^7$ is, independently at each occurrence, H or $C_1$-$C_4$ alkyl, or one of said $R^6$ or one of said $R^7$ and one of said $R^4$, together with the nitrogen and carbon atoms through which they are attached, form a monocyclic or bicyclic heterocyclic ring of 3 to 12 atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl.

23. The compound of claim 1, wherein the pharmaceutically acceptable salt is a hydrochloride (HCl) salt.

24. A compound of formula II:

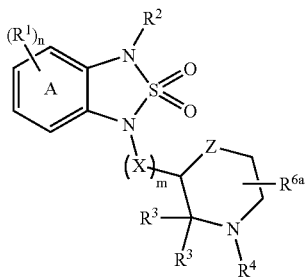

II or a pharmaceutically acceptable salt, stereoisomer or tautomer thereof;

wherein:

n is an integer from 0 to 4;

m is an integer from 1 to 6;

X is, independently at each occurrence, $C(R^7)_2$, $N(R^3)$, O, S, S(=O), or S(=O)$_2$;

Z is O, $N(R^3)$, S, or $C(R^7)_2$;

$R^1$ is, independently at each occurrence, H, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;

$R^2$ is aryl substituted with 0-3 $R^9$;

$R^3$ is, independently at each occurrence, H, $C_1$-$C_4$ alkyl, aryl substituted with 0-3 $R^{12}$, or heteroaryl substituted with 0-3 $R^{12}$;

$R^4$ is H, $C_1$-$C_6$ alkyl, arylalkyl substituted with 0-3 $R^{13}$ or heteroarylmethyl substituted with 0-3 $R^{13}$;

$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;

$R^{6a}$ is H, $C_1$-$C_4$ alkyl, $C_1$-$C_6$ alkoxy, halo, aryl substituted with 0-3 $R^1$, heteroaryl substituted with 0-3 $R^1$, —$N(R^3)_2$, —$S(R^3)$, or —$R^8$—O—$R^3$;

$R^7$ is, independently at each occurrence, H, hydroxy, $C_1$-$C_6$ alkoxy, or $C_1$-$C_4$ alkyl;

$R^8$ is, independently at each occurrence, straight or branched $C_1$-$C_6$ alkylenyl;

or one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl;

$R^9$ is, independently at each occurrence, alkyl, alkoxy, halo;

$R^{10}$ is, independently at each occurrence, alkyl, alkoxy, halo, $CF_3$, $OCF_3$, hydroxy, alkanoyloxy, nitro, nitrile, alkenyl, or alkynyl;

$R^{11}$ is, independently at each occurrence, alkyl, alkoxy, halo, $CF_3$, $OCF_3$, hydroxy, alkanoyloxy, nitro, nitrile, alkenyl, or alkynyl; and $R^{12}$ and $R^{13}$ are each, independently at each occurrence, alkyl, alkoxy, halo, $CF_3$, $OCF_3$, hydroxy, hydroxyalkyl, aminoalkyl, a heterocyclic ring, alkanoyloxy, nitro, nitrile, alkenyl, or alkynyl.

25. The compound of claim 24, wherein Z is O.

26. The compound of claim 24, wherein Z is $N(R^3)$.

27. The compound of claim 24, wherein X is $CH_2$ and m is 2 to 4.

28. The compound of claim 24, wherein:

ring A is composed of all carbon atoms;

$R^1$ is H;

$R^2$ is phenyl substituted with one to three fluoro (F) atoms;

each $R^3$ is H;

$R^4$ is H; and $R^{6a}$ is H.

29. The compound of claim 24, wherein the compound is:

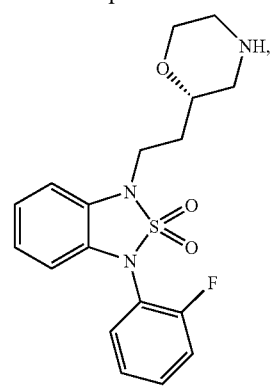

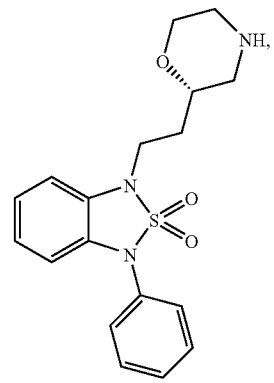

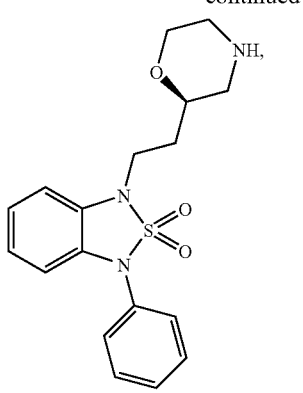
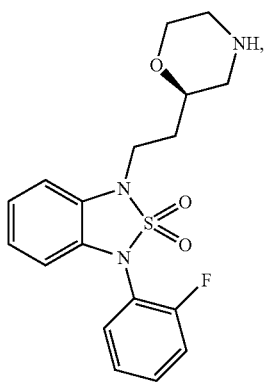
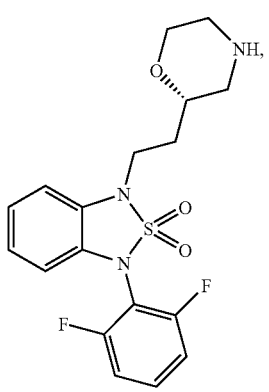
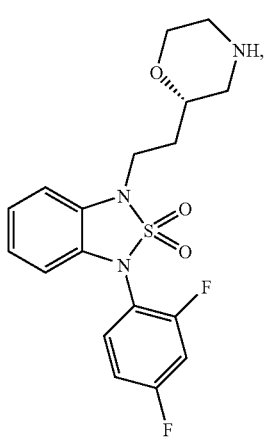
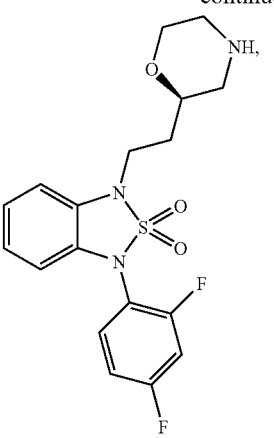
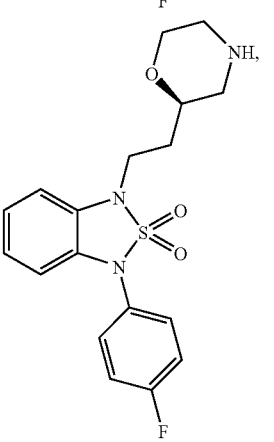
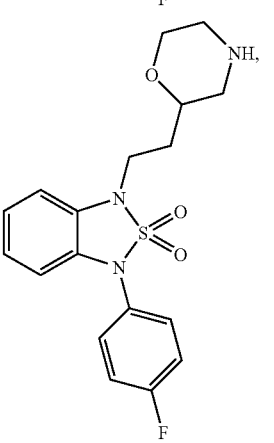
or

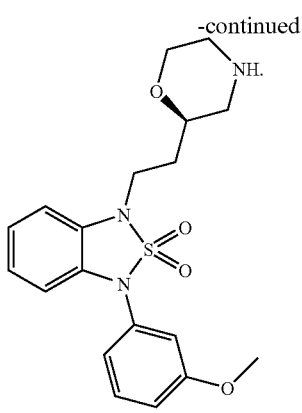

30. The compound of claim 1, selected from the group consisting of:

1-(morpholin-2-ylmethyl)-3-phenyl-1,3-dihydro-2,1,3-benzothiadiazole 2,2-dioxide;
1-[(2R)-morpholin-2-ylmethyl]-3-phenyl-1,3-dihydro-2,1,3-benzothiadiazole 2,2-dioxide;
1-[(2S)-morpholin-2-ylmethyl]-3-phenyl-1,3-dihydro-2,1,3-benzothiadiazole 2,2-dioxide;
1-[(4-methylmorpholin-2-yl)methyl]-3-phenyl-1,3-dihydro-2,1,3-benzothiadiazole 2,2-dioxide;
1-(2-chloro-4-fluorophenyl)-3-{2-[(3R,5S)-3,5-dimethylpiperazin-1-yl]ethyl}-1,3-dihydro-2,1,3-benzothiadiazole-2,2-dioxide;
1-(2-chloro-4-fluorophenyl)-3-{2-piperazin-1-ylethyl}-1,3-dihydro-2,1,3-benzothiadiazole-2,2-dioxide;
1-(4-fluoro-2-methylphenyl)-3-{2-piperazin-1-ylethyl}-1,3-dihydro-2,1,3-benzothiadiazole-2,2-dioxide;
1-(4-fluoro-2-methylphenyl)-3-{2-[(3R,5S)-3,5-dimethylpiperazin-1-yl]ethyl}-1,3-dihydro-2,1,3-benzothiadiazole-2,2-dioxide;
1-(4-fluoro-2-methoxyphenyl)-3-{2-piperazin-1-ylethyl}-1,3-dihydro-2,1,3-benzothiadiazole-2,2-dioxide;
1-[2-(2,5-diazabicyclo[2.2.1]hept-2-yl)ethyl]-3-phenyl-1,3-dihydro-2,1,3-benzothiadiazole 2,2-dioxide;
2-{2-[3-(2-fluorophenyl)-2,2-dioxido-2,1,3-benzothiadiazol-1(3H)-yl]ethoxy}ethanamine;
2-{2-[3-(2-fluorophenyl)-2,2-dioxido-2,1,3-benzothiadiazol-1(3H)-yl]ethoxy}-N-methylethanamine;
2-{2-[3-(2-fluorophenyl)-2,2-dioxido-2,1,3-benzothiadiazol-1(3H)-yl]ethoxy}-N,N-dimethylethanamine;
1-{2-[2-(3,5-dimethylpiperazin-1-yl)ethoxy]ethyl}-3-(2-fluorophenyl)-1,3-dihydro-2,1,3-benzothiadiazole 2,2-dioxide;
1-[5-(3,5-dimethylpiperazin-1-yl)pentyl]-3-(2-fluorophenyl)-1,3-dihydro-2,1,3-benzothiadiazole 2,2-dioxide;
(2R)-3-[3-(2-fluorophenyl)-2,2-dioxido-2,1,3-benzothiadiazol-1(3H)-yl]-2-methylpropan-1-amine;
(2S)-3-[3-(2-fluorophenyl)-2,2-dioxido-2,1,3-benzothiadiazol-1(3H)-yl]-2-methylpropan-1-amine;
4-[3-(2-fluorophenyl)-2,2-dioxido-2,1,3-benzothiadiazol-1(3H)-yl]butan-2-amine;
3-[3-(2-fluorophenyl)-2,2-dioxido-2,1,3-benzothiadiazol-1(3H)-yl]-N-methylbutan-1-amine;
4-[3-(2-fluorophenyl)-2,2-dioxido-2,1,3-benzothiadiazol-1(3H)-yl]-N-methylbutan-2-amine;
(2R)-3-[3-(2-fluorophenyl)-2,2-dioxido-2,1,3-benzothiadiazol-1(3H)-yl]-N,2-dimethylpropan-1-amine;
(2S)-3-[3-(2-fluorophenyl)-2,2-dioxido-2,1,3-benzothiadiazol-1(3H)-yl]-N,2-dimethylpropan-1-amine;
3-[3-(2-fluorophenyl)-2,2-dioxido-2,1,3-benzothiadiazol-1(3H)-yl]butan-1-amine;
1-Phenyl-3-(piperidin-4-ylmethyl)-1,3-dihydro-2,1,3-benzothiadiazole2,2-dioxide;
1-(2,6-Difluorophenyl)-3-(morpholin-2-ylmethyl)-1,3-dihydro-2,1,3-benzothiadiazole 2,2-dioxide;
1-(2,6-Difluorophenyl)-3-[(2R)-morpholin-2-ylmethyl]-1,3-dihydro-2,1,3-benzothiadiazole 2,2-dioxide;
1-(2,6-Difluorophenyl)-3-[(2S)-morpholin-2-ylmethyl]-1,3-dihydro-2,1,3-benzothiadiazole 2,2-dioxide;
1-(2,3-Difluorophenyl)-3-(morpholin-2-ylmethyl)-1,3-dihydro-2,1,3-benzothiadiazole 2,2-dioxide;
1-(Morpholin-2-ylmethyl)-3-[2-(trifluoromethoxy)phenyl]-1,3-dihydro-2,1,3-benzothiadiazole 2,2-dioxide;
1-Phenyl-3-(2-piperidin-4-ylethyl)-1,3-dihydro-2,1,3-benzothiadiazole 2,2-dioxide
1-Phenyl-3-(2-piperazin-1-ylethyl)-1,3-dihydro-2,1,3-benzothiadiazole-2,2-dioxide;
4-Fluoro-3-phenyl-1-(piperidin-4-ylmethyl)-1,3-dihydro-2,1,3-benzothiadiazole-2,2-dioxide;
4-Fluoro-3-phenyl-1-(2-piperidin-4-ylethyl)-1,3-dihydro-2,1,3-benzothiadiazole 2,2-dioxide;
4-Fluoro-3-phenyl-1-(2-piperazin-1-ylethyl)-1,3-dihydro-2,1,3-benzothiadiazole-2,2-dioxide;
4-Fluoro-3-(morpholin-2-ylmethyl)-1-phenyl-1,3-dihydro-2,1,3-benzothiadiazole-2,2-dioxide;
1-Phenyl-3-(3-piperidin-4-ylpropyl)-1,3-dihydro-2,1,3-benzothiadiazole-2,2-dioxide;
1-Phenyl-3-(2-piperidin-2-ylethyl)-1,3-dihydro-2,1,3-benzothiadiazole-2,2-dioxide
1-(2,6-Difluorophenyl)-3-(2-piperidin-4-ylethyl)-1,3-dihydro-2,1,3-benzothiadiazoie-2,2-dioxide;
1-(2,6-Difluorophenyl)-3-(2-piperazin-1-ylethyl)-1,3-dihydro-2,1,3-benzothiadiazole 2,2-dioxide;
1-Phenyl-3-(piperidin-3-ylmethyl)-1,3-dihydro-2,1,3-benzothiadiazole-2,2-dioxide;
1-Phenyl-3-[(3R)-piperidin-3-ylmethyl]-1,3-dihydro-2,1,3-benzothiadiazole-2,2-dioxide;
1-Phenyl-3-[(3S)-piperidin-3-ylmethyl]-1,3-dihydro-2,1,3-benzothiadiazole-2,2-dioxide;
1-Phenyl-3-(2-piperidin-3-ylethyl)-1,3-dihydro-2,1,3-benzothiadiazole-2,2-dioxide;
1-Phenyl-3-{2-[(3S)-piperidin-3-yl]ethyl}-1,3-dihydro-2,1,3-benzothiadiazole-2,2-dioxide;
1-Phenyl-3-{2-[(3R)-piperidin-3-yl]ethyl}-1,3-dihydro-2,1,3-benzothiadiazole-2,2-dioxide;
1-(2,3-Difluorophenyl)-3-(2-piperidin-4-ylethyl)-1,3-dihydro-2,1,3-benzothiadiazole-2,2-dioxide;
1-(2,5-Difluorophenyl)-3-(2-piperidin-4-ylethyl)-1,3-dihydro-2,1,3-benzothiadiazole-2,2-dioxide;
1-(2,3-Difluorophenyl)-3-(2-piperazin-1-ylethyl)-1,3-dihydro-2,1,3-benzothiadiazole-2,2-dioxide;
1-(2,5-Difluorophenyl)-3-(2-piperazin-1-ylethyl)-1,3-dihydro-2,1,3-benzothiadiazole-2,2-dioxide;
1-[2-(cis-3,5-Dimethylpiperazin-1-yl)ethyl]-3-phenyl-1,3-dihydro-2,1,3-benzothiadiazole-2,2-dioxide;
1-(2-Fluorophenyl)-3-(2-piperazin-1-ylethyl)-1,3-dihydro-2,1,3-benzothiadiazole-2,2-dioxide;
1-[2-(cis-3,5-Dimethylpiperazin-1-yl)ethyl]-3-(2-fluorophenyl)-1,3-dihydro-2,1,3-benzothiadiazole-2,2-dioxide;
1-[3-(cis-3,5-Dimethylpiperazin-1-yl)propyl]-3-phenyl-1,3-dihydro-2,1,3-benzothiadiazole 2,2-dioxide;

1-(2,6-Difluorophenyl)-3-[2-(cis-3,5-dimethylpiperazin-1-yl)ethyl]-1,3-dihydro-2,1,3-benzothiadiazole-2,2-dioxide;
1-(2-Piperazin-1-ylethyl)-3-(2,4,6-trifluorophenyl)-1,3-dihydro-2,1,3-benzothiadiazole-2,2-dioxide;
1-[2-(cis-3,5-Dimethylpiperazin-1-yl)ethyl]-3-(2,4,6-trifluorophenyl)-1,3-dihydro-2,1,3-benzothiadiazole-2,2-dioxide;
1-Phenyl-3-(3-piperazin-1-ylpropyl)-1,3-dihydro-2,1,3-benzothiadiazole-2,2-dioxide;
1-(4-Fluorophenyl)-3-(2-piperazin-1-ylethyl)-1,3-dihydro-2,1,3-benzothiadiazoie-2,2-dioxide;
1-[2-(cis-3,5-Dimethylpiperazin-1-yl)ethyl]-3-(4-fluorophenyl)-1,3-dihydro-2,1,3-benzothiadiazole-2,2-dioxide;
1-(2,4-difluorophenyl)-3-(2-piperazin-1-ylethyl)-1,3-dihydro-2,1,3-benzothiadiazole 2,2-dioxide;
1-(2,4-difluorophenyl)-3-[2-(3,5-dimethylpiperazin-1-yl)ethyl]-1,3-dihydro-2,1,3-benzothiadiazole-2,2-dioxide;
1-[2-(3,5-dimethylpiperazin-1-yl)ethyl]-4-fluoro-3-(2-fluorophenyl)-1,3-dihydro-2,1,3-benzothiadiazole 2,2-dioxide;
1-(2-{[3-(2,3-difluorophenyl)-2,2-dioxido-2,1,3-benzothiadiazol-1(3H)-yl]methyl}phenyl)-N-methylmethanamine;
3-[3-(2,3-difluorophenyl)-2,2-dioxido-2,1,3-benzothiadiazol-1(3H)-yl]-N-methyl-1-phenylpropan-1-amine;
3-[3-(2-fluorophenyl)-2,2-dioxido-2,1,3-benzothiadiazol-1(3H)-yl]-N-methyl-1-phenylpropan-1-amine;
4-[3-(2-fluorophenyl)-2,2-dioxido-2,1,3-benzothiadiazol-1(3H)-yl]-N-methylbut-2-yn-1-amine;
4-[3-(2-fluorophenyl)-2,2-dioxido-2,1,3-benzothiadiazol-1(3H)-yl]-N,N-dimethylbut-2-yn-1-amine;
(2E)-4-[3-(2-fluorophenyl)-2,2-dioxido-2,1,3-benzothiadiazol-1(3H)-yl]-N-methylbut-2-en-1-amine;
(2E)-4-[3-(2-fluorophenyl)-2,2-dioxido-2,1,3-benzothiadiazol-1(3H)-yl]-N,N-dimethylbut-2-en-1-amine;
3-{2-[(3R,5S)-3,5-dimethylpiperazin-1-yl]ethyl}-4-fluoro-1-(2-fluorophenyl)-1,3-dihydro-2,1,3-benzothiadiazole 2,2-dioxide;
2,2-difluoro-3-[3-(2-fluorophenyl)-2,2-dioxido-2,1,3-benzothiadiazol-1(3H)-yl]-N-methylpropan-1-amine;
1-(2-Fluorophenyl)-3-(2-piperidin-4-ylethyl)-1,3-dihydro-2,1,3-benzothiadiazole 2,2-dioxide;
1-[2-(1,4-Diazepan-1-yl)ethyl]-3-phenyl-1,3-dihydro-2,1,3-benzothiadiazole-2,2-dioxide;
1-(2,4-Difluorophenyl)-4-fluoro-3-(2-piperazin-1-ylethyl)-1,3-dihydro-2,1,3-benzothiadiazole-2,2-dioxide;
3-(2,4-Difluorophenyl)-4-fluoro-1-(2-piperazin-1-ylethyl)-1,3-dihydro-2,1,3-benzothiadiazole-2,2-dioxide
1-[2-(1,4-Diazepan-1-yl)ethyl]-3-(2,4,6-trifluorophenyl)-1,3-dihydro-2,1,3-benzothiadiazole-2,2-dioxide
1-{2-[(1S,4S)-2,5-Diazabicyclo[2.2.1]hept-2-yl]ethyl}-3-(2,4,6-trifluorophenyl)-1,3-dihydro-2,1,3-benzothiadiazole-2,2-dioxide;
3-[2-(1,4-Diazepan-1-yl)ethyl]-1-(2,4-difluorophenyl)-4-fluoro-1,3-dihydro-2,1,3-benzothiadiazole 2,2-dioxide;
1-[2-(1,4-Diazepan-1-yl)ethyl]-3-(2-fluorophenyl)-1,3-dihydro-2,1,3-benzothiadiazole 2,2-dioxide;
1-{2-[(1S,4S)-2,5-diazabicyclo[2.2.1]hept-2-yl]ethyl}-3-(2-fluorophenyl)-1,3-dihydro-2,1,3-benzothiadiazole 2,2-dioxide;
1-Phenyl-3-(2-piperidin-1-ylethyl)-1,3-dihydro-2,1,3-benzothiadiazole-2,2-dioxide;
1-(2,4-Difluorophenyl)-3-[2-(cis-3,5-dimethylpiperazin-1-yl)ethyl]-4-fluoro-1,3-dihydro-2,1,3-benzothiadiazole 2,2-dioxide;
1-[3-(1,4-Diazepan-1-yl)propyl]-3-phenyl-1,3-dihydro-2,1,3-benzothiadiazole-2,2-dioxide;
1-[2-(1,4-Diazepan-1-yl)ethyl]-3-(2,6-difluorophenyl)-1,3-dihydro-2,1,3-benzothiadiazole-2,2-dioxide;
1-[2-(1,4-Diazepan-1-yl)ethyl]-3-(2,4-difluorophenyl)-1,3-dihydro-2,1,3-benzothiadiazole-2,2-dioxide;
1-{2-[(1S,4S)-2,5-Diazabicyclo[2.2.1]hept-2-yl]ethyl}-3-(2,4-difluorophenyl)-1,3-dihydro-2,1,3-benzothiadiazole-2,2-dioxide;
1-(2,4-Difluorophenyl)-3-(2-piperidin-4-ylethyl)-1,3-dihydro-2,1,3-benzothiadiazole-2,2-dioxide;
1-(2,4-Difluorophenyl)-3-[2-(4-methylpiperazin-1-yl)ethyl]-1,3-dihydro-2,1,3-benzothiadiazole 2,2-dioxide;
1-(2,4-Difluorophenyl)-4-fluoro-3-[2-(4-methylpiperazin-1-yl)ethyl]-1,3-dihydro-2,1,3-benzothiadiazole 2,2-dioxide;
1-(2,4-Difluorophenyl)-3-[2-(4-methyl-1,4-diazepan-1-yl)ethyl]-1,3-dihydro-2,1,3-benzothiadiazole 2,2-dioxide;
1-[2-(4-Methyl-1,4-diazepan-1-yl)ethyl]-3-(2,4,6-trifluorophenyl)-1,3-dihydro-2,1,3-benzothiadiazole 2,2-dioxide;
N-{2-[3-(2-Fluorophenyl)-2,2-dioxido-2,1,3-benzothiadiazol-1(3H)-yl]ethyl}-N,N'-dimethylethane-1,2-diamine;
N-{2-[3-(2,4-Difluorophenyl)-2,2-dioxido-2,1,3-benzothiadiazol-1(3H)-yl]ethyl}-N,N'-dimethylethane-1,2-diamine;
N-{2-[2,2-Dioxido-3-(2,4,6-trifluorophenyl)-2,1,3-benzothiadiazol-1(3H)-yl]ethyl}-N,N'-dimethylethane-1,2-diamine;
1-{3-[3-(2-fluorophenyl)-2,2-dioxido-2,1,3-benzothiadiazol-1(3H)-yl]propyl}piperidin-4-amine;
1-[3-(2,2-dioxido-3-phenyl-2,1,3-benzothiadiazol-1(3H)-yl)propyl]piperidin-4-amine;
1-{2-[3-(2-fluorophenyl)-2,2-dioxido-2,1,3-benzothiadiazol-1(3H)-yl]ethyl}piperidin-4-amine;
1-{2-[3-(2-fluorophenyl)-2,2-dioxido-2,1,3-benzothiadiazol-1(3H)-yl]ethyl}-N-methylpiperidin-4-amine;
1-{2-[3-phenyl-2,2-dioxido-2,1,3-benzothiadiazol-1(3H)-yl]ethyl}piperidin-4-amine;
1-{2-[3-phenyl-2,2-dioxido-2,1,3-benzothiadiazol-1(3H)-yl]ethyl}-N-methylpiperidin-4-amine;
1-{1-[2-(2,2-dioxido-3-phenyl-2,1,3-benzothiadiazol-1(3H)-yl)ethyl]pyrrolidin-3-yl}methanamine;
1-phenyl-3-[2-(4-pyrrolidin-1-ylpiperidin-1-yl)ethyl]-1,3-dihydro-2,1,3-benzothiadiazole 2,2-dioxide;
2-{2-[3-(2-chloro-4-fluorophenyl)-2,2-dioxido-2,1,3-benzothiadiazol-1(3H)-yl]ethoxy}-N-methylethanamine;
2-{2-[3-(2-chloro-4-fluorophenyl)-2,2-dioxido-2,1,3-benzothiadiazol-1(3H)-yl]ethoxyl}-N,N-dimethylethanamine;
1-(4-chloro-2-fluorophenyl)-3-(2-piperazin-1-yl-ethyl)-1,3-dihydro-2,1,3-benzothiadiazole 2,2-dioxide;
1-(4-chloro-2-fluorophenyl)-3-{2-[(3R,5S)-3,5-dimethylpiperazin-1-yl]ethyl}-1,3-dihydro-2,1,3-benzothiadiazole 2,2-dioxide;
1-(4-chloro-2-fluorophenyl)-3-(2-piperidin-4-ylethyl)-1,3-dihydro-2,1,3-benzothiadiazole 2,2-dioxide;
1-(4-chloro-2-methylphenyl)-3-{2-[(3R,5S)-3,5-dimethylpiperazin-1-yl]ethyl}-1,3-dihydro-2,1,3-benzothiadiazole 2,2-dioxide;
1-(4-chloro-2-methylphenyl)-3-(2-piperazin-1-ylethyl)-1,3-dihydro-2,1,3-benzothiadiazole 2,2-dioxide;
1-(tert-butylamino)-4-(2,2-dioxido-3-phenyl-2,1,3-benzothiadiazol-1(3H)-yl)butan-2-one;

4-(2,2-dioxido-3-phenyl-2,1,3-benzothiadiazol-1(3H)-yl)-1-(isopropylamino)butan-2-one;
1-(cyclopropylamino)-4-(2,2-dioxido-3-phenyl-2,1,3-benzothiadiazol-1(3H)-yl)butan-2-one;
4-(2,2-dioxido-3-phenyl-2,1,3-benzothiadiazol-1(3H)-yl)-1-(methylamino)butan-2-one;
4-[3-(2-fluorophenyl)-2,2-dioxido-2,1,3-benzothiadiazol-1(3H)-yl]-1-(methylamino)butan-2-one;
(2Z)-4-(2,2-dioxido-3-phenyl-2,1,3-benzothiadiazol-1(3H)-yl)-1-(methylamino) butan-2-one oxime;
(2S)-4-[3-(2-fluorophenyl)-2,2-dioxido-2,1,3-benzothiadiazol-1(3H)-yl]-2-methoxy-N-methylbutan-1-amine;
(2S)-2-methoxy-N-methyl-4-[3-(2-methylphenyl)-2,2-dioxido-2,1,3-benzothiadiazol-1(3H)-yl]butan-1-amine;
(2S)-2-methoxy-4-[3-(3-methoxyphenyl)-2,2-dioxido-2,1,3-benzothiadiazol-1(3H)-yl]-N-methylbutan-1-amine;
4-(2,2-dioxido-3-phenyl-2,1,3-benzothiadiazol-1(3H)-yl)-2-methoxy-N-methylbutan-1-amine;
(2R)-4-(2,2-dioxido-3-phenyl-2,1,3-benzothiadiazol-1(3H)-yl)-2-methoxy-N-methylbutan-1-amine;
(2S)-4-(2,2-dioxido-3-phenyl-2,1,3-benzothiadiazol-1(3H)-yl)-2-methoxy-N-methylbutan-1-amine;
N-{(2S)-4-[3-(2-fluorophenyl)-2,2-dioxido-2,1,3-benzothiadiazol-1(3H)-yl]-2-methoxybutyl}cyclopropanamine;
N-{(2S)-2-methoxy-4-[3-(2-methylphenyl)-2,2-dioxido-2,1,3-benzothiadiazol-1(3H)-yl]butyl}cyclopropanamine;
N-{(2S)-2-methoxy-4-[3-(3-methoxyphenyl)-2,2-dioxido-2,1,3-benzothiadiazol-1(3H)-yl]butyl}cyclopropanamine;
N-{(2S)-4-[3-(2,4-difluorophenyl)-2,2-dioxido-2,1,3-benzothiadiazol-1-(3H)-yl]-2-methoxybutyl}cyclopropanamine;
N-{(2S)-4-[3-(2,5-difluorophenyl)-2,2-dioxido-2,1,3-benzothiadiazol-1(3H)-yl]-2-methoxybutyl}cyclopropanamine;
N-{(2S)-4-[3-(2,6-difluorophenyl)-2,2-dioxido-2,1,3-benzothiadiazol-1(3H)-yl]-2-methoxybutyl}cyclopropanamine;
2S)-4-[3-(2,6-difluorophenyl)-2,2-dioxido-2,1,3-benzothiadiazol-1(3H)-yl]-2-methoxy-N-methylbutan-1-amine;
(2S)-4-[3-(2,4-difluorophenyl)-2,2-dioxido-2,1,3-benzothiadiazol-1(3H)-yl]-2-methoxy-N-methylbutan-1-amine;
1-(2-morpholin-2-ylethyl)-3-phenyl-1,3-dihydro-2,1,3-benzothiadiazole 2,2-dioxide;
1-{2-[(2S)-morpholin-2-yl]ethyl}-3-phenyl-1,3-dihydro-2,1,3-benzothiadiazole 2,2-dioxide;
1-{2-[(2R)-morpholin-2-yl]ethyl}-3-phenyl-1,3-dihydro-2,1,3-benzothiadiazole 2,2-dioxide;
1-(4-fluorophenyl)-3-(2-morpholin-2-ylethyl)-1,3-dihydro-2,1,3-benzothiadiazole 2,2-dioxide;
1-(4-fluorophenyl)-3-{2-[(2S)-morpholin-2-yl]ethyl}-1,3-dihydro-2,1,3-benzothiadiazole 2,2-dioxide;
1-(4-fluorophenyl)-3-{2-[(2R)-morpholin-2-yl]ethyl}-1,3-dihydro-2,1,3-benzothiadiazole 2,2-dioxide;
1-(2,4-difluorophenyl)-3-(2-morpholin-2-ylethyl)-1,3-dihydro-2,1,3-benzothiadiazole 2,2-dioxide;
1-(2,4-difluorophenyl)-3-{2-[(2S)-morpholin-2-yl]ethyl}-1,3-dihydro-2,1,3-benzothiadiazole 2,2-dioxide;
1-(2,4-difluorophenyl)-3-{2-[(2R)-morpholin-2-yl]ethyl}-1,3-dihydro-2,1,3-benzothiadiazole 2,2-dioxide;
1-(2-morpholin-2-ylethyl)-3-(2,4,6-trifluorophenyl)-1,3-dihydro-2,1,3-benzothiadiazole 2,2-dioxide;
1-{2-[(2S)-morpholin-2-yl]ethyl}-3-(2,4,6-trifluorophenyl)-1,3-dihydro-2,1,3-benzothiadiazole 2,2-dioxide;
1-{2-[(2R)-morpholin-2-yl]ethyl}-3-(2,4,6-trifluorophenyl)-1,3-dihydro-2,1,3-benzothiadiazole 2,2-dioxide;
1-(3-methoxyphenyl)-3-{2-[(2S)-morpholin-2-yl]ethyl}-1,3-dihydro-2,1,3-benzothiadiazole 2,2-dioxide;
1-(3-methoxyphenyl)-3-{2-[(2R)-morpholin-2-yl]ethyl}-1,3-dihydro-2,1,3-benzothiadiazole 2,2-dioxide;
1-(2-fluorophenyl)-3-{2-[(2S)-morpholin-2-yl]ethyl}-1,3-dihydro-2,1,3-benzothiadiazole 2,2-dioxide;
1-(2-fluorophenyl)-3-{2-[(2R)-morpholin-2-yl]ethyl}-1,3-dihydro-2,1,3-benzothiadiazole 2,2-dioxide;
1-(2,6-difluorophenyl)-3-{2-[(2S)-morpholin-2-yl]ethyl}-1,3-dihydro-2,1,3-benzothiadiazole 2,2-dioxide;
1-(3-{[3-(2-fluorophenyl)-2,2-dioxido-2,1,3 benzothiadiazol-1(3H)-yl]methyl}phenyl)-N-methylmethanamine;
1-(3-{[3-(2-fluorophenyl)-2,2-dioxido-2,1,3-benzothiadiazol-1(3H)-yl]methyl}phenyl)methanamine;
1-(3-{[3-(2-fluorophenyl)-2,2-dioxido-2,1,3-benzothiadiazol-1(3H)-yl]methyl}phenyl)-N,N-dimethylmethanamine;
1-(4-{[3-(2-fluorophenyl)-2,2-dioxido-2,1,3-benzothiadiazol-1(3H)-yl]methyl}phenyl)-N,N-dimethylmethanamine;
1-(4-{[3-(2-fluorophenyl)-2,2-dioxido-2,1,3-benzothiadiazol-1(3H)-yl]methyl}phenyl)methanamine;
1-(4-{[3-(2-fluorophenyl)-2,2-dioxido-2,1,3-benzothiadiazol-1(3H)-yl]methyl}phenyl)-N-methylmethanamine;
(2Z)-4-[3-(2-fluoro-4-methylphenyl)-2,2-dioxido-2,1,3-benzothiadiazol-1(3H)-yl]-N-methylbut-2-en-1-amine;
(2Z)-4-[3-(2-fluoro-4-methylphenyl)-2,2-dioxido-2,1,3-benzothiadiazol-1(3H)-yl]but-2-en-1-amine;
(2Z)-4-[3-(2-fluoro-4-methylphenyl)-2,2-dioxido-2,1,3-benzothiadiazol-1(3H)-yl]-N,N-dimethylbut-2-en-1-amine;
(2Z)-N-ethyl-4-[3-(2-fluoro-4-methylphenyl)-2,2-dioxido-2,1,3-benzothiadiazol-1(3H)-yl]but-2-en-1-amine;
1-(3,4-difluorophenyl)-3-(2-piperazin-1-ylethyl)-1,3-dihydro-2,1,3-benzothiadiazole 2,2-dioxide;
1-(3,4-difluorophenyl)-3-(3-piperazin-1-ylpropyl)-1,3-dihydro-2,1,3-benzothiadiazole 2,2-dioxide;
1-(3,4-difluorophenyl)-3-[3-(3,5-dimethylpiperazin-1-yl)propyl]-1,3-dihydro-2,1,3-benzothiadiazole 2,2-dioxide;
2-{2-[3-(3,4-difluorophenyl)-2,2-dioxido-2,1,3-benzothiadiazol-1(3H)-yl]ethoxy}-N-methylethanamine;
1-(2-piperazin-1-ylethyl)-3-(2,3,4-trifluorophenyl)-1,3-dihydro-2,1,3-benzothiadiazole 2,2-dioxide;
1-(2-methylphenyl)-3-(2-piperazin-1-ylethyl)-1,3-dihydro-2,1,3-benzothiadiazole 2,2-dioxide;
1-(2-chlorophenyl)-3-(2-piperazin-1-ylethyl)-1,3-dihydro-2,1,3-benzothiadiazole 2,2-dioxide;
2-{2-[3-(2,4-difluorophenyl)-2,2-dioxido-2,1,3-benzothiadiazol-1(3H)-yl]ethoxy}-N-methylethanamine;
2-{2-[3-(2,4-difluorophenyl)-2,2-dioxido-2,1,3-benzothiadiazol-1(3H)-yl]ethoxy}ethanamine;
2-{2-[3-(2,4-difluorophenyl)-2,2-dioxido-2,1,3-benzothiadiazol-1(3H)-yl]ethoxy}-N,N-dimethylethanamine;
(2E)-4-[3-(2,4-difluorophenyl)-2,2-dioxido-2,1,3-benzothiadiazol-1(3H)-yl]-N-methylbut-2-en-1-amine;

(2E)-4-[3-(2,4-difluorophenyl)-2,2-dioxido-2,1,3-benzothiadiazol-1(3H)-yl]-N,N-dimethylbut-2-en-1-amine;
(2E)-4-[3-(2,4-difluorophenyl)-2,2-dioxido-2,1,3-benzothiadiazol-1(3H)-yl]but-2-en-1-amine;
N-(2-{2-[3-(2,6-difluorophenyl)-2,2-dioxido-2,1,3-benzothiadiazol-1(3H)-yl]ethoxy}ethyl)cyclopropanamine;
N-(2-{2-[3-(2,6-difluorophenyl)-2,2-dioxido-2,1,3-benzothiadiazol-1(3H)-yl]ethoxy}ethyl)cyclobutanamine;
N-(2-{2-[3-(2,6-difluorophenyl)-2,2-dioxido-2,1,3-benzothiadiazol-1(3H)-yl]ethoxy}ethyl)cyclopentanamine;
2-{2-[3-(2,6-difluorophenyl)-2,2-dioxido-2,1,3-benzothiadiazol-1(3H)-yl]ethoxy}-N-methylethanamine;
2-{2-[3-(2,6-difluorophenyl)-2,2-dioxido-2,1,3-benzothiadiazol-1(3H)-yl]ethoxy}-N-ethylethanamine;
N-(2-{2-[3-(2,6-difluorophenyl)-2,2-dioxido-2,1,3-benzothiadiazol-1(3H)-yl]ethoxy}ethyl)propan-2-amine;
1-(4-chlorophenyl)-3-(4-morpholin-4-ylbutyl)-1,3-dihydro-2,1,3-benzothiadiazole 2,2-dioxide;
1-(2-Fluorophenyl)-4-fluoro-3-{2-[(2R)-morpholin-2-yl]ethyl}-1,3-dihydro-2,1,3-benzothiadiazole 2,2-dioxide;
1-(2-Fluorophenyl)-4-fluoro-3-{2-[(2S)-morpholin-2-yl]ethyl}-1,3-dihydro-2,1,3-benzothiadiazole 2,2-dioxide;
1-(2-Fluorophenyl)-5-fluoro-3-{2-[(2R)-morpholin-2-yl]ethyl}-1,3-dihydro-2,1,3-benzothiadiazole 2,2-dioxide;
1-(2-Fluorophenyl)-5-fluoro-3-{2-[(2S)-morpholin-2-yl]ethyl}-1,3-dihydro-2,1,3-benzothiadiazole 2,2-dioxide;
1-(2-Fluorophenyl)-6-fluoro-3-{2-[(2R)-morpholin-2-yl]ethyl}-1,3-dihydro-2,1,3-benzothiadiazole 2,2-dioxide;
1-(2-Fluorophenyl)-6-fluoro-3-{2-[(2S)-morpholin-2-yl]ethyl}-1,3-dihydro-2,1,3-benzothiadiazole 2,2-dioxide;
1-(2-Fluorophenyl)-7-fluoro-3-{2-[(2R)-morpholin-2-yl]ethyl}-1,3-dihydro-2,1,3-benzothiadiazole 2,2-dioxide;
1-(2-Fluorophenyl)-7-fluoro-3-{2-[(2S)-morpholin-2-yl]ethyl}-1,3-dihydro-2,1,3-benzothiadiazole 2,2-dioxide;
1-(2,6-Difluorophenyl)-4-fluoro-3-{2-[(2R)-morpholin-2-yl]ethyl}-1,3-dihydro-2,1,3-benzothiadiazole 2,2-dioxide;
1-(2,6-Difluorophenyl)-4-fluoro-3-{2-[(2S)-morpholin-2-yl]ethyl}-1,3-dihydro-2,1,3-benzothiadiazole 2,2-dioxide;
1-(2,6-Difluorophenyl)-5-fluoro-3-{2-[(2R)-morpholin-2-yl]ethyl}-1,3-dihydro-2,1,3-benzothiadiazole 2,2-dioxide;
1-(2,6-Difluorophenyl)-5-fluoro-3-{2-[(2S)-morpholin-2-yl]ethyl}-1,3-dihydro-2,1,3-benzothiadiazole 2,2-dioxide;
1-(2,6-Difluorophenyl)-6-fluoro-3-{2-[(2R)-morpholin-2-yl]ethyl}-1,3-dihydro-2,1,3-benzothiadiazole 2,2-dioxide;
1-(2,6-Difluorophenyl)-6-fluoro-3-{2-[(2S)-morpholin-2-yl]ethyl}-1,3-dihydro-2,1,3-benzothiadiazole 2,2-dioxide;
1-(2,6-Difluorophenyl)-7-fluoro-3-{2-[(2R)-morpholin-2-yl]ethyl}-1,3-dihydro-2,1,3-benzothiadiazole 2,2-dioxide; and
1-(2,6-Difluorophenyl)-7-fluoro-3-{2-[(2S)-morpholin-2-yl]ethyl}-1,3-dihydro-2,1,3-benzothiadiazole 2,2-dioxide; and
pharmaceutically acceptable salts thereof.

31. A composition, comprising:
a. at least one compound of formula I:

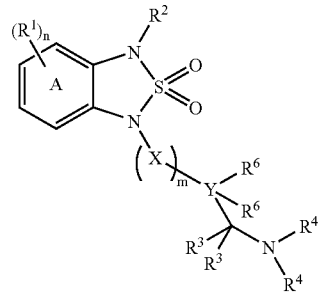

or a pharmaceutically acceptable salt, stereoisomer or tautomer thereof;

wherein:

n is an integer from 0 to 4;

m is an integer from 0 to 6;

X is, independently at each occurrence, $C(R^7)_2$, $N(R^3)$, O, S, $S(=O)$, or $S(=O)_2$;

Y is C; or

Y and an adjacent X together form —$CR^7$=$CR^7$—, —C≡C—, or arylenyl substituted with 0-3 $R^{10}$;

$R^1$ is, independently at each occurrence, H, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;

$R^2$ is aryl substituted with 0-3 $R^9$;

$R^3$ is, independently at each occurrence, H, halo, hydroxy, alkyl substituted with 0-3 $R^{13}$, a heterocyclic ring, aryl substituted with 0-3 $R^{12}$, or heteroaryl substituted with 0-3 $R^{12}$;

$R^4$ is, independently at each occurrence, H, alkyl substituted with 0-3 $R^{13}$, arylalkyl substituted with 0-3 $R^{13}$ or heteroarylmethyl substituted with 0-3 $R^{13}$;

$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;

$R^6$ is, independently at each occurrence, H, hydroxy, $C_1$-$C_4$ alkyl, $C_1$-$C_6$ alkoxy, halo, aryl substituted with 0-3 $R^1$, heteroaryl substituted with 0-3 $R^1$, —$N(R^3)_2$, —$S(R^3)$, or —$R^8$—O—$R^3$; or both $R^6$ groups form a cycloalkyl, a heterocyclic ring, =O or =N—OH;

provided that if each $R^3$ is H, each X is $CH_2$, and either each $R^6$ is H or one $R^6$ is hydroxy; then, both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, or a heterocyclic ring, F, or $CF_3$; and where any additional N atom may be optionally substituted with $C_1$-$C_4$ alkyl;

$R^7$ is, independently at each occurrence, H, hydroxy, alkoxy, or $C_1$-$C_4$ alkyl;

$R^8$ is, independently at each occurrence, straight or branched alkylenyl;

or one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, F, or $CF_3$; and where any additional N atom may be optionally substituted with alkyl;

or both of said $R^4$, together with the nitrogen through which they are attached, form monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, a heterocyclic ring, F, or $CF_3$; and where any additional N atom may be optionally substituted with alkyl;

or one of said $R^6$ or one of said $R^7$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl; provided that $R^4$ and $R^7$, taken together, do not form a piperidinyl ring;

$R^9$ is, independently at each occurrence, alkyl, alkoxy, halo;

$R^{10}$ is, independently at each occurrence, alkyl, alkoxy, halo, $CF_3$, $OCF_3$, hydroxy, alkanoyloxy, nitro, nitrile, alkenyl, or alkynyl;

$R^{11}$ is, independently at each occurrence, alkyl, alkoxy, halo, $CF_3$, $OCF_3$, hydroxy, alkanoyloxy, nitro, nitrile, alkenyl, or alkynyl; and $R^{12}$ and $R^{13}$ are each, independently at each occurrence, alkyl, alkoxy, halo, $CF_3$, $OCF_3$, hydroxy, hydroxyalkyl, aminoalkyl, a heterocyclic ring, alkanoyloxy, nitro, nitrile, alkenyl, or alkynyl; and b. at least one pharmaceutically acceptable carrier.

32. A process for the preparation of a compound of formula I:

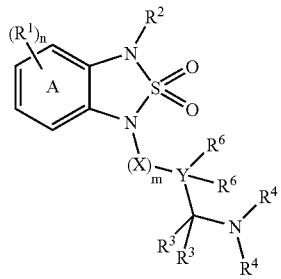

or a pharmaceutically acceptable salt, stereoisomer or tautomer thereof;

wherein:

n is an integer from 0 to 4;

m is an integer from 0 to 6;

X is, independently at each occurrence, $C(R^7)_2$, $N(R^3)$, O, S, S(=O), or S(=O)$_2$;

Y is C; or

Y and an adjacent X together form —$CR^7$=$CR^7$—, —C≡C—, or arylenyl substituted with 0-3 $R^{10}$;

$R^1$ is, independently at each occurrence, H, alkyl, alkoxy, halo, $CF_3$, $OCF_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;

$R^2$ is aryl substituted with 0-3 $R^9$;

$R^3$ is, independently at each occurrence, H, halo, hydroxy, alkyl substituted with 0-3 $R^{13}$, a heterocyclic ring, aryl substituted with 0-3 $R^{12}$, or heteroaryl substituted with 0-3 $R^{12}$;

$R^4$ is, independently at each occurrence, H, alkyl substituted with 0-3 $R^{13}$, arylalkyl substituted with 0-3 $R^{13}$ or heteroarylmethyl substituted with 0-3 $R^{13}$;

$R^5$ is, independently at each occurrence, alkyl, alkoxy, halo, $CF_3$, $OCF_3$, hydroxy, alkanoyloxy, nitro, nitrile, alkenyl, alkynyl, alkylsulfoxide, alkylsulfone, alkylsulfonamide, or alkylamido;

$R^6$ is, independently at each occurrence, H, hydroxy, $C_1$-$C_4$ alkyl, $C_1$-$C_6$ alkoxy, halo, aryl substituted with 0-3 $R^1$, heteroaryl substituted with 0-3 $R^1$, —$N(R^3)_2$, —$S(R^3)$, or —$R^8$—O—$R^3$; or both $R^6$ groups form a cycloalkyl, a heterocyclic ring, =O or =N—OH;

provided that if each $R^3$ is H, each X is $CH_2$, and either each $R^6$ is H or one $R^6$ is hydroxy; then, both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, or a heterocyclic ring, F, or $CF_3$; and where any additional N atom may be optionally substituted with $C_1$-$C_4$ alkyl;

$R^7$ is, independently at each occurrence, H, hydroxy, alkoxy, or $C_1$-$C_4$ alkyl;

$R^8$ is, independently at each occurrence, straight or branched alkylenyl;

or one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, F, or $CF_3$; and where any additional N atom may be optionally substituted with alkyl;

or both of said $R^4$, together with the nitrogen through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two alkyl, hydroxyalkyl, aminoalkyl, a heterocyclic ring, F, or $CF_3$; and where any additional N atom may be optionally substituted with alkyl;

or one of said $R^6$ or one of said $R^7$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or $SO_2$, and where any carbon ring atom may be optionally substituted with one or two $C_1$-$C_4$ alkyl, F, or $CF_3$; and where any additional N atom may be optionally substituted with $C_1$-$C_4$ alkyl; provided that $R^4$ and $R^7$, taken together, do not form a piperidinyl ring;

$R^9$ is, independently at each occurrence, alkyl, alkoxy,;

$R^{10}$ is, independently at each occurrence, alkyl, alkoxy, halo, $CF_3$, $OCF_3$, hydroxy, alkanoyloxy, nitro, nitrile, alkenyl, or alkynyl;

$R^{11}$ is, independently at each occurrence, alkyl, alkoxy, halo, $CF_3$, $OCF_3$, hydroxy, alkanoyloxy, nitro, nitrile, alkenyl, or alkynyl; and $R^{12}$ and $R^{13}$ are each, independently at each occurrence, alkyl, alkoxy, halo, $CF_3$, $OCF_3$, hydroxy, hydroxyalkyl, aminoalkyl, a heterocyclic ring, alkanoyloxy, nitro, nitrile, alkenyl, or alkynyl; and the process comprising:

(d) reacting a compound of formula IA:

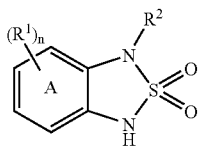

IA with a compound of formula IB:

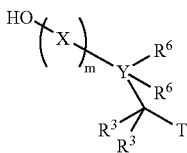

IB wherein

T is an —$N(R^4)_2$ or an activating group;

wherein, if T is —$N(R^4)_2$, then the compound of formula I is formed; or if T is an activating group, then a compound of formula IC is formed:

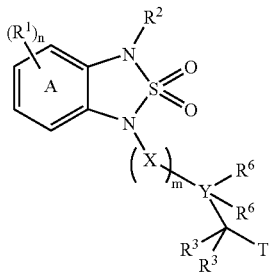

IC and the process further comprises:

(e) reacting the compound formula IC with —$N(R^4)R^P$ to form a compound of formula ID:

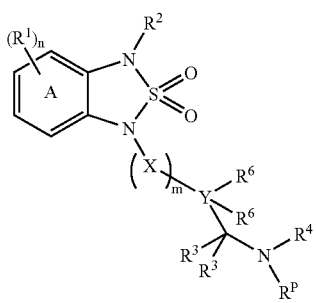

ID wherein $R^P$ is $R^4$ or a protecting group;

wherein, if $R^P$ is $R^4$, the compound of formula I is formed; or if $R^P$ is a protecting group, the process further comprises:

(f) deprotecting the compound of formula ID to form a deprotected compound; and (g) reacting the deprotected compound with an activated-$R^4$ group, provided that $R^4$ in the activated-$R^4$ group is not H;

wherein the compound of formula I is formed.

33. The process of claim 32, wherein step (d) further comprises contacting the compound of formula IA and IB with dialkyl azodicarboxylate and triphenylphosphine.

34. The process of claim 33, wherein the dialkyl azodicarboxylate is diisopropyl azodicarboxylate.

35. The process of claim 32, wherein the activating group is selected from the group consisting of halo, tosylate, mesylate, triflate, and oxo.

36. The process of claim 35, wherein the activating group is Br.

37. The process of claim 32, wherein the protecting group is selected from the group consisting of BOC, benzyl, acetyl, PMB, alkyl, Fmoc, Cbz, trifluoroacetyl, tosyl and triphenylmethyl.

38. The process of claim 37, wherein the protecting group is BOC.

39. The process of claim 32, wherein the deprotecting step is performed in the presence of at least one agent selected from hydrochloric acid (HCl), tin(II)chloride, ammonium chloride, zinc, trifluoroacetic acid (TFA), tosic acid, a halotrimethylsilane, or aluminum chloride.

40. The process of claim 32, wherein any one of steps (d)-(g) is performed at or above 30° C. or any one of steps (d)-(g) includes a purification step comprising at least one of: filtration, extraction, chromatography, trituration, or recrystallization.

41. The process of claim 32, wherein the activated-$R^4$ group is halo-$R^4$ or O=$R^4$.

42. The process of claim 32, wherein the compound of formula IA is prepared by:

(a) reacting a compound of formula IE:

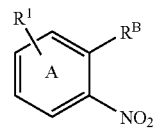

IE wherein $R^B$ is F or Cl;

with $R^2$—$NH_2$ to form a compound of formula IF:

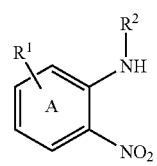

IF (b) hydrogenating the compound of formula IF to form a compound of formula IG:

$$\text{IG}$$

[Structure: benzene ring A with $R^1$, $R^2$, NH, and NH$_2$ substituents]

and (c) reacting the compound of formula IG with sulfamide in diglyme to form the compound of formula IA.

43. The process of claim 42, wherein the hydrogenating step is performed in the presence of hydrogen (H$_2$) and Pd/C.

44. The process of claim 42, wherein any one of steps (a)-(c) is performed at or above 30° C.

45. The process of claim 42, wherein any one of steps (a)-(c) includes a purification step comprising at least one of: filtration, extraction, chromatography, trituration, or recystallization.

46. A process for the preparation of a compound of formula I:

$$\text{I}$$

[Structure of formula I with substituents $(R^1)_n$, A, $R^2$, N, S(=O)$_2$, X, Y, $R^6$, $R^6$, $R^3$, $R^3$, N, $R^4$, $R^4$, m]

or a pharmaceutically acceptable salt, stereoisomer or tautomer thereof;
wherein:

n is an integer from 0 to 4;

m is an integer from 0 to 6;

X is, independently at each occurrence, $C(R^7)_2$, $N(R^3)$, O, S, S(=O), or S(=O)$_2$;

Y is C; or

Y and an adjacent X together form —$CR^7$=$CR^7$—, —C≡C—, or arylenyl substituted with 0-3 $R^{10}$;

$R^1$ is, independently at each occurrence, H, alkyl, alkoxy, halo, CF$_3$, OCF$_3$, hydroxy, alkanoyloxy, nitro, nitrile, alkenyl, alkynyl, aryl substituted with 0-3 $R^{11}$, heteroaryl substituted with 0-3 $R^{11}$, alkylsulfoxide, alkylsulfone, alkylsulfonamide, arylsulfonamide substituted with 0-3 $R^5$, alkylamido, or arylamido substituted with 0-3 $R^5$;

$R^2$ is aryl substituted with 0-3 $R^9$;

$R^3$ is, independently at each occurrence, H, halo, hydroxy, alkyl substituted with 0-3 $R^{13}$, a heterocyclic ring, aryl substituted with 0-3 $R^{12}$, or heteroaryl substituted with 0-3 $R^{12}$;

$R^4$ is, independently at each occurrence, H, alkyl substituted with 0-3 $R^{13}$, arylalkyl substituted with 0-3 $R^{13}$ or heteroarylmethyl substituted with 0-3 $R^{13}$;

$R^5$ is, independently at each occurrence, alkyl, alkoxy, halo, CF$_3$, OCF$_3$, hydroxy, alkanoyloxy, nitro, nitrile, alkenyl, alkynyl, alkylsulfoxide, alkylsulfone, alkylsulfonamide, or alkylamido;

$R^6$ is, independently at each occurrence, H, hydroxy, $C_1$-$C_4$ alkyl, $C_1$-$C_6$ alkoxy, halo, aryl substituted with 0-3 $R^1$, heteroaryl substituted with 0-3 $R^1$, —$N(R^3)_2$, —$S(R^3)$, or —$R^8$—O—$R^3$; or both $R^6$ groups form a cycloalkyl, a heterocyclic ring, =O or =N—OH;

provided that if each $R^3$ is H, each X is CH$_2$, and either each $R^6$ is H or one $R^6$ is hydroxy; then, both of said $R^4$, together with the nitrogen through which they are attached, form a monocyclic or bicyclic heterocyclic ring of 3 to 12 ring atoms, where one carbon may be optionally replaced with N, O, S, or SO$_2$, and where any carbon ring atom may be optionally substituted with one or two alkyl, hydroxyalkyl, aminoalkyl, or a heterocyclic ring, F, or CF$_3$; and where any additional N atom may be optionally substituted with $C_1$-$C_4$ alkyl;

$R^7$ is, independently at each occurrence, H, hydroxy, alkoxy, or $C_1$-$C_4$ alkyl;

$R^8$ is, independently at each occurrence, straight or branched alkylenyl;

or one of said $R^3$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or SO$_2$, and where any carbon ring atom may be optionally substituted with one or two alkyl, F, or CF$_3$; and where any additional N atom may be optionally substituted with alkyl;

or both of said $R^4$, together with the nitrogen through which they are attached, form a monocyclic or bicyclic heterocyclic ring of 3 to 12 ring atoms, where one carbon may be optionally replaced with N, O, S, or SO$_2$, and where any carbon ring atom may be optionally substituted with one or two alkyl, hydroxyalkyl, aminoalkyl, a heterocyclic ring, F, or CF$_3$; and where any additional N atom may be optionally substituted with alkyl;

or one of said $R^6$ or one of said $R^7$ and one of said $R^4$, together with the nitrogen and carbon atoms through which they are attached, form a monocyclic or bicyclic heterocyclic ring of 3 to 12 ring atoms, where one carbon may be optionally replaced with N, O, S, or SO$_2$, and where any carbon ring atom may be optionally substituted with one or two $C_1$-$C_4$ alkyl, F, or CF$_3$; and where any additional N atom may be optionally substituted with $C_1$-$C_4$ alkyl; provided that $R^4$ and $R^7$, taken together, do not form a piperidinyl ring;

$R^9$ is, independently at each occurrence, alkyl, alkoxy, halo;

$R^{10}$ is, independently at each occurrence, alkyl, alkoxy, halo, CF$_3$, OCF$_3$, hydroxy, alkanoyloxy, nitro, nitrile, alkenyl, or alkynyl;

$R^{11}$ is, independently at each occurrence, alkyl, alkoxy, halo, CF$_3$, OCF$_3$, hydroxy, alkanoyloxy, nitro, nitrile, alkenyl, or alkynyl; and $R^{12}$ and $R^{13}$ are each, independently at each occurrence, alkyl, alkoxy, halo, CF$_3$, OCF$_3$, hydroxy, hydroxyalkyl, aminoalkyl, a heterocyclic ring, alkanoyloxy, nitro, nitrile, alkenyl, or alkynyl; and the process comprising:

(d) reacting $R^2(BOH)_2$ and a transitional metal salt with a compound of formula IH:

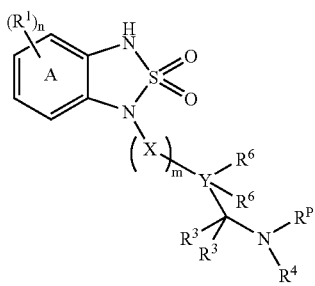

IH wherein
$R^P$ is $R^4$ or a protecting group; and
if $R^P$ is $R^4$, the compound of formula I is formed; or
if $R^P$ is a protecting group, the process further comprises:
(e) deprotecting the compound of formula IH to form a deprotected compound; and
(g) reacting the deprotected compound with an activated-$R^4$ group, provided that $R^4$ group in the activated-$R^4$ group is not H;
wherein the compound of formula I is formed.

47. The process of claim 46, wherein the transitional metal salt is copper(II)acetate.

48. The process of claim 46, wherein the activated-$R^4$ group is halo-$R^4$ or O=$R^4$.

49. The process of claim 46, wherein the protecting group is selected from the group consisting of BOC, benzyl, acetyl, PMB, alkyl, Fmoc, Cbz, trifluoroacetyl, tosyl and triphenylmethyl.

50. The process of claim 49, wherein the protecting group is BOC.

51. The process of claim 46, wherein the deprotecting step is performed in the presence of at least one agent selected from hydrochloric acid (HCl), tin(II)chloride, ammonium chloride, zinc, trifluoroacetic acid (TFA), tosic acid, a halotrimethylsilane, or aluminum chloride.

52. The process of claim 46, wherein any one of steps (d)-(g) is performed at or above 30° C. or any one of steps (d)-(g) includes a purification step comprising at least one of: filtration, extraction, chromatography, trituration, or recrystalization.

53. The process of claim 46, wherein the compound of formula IH is prepared by:
(a) reacting a compound of formula IJ:

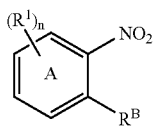

IJ wherein $R^B$ is F or Cl;
with a compound of formula IK:

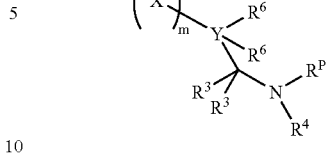

IK to form a compound of formula IL:

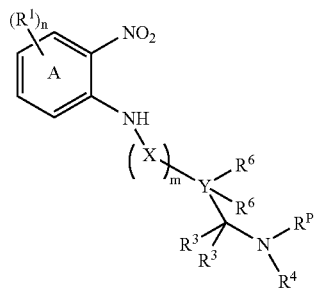

IL (b) hydrogenating the compound of formula IL to form a compound of formula IM:

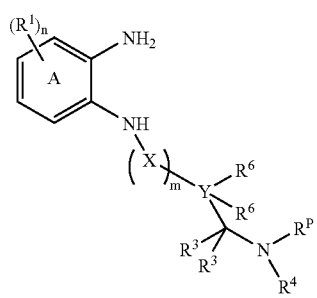

IM and (c) reacting the compound of formula IM with sulfamide and diglyme to form the compound of formula IH.

54. The process of claim 53, wherein the hydrogenating step is performed in the presence of hydrogen ($H_2$) and Pd/C.

55. The process of claim 53, wherein any one of steps (a)-(c) is performed at or above 30° C.

56. The process of claim 53, wherein any one of steps (a)-(c) includes a purification step comprising at least one of: filtration, extraction, chromatography, trituration, or recrystalization.

57. The compound named 1-(2,6-difluorophenyl)-3-(2-piperazin-1-ylethyl)-1,3-dihydro-2,1,3-benzothiadiazole-2,2-dioxide or a pharmaceutically acceptable salt thereof.

58. A composition comprising 1-(2,6-difluorophenyl)-3-(2-piperazin-1-ylethyl)-1,3-dihydro-2,1,3-benzothiadiazole-2,2-dioxide or a pharmaceutically acceptable salt thereof; and at least one pharmaceutically acceptable carrier.

* * * * *